(12) United States Patent
Lanza et al.

(10) Patent No.: US 12,209,255 B2
(45) Date of Patent: Jan. 28, 2025

(54) MESENCHYMAL-LIKE STEM CELLS DERIVED FROM HUMAN EMBRYONIC STEM CELLS, METHODS AND USES THEREOF

(71) Applicant: Astellas Institute for Regenerative Medicine, Westborough, MA (US)

(72) Inventors: Robert P. Lanza, Clinton, MA (US); Erin Kimbrel, Sudbury, MA (US)

(73) Assignee: Astellas Institute for Regenerative Medicine, Westborough, MA (US)

(*) Notice: Subject to any disclaimer, the term of this patent is extended or adjusted under 35 U.S.C. 154(b) by 262 days.

(21) Appl. No.: 16/745,944

(22) Filed: Jan. 17, 2020

(65) Prior Publication Data
US 2020/0392463 A1 Dec. 17, 2020

Related U.S. Application Data

(60) Continuation of application No. 15/656,473, filed on Jul. 21, 2017, now Pat. No. 10,557,122, which is a division of application No. 14/413,290, filed as application No. PCT/US2013/048291 on Jun. 27, 2013, now Pat. No. 9,745,551.

(60) Provisional application No. 61/762,961, filed on Feb. 11, 2013, provisional application No. 61/670,787, filed on Jul. 12, 2012.

(51) Int. Cl.
| | |
|---|---|
| *C12N 5/0775* | (2010.01) |
| *A61K 35/28* | (2015.01) |
| *A61K 35/51* | (2015.01) |
| *C12N 5/071* | (2010.01) |
| *C12N 5/0789* | (2010.01) |
| *C12N 13/00* | (2006.01) |
| *C12N 15/01* | (2006.01) |

(52) U.S. Cl.
CPC ............ *C12N 5/0662* (2013.01); *A61K 35/28* (2013.01); *A61K 35/51* (2013.01); *C12N 5/0647* (2013.01); *C12N 5/0692* (2013.01); *C12N 13/00* (2013.01); *C12N 15/01* (2013.01); *C12N 2501/10* (2013.01); *C12N 2501/115* (2013.01); *C12N 2501/145* (2013.01); *C12N 2501/155* (2013.01); *C12N 2501/165* (2013.01); *C12N 2501/26* (2013.01); *C12N 2506/02* (2013.01); *C12N 2533/90* (2013.01)

(58) Field of Classification Search
CPC .. C12N 5/0662; C12N 5/0647; C12N 5/0692; C12N 13/00; C12N 15/01; C12N 2501/10; C12N 2501/115; C12N 2501/145; C12N 2501/155; C12N 2501/165; C12N 2501/26; C12N 2506/02; C12N 2533/90; A61K 35/28; A61K 35/51
USPC .......................................... 424/93.7; 435/377
See application file for complete search history.

(56) References Cited

U.S. PATENT DOCUMENTS

| | | |
|---|---|---|
| 5,128,259 A | 7/1992 | Morgan |
| 5,599,705 A | 2/1997 | Cameron |
| 5,635,387 A | 6/1997 | Fei et al. |
| 5,914,268 A | 6/1999 | Keller et al. |
| 6,429,012 B1 | 8/2002 | Kraus et al. |
| 6,479,286 B1 | 11/2002 | Nelson et al. |
| 6,602,711 B1 | 8/2003 | Thomson et al. |
| 7,220,584 B2 | 5/2007 | Thomson et al. |
| 7,374,934 B2 | 5/2008 | Keller et al. |
| 7,592,176 B2 | 9/2009 | Pike et al. |
| 7,794,704 B2 | 9/2010 | Klimanskaya et al. |
| 7,998,472 B2 | 8/2011 | Huss et al. |
| 8,017,393 B2 | 9/2011 | Lanza et al. |
| 8,198,085 B2 | 6/2012 | Kanias et al. |
| 8,372,642 B2 | 2/2013 | Rajesh et al. |
| 8,679,834 B2 | 3/2014 | Lombardo et al. |
| 8,685,728 B2 | 4/2014 | Shi et al. |
| 8,822,218 B2 | 9/2014 | Kimbrel et al. |
| 8,868,631 B2 | 10/2014 | Pham et al. |
| 8,961,956 B2 | 2/2015 | Kimbrel et al. |
| 8,962,321 B2 | 2/2015 | Kimbrel et al. |
| 8,986,996 B2 | 3/2015 | Cho et al. |
| 9,109,202 B2 | 8/2015 | Spanholtz |

(Continued)

FOREIGN PATENT DOCUMENTS

| | | |
|---|---|---|
| AU | 2009244231 A1 | 11/2009 |
| AU | 2009244236 A1 | 11/2009 |

(Continued)

OTHER PUBLICATIONS

Tran et al.("Wnt3a-Induced Mesoderm Formation and Cardiomyogenesis in Human Embryonic Stem Cells," Stem Cells 2009;27: 1869-1878) (Year: 2009).*

(Continued)

*Primary Examiner* — Valarie E Bertoglio
(74) *Attorney, Agent, or Firm* — Wolf, Greenfield & Sacks, P.C.

(57) ABSTRACT

The present invention relates to methods of generating and expanding hitman embryonic stem cell derived mesenchymal-like stem/stromal cells. These hES-MSCs are characterized at least in part by the low level of expression of IL-6. These cells are useful for the prevention and treatment of T cell related autoimmune disease, especially multiple sclerosis, as well as for delivering agents across the blood-brain barrier and the blood-spinal cord barrier. Also provided is a method of selecting clinical grade hES-MSC and a method of modifying MSC to produced a MSC with specific biomarker profile. The modified MSC are useful for treatment of various diseases.

9 Claims, 34 Drawing Sheets

(56) References Cited

U.S. PATENT DOCUMENTS

| | | |
|---|---|---|
| 9,121,008 B2 | 9/2015 | Tsai |
| 9,301,979 B2 | 4/2016 | Cho et al. |
| 9,371,515 B2 | 6/2016 | Badoer et al. |
| 9,381,216 B2 | 7/2016 | Ghosh |
| 9,410,123 B2 | 8/2016 | Lanza et al. |
| 9,415,036 B2 | 8/2016 | Bastianelli |
| 9,655,925 B2 | 5/2017 | Lowdell et al. |
| 9,694,035 B2 | 7/2017 | Aggarwal et al. |
| 9,745,551 B2 | 8/2017 | Wang et al. |
| 9,938,500 B2 | 4/2018 | Lanza et al. |
| 9,943,547 B2 | 4/2018 | Aggarwal et al. |
| 9,988,602 B2 | 6/2018 | Lanza et al. |
| 9,988,603 B2 | 6/2018 | Li et al. |
| 10,046,011 B2 | 8/2018 | Wang et al. |
| 10,047,344 B2 | 8/2018 | Poon et al. |
| 10,363,276 B2 | 7/2019 | Yarmush et al. |
| 10,550,369 B2 | 2/2020 | Tom et al. |
| 10,557,122 B2 | 2/2020 | Wang et al. |
| 10,624,930 B2 | 4/2020 | Itescu et al. |
| 10,668,101 B2 | 6/2020 | Aggarwal et al. |
| 10,716,814 B2 | 7/2020 | Aggarwal et al. |
| 2002/0035735 A1 | 3/2002 | Schatten et al. |
| 2002/0103542 A1 | 8/2002 | Bilbo |
| 2003/0166273 A1 | 9/2003 | Kaufman et al. |
| 2003/0175954 A1 | 9/2003 | Shamblott et al. |
| 2003/0180265 A1 | 9/2003 | Scott et al. |
| 2004/0013676 A1 | 1/2004 | Bae et al. |
| 2004/0052771 A1 | 3/2004 | Lim |
| 2004/0229350 A1 | 11/2004 | Strelchenko et al. |
| 2005/0032210 A1 | 2/2005 | Sato et al. |
| 2005/0042751 A1 | 2/2005 | Goldman et al. |
| 2005/0153443 A1 | 7/2005 | Lanza et al. |
| 2005/0221482 A1 | 10/2005 | Burt et al. |
| 2005/0221487 A1 | 10/2005 | Zon et al. |
| 2006/0031955 A1 | 2/2006 | West et al. |
| 2006/0099198 A1 | 5/2006 | Thomson et al. |
| 2007/0031386 A1 | 2/2007 | Klimanskaya |
| 2007/0042344 A1 | 2/2007 | Choi et al. |
| 2007/0067860 A1 | 3/2007 | West et al. |
| 2007/0141703 A1 | 6/2007 | Stanley et al. |
| 2007/0218552 A1 | 9/2007 | Giarratana et al. |
| 2007/0298496 A1 | 12/2007 | Kuo et al. |
| 2008/0003674 A1 | 1/2008 | Slukvin et al. |
| 2008/0014180 A1 | 1/2008 | Lanza et al. |
| 2008/0014183 A1 | 1/2008 | Okano et al. |
| 2008/0057041 A1 | 3/2008 | Chung et al. |
| 2008/0095749 A1 | 4/2008 | Aggarwal et al. |
| 2008/0108044 A1 | 5/2008 | Rajesh et al. |
| 2008/0160564 A1 | 7/2008 | Rich |
| 2008/0166327 A1 | 7/2008 | Asahara et al. |
| 2008/0166751 A1 | 7/2008 | Asahara et al. |
| 2009/0010896 A1 | 1/2009 | Centeno et al. |
| 2009/0081784 A1 | 3/2009 | Vodyanyk et al. |
| 2009/0232777 A1 | 9/2009 | Lundgren-Akerlund et al. |
| 2009/0246875 A1 | 10/2009 | Yamanaka et al. |
| 2009/0271335 A1 | 10/2009 | West et al. |
| 2009/0304642 A1* | 12/2009 | Bakre ............... A61K 38/1709 435/377 |
| 2009/0304646 A1 | 12/2009 | Sakurada et al. |
| 2010/0167404 A1 | 7/2010 | West et al. |
| 2010/0240132 A1 | 9/2010 | Lanza et al. |
| 2010/0323027 A1 | 12/2010 | Lim et al. |
| 2011/0027886 A1* | 2/2011 | Han ..................... C12N 5/0692 435/406 |
| 2011/0064705 A1 | 3/2011 | Lanza et al. |
| 2011/0086424 A1 | 4/2011 | Lanza et al. |
| 2011/0123498 A1 | 5/2011 | Westenfelder |
| 2011/0129918 A1 | 6/2011 | Hung |
| 2011/0151554 A1 | 6/2011 | Yuo et al. |
| 2011/0195054 A1 | 8/2011 | Cohen et al. |
| 2011/0236971 A2 | 9/2011 | Vodyanyk et al. |
| 2012/0027731 A1 | 2/2012 | Lanza et al. |
| 2012/0077181 A1 | 3/2012 | Schmidt et al. |
| 2012/0087933 A1 | 4/2012 | Tom et al. |
| 2012/0114618 A1 | 8/2012 | Corp |
| 2013/0183272 A1 | 7/2013 | Kimbrel et al. |
| 2014/0057348 A1 | 2/2014 | West et al. |
| 2014/0072537 A1 | 3/2014 | Kimbrel et al. |
| 2015/0140657 A1 | 5/2015 | Kimbrel et al. |
| 2015/0203820 A1 | 7/2015 | Wang et al. |
| 2015/0272994 A1 | 10/2015 | Kimbrel et al. |
| 2016/0011545 A1 | 1/2016 | Kakishima et al. |
| 2016/0038543 A1 | 2/2016 | Kimbrel et al. |
| 2017/0121681 A1 | 5/2017 | Lanza et al. |
| 2017/0152481 A1 | 6/2017 | Lanza et al. |
| 2017/0239295 A1 | 8/2017 | Cho et al. |
| 2017/0252374 A1 | 9/2017 | Kimbrel et al. |
| 2018/0010098 A1 | 1/2018 | Wang et al. |
| 2018/0333436 A1 | 11/2018 | Yoshifumi et al. |
| 2018/0362922 A1 | 12/2018 | Kenichi et al. |
| 2018/0362933 A1 | 12/2018 | Kenichi et al. |
| 2019/0002828 A1 | 1/2019 | Lanza et al. |
| 2019/0002829 A1 | 1/2019 | Li et al. |
| 2019/0017027 A1 | 1/2019 | Lanza et al. |
| 2019/0046577 A1 | 2/2019 | Shi et al. |
| 2019/0048054 A1 | 2/2019 | Prockop et al. |
| 2019/0064186 A1 | 2/2019 | Herbert |
| 2019/0071637 A1 | 3/2019 | Slukvin et al. |
| 2019/0117701 A1 | 4/2019 | Ikeyama et al. |
| 2019/0175656 A1 | 6/2019 | Kimbrel et al. |
| 2019/0177685 A1 | 6/2019 | Gronthos et al. |
| 2019/0262404 A1 | 8/2019 | Song et al. |
| 2019/0314417 A1 | 10/2019 | Womba et al. |
| 2020/0009193 A1 | 1/2020 | Han et al. |
| 2020/0040305 A1 | 2/2020 | Ino et al. |
| 2020/0056156 A1 | 2/2020 | Ino et al. |
| 2020/0101118 A1 | 4/2020 | Ghosh |
| 2020/0131475 A1 | 4/2020 | Kimbrel et al. |
| 2020/0157503 A1 | 5/2020 | Lanza et al. |
| 2020/0392463 A1 | 12/2020 | Wang et al. |
| 2021/0182552 A1 | 6/2021 | Kimbrel et al. |
| 2022/0160778 A1 | 5/2022 | Kimbrel et al. |

FOREIGN PATENT DOCUMENTS

| | | |
|---|---|---|
| AU | 2013201444 A1 | 3/2013 |
| CA | 2792802 A1 | 9/2011 |
| CN | 1556197 A | 12/2004 |
| CN | 101045914 A | 10/2007 |
| CN | 101045915 A | 10/2007 |
| CN | 101384706 A | 3/2009 |
| CN | 101528915 A | 9/2009 |
| CN | 101815522 A | 8/2010 |
| CN | 102083960 A | 6/2011 |
| CN | 102083963 A | 6/2011 |
| CN | 102660495 A | 9/2012 |
| CN | 102822332 A | 12/2012 |
| CN | ZL200980125862 A | 12/2014 |
| CN | 104328087 A | 2/2015 |
| CN | 106434527 A | 2/2017 |
| EP | 1454641 A2 | 9/2004 |
| EP | 2013331 A2 | 1/2009 |
| EP | 2288690 A2 | 3/2011 |
| EP | 2291513 A2 | 3/2011 |
| EP | 2377923 A1 | 10/2011 |
| EP | 2377924 A1 | 10/2011 |
| EP | 2377925 A1 | 10/2011 |
| EP | 2426197 A1 | 3/2012 |
| EP | 1727892 B1 | 5/2012 |
| EP | 2507359 A1 | 10/2012 |
| EP | 2507365 A1 | 10/2012 |
| EP | 2712921 A1 | 4/2014 |
| EP | 2162534 B1 | 7/2014 |
| EP | 3369810 A1 | 9/2015 |
| EP | 3020405 A1 | 5/2016 |
| EP | 2451943 B1 | 11/2016 |
| EP | 3154565 A1 | 4/2017 |
| EP | 2298862 B1 | 8/2017 |
| EP | 2961430 B1 | 8/2017 |
| EP | 3287520 A1 | 2/2018 |
| EP | 3342858 A1 | 7/2018 |
| EP | 2185165 B1 | 10/2018 |
| EP | 3450548 A1 | 3/2019 |
| EP | 2931877 B1 | 7/2019 |

(56) References Cited

FOREIGN PATENT DOCUMENTS

| | | |
|---|---|---|
| EP | 2257289 B1 | 9/2019 |
| EP | 3430129 A4 | 10/2019 |
| EP | 3586853 A1 | 1/2020 |
| EP | 3608400 A1 | 2/2020 |
| EP | 3619294 A1 | 3/2020 |
| JP | S64-16581 A | 1/1989 |
| JP | 2002-515756 A | 5/2002 |
| JP | 2004-504834 A | 2/2004 |
| JP | 2004-531262 A | 10/2004 |
| JP | 2005-509422 A | 4/2005 |
| JP | 2005-511084 A | 4/2005 |
| JP | 2005-528362 A | 9/2005 |
| JP | 2006-230316 A | 9/2006 |
| JP | 2007-089432 A | 4/2007 |
| JP | 2007-536915 A | 12/2007 |
| JP | 2008-535493 A | 9/2008 |
| JP | 2009-531021 A | 9/2009 |
| JP | 2009-533059 A | 9/2009 |
| JP | 2010-532370 A | 10/2010 |
| JP | 2010-252778 A | 11/2010 |
| JP | 2011-519576 A | 7/2011 |
| JP | 2011-519577 A | 7/2011 |
| JP | 2011-520434 A | 7/2011 |
| JP | 2013-512673 A | 4/2013 |
| JP | 2013-512676 A | 4/2013 |
| JP | 2013-126423 A | 6/2013 |
| JP | 5630781 B2 | 11/2014 |
| JP | 2015-57070 A | 3/2015 |
| JP | 2015-61539 A | 4/2015 |
| JP | 5748654 B2 | 7/2015 |
| JP | 2016-063838 A | 4/2016 |
| KR | 2007-0114449 A | 12/2007 |
| KR | 1477016 B1 | 12/2014 |
| NZ | 518191 A | 1/2004 |
| NZ | 572842 A | 1/2012 |
| WO | WO 95/17500 A1 | 6/1995 |
| WO | 199964566 A2 | 12/1999 |
| WO | WO 99/67360 A2 | 12/1999 |
| WO | WO 00/11139 A1 | 3/2000 |
| WO | WO 01/36589 A2 | 5/2001 |
| WO | WO 2002/078449 A2 | 10/2002 |
| WO | WO 03/042405 A2 | 5/2003 |
| WO | WO 03/046141 A2 | 6/2003 |
| WO | WO 03/050251 A2 | 6/2003 |
| WO | WO 2003/080116 A1 | 10/2003 |
| WO | WO 2004/007698 A1 | 1/2004 |
| WO | 2004022078 A1 | 3/2004 |
| WO | WO 2004/029231 A1 | 4/2004 |
| WO | WO 2004/044146 A2 | 5/2004 |
| WO | WO 2004/098285 A2 | 11/2004 |
| WO | WO 2005/040391 A1 | 5/2005 |
| WO | WO 2005/049812 A1 | 6/2005 |
| WO | 2005063303 A1 | 7/2005 |
| WO | WO 2005/068610 A1 | 7/2005 |
| WO | WO 2005/078073 A2 | 8/2005 |
| WO | WO 2005/108981 A1 | 11/2005 |
| WO | WO 2005/118780 A1 | 12/2005 |
| WO | WO 2006/050330 A2 | 5/2006 |
| WO | WO 2006/090882 A1 | 8/2006 |
| WO | WO 2006/127150 A2 | 11/2006 |
| WO | WO 2006/130504 A2 | 12/2006 |
| WO | WO 2006/130651 A2 | 12/2006 |
| WO | WO 2007/005595 A1 | 1/2007 |
| WO | WO 2007/019398 A1 | 2/2007 |
| WO | WO 2007/032634 A1 | 3/2007 |
| WO | WO 2007/037682 A1 | 4/2007 |
| WO | WO 2007/047894 A2 | 4/2007 |
| WO | WO 2007/062198 A1 | 5/2007 |
| WO | WO 2007/093412 A2 | 8/2007 |
| WO | WO 2007/095064 A2 | 8/2007 |
| WO | WO 2007/120811 A2 | 10/2007 |
| WO | WO 2008/058779 A1 | 5/2008 |
| WO | WO 2008/103462 A2 | 8/2008 |
| WO | WO 2008/151386 A1 | 12/2008 |
| WO | WO 2009/006161 A1 | 1/2009 |
| WO | WO 2009/045360 A2 | 4/2009 |
| WO | WO 2009/051671 A1 | 4/2009 |
| WO | WO 2009/052389 A1 | 4/2009 |
| WO | WO 2009/104825 A1 | 8/2009 |
| WO | WO 2009/135905 A2 | 11/2009 |
| WO | WO 2009/137624 A2 | 11/2009 |
| WO | WO 2009/137629 A2 | 11/2009 |
| WO | WO 2010/017216 A2 | 2/2010 |
| WO | WO 2010/025506 A1 | 3/2010 |
| WO | WO 2010/138517 A1 | 12/2010 |
| WO | 2011047345 A2 | 4/2011 |
| WO | WO 2011/063005 A2 | 5/2011 |
| WO | WO 2011/068896 A1 | 6/2011 |
| WO | WO 2011/069127 A1 | 6/2011 |
| WO | WO 2011/097242 A2 | 8/2011 |
| WO | WO 2011/107437 A1 | 9/2011 |
| WO | WO 2011/116117 A2 | 9/2011 |
| WO | 2011124741 A1 | 10/2011 |
| WO | 2012026712 A2 | 3/2012 |
| WO | 2013082543 A1 | 6/2013 |
| WO | WO 2013/108949 A1 | 7/2013 |
| WO | 2014011407 A2 | 1/2014 |
| WO | WO 2015/189063 A1 | 12/2015 |
| WO | WO 2018/202853 A1 | 11/2018 |

OTHER PUBLICATIONS

Li, 2018, Cell death and Disease. 9:892, 9 pages.*
Amit, 2010, Stem Cell Reviews and Reports, 6:248-259.*
P Mafi et al. "Adult Mesenchymal Stem Cells and Cell Surface Characterization—A Systematic Review of the Literature," The Open Orthopaedics Journal, 2011, 5: 253-260.
M Dominici et al. "Minimal criteria for defining multipotent mesenchymal stromal cells," The International Society for Cellular Therap poistion statement, Cytotherapy (2006) vol. 8, No. 4, 315-317.
Irina V. Balyvasnikova et al. "Genetific Modification of Mesenchymal Stem Cells to Express a Single-Chain Antiboyd Against EGFRvIII on the Cell Surface", J Tissue Eng Regen Med. Jun. 2010: 247-258.
Bouffi, C et al. IL-6-Dependent PGE2 Secretion By Masenchymal Stem Cells Inhibits Local Inflammation in Experimental Arthritis. PLoS ONE. Dec. 2012, vol. 5; pp. 1-12.
Jing D. et al. Hematopoietic Stem Cells in Co-Culture with Mesenchymal Stromal Cells—Modeling the Niche Compartmnets in Citro. Heematologica. Sep. 30, 2009, vol. 95; pp. 542-550.
Min, C-K et al. "IL_10 Transduced Bone Marrow Meschumal Stem Cells Cn Attenuate the Severity of Actute Grat-Versus-Host Diseases after Experimental Allogeneic Stem Cell Transplanation" Feb. 12, 2007.
Peng, Fei, et al. "The effect of noncoherent red light irradiation on proliferation and osteogenic differentiation of bone marrow mesenchymal stem cells." Lasers in medical science 27.3 (2012): 645-653.
Saito, Shigeki, et al. "Mesenchymal stem cells stably transduced with a dominant-negative inhibitor of CCL2 greatly attenuate bleomycin-induced lung damage." The American journal of pathology 179.3 (2011): 1088-1094.
Al Jumah et al. The Immunomodulatory and Neuroprotective Effects of Mesenchymal Stem Cells (MSCs) in Experimental Autoimmune Encephalomyelitis (EAE): A Model of Multiple Sclerosis (MS). International journal of molecular sciences 13, 2012. pp. 9298-9331.
Anton et al. "Macrophage-associated mesenchymal stem cells assume an activated, migratory, pro-inflammatory phenotype with increased IL-6 and CXCL10 secretion." PLoS One 7, 2012, e35036.
Auletta et al. "The potential of mesenchymal stromal cells as a novel cellular therapy for multiple sclerosis." Immunotherapy 4, 2012. pp. 529-547.
Barberi et al. "Derivation of multipotent mesenchymal precursors from human embryonic stem cells." PLoS Med 2, 2005, e161.
Becher et al. "Experimental autoimmune encephalitis and inflammation in the absence of interleukin-12." The Journal of clinical investigation, 2012, 110: 493-497.

(56) References Cited

OTHER PUBLICATIONS

Benito-Leon. "Are the prevalence and incidence of multiple sclerosis changing?" Neuroepidemiology 2011, 36, pp. 148-149.
Briquet et al. "Prolonged ex vivo culture of human bone marrow mesenchymal stem cells influences their supportive activity toward NOD/SCID-repopulating cells and committed progenitor cells of B lymphoid and myeloid lineages." Haematologica. 2010i 95:47-56. doi:10.3324/haematol.2009.008524. 89 pages.
Brown et al. "The derivation of mesenchymal stem cells from human embryonic stem cells." Cells Tissues Organs 2009, 189, pp. 256-260.
Chao et al. "Mesenchymal stem cell transplantation attenuates blood brain barrier damage and neuroinflammation and protects dopaminergic neurons against MPTP toxicity in the substantia nigra in a model of Parkinson's disease." Journal of Neuroimmunology 2009, 216, pp. 39-50.
Chaudhary et al. "Lipoic acid inhibits expression of ICAM-1 and VCAM-1 by CNS endothelial cells and T cell migration into the spinal cord in experimental autoimmune encephalomyelitis." Journal of Neuroimmunology 2006 175: pp. 87-96.
Chyou et al. "Fibroblast-type reticular stromal cells regulate the lymph node vasculature." J Immunol 2008, 181, pp. 3887-3896.
Connick et al. "Autologous mesenchymal stem cells for the treatment of secondary progressive multiple sclerosis: an open-label phase 2a proof-of concept study." Lancet Neurology 2012, 11, pp. 150-156.
Correale et al. "The blood-brain-barrier in multiple sclerosis: functional roles and therapeutic targeting." Autoimmunity 2012 40, pp. 148-160.
Costa et al. "The hESC line Envy expresses high levels of GFP in all differentiated progeny." Nat Methods 2005 2, pp. 259-260.
Crocker et al. "Cell and agonist-specific regulation of genes for matrix metalloproteinases and their tissue inhibitors by primary glial cells." Journal of Neurochemistry, 2006, 98, 812-823.
Cuccurullo et al. "Suppression of RAGE as a basis of simvastatin-dependent plaque stabilization in type 2 diabetes." Arteriosclerosis, thrombosis, and vascular biology 2006, 26: 2716-2723.
Cunnea et al. "Gene expression analysis of the microvascular compartment in multiple sclerosis using laser microdissected blood vessels." Acta Neuropathologica 2010, 119: 601-615.
Dai et al. "Interleukin-10 plays a crucial role in suppression of experimental autoimmune encephalomyelitis by Bowman-Birk inhibitor." Journal of Neuroimmunology 2012, 245: 1-7.
De Lima et al. "Cord-Blood Engraftment with Ex Vivo Mesenchymal-Cell Coculture." The New England Journal of Medicine, 2012; 367;24: pp. 2305-2315.
Dienz et al. "The effects of IL-6 on CD4 T cell responses." Clinical Immunology 2009, 130, 27-33.
Djouad et al. "Immunosuppressive effect of mesenchymal stem cells favors tumor growth in allogeneic animals." Blood 2003, 102, 3837-3844.
Dong. "TH17 cells in development: an updated view of their molecular identity and genetic programming." Nat Rev Immunol 2008, 8, 337-348.
Draper et al. "Surface antigens of human embryonic stem cells: changes upon differentiation in culture." Journal of Anatomy 2002, 200, 249-258.
Drukker et al. "Characterization of the expression of MHC proteins in human embryonic stem cells." Proceedings of the National Academy of Sciences of the United States of America 2002, 99, 9864-9869.
Drukker et al. "Human embryonic stem cells and their differentiated derivatives are less susceptible to immune rejection than adult cells." Stem Cells, 2006, 24, 221-229.
English et al. "IFN-gamma and TNF alpha differentially regulate immunomodulation by murine mesenchymal stem cells." Immunology Letters, vol. 110, 2, Jun. 15, 2007, pp. 91-100.
Ge et al. "The CCL2 synthesis inhibitor bindarit targets cells of the neurovascular unit, and suppresses experimental autoimmune encephalomyelitis." J Neuroinflammation 2012, 9, 171.
Gijbels et al. "Administration of neutralizing antibodies to interleukin-6 (IL-6) reduces experimental autoimmune encephalomyelitis and is associated with elevated levels of IL-6 bioactivity in central nervous system and circulation." Mol Med 1995, 1, 795-805.
Gordon et al. "Human mesenchymal stem cells abrogate experimental allergic encephalomyelitis after intraperitoneal injection, and with sparse CNS infiltration." Neuroscience Letters, 2008, 448, 71-73.
Gordon et al. "Human mesenchymal stem cells infiltrate the spinal cord, reduce demyelination, and localize to white matter lesions in experimental autoimmune encephalomyelitis." J Neuropathol Exp Neurol 2010, 69, 1087-1095.
Grinnemo et al. "Xenoreactivity and engraftment of human mesenchymal stem cells transplanted into infarcted rat myocardium." J Thorac Cardiovasc Surg 2004, 127, 1293-1300.
Hansen et al. "Regulatory T cells as targets for immunotherapy of autoimmunity and inflammation." Inflamm Allergy Drug Targets 7, 2008. pp. 217-223.
Hofstetter et al. "Marrow stromal cells form guiding strands in the injured spinal cord and promote recovery." Proceedings of the National Academy of Sciences of the United States of America 2002, 99, 2199-2204.
Huber et al. "Haemangioblast commitment is initiated in the primitive streak of the mouse embryo." Nature 2004, 432, 625-630.
Huss et al. "TGF-beta signaling via Smad4 drives IL-10 production in effector Th1 cells and reduces T-cell trafficking in EAE." European Journal of Immunology 2011. 41: 2987-2996.
Hwang et al. "In vivo commitment and functional tissue regeneration using human embryonic stem cell derived mesenchymal cells." Proc Natl Acad Sci U S A 2008, 105, 20641-20646.
International Preliminary Report on Patentability in corresponding PCT Application No. PCT/US2013/048291, mailed Jan. 13, 2015.
International Search Report in corresponding International Patent Application No. PCT/US2013/048291, mailed Feb. 21, 2014.
Javazon et al. "Mesenchymal stem cells: paradoxes of passaging." Exp Hematol 2004, 32, 414-425.
Jing et al. "Hematopoietic Stem Cells In Co-Culture With Mesenchymal Stromal Cells Modeling The Niche Compartments In Vitro." Haematologica. Sep. 30, 2009, vol. 95; pp. 542-550.
Karussis et al. "Safety and immunological effects of mesenchymal stem cell transplantation in patients with multiple sclerosis and amyotrophic lateral sclerosis." Arch Neurol 2010, 67, 1187-1194.
Kern et al. "Comparative Analysi of Msenchymal Stem Cells from Bone Marrow, Umbilical Cord Blood, or Adipose Tissue." Stem Cells, 2006; 24: pp. 1294-1301.
Klimanskaya et al. "Human embryonic stem cell lines derived from single blastomeres." Nature 2006, 444, 481-485.
Kurtzke. "Rating neurologic impairment in multiple sclerosis: an expanded disability status scale (EDSS)." Neurology, 1983, 33 (11): 1444-52.
Leech et al. "Cutting Edge: IL-6-Dependent Autoimmune Disease: Dendritic Cells as a Sufficient, but Transient, Source." J Immunol., 2013; 190:881-885.
Leslie et al. "Pharmaceuticals Utilized In Stem Cell Transplant." Feb. 2009. Retrieved from the Internet URL: http://www.cibmtr.org/Meetings/Materials/CRPDMC/Documents/2009/Feb2009/LeslieJ_PreTEDdrugs.pdf.
Lin et al. "Human embryonic stem cell derivation, maintenance, and differentiation to trophoblast." Methods in Molecular Biology 2010, 636, 1-24.
Liu et al. "Human Umbilical Cord Stem Cells Ameliorate Experimental Autoimmune Encephalomyelitis by Regulating Immunoinflammation and Remyelination." Stem Cells and Development; 2013; vol. 22, No. 7, pp. 1053-1062.
Lu et al. "Generation of functional hemangioblasts from human embryonic stem cells." Nat Methods 2007, 4, 501-509.
Lu et al. "Hemangioblasts from human embryonic stem cells generate multilayered blood vessels with functional smooth muscle cells." Regenerative medicine 4, 2009. pp. 37-47.
Lu et al. "Robust generation of hemangioblastic progenitors from human embryonic stem cells." Regen Med 2008, 3, 693-704.
Ludwig et al. "Derivation of human embryonic stem cells in defined conditions." Nat Biotechnol, 2006, 24: 185-187.

(56) References Cited

OTHER PUBLICATIONS

Mafi et al. "Adult Mesenchymal Stem Cells and Cell Surface Characterization—A Systematic Review of the Literature." The Open Orthopaedics Journal. Apr. 21, 2011, vol. 5; pp. 253-260.

Mahad et al. "The role of MCP-1 (CCL2) and CCR2 in multiple sclerosis and experimental autoimmune encephalomyelitis (EAE)." Seminars in Immunology 2003, 15: 23-32.

McFarland et al. "Multiple sclerosis: a complicated picture of autoimmunity." Nat Immunol 2007, 8, 913-919.

Menge et al. "Mesenchymal Stem Cells Regulate Blood-Brain Barrier Integrity Through TIMP3 Release After Traumatic Brain Injury." Science Translational Medicine 2012, 4, 161ra150.

Minagar et al. "Emerging roles of endothelial cells in multiple sclerosis pathophysiology and therapy." Neurological research 34, 2012. pp. 738-745.

Mohyeddin et al. "Does mesenchymal stem cell therapy help multiple sclerosis patients?" Report of a pilot study. Iranian Journal of Immunology: IJI 4, 2007. pp. 50-57.

Moore et al. "Astrocytic tissue inhibitor of metalloproteinase-1 (TIMP-1) promotes oligodendrocyte differentiation and enhances CNS myelination." The Journal of Neuroscience: The Official Journal of the Society for Neuroscience, 2011, 31, 6247-6254.

Morando et al. "The therapeutic effect of mesenchymal stem cell transplantation in experimental autoimmune encephalomyelitis is mediated by peripheral and central mechanisms." Stem Cell Res Ther, 2012, 3, 3.

No Author. "Human Mesenchymal Stem Cells and Multipotent Cord Blood Unrestricted Somatic Stem Cell Protocol: Thawing and Plating." Thermo Scientific. 2009 http://www.thermoscientific.fr/eThermo/CMA/PDFsNariousJFile_ 4338.pdf>; p. 2.

Ohtaki et al. "Stem/progenitor cells from bone marrow decrease neuronal death in global ischemia by modulation of inflammatory/immune responses." Proc Natl Acad Sci USA, 2008, 105, 14638-14643.

Olivier et al. "Differentiation of human embryonic stem cells into bipotent mesenchymal stem cells." Stem Cells, 2006, 24, 1914-1922.

Patanella et al. "Correlations between peripheral blood mononuclear cell production of BDNF, TNF-alpha, IL-6, IL-10 and cognitive performances in multiple sclerosis patients." J Neurosci Res 2010, 88, 1106-1112.

Payne et al. "Distinct immunomodulatory and migratory mechanisms underpin the therapeutic potential of human mesenchymal stem cells in autoimmune demyelination." Cell Transplant; 2013; vol. 22, pp. 1409-1425.

Peng et al. "The Effect of Noncoherent Red Light Irradiation on Proliferation and Osteogenic Differentiation of Bone Marrow Mesenchymal Stem Cells." Lasers Med Sci. Oct. 21, 2011, vol. 27; pp. 645-653.

Peron et al. "Human endometrial-derived mesenchymal stem cells suppress inflammation in the central nervous system of EAE mice." Stem Cell Rev 2012, 8, 940-952.

Pittenger et al. "Multilineage potential of adult human mesenchymal stem cells." Science, 1999, 284, 143-147.

Pomper et al. "Serial imaging of human embryonic stem-cell engraftment and teratoma formation in live mouse models." Cell Res, 2009, 19, 370-379.

Quintana et al. "Site-specific production of IL-6 in the central nervous system retargets and enhances the inflammatory response in experimental autoimmune encephalomyelitis." Journal of Immunology, 2009, 183, 2079-2088.

Rafei et al. "Allogeneic mesenchymal stem cells for treatment of experimental autoimmune encephalomyelitis." Mol Ther, 2009, 17, 1799-1803.

Rochman et al. "IL-6 increases primed cell expansion and survival." Journal of Immunology, 2005, 174, 4761-4767.

Ryan et al. "Interferon-gamma does not break, but promotes the immunosuppressive capacity of adult human mesenchymal stem cells." Clin Exp Immunol, 2007, 149, 353-363.

Saito et al. "Mesenchymal Stem Cells Stably Transduced With a Dominant-Negative Inhibitor of CCL2 Greatly Attenuate Bleomycin-Induced Lung Damage." The American Journal of Pathology. Sep. 3, 2011. vol. 179; pp. 1088-1094.

Sanchez et al. "Enrichment of human ESC derived multipotent mesenchymal stem cells with immunosuppressive and anti-inflammatory properties capable to protect against experimental inflammatory bowel disease." Stem Cells, 2011, 29, 251-262.

Sato et al. "Maintenance of pluripotency in human and mouse embryonic stem cells through activation of Wnt signaling by a pharmacological GSK-3-specific inhibitor." Nature Medicine, Jan. 2004, vol. 10, No. 1, pp. 55-63.

See et al. "Therapeutic Effects of Human STR0-3-Selected Mesenchymal Precursor Cells and Their Soluble Factors In Experimental Myocardial Ischemia." J Cell Mal Med. Oct. 2011. vol. 15; pp. 2117-2129.

Sethe et al. "Aging of mesenchymal stem cells." Ageing Res Rev, 2006, 5, 91-116.

Solchaga et al. "Chondrogenic differentiation of bone marrow-derived mesenchymal stem cells: tips and tricks." Methods in Molecular Biology, 2011, 698, 253-278.

Stromnes et al. "Active induction of experimental allergic encephalomyelitis." Nat Protoc, 2006, 1, 1810-1819.

Thomson et al. "Embryonic stem cell lines derived from human blastocysts." Science, 1998, 282, 1145-1147.

Tse et al. "Suppression of allogeneic T-cell proliferation by human marrow stromal cells: implications in transplantation." Transplantation 2003, 75, 389-397.

TYNDALL. "Successes and failures of stem cell transplantation in autoimmune diseases." Hematology Am Soc Hematol Educ Program 2011, 280-284.

Uccelli et al. "Why should mesenchymal stem cells (MSCs) cure autoimmune diseases?" Curr Opin Immunol. 2010, 22, 768-774.

Waterman et al. "A new mesenchymal stem cell (MSC) paradigm: polarization into a pro-inflammatory MSC1 or an Immunosuppressive MSC2 phenotype." PLoS One 5, 2010; vol. 5, Issue 4, e10088; pp. 1-14.

Weber et al. "Current treatment strategies for multiple sclerosis—efficacy versus neurological adverse effects." Current Pharmaceutical Design 18, 2012. pp. 209-219.

Wong. "Mesenchymal stem cells: angels or demons?" J Biomed Biotechnol 2011, 459510.

Yamout et al. "Bone marrow mesenchymal stem cell transplantation in patients with multiple sclerosis: a pilot study." J Neuroimmunol, 2010, 227, 185-189.

Zappia et al. "Mesenchymal stem cells ameliorate experimental autoimmune encephalomyelitis inducing T-cell anergy." Blood, 2005, 106, 1755-1761.

Zhang et al. "Human bone marrow stromal cell treatment improves neurological functional recovery in EAE mice." Exp Neurol, 2005, 195, 16-26.

Burden of Disease: Chronic Inflammation and Inflammatory pp. 1-5, 2017.

Naldini Luigi. "Ex vivo gene transfer and correction for cell-based therapies." Nature Reviews Genetics 12.5 (2011): 301-315.

Nguyen, et al. . Wu. "Methods to assess stem cell lineage, fate and function." Advanced drug delivery reviews 62.12 (2010): 1175-1186.

Brunt et al. . "Stem cells and regenerative medicine-future perspectives." Canadian journal of physiology and pharmacology 90.3 (2012): 327-335.

Cohen, Jeffrey A. "Mesenchymal stem cell transplantation in multiple sclerosis." Journal of the neurological sciences 333.1-2 (2013): 43-49.

Rose, Noel R. "Prediction and prevention of autoimmune disease in the 21st century: a review and preview." American Journal of Epidemiology 183.5 (2016): 403-406.

Wang, Li-Tzu, et al. "Human mesenchymal stem cells (MSCs) for treatment towards immune-and inflammation-mediated diseases: review of current clinical trials." Journal of biomedical science 23.1 (2016): 1-13.

(56) References Cited

OTHER PUBLICATIONS

Constantinescu, Cris S., et al. "Experimental autoimmune encephalomyelitis (EAE) as a model for multiple sclerosis (MS)." British journal of pharmacology 164.4 (2011): 1079-1106.
Canadian Office Action in Corresponding Canadian Application No. 2,876,499 mailed Apr. 28, 2020. 4 pages.
Chinese Office Action in Corresponding Chinese Application No. 201380037010.6, mailed May 25, 2016, 13 pages. English translation attached.
International Preliminary Report on Patentability mailed Jun. 12, 2014 for Application No. PCT/US2012/067464.
International Search Report and Written Opinion mailed Mar. 28, 2013 for Application No. PCT/US2012/067464.
Supplemental Partial European Search Report mailed Jun. 18, 2015 for Application No. EP 12854438.4.
Extended European Search Report mailed Oct. 13, 2015 for EP 12854438.4.
Extended European Search Report and Written Opinion dated Feb. 5, 2019 for EP 18186151.9.
[No Author Listed] *Astellas Institute for Regenerative Medicine v. IMSTEM Biotechnology, Inc.* Case 1:17-cv-12239. Document 1. Complaint. Filed Nov. 13, 2017.
[No Author Listed] *Astellas Institute for Regenerative Medicine v. IMSTEM Biotechnology, Inc.* Case 1:17-cv-12239. Document 136-4. Exhibit 4 (Emails). Dated Jan. 2, 2020.
[No Author Listed] *Astellas Institute for Regenerative Medicine v. IMSTEM Biotechnology, Inc.* Case 1:17-cv-12239. Document 136-5. Exhibit 5 (Emails). Dated Jan. 2, 2020.
[No Author Listed] *Astellas Institute for Regenerative Medicine v. IMSTEM Biotechnology, Inc.* Case 1:17-cv-12239. Document 136-6. Exhibit 6 (Emails). Dated Jan. 2, 2020.
[No Author Listed] *Astellas Institute for Regenerative Medicine v. IMSTEM Biotechnology, Inc.* Case 1:17-cv-12239. Document 136-7. Exhibit 7 (Emails). Dated Jan. 2, 2020.
[No Author Listed] *Astellas Institute for Regenerative Medicine v. IMSTEM Biotechnology, Inc.* Case 1:17-cv-12239-ADB. Document 103. Joint Motion to Modify Scheduling Order. Dated Sep. 18, 2019.
[No Author Listed] *Astellas Institute for Regenerative Medicine v. IMSTEM Biotechnology, Inc.* Case 1:17-cv-12239-ADB. Document 103-1. Exhibit A ([Proposed] Scheduling Order). Dated Sep. 18, 2019.
[No Author Listed] *Astellas Institute for Regenerative Medicine v. IMSTEM Biotechnology, Inc.* Case 1:17-cv-12239-ADB. Document 106. Amended Scheduling Order and Pretrial Order. Dated Sep. 26, 2019.
[No Author Listed] *Astellas Institute for Regenerative Medicine v. IMSTEM Biotechnology, Inc.* Case 1:17-cv-12239-ADB. Document 109. Defendants' Opposition to Plaintiffs' Motion for Leave to File an Amended Complaint. Dated Oct. 1, 2019.
[No Author Listed] *Astellas Institute for Regenerative Medicine v. IMSTEM Biotechnology, Inc.* Case 1:17-cv-12239-ADB. Document 110. Declaration of Benjamin M. Stern in Support of Defendants' Opposition to Plaintiffs' Motion for Leave to File an Amended Complaint. Dated Oct. 1, 2019.
[No Author Listed] *Astellas Institute for Regenerative Medicine v. IMSTEM Biotechnology, Inc.* Case 1:17-cv-12239-ADB. Document 110-1. Exhibit 1 to the Sep. 27, 2019 Stern Declaration (Documents for U.S. Appl. No. 14/413,290). Dated Oct. 1, 2019.
[No Author Listed] *Astellas Institute for Regenerative Medicine v. IMSTEM Biotechnology, Inc.* Case 1:17-cv-12239-ADB. Document 110-4. Exhibit 4 to the Sep. 27, 2019 Stern Declaration (Email). Dated Oct. 1, 2019.
[No Author Listed] *Astellas Institute for Regenerative Medicine v. IMSTEM Biotechnology, Inc.* Case 1:17-cv-12239-ADB. Document 110-8. Exhibit 8 to the Sep. 27, 2019 Stern Declaration (Videotaped Deposition of Ren-He Xu). Dated Oct. 1, 2019.

[No Author Listed] *Astellas Institute for Regenerative Medicine v. IMSTEM Biotechnology, Inc.* Case 1:17-cv-12239-ADB. Document 111. Memorandum and Order on Plaintiffs' Motion to Amend. Dated Oct. 2, 2019.
[No Author Listed] *Astellas Institute for Regenerative Medicine v. IMSTEM Biotechnology, Inc.* Case 1:17-cv-12239-ADB. Document 113. First Amended Complaint. Dated Oct. 3, 2019.
[No Author Listed] *Astellas Institute for Regenerative Medicine v. IMSTEM Biotechnology, Inc.* Case 1:17-cv-12239-ADB. Document 113-1. Exhibit A (United States Patent No. U.S. Pat. No. 9,745,551 B2). Dated Oct. 3, 2019.
[No Author Listed] *Astellas Institute for Regenerative Medicine v. IMSTEM Biotechnology, Inc.* Case 1:17-cv-12239-ADB. Document 113-2. Exhibit B (Human ESC—Derived MSCs Outperform Bone Marrow MSCs in the Treatment of an EAE Model of Multiple Sclerosis). Dated Oct. 3, 2019.
[No Author Listed] *Astellas Institute for Regenerative Medicine v. IMSTEM Biotechnology, Inc.* Case 1:17-cv-12239-ADB. Document 113-3. Exhibit C (Generation of functional hemangioblasts from human embryonic stem cells). Dated Oct. 3, 2019.
[No Author Listed] *Astellas Institute for Regenerative Medicine v. IMSTEM Biotechnology, Inc.* Case 1:17-cv-12239-ADB. Document 113-4. Exhibit D (Mesenchymal Stem Cell Population Derived from Human Pluripotent Stem Cells Displays Potent Immunomodulatory and Therapeutic Properties). Dated Oct. 3, 2019.
[No Author Listed] *Astellas Institute for Regenerative Medicine v. IMSTEM Biotechnology, Inc.* Case 1:17-cv-12239-ADB. Document 113-5. Exhibit E (Documents for U.S. Appl. No. 14/413,290). Dated Oct. 3, 2019.
[No Author Listed] *Astellas Institute for Regenerative Medicine v. IMSTEM Biotechnology, Inc.* Case 1:17-cv-12239-ADB. Document 114. Defendants' Second Amended Answer. Dated Oct. 17, 2019.
[No Author Listed] *Astellas Institute for Regenerative Medicine v. IMSTEM Biotechnology, Inc.* Case 1:17-cv-12239-ADB. Document 117. Verrill Dana LLP's Motion to Withdraw as Counsel for Defendants. Dated Nov. 15, 2019.
[No Author Listed] *Astellas Institute for Regenerative Medicine v. IMSTEM Biotechnology, Inc.* Case 1:17-cv-12239-ADB. Document 118. Plaintiffs' Opposition to Verrill Dana LLP's Motion to Withdraw as Counsel for Defendants. Dated Nov. 18, 2019.
[No Author Listed] *Astellas Institute for Regenerative Medicine v. IMSTEM Biotechnology, Inc.* Case 1:17-cv-12239-ADB. Document 119. Notice of Electronic Filing. Dated Nov. 19, 2019.
[No Author Listed] *Astellas Institute for Regenerative Medicine v. IMSTEM Biotechnology, Inc.* Case 1:17-cv-12239-ADB. Document 120. Motion for Dispositive Motion Briefing Limits. Dated Dec. 13, 2019.
[No Author Listed] *Astellas Institute for Regenerative Medicine v. IMSTEM Biotechnology, Inc.* Case 1:17-cv-12239-ADB. Document 122. Defendants' Opposition to Plaintiffs' Motion for Order to Set Dispositive Motion Briefing Limits. Dated Dec. 17, 2019.
[No Author Listed] *Astellas Institute for Regenerative Medicine v. IMSTEM Biotechnology, Inc.* Case 1:17-cv-12239-ADB. Document 124. Notice of Electronic Filing. Dated Dec. 18, 2019.
[No Author Listed] *Astellas Institute for Regenerative Medicine v. IMSTEM Biotechnology, Inc.* Case 1:17-cv-12239-ADB. Document 127. Astellas' Motion for Partial Summary Judgment. Dated Dec. 19, 2019.
[No Author Listed] *Astellas Institute for Regenerative Medicine v. IMSTEM Biotechnology, Inc.* Case 1:17-cv-12239-ADB. Document 128. Memorandum of Points and Authorities in Support of Astellas' Motion for Partial Summary Judgment. Dated Dec. 19, 2019.
[No. Author Listed] *Astellas Institute for Regenerative Medicine v. IMSTEM Biotechnology, Inc.* Case 1:17-cv-12239-ADB. Document 129. Declaration of Lauren K. Sharkey in Support of Astellas' Motion for Summary Judgment. Dated Dec. 19, 2019.
[No Author Listed] *Astellas Institute for Regenerative Medicine v. IMSTEM Biotechnology, Inc.* Case 1:17-cv-12239-ADB. Document 129-12. Exhibit 12 to Sharkey Declaration (Expert Rebuttal Report of Bruce Bunnell, Ph.D.). Dated Dec. 19, 2019.
[No Author Listed] *Astellas Institute for Regenerative Medicine v. IMSTEM Biotechnology, Inc.* Case 1:17-cv-12239-ADB. Document

(56) References Cited

OTHER PUBLICATIONS 129-13. Exhibit 13 to Sharkey Declaration (Expert Rebuttal Report of John M. Perry, Ph.D.). Dated Dec. 19, 2019.
[No Author Listed] *Astellas Institute for Regenerative Medicine* v. *IMSTEM Biotechnology, Inc.* Case 1:17-cv-12239-ADB. Document 129-14. Exhibit 14 to Sharkey Declaration (Opening Expert Report of Bruce Bunnell, Ph.D.). Dated Dec. 19, 2019.
[No Author Listed] *Astellas Institute for Regenerative Medicine* v. *IMSTEM Biotechnology, Inc.* Case 1:17-cv-12239-ADB. Document 129-16. Exhibit 16 to Sharkey Declaration (Video Deposition of Bryan Daniel Zerhusen, Ph.D., J.D.). Dated Dec. 19, 2019.
[No Author Listed] *Astellas Institute for Regenerative Medicine* v. *IMSTEM Biotechnology, Inc.* Case 1:17-cv-12239-ADB. Document 129-19. Exhibit 19 to Sharkey Declaration (Defendants' Objections and Responses to Plaintiffs' Fourth Set of Interrogatories (No. 36). Dated Dec. 19, 2019.
[No Author Listed] *Astellas Institute for Regenerative Medicine* v. *IMSTEM Biotechnology, Inc.* Case 1:17-cv-12239-ADB. Document 129-2. Exhibit 2 to Sharkey Declaration (United States Patent U.S. Pat. No. 9,745,551 B2). Dated Dec. 19, 2019.
[No Author Listed] *Astellas Institute for Regenerative Medicine* v. *IMSTEM Biotechnology, Inc.* Case 1:17-cv-12239-ADB. Document 129-20. Exhibit 20 to Sharkey Declaration (Email Regarding Defendants' Deficient Response to Plaintiffs' Fourth Set of Interrogatories (No. 36). Dated Dec. 19, 2019.
[No Author Listed] *Astellas Institute for Regenerative Medicine* v. *IMSTEM Biotechnology, Inc.* Case 1:17-cv-12239-ADB. Document 129-33. Exhibit 33 to Sharkey Declaration (Plaintiffs' Third Set of Interrogatories (Nos. 31-35). Dated Dec. 19, 2019.
[No Author Listed] *Astellas Institute for Regenerative Medicine* v. *IMSTEM Biotechnology, Inc.* Case 1:17-cv-12239-ADB. Document 129-37. Exhibit 37 to Sharkey Declaration (Expert Report of Dr. Bryan Zerhusen). Dated Dec. 19, 2019.
[No Author Listed] *Astellas Institute for Regenerative Medicine* v. *IMSTEM Biotechnology, Inc.* Case 1:17-cv-12239-ADB. Document 129-4. Exhibit 4 to Sharkey Declaration (Documents for U.S. Application Titled "Using mesenchymal-like stem cells derived from human embryonic stem cell-differentiated hemangioblast to treat multiple sclerosis and other autoimmune diseases"). Dated Dec. 19, 2019.
[No Author Listed] *Astellas Institute for Regenerative Medicine* v. *IMSTEM Biotechnology, Inc.* Case 1:17-cv-12239-ADB. Document 129-7. Exhibit 7 to Sharkey Declaration (Plaintiffs' First Set of Interrogatories [Nos. 1-21]). Dated Dec. 19, 2019.
[No Author Listed] *Astellas Institute for Regenerative Medicine* v. *IMSTEM Biotechnology, Inc.* Case 1:17-cv-12239-ADB. Document 130. Astellas' Statement of Undisputed Material Facts in Support of Its Motion for Partial Summary Judgment. Dated Dec. 19, 2019.
[No Author Listed] *Astellas Institute for Regenerative Medicine* v. *IMSTEM Biotechnology, Inc.* Case 1:17-cv-12239-ADB. Document 131. Defendants' Motion for Partial Summary Judgment. Dated Dec. 19, 2019.
[No Author Listed] *Astellas Institute for Regenerative Medicine* v. *IMSTEM Biotechnology, Inc.* Case 1:17-cv-12239-ADB. Document 135. Defendants' Corrected Memorandum of Law in Support of their Motion for Partial Summary Judgment. Dated Jan. 2, 2020.
[No Author Listed] *Astellas Institute for Regenerative Medicine* v. *IMSTEM Biotechnology, Inc.* Case 1:17-cv-12239-ADB. Document 136. Corrected Declaration of Timothy R. Shannon in Support of Defendants' Motion for Partial Summary Judgment. Dated Jan. 2, 2020.
[No Author Listed] *Astellas Institute for Regenerative Medicine* v. *IMSTEM Biotechnology, Inc.* Case 1:17-cv-12239-ADB. Document 136-1. Exhibit 1 (Emails). Dated Jan. 2, 2020.
[No Author Listed] *Astellas Institute for Regenerative Medicine* v. *IMSTEM Biotechnology, Inc.* Case 1:17-cv-12239-ADB. Document 136-10. Exhibit 10 (United States Patent No. U.S. Pat. No. 8,962,321 B2). Dated Jan. 2, 2020.
[No Author Listed] *Astellas Institute for Regenerative Medicine* v. *IMSTEM Biotechnology, Inc.* Case 1:17-cv-12239-ADB. Document 136-11. Exhibit 11 (Emails). Dated Jan. 2, 2020.
[No Author Listed] *Astellas Institute for Regenerative Medicine* v. *IMSTEM Biotechnology, Inc.* Case 1:17-cv-12239-ADB. Document 136-12. Exhibit 12 (Material Transfer Agreement). Dated Jan. 2, 2020.
[No Author Listed] *Astellas Institute for Regenerative Medicine* v. IMSTEM Biotechnology, Inc. Case 1:17-cv-12239-ADB. Document 136-13. Exhibit 13 (Emails). Dated Jan. 2, 2020.
[No Author Listed] *Astellas Institute for Regenerative Medicine* v. *IMSTEM Biotechnology, Inc.* Case 1:17-cv-12239-ADB. Document 136-14. Exhibit 14 (Email). Dated Jan. 2, 2020.
[No Author Listed] *Astellas Institute for Regenerative Medicine* v. *IMSTEM Biotechnology, Inc.* Case 1:17-cv-12239-ADB. Document 136-15. Exhibit 15 (Emails). Dated Jan. 2, 2020.
[No Author Listed] *Astellas Institute for Regenerative Medicine* v. *IMSTEM Biotechnology, Inc.* Case 1:17-cv-12239-ADB. Document 136-16. Exhibit 16 (IMSTEM Biotechnology, Inc. Incorporation Agreement). Dated Jan. 2, 2020.
[No Author Listed] *Astellas Institute for Regenerative Medicine* v. *IMSTEM Biotechnology, Inc.* Case 1:17-cv-12239-ADB. Document 136-17. Exhibit 17 (Documents for U.S. Appl. No. 61/670,787). Dated Jan. 2, 2020.
[No Author Listed] *Astellas Institute for Regenerative Medicine* v. *IMSTEM Biotechnology, Inc.* Case 1:17-cv-12239-ADB. Document 136-18. Exhibit 18 (Documents for U.S. Appl. No. 61/762,961). Dated Jan. 2, 2020.
[No Author Listed] *Astellas Institute for Regenerative Medicine* v. *IMSTEM Biotechnology, Inc.* Case 1:17-cv-12239-ADB. Document 136-2. Exhibit 2 (Email). Dated Jan. 2, 2020.
[No Author Listed] *Astellas Institute for Regenerative Medicine* v. *IMSTEM Biotechnology, Inc.* Case 1:17-cv-12239-ADB. Document 136-20. Exhibit 20 (Patent Cooperation Treaty [PCT] Publication No. WO 2013/082543 A1). Dated Jan. 2, 2020.
[No Author Listed] *Astellas Institute for Regenerative Medicine* v. *IMSTEM Biotechnology, Inc.* Case 1:17-cv-12239-ADB. Document 136-22. Exhibit 22 (Stem cell grants target multiple sclerosis, epilepsy, cancer). Dated Jan. 2, 2020.
[No Author Listed] *Astellas Institute for Regenerative Medicine* v. *IMSTEM Biotechnology, Inc.* Case 1:17-cv-12239-ADB. Document 136-23. Exhibit 33 (Patent Cooperation Treaty [PCT] Publication No. WO 2014/011407 A2). Dated Jan. 2, 2020.
[No Author Listed] *Astellas Institute for Regenerative Medicine* v. *IMSTEM Biotechnology, Inc.* Case 1:17-cv-12239-ADB. Document 136-25. Exhibit 25 (Plaintiffs' Privilege Log). Dated Jan. 2, 2020.
[No Author Listed] *Astellas Institute for Regenerative Medicine* v. *IMSTEM Biotechnology, Inc.* Case 1:17-cv-12239-ADB. Document 136-3. Exhibit 3 (Emails). Dated Jan. 2, 2020.
[No Author Listed] *Astellas Institute for Regenerative Medicine* v. *IMSTEM Biotechnology, Inc.* Case 1:17-cv-12239-ADB. Document 136-31. Exhibit 31 (U.S. Appl. No. 14/413,290). Dated Jan. 2, 2020.
[No Author Listed] *Astellas Institute for Regenerative Medicine* v. *IMSTEM Biotechnology, Inc.* Case 1:17-cv-12239-ADB. Document 136-32. Exhibit 32 (United States Patent No. U.S. Pat. No. 8,961,956 B2). Dated Jan. 2, 2020.
[No Author Listed] *Astellas Institute for Regenerative Medicine* v. *IMSTEM Biotechnology, Inc.* Case 1:17-cv-12239-ADB. Document 136-33. Exhibit 33 (United States Patent No. U.S. Pat. No. 8,962,321 B2). Dated Jan. 2, 2020.
[No Author Listed] *Astellas Institute for Regenerative Medicine* v. *IMSTEM Biotechnology, Inc.* Case 1:17-cv-12239-ADB. Document 136-35. Exhibit 35 (Documents for U.S. Appl. No. 14/413,290). Dated Jan. 2, 2020.
[No Author Listed] *Astellas Institute for Regenerative Medicine* v. *IMSTEM Biotechnology, Inc.* Case 1:17-cv-12239-ADB. Document 136-36. Exhibit 36 (United States Patent No. U.S. Pat. No. 9,745,551 B2). Dated Jan. 2, 2020.
[No Author Listed] *Astellas Institute for Regenerative Medicine* v. *IMSTEM Biotechnology, Inc.* Case 1:17-cv-12239-ADB. Document 136-37. Exhibit 37 (Video Deposition of Bryan Daniel Zerhusen, Ph.D., J.D.). Dated Jan. 2, 2020.

(56) References Cited

OTHER PUBLICATIONS

[No Author Listed] *Astellas Institute for Regenerative Medicine* v. *IMSTEM Biotechnology, Inc.* Case 1:17-cv-12239-ADB. Document 136-38. Exhibit 38 (Opening Expert Report of Lisa Fortier, DVM, Ph.D.). Dated Jan. 2, 2020.
[No Author Listed] *Astellas Institute for Regenerative Medicine* v. *IMSTEM Biotechnology, Inc.* Case 1:17-cv-12239-ADB. Document 136-39. Exhibit 39 (Expert Report of Gregory K. Bell, Ph.D.). Dated Jan. 2, 2020.
[No Author Listed] *Astellas Institute for Regenerative Medicine* v. *IMSTEM Biotechnology, Inc.* Case 1:17-cv-12239-ADB. Document 136-8. Exhibit 8 (Documents for U.S. Appl. No. 61/565,358). Dated Jan. 2, 2020.
[No Author Listed] *Astellas Institute for Regenerative Medicine* v. *IMSTEM Biotechnology, Inc.* Case 1:17-cv-12239-ADB. Document 136-9. Exhibit 9 (United States Patent No. U.S. Pat. No. 8,961,956 B2). Dated Jan. 2, 2020.
[No Author Listed] *Astellas Institute for Regenerative Medicine* v. *IMSTEM Biotechnology, Inc.* Case 1:17-cv-12239-ADB. Document 137. Defendants' Corrected Statement of Undisputed Material Facts in Support of Their Motion for Partial Summary Judgment. Dated Jan. 2, 2020.
[No Author Listed] *Astellas Institute for Regenerative Medicine* v. *IMSTEM Biotechnology, Inc.* Case 1:17-cv-12239-ADB. Document 142. Astellas' Opposition to Defendants' Motion for Partial Summary Judgment. Dated Jan. 10, 2020.
[No Author Listed] *Astellas Institute for Regenerative Medicine* v. *IMSTEM Biotechnology, Inc.* Case 1:17-cv-12239-ADB. Document 143. Declaration of Lauren K. Sharkey in Support of Astellas' Opposition to Defendants' Motion for Partial Summary Judgment. Dated Jan. 10, 2020.
[No Author Listed] *Astellas Institute for Regenerative Medicine* v. *IMSTEM Biotechnology, Inc.* Case 1:17-cv-12239-ADB. Document 143-16. Exhibit 53 to Sharkey Declaration (Expert Report of Dr. Bryan Zerhusen). Dated Jan. 10, 2020.
[No Author Listed] *Astellas Institute for Regenerative Medicine* v. *IMSTEM Biotechnology, Inc.* Case 1:17-cv-12239-ADB. Document 143-17. Exhibit 54 to Sharkey Declaration (Video Deposition of Bryan Daniel Zerhusen, Ph.D., J.D.). Dated Jan. 10, 2020.
[No Author Listed] *Astellas Institute for Regenerative Medicine* v. *IMSTEM Biotechnology, Inc.* Case 1:17-cv-12239-ADB. Document 143-32. Exhibit 69 to Sharkey Declaration (Documents for U.S. Appl. No. 14/413,290). Dated Jan. 10, 2020.
[No Author Listed] *Astellas Institute for Regenerative Medicine* v. *IMSTEM Biotechnology, Inc.* Case 1:17-cv-12239-ADB. Document 143-9. Exhibit 46 to Sharkey Declaration (Human ESC-Derived MSCs Outperform Bone Marrow MSCs in the Treatment of an EAE Model of Multiple Sclerosis). Dated Jan. 10, 2020.
[No Author Listed] *Astellas Institute for Regenerative Medicine* v. *IMSTEM Biotechnology, Inc.* Case 1:17-cv-12239-ADB. Document 144. Astellas' Responses to Defendants' Corrected Statement of Undisputed Material Facts and Supplemental Statements of Material Facts. Dated Jan. 10, 2020.
[No Author Listed] *Astellas Institute for Regenerative Medicine* v. *IMSTEM Biotechnology, Inc.* Case 1:17-cv-12239-ADB. Document 152. Defendants' Opposition to Astellas' Motion for Partial Summary Judgment. Dated Jan. 15, 2020.
[No Author Listed] *Astellas Institute for Regenerative Medicine* v. *IMSTEM Biotechnology, Inc.* Case 1:17-cv-12239-ADB. Document 153. Defendants' Opposition to Plaintiffs' Statement of Undisputed Material Facts in Support of Their Motion for Partial Summary Judgment & Counterstatement of Additional Material of Facts. Dated Jan. 15, 2020.
[No Author Listed] *Astellas Institute for Regenerative Medicine* v. *IMSTEM Biotechnology, Inc.* Case 1:17-cv-12239-ADB. Document 154. Declaration of Timothy R. Shannon In In Support of Defendants' Opposition to Plaintiffs' Motion for Partial Summary Judgment. Dated Jan. 15, 2020.
[No Author Listed] *Astellas Institute for Regenerative Medicine* v. *IMSTEM Biotechnology, Inc.* Case 1:17-cv-12239-ADB. Document 154-1. Exhibit 01 to Shannon Declaration ISO Opposition (United States Patent No. U.S. Pat. No. 8,962,321 B2). Dated Jan. 15, 2020.
[No Author Listed] *Astellas Institute for Regenerative Medicine* v. *IMSTEM Biotechnology, Inc.* Case 1:17-cv-12239-ADB. Document 154-10. Exhibit 10 to Shannon Declaration ISO Opposition (Documents for U.S. Appl. No. 14/413,290). Dated Jan. 15, 2020.
[No Author Listed] *Astellas Institute for Regenerative Medicine* v. *IMSTEM Biotechnology, Inc.* Case 1:17-cv-12239-ADB. Document 154-14. Exhibit 14 to Shannon Declaration ISO Opposition (Opening Expert Report of Bruce Bunnell, Ph.D.). Dated Jan. 15, 2020.
[No Author Listed] *Astellas Institute for Regenerative Medicine* v. *IMSTEM Biotechnology, Inc.* Case 1:17-cv-12239-ADB. Document 154-2. Exhibit 02 to Shannon Declaration ISO Opposition (Patent Cooperation Treaty [PCT] Publication No. WO 2013/082543 A1). Dated Jan. 15, 2020.
[No Author Listed] *Astellas Institute for Regenerative Medicine* v. *IMSTEM Biotechnology, Inc.* Case 1:17-cv-12239-ADB. Document 154-3. Exhibit 03 to Shannon Declaration ISO Opposition (Emails). Dated Jan. 15, 2020.
[No Author Listed] *Astellas Institute for Regenerative Medicine* v. *IMSTEM Biotechnology, Inc.* Case 1:17-cv-12239-ADB. Document 154-4. Exhibit 04 to Shannon Declaration ISO Opposition (Patent Cooperation Treaty [PCT] Publication No. WO 2014/011407 A2). Dated Jan. 15, 2020.
[No Author Listed] *Astellas Institute for Regenerative Medicine* v. *IMSTEM Biotechnology, Inc.* Case 1:17-cv-12239-ADB. Document 154-5. Exhibit 05 to Shannon Declaration ISO Opposition (Documents for U.S. Appl. No. 14/413,290). Dated Jan. 15, 2020.
[No Author Listed] *Astellas Institute for Regenerative Medicine* v. *IMSTEM Biotechnology, Inc.* Case 1:17-cv-12239-ADB. Document 154-6. Exhibit 06 to Shannon Declaration ISO Opposition (Documents for U.S. Appl. No. 14/413,290). Dated Jan. 15, 2020.
[No Author Listed] *Astellas Institute for Regenerative Medicine* v. *IMSTEM Biotechnology, Inc.* Case 1:17-cv-12239-ADB. Document 154-7. Exhibit 07 to Shannon Declaration ISO Opposition (Documents for U.S. Appl. No. 14/413,290). Dated Jan. 15, 2020.
[No Author Listed] *Astellas Institute for Regenerative Medicine* v. *IMSTEM Biotechnology, Inc.* Case 1:17-cv-12239-ADB. Document 154-8. Exhibit 08 to Shannon Declaration ISO Opposition (Documents for U.S. Appl. No. 14/413,290). Dated Jan. 15, 2020.
[No Author Listed] *Astellas Institute for Regenerative Medicine* v. *IMSTEM Biotechnology, Inc.* Case 1:17-cv-12239-ADB. Document 154-9. Exhibit 09 to Shannon Declaration ISO Opposition (Expert Report of Dr. Bryan Zerhusen). Dated Jan. 15, 2020.
[No Author Listed] *Astellas Institute for Regenerative Medicine* v. *IMSTEM Biotechnology, Inc.* Case 1:17-cv-12239-ADB. Document 155. Astellas' Reply in Support of Its Motion for Partial Summary Judgment. Dated Jan. 17, 2020.
[No Author Listed] *Astellas Institute for Regenerative Medicine* v. *IMSTEM Biotechnology, Inc.* Case 1:17-cv-12239-ADB. Document 156. Declaration of Lauren K. Sharkey in Support of Astellas' Reply in Support of Its Motion for Partial Summary Judgment. Dated Jan. 17, 2020.
[No Author Listed] *Astellas Institute for Regenerative Medicine* v. *IMSTEM Biotechnology, Inc.* Case 1:17-cv-12239-ADB. Document 156-1. Exhibit 73 to Sharkey Declaration (Video Deposition of Bryan Daniel Zerhusen, Ph.D., J.D.). Dated Jan. 17, 2020.
[No Author Listed] *Astellas Institute for Regenerative Medicine* v. *IMSTEM Biotechnology, Inc.* Case 1:17-cv-12239-ADB. Document 157. Astellas' Responses to Defendants' Counterstatement of Additional Material Facts. Dated Jan. 17, 2020.
[No Author Listed] *Astellas Institute for Regenerative Medicine* v. *IMSTEM Biotechnology, Inc.* Case 1:17-cv-12239-ADB. Document 158. Defendants' Opposition to Plaintiffs' Supplemental Statement of Facts. Dated Jan. 17, 2020.
[No Author Listed] *Astellas Institute for Regenerative Medicine* v. *IMSTEM Biotechnology, Inc.* Case 1:17-cv-12239-ADB. Document 159. Declaration of Timothy R. Shannon in Further Support of Defendants' Motion for Partial Summary Judgment. Dated Jan. 17, 2020.
[No Author Listed] *Astellas Institute for Regenerative Medicine* v. *IMSTEM Biotechnology, Inc.* Case 1:17-cv-12239-ADB. Document 159-1. Exhibit 1 to Shannon Declaration in Further Support of

(56) References Cited

OTHER PUBLICATIONS

Defendants' Motion for Partial Summary Judgment (Expert Report of Dr. Bryan Zerhusen). Dated Jan. 17, 2020.

[No Author Listed] *Astellas Institute for Regenerative Medicine v. IMSTEM Biotechnology, Inc.* Case 1:17-cv-12239-ADB. Document 159-2. Exhibit 2 to Shannon Declaration in Further Support of Defendants' Motion for Partial Summary Judgment (Plaintiffs' Privilege Log). Dated Jan. 17, 2020.

[No Author Listed] *Astellas Institute for Regenerative Medicine v. IMSTEM Biotechnology, Inc.* Case 1:17-cv-12239-ADB. Document 159-3. Exhibit 3 to Shannon Declaration in Further Support of Defendants' Motion for Partial Summary Judgment (Email). Dated Jan. 17, 2020.

[No Author Listed] *Astellas Institute for Regenerative Medicine v. IMSTEM Biotechnology, Inc.* Case 1:17-cv-12239-ADB. Document 159-4. Exhibit 4 to Shannon Declaration in Further Support of Defendants' Motion for Partial Summary Judgment (Continued Videotaped Deposition of Xiaofang Wang, MD, PhD). Dated Jan. 17, 2020.

[No Author Listed] *Astellas Institute for Regenerative Medicine v. IMSTEM Biotechnology, Inc.* Case 1:17-cv-12239-ADB. Document 159-5. Exhibit 5 to Shannon Declaration in Further Support of Defendants' Motion for Partial Summary Judgment (Presentation). Dated Jan. 17, 2020.

[No Author Listed] *Astellas Institute for Regenerative Medicine v. IMSTEM Biotechnology, Inc.* Case 1:17-cv-12239-ADB. Document 159-6. Exhibit 6 to Shannon Declaration in Further Support of Defendants' Motion for Partial Summary Judgment (Presentation). Dated Jan. 17, 2020.

[No Author Listed] *Astellas Institute for Regenerative Medicine v. IMSTEM Biotechnology, Inc.* Case 1:17-cv-12239-ADB. Document 159-7. Exhibit 7 to Shannon Declaration in Further Support of Defendants' Motion for Partial Summary Judgment (Email). Dated Jan. 17, 2020.

[No Author Listed] *Astellas Institute for Regenerative Medicine v. IMSTEM Biotechnology, Inc.* Case 1:17-cv-12239-ADB. Document 161. Defendants' Reply to Astellas' Opposition to Defendants' Motion for Partial Summary Judgment. Dated Jan. 17, 2020.

[No Author Listed] *Astellas Institute for Regenerative Medicine v. IMSTEM Biotechnology, Inc.* Case 1:17-cv-12239-ADB. Document 20. Defendants IMSTEM Biotechnology, Inc.'s and Xiaofang Wang's Answer and Counterclaims. Filed Jan. 10, 2018.

[No Author Listed] *Astellas Institute for Regenerative Medicine v. IMSTEM Biotechnology, Inc.* Case 1:17-cv-12239-ADB. Document 21. Plaintiffs Astellas' and SCRMI's Motion to Dismiss Defendants IMSTEM's and Xiaofang Wang's Counterclaims. Filed Jan. 31, 2018.

[No Author Listed] *Astellas Institute for Regenerative Medicine v. IMSTEM Biotechnology, Inc.* Case 1:17-cv-12239-ADB. Document 22. Plaintiffs Astellas' and SCRMI's Memorandum In Support of Their Motion to Dismiss Defendants IMSTEM's and Xiaofang Wang's Counterclaims. Filed Jan. 31, 2018.

[No Author Listed] *Astellas Institute for Regenerative Medicine v. IMSTEM Biotechnology, Inc.* Case 1:17-cv-12239-ADB. Document 23. Declaration of Rebecca L. Rabenstein In Support Of Plaintiffs Astellas' And SCRMI's Motion To Dismiss Defendants IMSTEM's And Xiaofang Wang's Counterclaims Filed Jan. 31, 2018.

[No Author Listed] *Astellas Institute for Regenerative Medicine v. IMSTEM Biotechnology, Inc.* Case 1:17-cv-12239-ADB. Document 28. Opposition to Plaintiffs' Motion to Dismiss IMSTEM and Xiaofang Wang's Counterclaims. Filed Mar. 16, 2018.

[No Author Listed] *Astellas Institute for Regenerative Medicine v. IMSTEM Biotechnology, Inc.* Case 1:17-cv-12239-ADB. Document 29. Declaration of Timothy R. Shannon In Support Of Defendants' Opposition To Plaintiffs' Motion To Dismiss IMSTEM's And Xiaofang Wang's Counterclaims. Filed Mar. 16, 2018.

[No Author Listed] *Astellas Institute for Regenerative Medicine v. IMSTEM Biotechnology, Inc.* Case 1:17-cv-12239-ADB. Document 32. Reply Brief In Support Of Plaintiffs' Motion to Dismiss IMSTEM's and Xiaofang Wang's Counterclaims. Filed Mar. 29, 2018.

[No Author Listed] *Astellas Institute for Regenerative Medicine v. IMSTEM Biotechnology, Inc.* Case 1:17-cv-12239-ADB. Document 33. Defendant Ren-He Xu's Answer. Filed Jun. 8, 2018.

[No Author Listed] *Astellas Institute for Regenerative Medicine v. IMSTEM Biotechnology, Inc.* Case 1:17-cv-12239-ADB. Document 37. Memorandum and Order on Motion To Dismiss. Filed Sep. 28, 2018.

[No Author Listed] *Astellas Institute for Regenerative Medicine v. IMSTEM Biotechnology, Inc.* Case 1:17-cv-12239-ADB. Document 42. Plaintiffs' Answer to Defendants' Counterclaims. Filed Oct. 12, 2018.

[No Author Listed] *Astellas Institute for Regenerative Medicine v. IMSTEM Biotechnology, Inc.* Case 1:17-cv-12239-ADB. Document 70. Defendants' Motion For Leave To File Amended Counterclaims. Filed Jul. 22, 2019.

[No Author Listed] *Astellas Institute for Regenerative Medicine v. IMSTEM Biotechnology, Inc.* Case 1:17-cv-12239-ADB. Document 71. Defendants' Memorandum of Law In Support Of their Motion For Leave To File Amended Counterclaims. Filed Jul. 22, 2019.

[No Author Listed] *Astellas Institute for Regenerative Medicine v. IMSTEM Biotechnology, Inc.* Case 1:17-cv-12239-ADB. Document 75. Plaintiffs' Opposition to Defendants' Motion For Leave To File Amended Counterclaims. Filed Jul. 30, 2019.

[No Author Listed] *Astellas Institute for Regenerative Medicine v. IMSTEM Biotechnology, Inc.* Case 1:17-cv-12239-ADB. Document 76. Declaration Of Lauren K. Sharkey In Support Of Plaintiffs' Opposition To Defendants' Motion For Leave To File Amended Counterclaims. Filed Jul. 30, 2019.

[No Author Listed] *Astellas Institute for Regenerative Medicine v. IMSTEM Biotechnology, Inc.* Case 1:17-cv-12239-ADB. Document 83. Reply to Plaintiffs' Opposition To Defendants' Motion For Leave To File Amended Counterclaims. Filed Aug. 6, 2019.

[No Author Listed] *Astellas Institute for Regenerative Medicine v. IMSTEM Biotechnology, Inc.* Case 1:17-cv-12239-ADB. Document 84. Declaration of Timothy R. Shannon In Support Of Defendants' Reply to Plaintiffs' Opposition to Defendants' Motion For Leave To File Amended Counterclaims. Filed Aug. 6, 2019.

[No Author Listed] *Astellas Institute for Regenerative Medicine v. IMSTEM Biotechnology, Inc.* Case 1:17-cv-12239-ADB. Document 85. Memorandum and Order on Defendants' Motion to Amend Counterclaims. Dated Aug. 21, 2019.

[No Author Listed] *Astellas Institute for Regenerative Medicine v. IMSTEM Biotechnology, Inc.* Case 1:17-cv-12239-ADB. Document 87. Transcript of Scheduling Conference Before the Honorable Allison D. Burroughs. Dated Aug. 21, 2019.

[No Author Listed] *Astellas Institute for Regenerative Medicine v. IMSTEM Biotechnology, Inc.* Case 1:17-cv-12239-ADB. Document 88. Transcript of Scheduling Conference Before the Honorable Allison D. Burroughs. Dated Aug. 27, 2019.

[No Author Listed] *Astellas Institute for Regenerative Medicine v. IMSTEM Biotechnology, Inc.* Case 1:17-cv-12239-ADB. Document 91. Defendants' Amended Answer and Counterclaims. Dated Aug. 28, 2019.

[No Author Listed] *Astellas Institute for Regenerative Medicine v. IMSTEM Biotechnology, Inc.* Case 1:17-cv-12239-ADB. Document 91-1. Exhibit A (United States Patent No. U.S. Pat. No. 8,961,956 B2). Dated Aug. 28, 2019.

[No Author Listed] *Astellas Institute for Regenerative Medicine v. IMSTEM Biotechnology, Inc.* Case 1:17-cv-12239-ADB. Document 91-2. Exhibit A-1 (United States Patent No. U.S. Pat. No. 8,962,321 B2). Dated Aug. 28, 2019.

[No Author Listed] *Astellas Institute for Regenerative Medicine v. IMSTEM Biotechnology, Inc.* Case 1:17-cv-12239-ADB. Document 91-3. Exhibit B (The Kinases MEKK2 and MEKK3 Regulate Transforming Growth Factor-ß-Mediated Helper T Cell Differentiation). Dated Aug. 28, 2019.

[No Author Listed] *Astellas Institute for Regenerative Medicine v. IMSTEM Biotechnology, Inc.* Case 1:17-cv-12239-ADB. Document 91-4. Exhibit C (Excerpts from plaintiffs' provisional U.S. Appl. No. 61/565,358). Dated Aug. 28, 2019.

(56) References Cited

OTHER PUBLICATIONS

[No Author Listed] *Astellas Institute for Regenerative Medicine* v. *IMSTEM Biotechnology, Inc.* Case 1:17-cv-12239-ADB. Document 92. Plaintiffs' Answer to Defendants' Amended Counterclaims. Dated Sep. 6, 2019.

[No Author Listed] *Astellas Institute for Regenerative Medicine* v. *IMSTEM Biotechnology, Inc.* Case 1:17-cv-12239-ADB. Document 95. Joint Stipulation Regarding U.S. Appl. No. 15/656,473. Dated Sep. 12, 2019.

[No Author Listed] *Astellas Institute for Regenerative Medicine* v. *IMSTEM Biotechnology, Inc.* Case 1:17-cv-12239-ADB. Document 96. Plaintiffs' Motion for Leave to File an Amended Complaint. Dated Sep. 13, 2019.

[No Author Listed] *Astellas Institute for Regenerative Medicine* v. *IMSTEM Biotechnology, Inc.* Case 1:17-cv-12239-ADB. Document 96-1. Exhibit A ([Proposed] First Amended Complaint). Dated Sep. 13, 2019.

[No Author Listed] *Astellas Institute for Regenerative Medicine* v. *IMSTEM Biotechnology, Inc.* Case 1:17-cv-12239-ADB. Document 96-2. Exhibit B ([Proposed] First Amended Complaint). Dated Sep. 13, 2019.

[No Author Listed] *Astellas Institute for Regenerative Medicine* v. *IMSTEM Biotechnology, Inc.* Case 1:17-cv-12239-ADB. Document 97. Plaintiffs' Memorandum In Support of Its Motion For Leave to File an Amended Complaint. Dated Sep. 13, 2019.

[No Author Listed] *Astellas Institute for Regenerative Medicine* v. *IMSTEM Biotechnology, Inc.* Case 1:17-cv-12239-ADB. Document 99. Declaration of Lauren K. Sharkey in Support of Plaintiffs' Motion for Leave to File an Amended Complaint. Dated Sep. 13, 2019.

[No Author Listed], Advanced Cell Technology, Inc. ACT secures first patent for generating hemangioblast cells to treat a broad spectrum of vascular and hematopoietic disorders. Sep. 19, 2011. http://www.advancedcell.com/news-and-media/press-releases/act—secures-first-patent-for-generating-hemangioblast-cells-to-treat-a-broad-spectrum-of-vascular-and-hematopoietic-disorders/ [Last accessed Aug. 18, 2014.].

[No Author Listed], Life technologies, Guidelines for Maintaining Cultured Cells. Retrieved online at: https://www.lifetechnologies.com/us/en/home/references/gibco-cell-culture-basics/cell-culture-protocols/maintaining-cultured-cells.html. 4 pages, (2014).

[No Author Listed], NIH, Stem Cells: Scientific Progress and Future Research Directions. National Institutes of Health, Department of Health and Human Services. pp. 1-4, Jun. 2001.

[No Author Listed], UCLA, Induced Pluripotent Stem Cells (iPS). Definition. 2016.

Aggarwal et al., Human mesenchymal stem cells modulate allogeneic immune cell responses. Blood. Feb. 15, 2005;105(4):1815-22. Epub Oct. 19, 2004.

Alikani et al., Nonviable human pre-implantation embryos as a source of stem cells for research and potential therapy. Stem Cell Rev. Dec. 2005;1(4):337-43.

Baek et al., Stroma-free mass production of clinical-grade red blood cells (RBCs) by using poloxamer 188 as an RBC survival enhancer. Transfusion. Nov. 2009;49(11):2285-95.

Bagamery et al., Are platelets activated after a rapid, one-step density gradient centrifugation? Evidence from flow cytometric analysis. Clin Lab Haematol. Feb. 2005;27(1):75-7.

Bai et al., Hepatocyte growth factor mediates mesenchymal stem cell-induced recovery in multiple sclerosis models. Nat Neurosci. Jun. 2012;15(6):862-70. doi: 10.1038/nn.3109.

Bai et al., Human bone marrow-derived mesenchymal stem cells induce Th2-polarized immune response and promote endogenous repair in animal models of multiple sclerosis. Glia. Aug. 15, 2009;57(11):1192-203. doi: 10.1002/glia.20841.

Baker et al., Models of multiple sclerosis. ACNR. Jan. 2007;6(6):10-12.

Barlow et al., Comparison of human placenta—and bone marrow-derived multipotent mesenchymal stem cells. Stem Cells Dev. Dec. 2008;17(6):1095-107. doi: 10.1089/scd.2007.0154. Abstract Only.

Barry et al., The SH-3 and SH-4 antibodies recognize distinct epitopes on CD73 from human mesenchymal stem cells. Biochem Biophys Res Commun. Nov. 30, 2001;289(2):519-24. Abstract Only.

Bartholomaus et al., Effector T cell interactions with meningeal vascular structures in nascent autoimmune CNS lesions. Nature. Nov. 5, 2009;462(7269):94-8. doi: 10.1038/nature08478. Epub Oct. 14, 2009. Abstract Only.

Becker, Stem cell grants target multiple sclerosis, epilepsy, cancer. The CT Mirror. Jun. 13, 2013. 4 pages. Available online at https://ctmirror.org/2013/06/13/stem-cell-grants-target-multiple-sclerosis-epilepsy-cancer/.

Ben-Ami et al., Mesenchymal stem cells as an immunomodulatory therapeutic strategy for autoimmune diseases. Autoimmun Rev. May 2011;10(7):410-5. doi: 10.1016/j.autrev.2011.01.005. Epub Jan. 20, 2011. Review. PubMed PMID: 21256250.

Bennett et al., Blood-brain barrier disruption and enhanced vascular permeability in the multiple sclerosis model EAE. J Neuroimmunol. Dec. 15, 2010;229(1-2):180-91. doi: 10.1016/j.jneuroim.2010.08.011. Epub Sep. 15, 2010. Abstract Only.

Bhatia, Hematopoiesis from human embryonic stem cells. Ann N Y Acad Sci. Jun. 2007;1106:219-22.

Bocelli-Tyndall et al., Bone marrow mesenchymal stromal cells (BM-MSCs) from healthy donors and auto-immune disease patients reduce the proliferation of autologous—and allogeneicstimulated lymphocytes in vitro. Rheumatology (Oxford). Mar. 2007;46(3):403-8. Epub Aug. 18, 2006.

Bonab et al., Aging of mesenchymal stem cell in vitro. BMC Cell Biol. Mar. 10, 2006;7:14.

Bonfield et al., Defining human mesenchymal stem cell efficacy in vivo. J Inflamm (Lond). Oct. 25, 2010;7:51. doi: 10.1186/1476-9255-7-51.

Bordoni et al., Hepatocyte-conditioned medium sustains endothelial differentiation of human hematopoietic-endothelial progenitors. Hepatology. May 2007;45(5):1218-28.

Bowles et al., HOXB4 overexpression promotes hematopoietic development by human embryonic stem cells. Stem Cells. May 2006;24(5):1359-69.

Bruder et al., Growth kinetics, self-renewal, and the osteogenic potential of purified human mesenchymal stem cells during extensive subcultivation and following cryopreservation. J Cell Biochem. Feb. 1997;64(2):278-94.

Bruno et al., Isolation and Characterization of Resident Mesenchymal Stem Cells in Human Glomeruli. Methods Mol Biol. 2012;879:367-80. doi: 10.1007/978-1-61779-815-3_22.

Carrion et al., Opposing effect of mesenchymal stem cells on Th1 and Th17 cell polarization according to the state of CD4+ T cell activation. Immunol Lett. Mar. 30, 2011;135(1-2):10-6. doi: 10.1016/j.imlet.2010.09.006. Epub Oct. 1, 2010. Abstract Only.

Carroll et al., Update on stem cell therapy for cerebral palsy. Expert Opin Biol Ther. Apr. 2011;11(4):463-71. doi: 10.1517/14712598.2011.557060. Epub Feb. 8, 2011. Review.

Celebi et al., Irradiated Mesenchymal Stem Cells improve the ex vivo expansion of Hematopoietic Progenitors by partly mimicking the bone marrow endosteal environment. J Immunol Methods. Jul. 29, 2011;370(1-2):93-103. doi: 10.1016/j.jim.2011.06.006. Epub Jun. 15, 2011.

Cerdan et al., Hematopoietic Differentiation. Embryonic Stem Cells. Chapter 5, pp. 53-83, (2007).

Chamberlain et al., Mesenchymal stem cells exhibit firm adhesion, crawling, spreading and transmigration across aortic endothelial cells: effects of chemokines and shear. PLoS One. 2011;6(9):e25663. doi: 10.1371/journal.pone.0025663. Epub Sep. 28, 2011.

Chang et al., The kinases MEKK2 and MEKK3 regulate transforming growth factor-β-mediated helper T cell differentiation. Immunity. Feb. 25, 2011;34(2):201-12. doi: 10.1016/j.immuni.2011.01.017. Epub Feb. 17, 2011.

Chan-Ling et al., Hematopoietic stem cells provide repair functions after laser-induced Bruch's membrane rupture model of choroidal neovascularization. Am J Pathol. Mar. 2006;168(3):1031-44.

Charbord et al., Bone marrow mesenchymal stem cells: historical overview and concepts. Hum Gene Ther. Sep. 2010;21(9):1045-56. doi: 10.1089/hum.2010.115. Review.

(56) References Cited

OTHER PUBLICATIONS

Chen et al., Enabling a robust scalable manufacturing process for therapeutic exosomes through oncogenic immortalization of human ESC-derived MSCs. J Transl Med. Apr. 25, 2011;9:47. doi: 10.1186/1479-5876-9-47.

Chen et al., Small molecule mesengenic induction of human induced pluripotent stem cells to generate mesenchymal stem/stromal cells. Stem Cells Transl Med. Feb. 2012;1(2):83-95. doi: 10.5966/sctm.2011-0022. Epub Feb. 7, 2012.

Cheng et al., Human mesenchymal stem cells support megakaryocyte and pro-platelet formation from CD34(+) hematopoietic progenitor cells. J Cell Physiol. Jul. 2000;184(1):58-69.

Chippendale et al., Isolation of mesenchymal stem cells from bone marrow aspirate. Comprehensive Biotech. Jul. 2011;2(5):15-123.

Choi et al., A common precursor for hematopoietic and endothelial cells. Development. Feb. 1998;125(4):725-32.

Choi et al., In vitro development of a hemangioblast from a human embryonic stem cell, SNUhES#3. Life Sci. Jul. 3, 2009;85(1-2):39-45.

Chun et al., Megakaryocyte Production from Feeder Cell-Free Cultures of Human Embryonic Stem Cells (hESC). Blood, 2009;114: Abstract 2528.

Chung et al., Human embryonic stem cell lines generated without embryo destruction. Cell Stem Cell. Feb. 7, 2008;2(2):113-7. doi: 10.1016/j.stem.2007.12.013. Epub Jan. 10, 2008.

Cibelli et al., Parthenogenetic stem cells in nonhuman primates. Science. Feb. 1, 2002;295(5556):819.

Cibelli et al., Somatic Cell Nuclear Transfer in Humans: Pronuclear and Early Embryonic Development. ebiomed: The Journal of Regenerative Medicine. Nov. 26, 2001;2(5):25-31.

Ciraci et al., Adult human circulating CD34-Lin-CD45-CD133— cells can differentiate into hematopoietic and endothelial cells. Blood. Aug. 25, 2011;118(8):2105-15. doi: 10.1182/blood-2010-10-316596. Epub Jun. 29, 2011.

Colter et al., Identification of a subpopulation of rapidly self-renewing and multipotential adult stem cells in colonies of human marrow stromal cells. Proc Natl Acad Sci U S A. Jul. 3, 2001;98(14):7841-5. Epub Jun. 26, 2001.

Conget et al., Phenotypical and functional properties of human bone marrow mesenchymal progenitor cells. J Cell Physiol. Oct. 1999;181(1):67-73.

Connick et al., The mesenchymal stem cells in multiple sclerosis (MSCIMS) trial protocol and baseline cohort characteristics: an open-label pre-test: post-test study with blinded outcome assessments. Trials. Mar. 2, 2011;12:62. doi: 10.1186/1745-6215-12-62.

Copland et al., The clinical time-course of experimental autoimmune uveoretinitis using topical endoscopic fundal imaging with histologic and cellular infiltrate correlation. Invest Ophthalmol Vis Sci. Dec. 2008;49(12):5458-65. doi: 10.1167/iovs.08-2348. Epub Aug. 29, 2008.

Dang et al., Efficiency of embryoid body formation and hematopoietic development from embryonic stem cells in different culture systems. Biotechnol Bioeng. 2002;78(4):442-453.

Darlington et al., Reciprocal Th1 and Th17 regulation by mesenchymal stem cells: Implication for multiple sclerosis. Ann Neurol. Oct. 2010;68(4):540-5. doi: 10.1002/ana.22065. Abstract Only.

Dazzi et al., Mesenchymal stem cells and autoimmune diseases. Best Pract Res Clin Haematol. Mar. 2011;24(1):49-57. doi: 10.1016/j.beha.2011.01.002. Epub Feb. 23, 2011. Abstract Only.

De Becker et al., Migration of culture-expanded human mesenchymal stem cells through bone marrow endothelium is regulated by matrix metalloproteinase-2 and tissue inhibitor of metalloproteinase-3. Haematologica. Apr. 2007;92(4):440-9.

Deacon et al., The use of gamma-irradiation and ultraviolet-irradiation in the preparation of human melanoma cells for use in autologous whole-cell vaccines. BMC Cancer. Dec. 4, 2008;8:360. doi: 10.1186/1471-2407-8-360.

Deans et al., Mesenchymal stem cells: biology and potential clinical uses. Exp Hematol. Aug. 2000;28(8):875-84. doi: 10.1016/s0301-472x(00)00482-3.

Dolzhanskiy et al., The development of human megakaryocytes: III. Development of mature megakaryocytes from highly purified committed progenitors in synthetic culture media and inhibition of thrombopoietin-induced polyploidization by interleukin-3. Blood. Jan. 15, 1997;89(2):426-34.

Dore et al., Transcription factor networks in erythroid cell and megakaryocyte development. Blood. Jul. 14, 2011;118(2):231-9.

Douay et al., Stem cells—a source of adult red blood cells for transfusion purposes: present and future. Crit Care Clin. Apr. 2009;25(2):383-98.

Duijvestein et al., Pretreatment with interferon-γ enhances the therapeutic activity of mesenchymal stromal cells in animal models of colitis. Stem Cells. Oct. 2011;29(10):1549-58. doi: 10.1002/stem.698.

Fedele et al., CD38 is expressed on human mature monocyte-derived dendritic cells and is functionally involved in CD83 expression and IL-12 induction. Eur J Immunol. May 2004;34(5):1342-50.

Ferrer et al., Treatment of perianal fistulas with human embryonic stem cell-derived mesenchymal stem cells: a canine model of human fistulizing Crohn's disease. Regen Med. Jan. 2016;11(1):33-43. doi: 10.2217/rme.15.69. Epub Sep. 21, 2015.

Franco Lambert et al., Differentiation of human adipose-derived adult stem cells into neuronal tissue: does it work? Differentiation. Mar. 2009;77(3):221-8. doi: 10.1016/j.diff.2008.10.016. Epub Jan. 24, 2009. Review.

Fu et al., Comparison of immunological characteristics of mesenchymal stem cells derived from human embryonic stem cells and bone marrow. Tissue Eng Part A. Feb. 2015;21(3-4):616-26. doi: 10.1089/ten.TEA.2013.0651. Epub Jan. 8, 2015.

Fujimoto et al., Production of functional platelets by differentiated embryonic stem (ES) cells in vitro. Blood. Dec. 1, 2003;102(12):4044-51.

Furlan et al., Animal models of multiple sclerosis. Methods Mol Biol. 2009;549:157-73. doi: 10.1007/978-1-60327-931-4_11.

Geens et al., Human embryonic stem cell lines derived from single blastomeres of two 4-cell stage embryos. Hum Reprod. Nov. 2009;24(11):2709-17.

Giarratana et al., Ex vivo generation of fully mature human red blood cells from hematopoietic stem cells. Nat Biotechnol. Jan. 2005;23(1):69-74.

Giuliani et al., Long-lasting inhibitory effects of fetal liver mesenchymal stem cells on T-lymphocyte proliferation. PLoS One. 2011;6(5):e19988. doi: 10.1371/journal.pone.0019988. Epub May 19, 2011.

Gnecchi et al., Bone marrow-derived mesenchymal stem cells: isolation, expansion, characterization, viral transduction, and production of conditioned medium. Methods Mol Biol. 2009;482:281-94. doi: 10.1007/978-1-59745-060-7_18.

Gonzalez et al., Treatment of experimental arthritis by inducing immune tolerance with human adipose-derived mesenchymal stem cells. Arthritis Rheum. Apr. 2009;60(4):1006-19. doi: 10.1002/art.24405.

Gordon et al.,, Human mesenchymal stem cells abrogate experimental allergic encephalomyelitis after intraperitoneal injection, and with sparse CNS infiltration. Neurosci Lett. Dec. 19, 2008;448(1):71-3. doi: 10.1016/j.neulet.2008.10.040. Epub Oct. 17, 2008.

Gotherstrom et al., Difference in gene expression between human fetal liver and adult bone marrow mesenchymal stem cells. Haematologica. Aug. 2005;90(8):1017-26.

Gotherstrom et al., Immunologic properties of human fetal mesenchymal stem cells. Am J Obstet Gynecol. Jan. 2004;190(1):239-45. Abstract Only.

Grant et al., Adult hematopoietic stem cells provide functional hemangioblast activity during retinal neovascularization. Nat Med. Jun. 2002;8(6):607-12.

Gregory et al., Non-hematopoietic bone marrow stem cells: molecular control of expansion and differentiation. Exp Cell Res. Jun. 10, 2005;306(2):330-5. Epub Apr. 15, 2005. Review.

Gruenloh et al., Characterization and in vivo testing of mesenchymal stem cells derived from human embryonic stem cells. Tissue Eng Part A. Jun. 2011;17(11-12):1517-25. doi: 10.1089/ten.TEA.2010.0460. Epub Mar. 4, 2011.

(56) References Cited

OTHER PUBLICATIONS

Gu et al., Transplantation of umbilical cord mesenchymal stem cells alleviates lupus nephritis in MRL/lpr mice. Lupus. Nov. 2010;19(13):1502-14. doi: 10.1177/0961203310373782. Epub Jul. 20, 2010.

Guillot et al., Human first-trimester fetal MSC express pluripotency markers and grow faster and have longer telomeres than adult MSC. Stem Cells. Mar. 2007;25(3):646-54. Epub Nov. 22, 2006.

Guo et al., Hemangioblastic characteristics of fetal bone marrow-derived Flk1(+)CD31(-)CD34(-) cells. Exp Hematol. Jul. 2003;31(7):650-8.

Haruta et al., In vitro and in vivo characterization of pigment epithelial cells differentiated from primate embryonic stem cells. Invest Ophthalmol Vis Sci. Mar. 2004;45(3):1020-5.

Hematti et al., Nonhuman primate embryonic stem cells as a preclinical model for hematopoietic and vascular repair. Exp Hematol. Sep. 2005;33(9):980-6.

Hematti, Human embryonic stem cell-derived mesenchymal progenitors: an overview. Methods Mol Biol. 2011;690:163-74. doi: 10.1007/978-1-60761-962-8_11. Review.

Hiroyama et al., Establishment of mouse embryonic stem cell-derived erythroid progenitor cell lines able to produce functional red blood cells. PLoS One. Feb. 6, 2008;3(2):e1544, 11 pages.

Huang et al., The promise of cytokine antibody arrays in the drug discovery process. Expert Opin Ther Targets. Jun. 2005;9(3):601-15. Review.

Huangfu et al., Induction of pluripotent stem cells from primary human fibroblasts with only Oct4 and Sox2. Nat Biotechnol. Nov. 2008;26(11):1269-75.

Hwang et al., Comparison of cytokine expression in mesenchymal stem cells from human placenta, cord blood, and bone marrow. J Korean Med Sci. Aug. 2009;24(4):547-54. doi: 10.3346/jkms.2009.24.4.547. Epub Jul. 29, 2009.

Hyland et al., Challenges to clinical trials in multiple sclerosis: outcome measures in the era of disease-modifying drugs. Curr Opin Neurol. Jun. 2011;24(3):255-61. doi: 10.1097/WCO. 0b013e3283460542. Review.

Ireland, Visualizing Human Biology, Third Edition. Wiley and Sons Inc., 3 pages, (2008).

Isakova et al., Age—and dose-related effects on MSC engraftment levels and anatomical distribution in the central nervous systems of nonhuman primates: identification of novel MSC subpopulations that respond to guidance cues in brain. Stem Cells. Dec. 2007;25(12):3261-70. Epub Oct. 11, 2007.

Itskovitz-Eldor et al., Differentiation of human embryonic stem cells into embryoid bodies compromising the three embryonic germ layers. Mol Med. Feb. 2000;6(2):88-95.

Jarnjak-Jankovic et al., A full scale comparative study of methods for generation of functional Dendritic cells for use as cancer vaccines. BMC Cancer. Jul. 3, 2007;7:119. 9 pages.

Ji et al., Mesenchymal stem cell transplantation inhibits abnormal activation of Akt/GSK3β signaling pathway in T cells from systemic lupus erythematosus mice. Cell Physiol Biochem. 2012;29(5-6):705-12. doi: 10.1159/000178590. Epub May 11, 2012.

Jo et al., Fetal mesenchymal stem cells derived from human umbilical cord sustain primitive characteristics during extensive expansion. Cell Tissue Res. Dec. 2008;334(3):423-33. doi: 10.1007/s00441-008-0696-3.

Karlsson et al., Human embryonic stem cell-derived mesenchymal progenitors—potential in regenerative medicine. Stem Cell Res. Jul. 2009;3(1):39-50. doi: 10.1016/j.scr.2009.05.002. Epub May 19, 2009. Abstract Only.

Kassis et al., Neuroprotection and immunomodulation with mesenchymal stem cells in chronic experimental autoimmune encephalomyelitis. Arch Neurol. Jun. 2008;65(6):753-61. doi: 10.1001/archneur.65.6.753.

Kaufman et al., Hematopoietic colony-forming cells derived from human embryonic stem cells. Proc Natl Acad Sci U S A. Sep. 11, 2001;98(19):10716-21.

Kennedy et al., A common precursor for primitive erythropoiesis and definitive haematopoiesis. Nature. Apr. 3, 1997;386(6624):488-93. Abstract Only.

Kennedy et al., Development of the hemangioblast defines the onset of hematopoiesis in human ES cell differentiation cultures. Blood. Apr. 1, 2007;109(7):2679-87.

Kilpinen et al., Aging bone marrow mesenchymal stromal cells have altered membrane glycerophospholipid composition and functionality. J Lipid Res. Mar. 2013;54(3):622-35. doi: 10.1194/jlr. M030650.

Kimbrel et al., Generation of functional lymphoid (natural killer) cells from human ESC-derived hemangioblasts. Blood. 2009; 114:1502. Abstract.

Kimbrel et al., Mesenchymal stem cell population derived from human pluripotent stem cells displays potent immunomodulatory and therapeutic properties. Stem Cells Dev. Jul. 15, 2014;23(14):1611-24. doi: 10.1089/scd.2013.0554. Epub May 2, 2014.

Kinnaird et al., Marrow-derived stromal cells express genes encoding a broad spectrum of arteriogenic cytokines and promote in vitro and in vivo arteriogenesis through paracrine mechanisms. Circ Res. Mar. 19, 2004;94(5):678-85. doi: 10.1161/01.RES.0000118601. 37875.AC. Epub Jan. 22, 2004.

Klimanskaya et al., Approaches for Derivation and Maintenance of Human Embryonic Stem Cells: Detailed Procedures and Alternatives. Essentials of Stem Cell Biology, Third Edition. Academic Press. Chapter 29, pp. 409-434, (2014).

Klimanskaya et al., Approaches for Derivation and Maintenance of Human ES Cells: Detailed Procedures and Alternatives. Handbook of Stem Cells. Elsevier Academic Press, Amsterdam. vol. 1, Embryonic Stem Cells. Robert Lanza (Ed). Chapter 41, (2004).

Klimanskaya et al., Human embryonic stem cells derived without feeder cells. Lancet. May 7-13, 2005;365(9471): 1636-41.

Ksiazek, A comprehensive review on mesenchymal stem cell growth and senescence. Rejuvenation Res. Apr. 2009;12(2):105-16. doi: 10.1089/rej.2009.0830. Review.

Lai et al., Exosome secreted by MSC reduces myocardial ischemia/reperfusion injury. Stem Cell Res. May 2010;4(3):214-22. doi: 10.1016/j.scr.2009.12.003. Epub Jan. 4, 2010.

Lazarevic et al., T-bet represses T(H)17 differentiation by preventing Runx1-mediated activation of the gene encoding RORγt. Nat Immunol. Jan. 2011; 12(1):96-104. doi: 10.1038/ni.1969. Epub Dec. 12, 2010.

Le Blanc et al., HLA expression and immunologic properties of differentiated and undifferentiated mesenchymal stem cells. Exp Hematol. Oct. 2003;31(10):890-6. Abstract Only.

Lechmann et al., CD83 on dendritic cells: more than just a marker for maturation. Trends Immunol. Jun. 2002;23(6):273-5.

Lee et al., Human umbilical cord blood-derived mesenchymal stem cells improve neuropathology and cognitive impairment in an Alzheimer's disease mouse model through modulation of neuroinflammation. Neurobiol Aging. Mar. 2012;33(3):588-602. doi: 10.1016/j.neurobiolaging.2010.03.024. Epub May 14, 2010. Abstract Only.

Lee et al., Safety and feasibility of countering neurological impairment by intravenous administration of autologous cord blood in cerebral palsy. J Transl Med. Mar. 23, 2012;10:58. doi: 10.1186/1479-5876-10-58.

Li et al., [In vitro differentiation into megakaryocytes and generation of platelets from CD34+ cells of umbilical cord blood]. Zhong Nan Da Xue Xue Bao Yi Xue Ban. Oct. 2006;31(5):776-81. Chinese.

Li et al., Human embryonic stem cell-derived mesenchymal stroma cells (hES-MSCs) engraft in vivo and support hematopoiesis without suppressing immune function: implications for off-the shelf ES-MSC therapies. PLoS One. 2013;8(1):e55319. doi: 10.1371/journal.pone.0055319. Epub Jan. 29, 2013.

Li et al., Large Scale Generation of Functional Megakaryocytes from Human Embryonic Stem Cells (hESCs) Under Stromal-Free Conditions. Blood, ASH Annual Meeting. 2009;114:Abstract 2540.

Lian et al., Derivation of clinically compliant MSCs from CD105+, CD24—differentiated human ESCs. Stem Cells. Feb. 2007;25(2):425-36. Epub Oct. 19, 2006.

Liang et al., Human umbilical cord mesenchymal stem cells ameliorate mice trinitrobenzene sulfonic acid (TNBS)-induced colitis.

(56) References Cited

OTHER PUBLICATIONS

Cell Transplant. 2011;20(9):1395-408. doi: 10.3727/096368910X557245. Epub Mar. 9, 2011.
Lin et al., Multilineage potential of homozygous stem cells derived from metaphase II oocytes. Stem Cells. 2003;21(2):152-61.
Loges et al., Identification of the adult human hemangioblast. Stem Cells Dev. Jun. 2004;13(3):229-42.
Lowry et al., Generation of human induced pluripotent stem cells from dermal fibroblasts. Proc Natl Acad Sci U S A. Feb. 26, 2008;105(8):2883-8.
Lu et al., Biologic properties and enucleation of red blood cells from human embryonic stem cells. Blood. Dec. 1, 2008;112(12):4475-84.
Lu et al., GeneChip analysis of human embryonic stem cell differentiation into hemangioblasts: an in silico dissection of mixed phenotypes. Genome Biol. 2007;8(11):R240, 19 pages.
Lu et al., Protocol for culturing, differentiating and expanding hES-BC cells. Supplemental Protocol. Nature Methods. 2007;4:1-3.
Lu et al., Recombinant HoxB4 fusion proteins enhance hematopoietic differentiation of human embryonic stem cells. Stem Cells Dev. Aug. 2007;16(4):547-59.
Ma et al., Generation of functional erythrocytes from human embryonic stem cell-derived definitive hematopoiesis. Proc Natl Acad Sci U S A. Sep. 2, 2008;105(35):13087-92.
Ma et al., Novel method for efficient production of multipotential hematopoietic progenitors from human embryonic stem cells. Int J Hematol. Jun. 2007;85(5):371-9.
Maherali et al., Guidelines and techniques for the generation of induced pluripotent stem cells. Cell Stem Cell. Dec. 4, 2008;3(6):595-605.
Mahmood et al., Enhanced differentiation of human embryonic stem cells to mesenchymal progenitors by inhibition of TGF-beta/activin/nodal signaling using SB-431542. J Bone Miner Res. Jun. 2010;25(6):1216-33. doi: 10.1002/jbmr.34.
Majumdar et al., Phenotypic and functional comparison of cultures of marrow-derived mesenchymal stem cells (MSCs) and stromal cells. J Cell Physiol. Jul. 1998; 176(1):57-66.
Martins-Taylor et al., Stem Cells and Tissue Regeneration. Chapter 3. 63-91.
Matsumoto et al., Stepwise development of hematopoietic stem cells from embryonic stem cells. PLoS One. 2009;4(3):e4820, 10 pages.
McFarland et al., Multiple sclerosis: a complicated picture of autoimmunity. Nat Immunol. Sep. 2007;8(9):913-9.
Meisel et al., Human bone marrow stromal cells inhibit allogeneic T-cell responses by indoleamine 2,3-dioxygenase-mediated tryptophan degradation. Blood. Jun. 15, 2004;103(12):4619-21. Epub Mar. 4, 2004.
Mercher et al., Notch signaling specifies megakaryocyte development from hematopoietic stem cells. Cell Stem Cell. Sep. 11, 2008;3(3):314-26.
Mikkola et al., The search for the hemangioblast. J Hematother Stem Cell Res. Feb. 2002;11(1):9-17. First Page Only.
Mitalipova et al., Human embryonic stem cell lines derived from discarded embryos. Stem Cells. 2003;21(5):521-6.
Mohanty et al., A small molecule modulator of prion protein increases human mesenchymal stem cell lifespan, ex vivo expansion, and engraftment to bone marrow in NOD/SCID mice. Stem Cells. Jun. 2012;30(6):1134-43. doi: 10.1002/stem.1065.
Musina et al., Comparison of mesenchymal stem cells obtained from different human tissues. Bull Exp Biol Med. Apr. 2005; 139(4):504-9. Abstract Only.
Nakamura, In vitro production of transfusable red blood cells. Biotechnol Genet Eng Rev. 2008;25:187-201.
Neildez-Nguyen et al., Human erythroid cells produced ex vivo at large scale differentiate into red blood cells in vivo. Nat Biotechnol. May 2002;20(5):467-72.
Newman et al., Treatment of inflammatory diseases with mesenchymal stem cells. Inflamm Allergy Drug Targets. Jun. 2009;8(2):110-23.

Nishikawa et al., Progressive lineage analysis by cell sorting and culture identifies FLK1+VE-cadherin+ cells at a diverging point of endothelial and hemopoietic lineages. Development. 1998;125(9):1747-1757.
Nishikii et al., Metalloproteinase regulation improves in vitro generation of efficacious platelets from mouse embryonic stem cells. J Exp Med. Aug. 4, 2008;205(8):1917-27.
Noth et al., Technology insight: adult mesenchymal stem cells for osteoarthritis therapy. Nat Clin Pract Rheumatol. Jul. 2008;4(7):371-80. doi: 10.1038/ncprheum0816. Epub May 13, 2008.
Olivier et al., Large-scale production of embryonic red blood cells from human embryonic stem cells. Exp Hematol. Dec. 2006;34(12):1635-42.
Ozawa et al., Erythroid cells play essential roles in angiogenesis by bone marrow cell implantation. J Mol Cell Cardiol. May 2006;40(5):629-38.
Parekkadan et al., Aire controls mesenchymal stem cell-mediated suppression in chronic colitis. Mol Ther. Jan. 2012;20(1):178-86. doi: 10.1038/mt.2011.192. Epub Sep. 27, 2011.
Park et al., Cytokine secretion profiling of human mesenchymal stem cells by antibody array. Int J Stem Cells. May 2009;2(1):59-68.
Park et al., Reprogramming of human somatic cells to pluripotency with defined factors. Nature. Jan. 10, 2008;451(7175):141-6.
Park et al., Transcription elongation factor Tcea3 regulates the pluripotent differentiation potential of mouse embryonic stem cells via the Lefty1-Nodal-Smad2 pathway. Stem Cells. Feb. 2013;31(2):282-92. doi: 10.1002/stem.1284.
Passegue et al., Normal and leukemic hematopoiesis: are leukemias a stem cell disorder or a reacquisition of stem cell characteristics? Proc Natl Acad Sci U S A. Sep. 30, 2003;100 Suppl 1:11842-9.
Pati et al., Bone marrow derived mesenchymal stem cells inhibit inflammation and preserve vascular endothelial integrity in the lungs after hemorrhagic shock. PLoS One. 2011;6(9):e25171. doi: 10.1371/journal.pone.0025171. Epub Sep. 28, 2011.
Pearson et al., The stepwise specification of embryonic stem cells to hematopoietic fate is driven by sequential exposure to Bmp4, activin A, bFGF and VEGF. Development. Apr. 2008;135(8):1525-35.
Perlingeiro et al., A role for thrombopoietin in hemangioblast development. Stem Cells. 2003;21(3):272-80.
Pick et al., Differentiation of human embryonic stem cells in serum-free medium reveals distinct roles for bone morphogenetic protein 4, vascular endothelial growth factor, stem cell factor, and fibroblast growth factor 2 in hematopoiesis. Stem Cells. Sep. 2007;25(9):2206-14.
Pilat et al., HOXB4 enforces equivalent fates of ES-cell-derived and adult hematopoietic cells. Proc Natl Acad Sci U S A. Aug. 23, 2005;102(34):12101-6.
Pizarro et al., Mouse models for the study of Crohn's disease. Trends Mol Med. May 2003;9(5):218-22. Abstract Only.
Pontikoglou et al., Bone marrow mesenchymal stem cells: biological properties and their role in hematopoiesis and hematopoietic stem cell transplantation. Stem Cell Rev. Sep. 2011;7(3):569-89. doi: 10.1007/s12015-011-9228-8. Review.
Pozzobon et al., Abstract P128: Human hemangioblast from bone marrow generates in vitro hematopoietic, endothelial and mesenchymal lineages. Abstracts: XXXII Annual ESAO Congress, Oct. 5-8, 2005, Bologna—Italy. Tissue Engineering I. The International Journal of Artificial Organs. 2005;28(9):934.
Purpura et al., Analysis of the temporal and concentration-dependent effects of BMP-4, VEGF, and TPO on development of embryonic stem cell-derived mesoderm and blood progenitors in a defined, serum-free media. Exp Hematol. Sep. 2008;36(9):1186-98.
Qiu et al., Globin switches in yolk sac-like primitive and fetal-like definitive red blood cells produced from human embryonic stem cells. Blood. Feb. 15, 2008;111(4):2400-8.
Rajesh et al., Differential requirements for hematopoietic commitment between human and rhesus embryonic stem cells. Stem Cells. Feb. 2007;25(2):490-9.
Ransohoff, Animal models of multiple sclerosis: the good, the bad and the bottom line. Nat Neurosci. Jul. 26, 2012;15(8):1074-7. doi: 10.1038/nn.3168.

(56) References Cited

OTHER PUBLICATIONS

Rasmusson et al., Immune modulation by mesenchymal stem cells. Exp Cell Res. Jul. 15, 2006;312(12):2169-79. Epub Apr. 24, 2006. Abstract Only.

Rasmusson et al., Mesenchymal stem cells stimulate antibody secretion in human B cells. Scand J Immunol. Apr. 2007;65(4):336-43.

Raynaud et al., Human embryonic stem cell derived mesenchymal progenitors express cardiac markers but do not form contractile cardiomyocytes. PLoS One. 2013;8(1):e54524. doi: 10.1371/journal.pone.0054524. Epub Jan. 16, 2013.

Reems et al., In vitro megakaryocyte production and platelet biogenesis: state of the art. Transfus Med Rev. Jan. 2010;24(1):33-43.

Reijo Pera et al., Gene expression profiles of human inner cell mass cells and embryonic stem cells. Differentiation. Jul. 2009;78(1):18-23.

Reubinoff et al., Embryonic stem cell lines from human blastocysts: somatic differentiation in vitro. Nat Biotechnol. Apr. 2000;18(4):399-404.

Revazova et al., Patient-specific stem cell lines derived from human parthenogenetic blastocysts. Cloning Stem Cells. 2007 Fall;9(3):432-49.

Rogers et al., Phospholipase Czeta causes Ca2+ oscillations and parthenogenetic activation of human oocytes. Reproduction. Dec. 2004;128(6):697-702.

Rombouts et al., Primary murine MSC show highly efficient homing to the bone marrow but lose homing ability following culture. Leukemia. Jan. 2003;17(1):160-70.

Sajic et al., Mesenchymal stem cells lack efficacy in the treatment of experimental autoimmune neuritis despite in vitro inhibition of T-cell proliferation. PLoS One. 2012;7(2):e30708. doi: 10.1371/journal.pone.0030708. Epub Feb. 16, 2012.

Salem et al., Mesenchymal stromal cells: current understanding and clinical status. Stem Cells. Mar. 31, 2010;28(3):585-96. doi: 10.1002/stem.269.

Sangiorgi et al., Modulation of Immunoregulatory Properties of Mesenchymal Stromal Cells by Toll-Like Receptors: Potential Applications on GVHD. Stem Cells Int. 2016;2016:9434250. Epub Sep. 21, 2016. Review.

Sato et al., Manipulation of self-renewal in human embryonic stem cells through a novel pharmacological GSK-3 inhibitor. Methods Mol Biol. 2006;331:115-28.

Sato et al., Stable generation of serum—and feeder-free embryonic stem cell-derived mice with full germline-competency by using a GSK3 specific inhibitor. Genesis. Jun. 2009;47(6):414-22. doi:10.1002/dvg.20514.

Sauvageau et al., Overexpression of HOXB4 in hematopoietic cells causes the selective expansion of more primitive populations in vitro and in vivo. Genes Dev. Jul. 15, 1995;9(14):1753-65.

Schäck, et al., Expression of CD24 in Human Bone Marrow-Derived Mesenchymal Stromal Cells is Regulated by TGFβ3 and Induces a Myofibroblast-Like Genotype. Stem Cells Int. 2016;2016:1319578. doi: 10.1155/2016/1319578. Epub Dec. 14, 2015.

Schenke-Layland et al., Reprogrammed mouse fibroblasts differentiate into cells of the cardiovascular and hematology lineages. Stem Cells. Jun. 2008;26(6):1537-46.

Seliger et al., Chemical production of excited states. Chemiluminescence of carcinogenic hydrocarbons accompanying their metabolic hydroxylation and a proposal for common active site geometries for hydroxylation. J Phys Chem. Sep. 1976;80(20):2296-306.

Selmani et al., Human leukocyte antigen-G5 secretion by human mesenchymal stem cells is required to suppress T lymphocyte and natural killer function and to induce CD4+CD25highFOXP3+ regulatory T cells. Stem Cells. Jan. 2008;26(1):212-22. Epub Oct. 11, 2007.

Senger, Pathways to Pregnancy and Parturition. Current Conceptions, Inc., Pullman, WA. Chapter 13, pp. 221-222, (1997).

Sheikh et al., Mesenchymal stem cell transplantation modulates neuroinflammation in focal cerebral ischemia: contribution of fractalkine and IL-5. Neurobiol Dis. Mar. 2011;41(3):717-24. doi: 10.1016/j.nbd.2010.12.009. Epub Dec. 17, 2010. Abstract Only.

Shinoda et al., alpha4-Integrin(+) endothelium derived from primate embryonic stem cells generates primitive and definitive hematopoietic cells. Blood. Mar. 15, 2007;109(6):2406-15.

Si et al., MSCs: Biological characteristics, clinical applications and their outstanding concerns. Ageing Res Rev. Jan. 2011;10(1):93-103. doi: 10.1016/j.arr.2010.08.005. Epub Aug. 19, 2010. Review.

Singer et al., Mesenchymal stem cells: mechanisms of inflammation. Annu Rev Pathol. 2011;6:457-78. doi: 10.1146/annurev-pathol-011110-130230. Abstract Only.

Sonoyama et al., Mesenchymal stem cell-mediated functional tooth regeneration in swine. PLoS One. Dec. 20, 2006;1(1):e79. doi: 10.1371/journal.pone.0000079.

Springer et al., VEGF gene delivery to muscle: potential role for vasculogenesis in adults. Mol Cell. Nov. 1998;2(5):549-58.

Stuve et al., Translational Research in Neurology and Neuroscience 2010. Arch Neurol. Nov. 2010;67(11):1307-1315. doi:10.1001/archneurol.2010.158.

Sun et al., An adult uterine hemangioblast: evidence for extramedullary self-renewal and clonal bilineage potential. Blood. Oct. 21, 2010;116(16):2932-41. doi: 10.1182/blood-2010-01-266882. Epub Jul. 6, 2010.

Sun et al., Mesenchymal stem cell transplantation reverses multiorgan dysfunction in systemic lupus erythematosus mice and humans. Stem Cells. Jun. 2009;27(6):1421-1432. doi:10.1002/stem.68.

Svingen et al., Hox transcription factors and their elusive mammalian gene targets. Heredity (Edinb). Aug. 2006;97(2):88-96.

Sze et al., Elucidating the secretion proteome of human embryonic stem cell-derived mesenchymal stem cells. Mol Cell Proteomics. Oct. 2007;6(10):1680-9. Epub Jun. 11, 2007.

T' Hart et al., EAE: imperfect but useful models of multiple sclerosis. Trends Mol Med. Mar. 2011;17(3):119-25. doi: 10.1016/j.molmed.2010.11.006. Epub Jan. 19, 2011.

Takahashi et al., Induction of pluripotent stem cells from adult human fibroblasts by defined factors. Cell. Nov. 30, 2007;131(5):861-72.

Takayama et al., Generation of functional platelets from human embryonic stem cells in vitro via ES-sacs, VEGF-promoted structures that concentrate hematopoietic progenitors. Blood. Jun. 1, 2008;111(11):5298-306.

Tan et al., Immunomudulative effects of mesenchymal stem cells derived from human embryonic stem cells in vivo and in vitro. J Zhejiang Univ Sci B. Jan. 2011;12(1):18-27. doi: 10.1631/jzus.B1000074.

Teo et al., Mesenchymal stem cells transmigrate between and directly through tumor necrosis factor-α-activated endothelial cells via both leukocyte-like and novel mechanisms. Stem Cells. Nov. 2012;30(11):2472-86. doi: 10.1002/stem.1198.

Thiel et al., Human embryonic stem cell-derived mesenchymal cells preserve kidney function and extend lifespan in NZB/W F1 mouse model of lupus nephritis. Sci Rep. Dec. 2, 2015;5:17685. doi: 10.1038/srep17685.

Tian et al., Cytokine requirements differ for stroma and embryoid body-mediated hematopoiesis from human embryonic stem cells. Exp Hematol. Oct. 2004;32(10):1000-9.

Tober et al., The megakaryocyte lineage originates from hemangioblast precursors and is an integral component both of primitive and of definitive hematopoiesis. Blood. Feb. 15, 2007;109(4):1433-41.

Tran et al., Efficient differentiation of human pluripotent stem cells into mesenchymal stem cells by modulating intracellular signaling pathways in a feeder/serum-free system. Stem Cells Dev. May 1, 2012;21(7):1165-75. doi: 10.1089/scd.2011.0346. Epub Sep. 27, 2011. Supplemental Material Included.

Trivedi et al., Derivation and immunological characterization of mesenchymal stromal cells from human embryonic stem cells. Exp Hematol. Mar. 2008;36(3):350-9. doi: 10.1016/j.exphem.2007.10.007. Epub Jan. 7, 2008.

Trivedi et al., Simultaneous generation of CD34+ primitive hematopoietic cells and CD73+ mesenchymal stem cells from

(56) References Cited

OTHER PUBLICATIONS human embryonic stem cells cocultured with murine OP9 stromal cells. Exp Hematol. Jan. 2007;35(1):146-54. Abstract Only.
Tseng et al., Generation of immunogenic dendritic cells from human embryonic stem cells without serum and feeder cells. Regen Med. Jul. 2009;4(4):513-26.
Uccelli et al., Mesenchymal stem cells as treatment for MS—progress to date. Mult Scler. Apr. 2013;19(5):515-9. doi: 10.1177/1352458512464686. Epub Nov. 1, 2012. Review.
Umeda et al., Development of primitive and definitive hematopoiesis from nonhuman primate embryonic stem cells in vitro. Development. Apr. 2004;131(8):1869-79.
Van De Velde et al., The four blastomeres of a 4-cell stage human embryo are able to develop individually into blastocysts with inner cell mass and trophectoderm. Hum Reprod. Aug. 2008;23(8):1742-7.
Van Velthoven et al., Repeated mesenchymal stem cell treatment after neonatal hypoxia-ischemia has distinct effects on formation and maturation of new neurons and oligodendrocytes leading to restoration of damage, corticospinal motor tract activity, and sensorimotor function. J Neurosci. Jul. 14, 2010;30(28):9603-11. doi: 10.1523/JNEUROSCI.1835-10.2010.
Verfaillie et al., Kinetics of engraftment of CD34(-) and CD34(+) cells from mobilized blood differs from that of CD34(-) and CD34(+) cells from bone marrow. Exp Hematol. Sep. 2000;28(9):1071-9.
Vodyanik et al., A mesoderm-derived precursor for mesenchymal stem and endothelial cells. Cell Stem Cell. Dec. 3, 2010;7(6):718-29. doi: 10.1016/j.stem.2010.11.011.
Vodyanik et al., Human embryonic stem cell-derived CD34+ cells: efficient production in the coculture with OP9 stromal cells and analysis of lymphohematopoietic potential. Blood. Jan. 15, 2005;105(2):617-26.
Volarevic et al., Concise review: Mesenchymal stem cell treatment of the complications of *diabetes mellitus*. Stem Cells. Jan. 2011;29(1):5-10. doi: 10.1002/stem.556. Review.
Wagner et al., Replicative senescence of mesenchymal stem cells: a continuous and organized process. PLoS One. May 21, 2008;3(5):e2213. doi: 10.1371/journal.pone.0002213.
Wakitani et al., Human autologous culture expanded bone marrow mesenchymal cell transplantation for repair of cartilage defects in osteoarthritic knees. Osteoarthritis Cartilage. Mar. 2002;10(3):199-206. Abstract Only.
Wang et al., Endothelial and hematopoietic cell fate of human embryonic stem cells originates from primitive endothelium with hemangioblastic properties. Immunity. Jul. 2004;21(1):31-41.
Wang et al., Human ESC-derived MSCs outperform bone marrow MSCs in the treatment of an EAE model of multiple sclerosis. Stem Cell Reports. Jun. 6, 2014;3(1):115-30. doi: 10.1016/j.stemcr.2014.04.020. eCollection Jul. 8, 2014.
Wang, Endothelial and hematopoietic cell fate of human embryonic stem cells. Trends Cardiovasc Med. Apr. 2006;16(3): 89-94.
Watanabe et al., A ROCK inhibitor permits survival of dissociated human embryonic stem cells. Nat Biotechnol. Jun. 2007;25(6):681-6.
Wei et al., One-step derivation of cardiomyocytes and mesenchymal stem cells from human pluripotent stem cells. Stem Cell Res. Sep. 2012;9(2):87-100. doi: 10.1016/j.scr.2012.04.003. Epub Apr. 24, 2012.
Wernig et al., n vitro reprogramming of fibroblasts into a pluripotent ES-cell-like state. Nature. Jul. 19, 2007;448(7151):318-24.
Woll et al., Human embryonic stem cell-derived NK cells acquire functional receptors and cytolytic activity. J Immunol. Oct. 15, 2005;175(8):5095-103.
Woll et al., Human embryonic stem cells differentiate into a homogeneous population of natural killer cells with potent in vivo antitumor activity. Blood. Jun. 11, 2009;113(24):6094-101.
Xiong, Molecular and developmental biology of the hemangioblast. Dev Dyn. May 2008;237(5):1218-31.

Xu et al., Feeder-free growth of undifferentiated human embryonic stem cells. Nat Biotechnol. Oct. 2001;19(10):971-4.
Yen et al., Brief report -- human embryonic stem cell-derived mesenchymal progenitors possess strong immunosuppressive effects toward natural killer cells as well as T lymphocytes. Stem Cells. Feb. 2009;27(2):451-6. doi: 10.1634/stemcells.2008-0390.
Yoder, A bipotent mesoderm subset identified via colony-forming assay. Cell Stem Cell. Dec. 3, 2010;7(6):643-4. doi: 10.1016/j.stem.2010.11.022.
Yu et al., Pluripotent stem cell lines. Genes Dev. Aug. 1, 2008;22(15):1987-97.
Yu et al., Retinoic acid enhances the generation of hematopoietic progenitors from human embryonic stem cell-derived hematovascular precursors. Blood. Dec. 2, 2010;116(23):4786-94. doi: 10.1182/blood-2010-01-263335. Epub Apr. 28, 2010.
Yuan et al., Stem cell science on the rise in China. Cell Stem Cell. Jan. 6, 2012;10(1):12-5.
Zambidis et al., Expression of angiotensin-converting enzyme (CD143) identifies and regulates primitive hemangioblasts derived from human pluripotent stem cells. Blood. Nov. 1, 2008;112(9):3601-14.
Zambidis et al., Hematopoietic differentiation of human embryonic stem cells progresses through sequential hematoendothelial, primitive, and definitive stages resembling human yolk sac development. Blood. Aug. 1, 2005;106(3):860-70.
Zhang et al., Bone marrow stromal cells reduce axonal loss in experimental autoimmune encephalomyelitis mice. J Neurosci Res. Aug. 1, 2006;84(3):587-95. Abstract Only.
Zhao et al., Effect of different hemopoietic microenvironment on the differentiation of hemopoietic cells from human embryonic stem cells. Zhong Nan Da Xue Xue Bao Yi Xue Ban. Dec. 2007;32(6):992-6.
Zheng et al., Concise Review: One Stone for Multiple Birds: Generating Universally Compatible Human Embryonic Stem Cells. Stem Cells. Sep. 2016;34(9):2269-75. doi: 10.1002/stem.2407. Epub Jun. 27, 2016. Review.
Zhou et al., Transplantation of human bone marrow mesenchymal stem cell ameliorates the autoimmune pathogenesis in MRL/lpr mice. Cell Mol Immunol. Dec. 2008;5(6):417-24. doi: 10.1038/cmi.2008.52.
Zwaka, Use of Genetically Modified Stem Cells in Experimental Gene Therapies. Stem Cell Information. NIH, National Institutes of Health, retrieved online at: https://web.archive.org/web/20171029014802/https://stemcells.nih.gov/info/Regenerative_Medicine/2006Chapter4.htm. Chapter 4, (2016).
U.S. District Court District of Massachusetts Memorandum and Order on Cross Motions for Summary Judgment for Civil Action No. 17-cv-12239-ADB. Document 163. Filed Mar. 4, 2020. 20 Pages.
U.S. District Court District of Massachusetts Defendants' Unopposed Motion for Leave to File Under Seal for Civil Action No. 17-cv-12239-ADB. Document 167. Filed Mar. 16, 2020. 3 Pages.
U.S. District Court District of Massachusetts Electronic Order Granting Document 167 for Civil Action No. 17-cv-12239-ADB. Document 168. Filed Mar. 16, 2020. 1 Page.
U.S. District Court District of Massachusetts Astellas' Omnibus Motion in Limine for Civil Action No. 17-cv-12239-ADB. Document 169. Filed Mar. 16, 2020. 3 Pages.
U.S. District Court District of Massachusetts Astellas' Memorandum in Support Of its Omnibus Motion in Limine for Civil Action No. 17-cv-12239-ADB. Document 170. Filed Mar. 16, 2020. 21 Pages.
U.S. District Court District of Massachusetts Astellas' Motion in Limine to Exclude Argument, Evidence, and Testimony Relating to Party Size, Wealth, and Any Impact Of Damages for Civil Action No. 17-cv-12239-ADB. Document 171. Filed Mar. 16, 2020. 3 Pages.
U.S. District Court District of Massachusetts Plaintiffs' Memorandum in Support Of its Motion in Limine to Exclude Argument, Evidence, and Testimony Relating to Party Size, Wealth, and Any Impact of Damages for Civil Action No. 17-cv-12239-ADB. Document 172. Filed Mar. 16, 2020. 7 Pages.
U.S. District Court District of Massachusetts Astellas' Motion in Limine to Exclude Argument, Evidence, and Testimony Conflicting

(56) References Cited

OTHER PUBLICATIONS

With Defendants' Admission in Pleadings for Civil Action No. 17-cv-12239-ADB. Document 173. Filed Mar. 16, 2020. 3 Pages.
U.S. District Court District of Massachusetts Astellas' Memorandum in Support Of its Motion in Limine to Exclude Argument, Evidence, and Testimony Conflicting With Defendants' Admission in Pleadings for Civil Action No. 17-cv-12239-ADB. Document 174. Filed Mar. 16, 2020. 8 Pages.
U.S. District Court District of Massachusetts Declaration of Yi Sun in Support Of Astellas' Motions in Limine for Civil Action No. 17-cv-12239-ADB. Document 175. Filed Mar. 16, 2020. 3 Pages.
U.S. District Court District of Massachusetts Exhibit 1 to Sun Declaration for Civil Action No. 17-cv-12239-ADB. Document 175-1. Filed Mar. 16, 2020. 2 Pages.
U.S. District Court District of Massachusetts Exhibit 2 to Sun Declaration for Civil Action No. 17-cv-12239-ADB. Document 175-2. Filed Mar. 16, 2020. 4 Pages.
U.S. District Court District of Massachusetts Exhibit 3 to Sun Declaration for Civil Action No. 17-cv-12239-ADB. Document 175-3. Filed Mar. 16, 2020. 5 Pages.
U.S. District Court District of Massachusetts Defendants' Motion in Limine Regarding U.S. Pat. No. 10,557,122 for Civil Action No. 17-cv-12239-ADB. Document 176. Filed Mar. 16, 2020. 3 Pages.
U.S. District Court District of Massachusetts Memorandum of Law of Defendants' Motion in Limine Regarding U.S. Pat. No. 10,557,122 for Civil Action No. 17-cv-12239-ADB. Document 177. Filed Mar. 16, 2020. 6 Pages.
U.S. District Court District of Massachusetts Defendants' Motion in Limine to Preclude Certain Evidence and Argument Relating to U.S. Pat. No. 9,745,551 for Civil Action No. 17-cv- 12239-ADB. Document 178. Filed Mar. 16, 2020. 3 Pages.
U.S. District Court District of Massachusetts Memorandum of Law in Support of Defendants' Motion in Limine to Preclude Certain Evidence and Argument Relating to U.S. Pat. No. 9,745,551 for Civil Action No. 17-cv-12239-ADB. Document 179. Filed Mar. 16, 2020. 13 Pages.
U.S. District Court District of Massachusetts Defendants' Motion in Limine to Preclude Evidence of Chinese Connections for Civil Action No. 17-cv-12239-ADB. Document 180. Filed Mar. 16, 2020. 3 Pages.
U.S. District Court District of Massachusetts Defendants' Memorandum of Law in Support of Motion in Limine to Preclude Evidence of Chinese Connections for Civil Action No. 17-cv-12239-ADB. Document 181. Filed Mar. 16, 2020. 10 Pages.
U.S. District Court District of Massachusetts Defendants' Motion in Limine to Preclude Improper Expert Testimony Regarding State Law Claims for Civil Action No. 17-cv-12239- ADB. Document 182. Filed Mar. 16, 2020. 3 Pages.
U.S. District Court District of Massachusetts Memorandum of Law in Support of Defendants' Motion in Limine to Preclude Improper Expert Testimony Regarding State Law Claims for Civil Action No. 17-cv-12239-ADB. Document 183. Filed Mar. 16, 2020. 14 Pages.
U.S. District Court District of Massachusetts Defendants' Motion in Limine to Preclude Improper Testimony Regarding Collaboration and Inventive Contribution for Civil Action No. 17-cv-12239-ADB. Document 184. Filed Mar. 16, 2020. 4 Pages.
U.S. District Court District of Massachusetts Memorandum of Law in Support of Defendants' Motion in Limine to Preclude Improper Testimony Regarding Collaboration and Inventive Contribution for Civil Action No. 17-cv-12239-ADB. Document 185. Filed Mar. 16, 2020. 12 Pages.
U.S. District Court District of Massachusetts Declaration of Timothy R. Shannon in Support of Defendants' Motions in Limine for Civil Action No. 17-cv-12239-ADB. Document 186. Filed Mar. 16, 2020. 3 Pages.
U.S. District Court District of Massachusetts Exhibit 1 to Shannon Declaration in Support of Defendants' Motions in Limine for Civil Action No. 17-cv-12239-ADB. Document 186-1. Filed Mar. 16, 2020. 1 Page.
U.S. District Court District of Massachusetts Exhibit 2 to Shannon Declaration in Support of Defendants' Motions in Limine for Civil Action No. 17-cv-12239-ADB. Document 186-2. Filed Mar. 16, 2020. 1 Page.
U.S. District Court District of Massachusetts Exhibit 3 to Shannon Declaration in Support of Defendants' Motions in Limine for Civil Action No. 17-cv-12239-ADB. Document 186-3. Filed Mar. 16, 2020. 1 Page.
U.S. District Court District of Massachusetts Exhibit 4 to Shannon Declaration in Support of Defendants' Motions in Limine for Civil Action No. 17-cv-12239-ADB. Document 186-4. Filed Mar. 16, 2020. 1 Page.
U.S. District Court District of Massachusetts Exhibit 5 to Shannon Declaration in Support of Defendants' Motions in Limine for Civil Action No. 17-cv-12239-ADB. Document 186-5. Filed Mar. 16, 2020. 1 Page.
U.S. District Court District of Massachusetts Exhibit 6 to Shannon Declaration in Support of Defendants' Motions in Limine for Civil Action No. 17-cv-12239-ADB. Document 186-6. Filed Mar. 16, 2020. 1 Page.
U.S. District Court District of Massachusetts Exhibit 7 to Shannon Declaration in Support of Defendants' Motions in Limine for Civil Action No. 17-cv-12239-ADB. Document 186-7. Filed Mar. 16, 2020. 1 Page.
U.S. District Court District of Massachusetts Exhibit 8 to Shannon Declaration in Support of Defendants' Motions in Limine for Civil Action No. 17-cv-12239-ADB. Document 186-8. Filed Mar. 16, 2020. 1 Page.
U.S. District Court District of Massachusetts Exhibit 9 to Shannon Declaration in Support of Defendants' Motions in Limine for Civil Action No. 17-cv-12239-ADB. Document 186-9. Filed Mar. 16, 2020. 3 Pages.
U.S. District Court District of Massachusetts Exhibit 10 to Shannon Declaration in Support of Defendants' Motions in Limine for Civil Action No. 17-cv-12239-ADB. Document 186-10. Filed Mar. 16, 2020. 5 Pages.
U.S. District Court District of Massachusetts Exhibit 11 to Shannon Declaration in Support of Defendants' Motions in Limine for Civil Action No. 17-cv-12239-ADB. Document 186-11. Filed Mar. 16, 2020. 3 Pages.
U.S. District Court District of Massachusetts Exhibit 12 to Shannon Declaration in Support of Defendants' Motions in Limine for Civil Action No. 17-cv-12239-ADB. Document 186-12. Filed Mar. 16, 2020. 4 Pages.
U.S. District Court District of Massachusetts Assented-To Defendants' Motion and Incorporated Memorandum for Continuance of Final Pre-Trial Conference and Trial for Civil Action No. 17-cv-12239-ADB. Document 187. Filed Mar. 25, 2020. 8 Pages.
U.S. District Court District of Massachusetts Declaration of Timothy R. Shannon in Support of Defendants' Motion for Continuance of Final Pre-Trial Conference and Trial for Civil Action No. 17-cv-12239-ADB. Document 188. Filed Mar. 25, 2020. 2 Pages.
U.S. District Court District of Massachusetts Exhibit 1 for Civil Action No. 17-cv-12239-ADB. Document 188-1. Filed Mar. 25, 2020. 4 Pages.
U.S. District Court District of Massachusetts Exhibit 2 for Civil Action No. 17-cv-12239-ADB. Document 188-2. Filed Mar. 25, 2020. 4 Pages.
U.S. District Court District of Massachusetts Exhibit 3 for Civil Action No. 17-cv-12239-ADB. Document 188-3. Filed Mar. 25, 2020. 3 Pages.
U.S. District Court District of Massachusetts Exhibit 4 for Civil Action No. 17-cv-12239-ADB. Document 188-4. Filed Mar. 25, 2020. 8 Pages.
U.S. District Court District of Massachusetts Electronic Order Granting Document 187 for Civil Action No. 17-cv-12239-ADB. Document 189. Filed Mar. 26, 2020. 2 Pages.
U.S. District Court District of Massachusetts Astellas' Opposition to Defendants' Motion in Limine to Preclude Evidence of Chinese Connections for Civil Action No. 17-cv-12239-ADB. Document 194. Filed Mar. 30, 2020. 19 Pages.

(56) References Cited

OTHER PUBLICATIONS

U.S. District Court District of Massachusetts Astellas' Opposition to Defendants' Motion in Limine Regarding U.S. Pat. No. 10,557,122 for Civil Action No. 17-cv-12239-ADB. Document 195. Filed Mar. 30, 2020. 7 Pages.
U.S. District Court District of Massachusetts Astellas' Opposition to Defendants' Motion in Limine to Preclude Improper Testimony Regarding Collaboration and Inventive Contribution for Civil Action No. 17-cv-12239-ADB. Document 196. Filed Mar. 30, 2020. 19 Pages.
U.S. District Court District of Massachusetts Astellas' Opposition to Defendants' Motion in Limine to Preclude Improper Expert Testimony Regarding State Law Claim for Civil Action No. 17-cv-12239-ADB. Document 197. Filed Mar. 30, 2020. 25 Pages.
U.S. District Court District of Massachusetts Astellas' Opposition to Defendants' Motion in Limine to Preclude Certain Evidence and Argument Relating to U.S. Pat. No. 9,745,551 for Civil Action No. 17-cv-12239-ADB. Document 198. Filed Mar. 30, 2020. 23 Pages.
U.S. District Court District of Massachusetts Declaration of Yi Sun in Support of Astellas' Oppositions to Defendants' Motions in Limine for Civil Action No. 17-cv-12239-ADB. Document 199. Filed Mar. 30, 2020. 6 Pages.
U.S. District Court District of Massachusetts Exhibit 1 to Sun Opposition Declaration for Civil Action No. 17-cv-12239-ADB. Document 199-1. Filed Mar. 30, 2020. 72 Pages.
U.S. District Court District of Massachusetts Exhibit 2 to Sun Opposition Declaration for Civil Action No. 17-cv-12239-ADB. Document 199-2. Filed Mar. 30, 2020. 4 Pages.
U.S. District Court District of Massachusetts Exhibit 3 to Sun Opposition Declaration for Civil Action No. 17-cv-12239-ADB. Document 199-3. Filed Mar. 30, 2020. 1 Page.
U.S. District Court District of Massachusetts Exhibit 4 to Sun Opposition Declaration for Civil Action No. 17-cv-12239-ADB. Document 199-4. Filed Mar. 30, 2020. 1 Page.
U.S. District Court District of Massachusetts Exhibit 5 to Sun Opposition Declaration for Civil Action No. 17-cv-12239-ADB. Document 199-5. Filed Mar. 30, 2020. 1 Page.
U.S. District Court District of Massachusetts Exhibit 6 to Sun Opposition Declaration for Civil Action No. 17-cv-12239-ADB. Document 199-6. Filed Mar. 30, 2020. 10 Pages.
U.S. District Court District of Massachusetts Exhibit 7 to Sun Opposition Declaration for Civil Action No. 17-cv-12239-ADB. Document 199-7. Filed Mar. 30, 2020. 1 Page.
U.S. District Court District of Massachusetts Exhibit 8 to Sun Opposition Declaration for Civil Action No. 17-cv-12239-ADB. Document 199-8. Filed Mar. 30, 2020. 1 Page.
U.S. District Court District of Massachusetts Exhibit 9 to Sun Opposition Declaration for Civil Action No. 17-cv-12239-ADB. Document 199-9. Filed Mar. 30, 2020. 36 Pages.
U.S. District Court District of Massachusetts Exhibit 10 to Sun Opposition Declaration for Civil Action No. 17-cv-12239-ADB. Document 199-10. Filed Mar. 30, 2020. 1 Page.
U.S. District Court District of Massachusetts Exhibit 11 to Sun Opposition Declaration for Civil Action No. 17-cv-12239-ADB. Document 199-11. Filed Mar. 30, 2020. 3 Pages.
U.S. District Court District of Massachusetts Exhibit 12 to Sun Opposition Declaration for Civil Action No. 17-cv-12239-ADB. Document 199-12. Filed Mar. 30, 2020. 1 Page.
U.S. District Court District of Massachusetts Exhibit 13 to Sun Opposition Declaration for Civil Action No. 17-cv-12239-ADB. Document 199-13. Filed Mar. 30, 2020. 1 Page.
U.S. District Court District of Massachusetts Exhibit 14 to Sun Opposition Declaration for Civil Action No. 17-cv-12239-ADB. Document 199-14. Filed Mar. 30, 2020. 1 Page.
U.S. District Court District of Massachusetts Exhibit 15 to Sun Opposition Declaration for Civil Action No. 17-cv-12239-ADB. Document 199-15. Filed Mar. 30, 2020. 6 Pages.
U.S. District Court District of Massachusetts Exhibit 16 to Sun Opposition Declaration for Civil Action No. 17-cv-12239-ADB. Document 199-16. Filed Mar. 30, 2020. 1 Page.
U.S. District Court District of Massachusetts Exhibit 17 to Sun Opposition Declaration for Civil Action No. 17-cv-12239-ADB. Document 199-17. Filed Mar. 30, 2020. 4 Pages.
U.S. District Court District of Massachusetts Exhibit 18 to Sun Opposition Declaration for Civil Action No. 17-cv-12239-ADB. Document 199-18. Filed Mar. 30, 2020. 1 Page.
U.S. District Court District of Massachusetts Exhibit 19 to Sun Opposition Declaration for Civil Action No. 17-cv-12239-ADB. Document 199-19. Filed Mar. 30, 2020. 16 Pages.
U.S. District Court District of Massachusetts Exhibit 20 to Sun Opposition Declaration for Civil Action No. 17-cv-12239-ADB. Document 199-20. Filed Mar. 30, 2020. 5 Pages.
U.S. District Court District of Massachusetts Exhibit 21 to Sun Opposition Declaration for Civil Action No. 17-cv-12239-ADB. Document 199-21. Filed Mar. 30, 2020. 1 Page.
U.S. District Court District of Massachusetts Exhibit 22 to Sun Opposition Declaration for Civil Action No. 17-cv-12239-ADB. Document 199-22. Filed Mar. 30, 2020. 1 Page.
U.S. District Court District of Massachusetts Exhibit 23 to Sun Opposition Declaration for Civil Action No. 17-cv-12239-ADB. Document 199-23. Filed Mar. 30, 2020. 1 Page.
U.S. District Court District of Massachusetts Exhibit 24 to Sun Opposition Declaration for Civil Action No. 17-cv-12239-ADB. Document 199-24. Filed Mar. 30, 2020. 86 Pages.
U.S. District Court District of Massachusetts Exhibit 25 to Sun Opposition Declaration for Civil Action No. 17-cv-12239-ADB. Document 199-25. Filed Mar. 30, 2020. 1 Page.
U.S. District Court District of Massachusetts Exhibit 26 to Sun Opposition Declaration for Civil Action No. 17-cv-12239-ADB. Document 199-26. Filed Mar. 30, 2020. 1 Page.
U.S. District Court District of Massachusetts Exhibit 27 to Sun Opposition Declaration for Civil Action No. 17-cv-12239-ADB. Document 199-27. Filed Mar. 30, 2020. 9 Pages.
U.S. District Court District of Massachusetts Exhibit 28 to Sun Opposition Declaration for Civil Action No. 17-cv-12239-ADB. Document 199-28. Filed Mar. 30, 2020. 1 Page.
U.S. District Court District of Massachusetts Exhibit 29 to Sun Opposition Declaration for Civil Action No. 17-cv-12239-ADB. Document 199-29. Filed Mar. 30, 2020. 1 Page.
U.S. District Court District of Massachusetts Exhibit 30 to Sun Opposition Declaration for Civil Action No. 17-cv-12239-ADB. Document 199-30. Filed Mar. 30, 2020. 1 Page.
U.S. District Court District of Massachusetts Exhibit 31 to Sun Opposition Declaration for Civil Action No. 17-cv-12239-ADB. Document 199-31. Filed Mar. 30, 2020. 1 Page.
U.S. District Court District of Massachusetts Defendants' Opposition to Plaintiffs' Motion in Limine to Exclude Argument, Evidence, and Testimony Relating to Party Size, Wealth, and Any Impact of Damages for Civil Action No. 17-cv-12239-ADB. Document 200. Filed Mar. 30, 2020. 5 Pages.
U.S. District Court District of Massachusetts Opposition to Plaintiffs' Motion in Limine to Exclude Argument, Evidence, and Testimony Conflicting With Defendants' Admission in Pleadings for Civil Action No. 17-cv-12239-ADB. Document 201. Filed Mar. 30, 2020. 8 Pages.
U.S. District Court District of Massachusetts Declaration of Timothy R. Shannon In Support of Defendants' Opposition to Plaintiffs' Motion in Limine to Exclude Argument, Evidence, and Testimony Conflicting With Defendants' Admission in Pleadings for Civil Action No. 17-cv- 12239-ADB. Document 202. Filed Mar. 30, 2020. 2 Pages.
U.S. District Court District of Massachusetts Exhibit 1 for Civil Action No. 17-cv-12239-ADB. Document 202-1. Filed Mar. 30, 2020. 3 Pages.
U.S. District Court District of Massachusetts Exhibit 2 for Civil Action No. 17-cv-12239-ADB. Document 202-2. Filed Mar. 30, 2020. 9 Pages.
U.S. District Court District of Massachusetts Exhibit 3 for Civil Action No. 17-cv-12239-ADB. Document 202-3. Filed Mar. 30, 2020. 7 Pages.
U.S. District Court District of Massachusetts Exhibit 4 for Civil Action No. 17-cv-12239-ADB. Document 202-4. Filed Mar. 30, 2020. 3 Pages.

(56) References Cited

OTHER PUBLICATIONS

U.S. District Court District of Massachusetts Exhibit 5 to Shannon Declaration in Support of Defendants' Opposition to Plaintiff's Motion in Limine to Exclude Admission in Pleadings for Civil Action No. 17-cv-12239-ADB. Document 202-5. Filed Mar. 30, 2020. 4 Pages.

U.S. District Court District of Massachusetts Defendants' Opposition to Plaintiff's Omnibus Motion in Limine for Civil Action No. 17-cv-12239-ADB. Document 203. Filed Mar. 31, 2020. 20 Pages.

U.S. District Court District of Massachusetts Declaration of Timothy R. Shannon in Support of Defendants' Opposition to Plaintiff's Omnibus Motion in Limine for Civil Action No. 17-cv- 12239-ADB. Document 204. Filed Mar. 31, 2020. 3 Pages.

U.S. District Court District of Massachusetts Exhibit 1 to Shannon Declaration in Support of Defendants' Opposition to Plaintiff's Omnibus Motion in Limine for Civil Action No. 17-cv- 12239-ADB. Document 204-1. Filed Mar. 31, 2020. 1 Page.

U.S. District Court District of Massachusetts Exhibit 2 to Shannon Declaration in Support of Defendants' Opposition to Plaintiff's Omnibus Motion in Limine for Civil Action No. 17-cv- 12239-ADB. Document 204-2. Filed Mar. 31, 2020. 6 Pages.

U.S. District Court District of Massachusetts Exhibit 3 to Shannon Declaration in Support of Defendants' Opposition to Plaintiff's Omnibus Motion in Limine for Civil Action No. 17-cv- 12239-ADB. Document 204-3. Filed Mar. 31, 2020. 20 Pages.

U.S. District Court District of Massachusetts Exhibit 4 to Shannon Declaration in Support of Defendants' Opposition to Plaintiff's Omnibus Motion in Limine for Civil Action No. 17-cv- 12239-ADB. Document 204-4. Filed Mar. 31, 2020. 4 Pages.

U.S. District Court District of Massachusetts Exhibit 5 to Shannon Declaration in Support of Defendants' Opposition to Plaintiff's Omnibus Motion in Limine for Civil Action No. 17-cv- 12239-ADB. Document 204-5. Filed Mar. 31, 2020. 21 Pages.

U.S. District Court District of Massachusetts Exhibit 6 to Shannon Declaration in Support of Defendants' Opposition to Plaintiff's Omnibus Motion in Limine for Civil Action No. 17-cv- 12239-ADB. Document 204-6. Filed Mar. 31, 2020. 19 Pages.

U.S. District Court District of Massachusetts Exhibit 7 to Shannon Declaration in Support of Defendants' Opposition to Plaintiff's Omnibus Motion in Limine for Civil Action No. 17-cv- 12239-ADB. Document 204-7. Filed Mar. 31, 2020. 6 Pages.

U.S. District Court District of Massachusetts Exhibit 8 to Shannon Declaration in Support of Defendants' Opposition to Plaintiff's Omnibus Motion in Limine for Civil Action No. 17-cv- 12239-ADB. Document 204-8. Filed Mar. 31, 2020. 1 Page.

U.S. District Court District of Massachusetts Exhibit 9 to Shannon Declaration in Support of Defendants' Opposition to Plaintiff's Omnibus Motion in Limine for Civil Action No. 17-cv- 12239-ADB. Document 204-9. Filed Mar. 31, 2020. 1 Page.

U.S. District Court District of Massachusetts Exhibit 10 to Shannon Declaration in Support of Defendants' Opposition to Plaintiff's Omnibus Motion in Limine for Civil Action No. 17-cv- 12239-ADB. Document 204-10. Filed Mar. 31, 2020. 1 Page.

U.S. District Court District of Massachusetts Exhibit 11 to Shannon Declaration in Support of Defendants' Opposition to Plaintiff's Omnibus Motion in Limine for Civil Action No. 17-cv- 12239-ADB. Document 204-11. Filed Mar. 31, 2020. 1 Page.

U.S. District Court District of Massachusetts Exhibit 12 to Shannon Declaration in Support of Defendants' Opposition to Plaintiff's Omnibus Motion in Limine for Civil Action No. 17-cv- 12239-ADB. Document 204-12. Filed Mar. 31, 2020. 1 Page.

U.S. District Court District of Massachusetts Exhibit 13 to Shannon Declaration in Support of Defendants' Opposition to Plaintiff's Omnibus Motion in Limine for Civil Action No. 17-cv- 12239-ADB. Document 204-13. Filed Mar. 31, 2020. 1 Page.

U.S. District Court District of Massachusetts Exhibit 14 to Shannon Declaration in Support of Defendants' Opposition to Plaintiff's Omnibus Motion in Limine for Civil Action No. 17-cv- 12239-ADB. Document 204-14. Filed Mar. 31, 2020. 1 Page.

U.S. District Court District of Massachusetts Exhibit 15 to Shannon Declaration in Support of Defendants' Opposition to Plaintiff's Omnibus Motion in Limine for Civil Action No. 17-cv- 12239-ADB. Document 204-15. Filed Mar. 31, 2020. 19 Pages.

U.S. District Court District of Massachusetts Unopposed Motion for Substitution of Parties for Civil Action No. 17-cv-12239-ADB. Document 205. Filed May 26, 2020. 4 Pages.

U.S. District Court District of Massachusetts Declaration of Lauren K. Sharkey in Support of Astellas' Unopposed Motion for Substitution of Parties for Civil Action No. 17-cv-12239-ADB. Document 206. Filed May 26, 2020. 3 Pages.

U.S. District Court District of Massachusetts Exhibit 1 for Civil Action No. 17-cv-12239-ADB. Document 206-1. Filed May 26, 2020. 3 Pages.

U.S. District Court District of Massachusetts Exhibit 2 for Civil Action No. 17-cv-12239-ADB. Document 206-2. Filed May 26, 2020. 3 Pages.

U.S. District Court District of Massachusetts Electronic Order Granting Document 205 for Civil Action No. 17-cv-12239-ADB. Document 207. Filed May 28, 2020. 1 Page.

U.S. District Court District of Massachusetts Electronic Clerk's Notes for Civil Action No. 17- cv-12239-ADB. Document 208. Filed Jun. 9, 2020. 1 Page.

U.S. District Court District of Massachusetts Electronic Order for Civil Action No. 17-cv-12239- ADB. Document 209. Filed Jun. 9, 2020. 1 Page.

U.S. District Court District of Massachusetts Pretrial Order for Civil Action No. 17-cv-12239- ADB. Document 210. Filed Jun. 10, 2020. 3 Pages.

U.S. District Court District of Massachusetts Defendants' Motion to Keep Trial Open to Facilitate Witness Testimony for Civil Action No. 17-cv-12239-ADB. Document 211. Filed Jul. 20, 2020. 3 Pages.

U.S. District Court District of Massachusetts Memorandum of Law in Support of Defendants' Motion to Keep Trial Open to Facilitate Witness Testimony for Civil Action No. 17-cv-12239- ADB. Document 212. Filed Jul. 20, 2020. 14 Pages.

U.S. District Court District of Massachusetts Declaration of Timothy R. Shannon in Support of Defendants' Motion and Incorporated Memorandum to Keep Trial Open to Facilitate Witness Testimony for Civil Action No. 17-cv-12239-ADB. Document 213. Filed Jul. 20, 2020. 6 Pages.

U.S. District Court District of Massachusetts Exhibit 1 for Civil Action No. 17-cv-12239-ADB. Document 213-1. Filed Jul. 20, 2020. 5 Pages.

U.S. District Court District of Massachusetts Exhibit 2 for Civil Action No. 17-cv-12239-ADB. Document 213-2. Filed Jul. 20, 2020. 8 Pages.

U.S. District Court District of Massachusetts Exhibit 3 for Civil Action No. 17-cv-12239-ADB. Document 213-3. Filed Jul. 20, 2020. 2 Pages.

U.S. District Court District of Massachusetts Exhibit 4 for Civil Action No. 17-cv-12239-ADB. Document 213-4. Filed Jul. 20, 2020. 28 Pages.

U.S. District Court District of Massachusetts Exhibit 5 for Civil Action No. 17-cv-12239-ADB. Document 213-5. Filed Jul. 20, 2020. 4 Pages.

U.S. District Court District of Massachusetts Exhibit 6 for Civil Action No. 17-cv-12239-ADB. Document 213-6. Filed Jul. 20, 2020. 4 Pages.

U.S. District Court District of Massachusetts Exhibit 7 for Civil Action No. 17-cv-12239-ADB. Document 213-7. Filed Jul. 20, 2020. 3 Pages.

U.S. District Court District of Massachusetts Exhibit 8 for Civil Action No. 17-cv-12239-ADB. Document 213-8. Filed Jul. 20, 2020. 20 Pages.

U.S. District Court District of Massachusetts Exhibit 9 for Civil Action No. 17-cv-12239-ADB. Document 213-9. Filed Jul. 20, 2020. 1 Page.

U.S. District Court District of Massachusetts Exhibit 10 for Civil Action No. 17-cv-12239-ADB. Document 213-10. Filed Jul. 20, 2020. 3 Pages.

(56) References Cited

OTHER PUBLICATIONS

U.S. District Court District of Massachusetts Exhibit 11 for Civil Action No. 17-cv-12239-ADB. Document 213-11. Filed Jul. 20, 2020. 3 Pages.
U.S. District Court District of Massachusetts Exhibit 12 for Civil Action No. 17-cv-12239-ADB. Document 213-12. Filed Jul. 20, 2020. 2 Pages.
U.S. District Court District of Massachusetts Exhibit 13 for Civil Action No. 17-cv-12239-ADB. Document 213-13. Filed Jul. 20, 2020. 5 Pages.
U.S. District Court District of Massachusetts Exhibit 14 for Civil Action No. 17-cv-12239-ADB. Document 213-14. Filed Jul. 20, 2020. 3 Pages.
U.S. District Court District of Massachusetts Exhibit 15 for Civil Action No. 17-cv-12239-ADB. Document 213-15. Filed Jul. 20, 2020. 18 Pages.
U.S. District Court District of Massachusetts Exhibit 16 for Civil Action No. 17-cv-12239-ADB. Document 213-16. Filed Jul. 20, 2020. 7 Pages.
U.S. District Court District of Massachusetts Exhibit 17 for Civil Action No. 17-cv-12239-ADB. Document 213-17. Filed Jul. 20, 2020. 2 Pages.
U.S. District Court District of Massachusetts Exhibit 18 for Civil Action No. 17-cv-12239-ADB. Document 213-18. Filed Jul. 20, 2020. 4 Pages.
U.S. District Court District of Massachusetts Exhibit 19 for Civil Action No. 17-cv-12239-ADB. Document 213-19. Filed Jul. 20, 2020. 1 Page.
U.S. District Court District of Massachusetts Exhibit 20 for Civil Action No. 17-cv-12239-ADB. Document 213-20. Filed Jul. 20, 2020. 6 Pages.
U.S. District Court District of Massachusetts Exhibit 21 for Civil Action No. 17-cv-12239-ADB. Document 213-21. Filed Jul. 20, 2020. 7 Pages.
U.S. District Court District of Massachusetts Exhibit 22 for Civil Action No. 17-cv-12239-ADB. Document 213-22. Filed Jul. 20, 2020. 5 Pages.
U.S. District Court District of Massachusetts Exhibit 23 for Civil Action No. 17-cv-12239-ADB. Document 213-23. Filed Jul. 20, 2020. 3 Pages.
U.S. District Court District of Massachusetts Exhibit 24 for Civil Action No. 17-cv-12239-ADB. Document 213-24. Filed Jul. 20, 2020. 2 Pages.
U.S. District Court District of Massachusetts Astellas' Opposition to Defendants' Motion to Keep Trial Open to Facilitate Witness Testimony for Civil Action No. 17-cv-12239-ADB. Document 216. Filed Jul. 28, 2020. 20 Pages.
U.S. District Court District of Massachusetts Declaration of Rebecca L. Rabenstein in Support of Astellas' Opposition to Defendants' Motion to Keep Trial Open to Facilitate Witness Testimony for Civil Action No. 17-cv-12239-ADB. Document 217. Filed Jul. 28, 2020. 4 Pages.
U.S. District Court District of Massachusetts Exhibit A to Rabenstein Declaration for Civil Action No. 17-cv-12239-ADB. Document 217-1. Filed Jul. 28, 2020. 3 Pages.
U.S. District Court District of Massachusetts Exhibit B to Rabenstein Declaration for Civil Action No. 17-cv-12239-ADB. Document 217-2. Filed Jul. 28, 2020. 9 Pages.
U.S. District Court District of Massachusetts Exhibit C to Rabenstein Declaration for Civil Action No. 17-cv-12239-ADB. Document 217-3. Filed Jul. 28, 2020. 2 Pages.
U.S. District Court District of Massachusetts Exhibit D to Rabenstein Declaration for Civil Action No. 17-cv-12239-ADB. Document 217-4. Filed Jul. 28, 2020. 3 Pages.
U.S. District Court District of Massachusetts Exhibit E to Rabenstein Declaration for Civil Action No. 17-cv-12239-ADB. Document 217-5. Filed Jul. 28, 2020. 1 Page.
U.S. District Court District of Massachusetts Exhibit F to Rabenstein Declaration for Civil Action No. 17-cv-12239-ADB. Document 217-6. Filed Jul. 28, 2020. 1 Page.
U.S. District Court District of Massachusetts Exhibit G to Rabenstein Declaration for Civil Action No. 17-cv-12239-ADB. Document 217-7. Filed Jul. 28, 2020. 1 Page.
U.S. District Court District of Massachusetts Exhibit H to Rabenstein Declaration for Civil Action No. 17-cv-12239-ADB. Document 217-8. Filed Jul. 28, 2020. 10 Pages.
U.S. District Court District of Massachusetts Exhibit I to Rabenstein Declaration for Civil Action No. 17-cv-12239-ADB. Document 217-9. Filed Jul. 28, 2020. 3 Pages.
U.S. District Court District of Massachusetts Exhibit J to Rabenstein Declaration for Civil Action No. 17-cv-12239-ADB. Document 217-10. Filed Jul. 28, 2020. 1 Page.
U.S. District Court District of Massachusetts Exhibit K to Rabenstein Declaration for Civil Action No. 17-cv-12239-ADB. Document 217-11. Filed Jul. 28, 2020. 1 Page.
U.S. District Court District of Massachusetts Exhibit L to Rabenstein Declaration for Civil Action No. 17-cv-12239-ADB. Document 217-12. Filed Jul. 28, 2020. 1 Page.
U.S. District Court District of Massachusetts Exhibit M to Rabenstein Declaration for Civil Action No. 17-cv-12239-ADB. Document 217-13. Filed Jul. 28, 2020. 26 Pages.
U.S. District Court District of Massachusetts Astellas' Pretrial Memorandum for Civil Action No. 17-cv-12239-ADB. Document 218. Filed Aug. 10, 2020. 30 Pages.
U.S. District Court District of Massachusetts Attachment A for Civil Action No. 17-cv-12239- ADB. Document 218-1. Filed Aug. 10, 2020. 8 Pages.
U.S. District Court District of Massachusetts Attachment B for Civil Action No. 17-cv-12239- ADB. Document 218-2. Filed Aug. 10, 2020. 8 Pages.
U.S. District Court District of Massachusetts Attachment C for Civil Action No. 17-cv-12239- ADB. Document 218-3. Filed Aug. 10, 2020. 63 Pages.
U.S. District Court District of Massachusetts Attachment D for Civil Action No. 17-cv-12239- ADB. Document 218-4. Filed Aug. 10, 2020. 5 Pages.
U.S. District Court District of Massachusetts Attachment E for Civil Action No. 17-cv-12239- ADB. Document 218-5. Filed Aug. 10, 2020. 4 Pages.
U.S. District Court District of Massachusetts Astellas' Trial Brief for Civil Action No. 17-cv- 12239-ADB. Document 219. Filed Aug. 10, 2020. 118 Pages.
U.S. District Court District of Massachusetts Defendants' Pretrial Memorandum for Civil Action No. 17-cv-12239-ADB. Document 220. Filed Aug. 10, 2020. 24 Pages.
U.S. District Court District of Massachusetts Facts Established By The Parties' Stipulation for Civil Action No. 17-cv-12239-ADB. Document 220-1. Filed Aug. 10, 2020. 7 Pages.
U.S. District Court District of Massachusetts Numbered Exhibits With No Objections for Civil Action No. 17-cv-12239-ADB. Document 220-2. Filed Aug. 10, 2020. 7 Pages.
U.S. District Court District of Massachusetts Lettered Exhibits With Objections for Civil Action No. 17-cv-12239-ADB. Document 220-3. Filed Aug. 10, 2020. 62 Pages.
U.S. District Court District of Massachusetts Defendants' Trial Memorandum With Proposed Findings of Fact and Conclusions of Law for Civil Action No. 17-cv-12239-ADB. Document 221. Filed Aug. 10, 2020. 63 Pages.
U.S. District Court District of Massachusetts Electronic Clerk's Notes for Civil Action No. 17- cv-12239-ADB. Document 222. Filed Aug. 12, 2020. 1 Page.
U.S. District Court District of Massachusetts Electronic Order for Civil Action No. 17-cv-12239- ADB. Document 223. Filed Aug. 12, 2020. 2 Pages.
U.S. District Court District of Massachusetts Electronic Order for Civil Action No. 17-cv-12239- ADB. Document 224. Filed Aug. 18, 2020. 2 Pages.
U.S. District Court District of Massachusetts Electronic Order for Civil Action No. 17-cv-12239- ADB. Document 225. Filed Aug. 18, 2020. 2 Pages.
U.S. District Court District of Massachusetts Frazier Letter in Response to Shannon Letter to Keep Trial Open for Civil Action No. 17-cv-12239-AD. Document 225. Filed Aug. 18, 2020. 2 Pages.

(56) References Cited

OTHER PUBLICATIONS

U.S. District Court District of Massachusetts Shannon Letter to Burroughs Regarding Motion to Keep Open for Civil Action No. 17-cv-12239-AD. Document 226. Filed Aug. 18, 2020. 1 Page.
U.S. District Court District of Massachusetts Astellas' Opposition to Defendants' Attempt to Raise a Last Minute, New, Unpled Affirmative Defense for Civil Action No. 17-cv-12239-AD. Document 227. Filed Aug. 20, 2020. 11 Pages.
U.S. District Court District of Massachusetts Shannon Letter to Burroughs for Civil Action No. 17-cv-12239-AD. Document 228. Filed Aug. 24, 2020. 1 Page.
U.S. District Court District of Massachusetts Shannon Letter to Burroughs for Civil Action No. 17-cv-12239-AD. Document 230. Filed Aug. 26, 2020. 1 Page.
U.S. District Court District of Massachusetts Electronic Clerk's Notes for Civil Action No. 17- cv-12239-ADB. Document 238. Filed Nov. 2, 2020. 2 Pages.
U.S. District Court District of Massachusetts Electronic Clerk's Notes for Civil Action No. 17- cv-12239-ADB. Document 239. Filed Nov. 3, 2020. 2 Pages.
U.S. District Court District of Massachusetts Electronic Clerk's Notes for Civil Action No. 17- CV-12239-ADB. Document 240. Filed Nov. 4, 2020. 2 Pages.
U.S. District Court District of Massachusetts Electronic Clerk's Notes for Civil Action No. 17- cv-12239-ADB. Document 241. Filed Nov. 5, 2020. 2 Pages.
U.S. District Court District of Massachusetts Electronic Clerk's Notes for Civil Action No. 17- cv-12239-ADB. Document 242. Filed Nov. 6, 2020. 2 Pages.
U.S. District Court District of Massachusetts Astellas' Findings of Fact and Conclusions of Law for Civil Action No. 17-cv-12239-ADB. Document 243. Filed Dec. 4, 2020. 58 Pages.
U.S. District Court District of Massachusetts Defendants' Post-Trial Proposed Findings of Fact and Conclusions of Law for Civil Action No. 17-cv-12239-ADB. Document 244. Filed Dec. 4, 2020. 58 Pages.
U.S. District Court District of Massachusetts Astellas' Response to Defendants' Proposed Findings of Fact and Conclusions of Law for Civil Action No. 17-cv-12239-ADB. Document 245. Filed Dec. 11, 2020. 16 Pages.
U.S. District Court District of Massachusetts Defendants' Response to Astellas' Post-Trial Proposed Findings of Fact and Conclusions of Law for Civil Action No. 17-cv-12239-ADB. Document 246. Filed Dec. 11, 2020. 13 Pages.
U.S. District Court District of Massachusetts Defendants' Assented-To Motion to Correct Record for Civil Action No. 17-cv-12239-ADB. Document 247. Filed Dec. 16, 2020. 4 Pages.
U.S. District Court District of Massachusetts Exhibit A for Civil Action No. 17-cv-12239-ADB. Document 247-1. Filed Dec. 16, 2020. 59 Pages.
U.S. District Court District of Massachusetts Electronic Order granting Document 247 for Civil Action No. 17-cv-12239-ADB. Document 248. Filed Dec. 17, 2020. 2 Pages.
U.S. District Court District of Massachusetts Findings of Fact and Conclusions of Law for Civil Action No. 17-cv-12239-ADB. Document 255. Filed Feb. 5, 2021. 48 Pages.

* cited by examiner

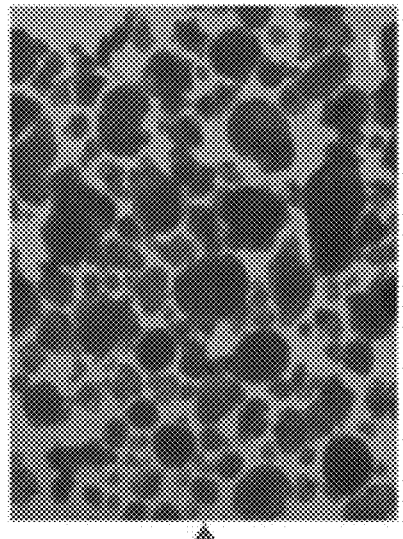
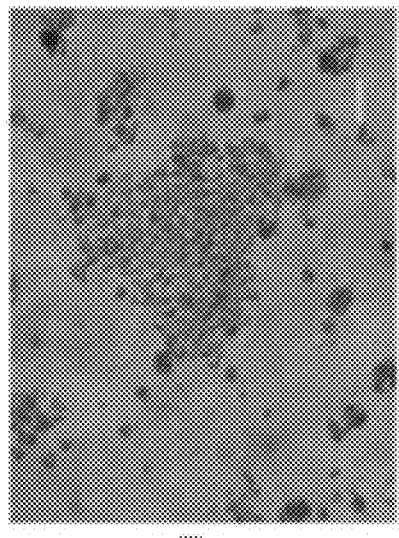
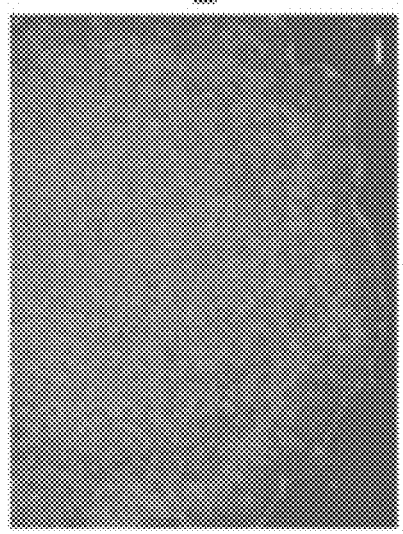
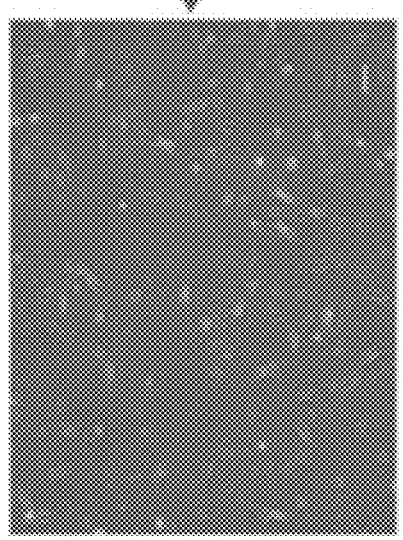
FIG. 1A hESC
FIG. 1B EB
FIG. 1C hES-MSC
FIG. 1D HB-enriched Day 9 Hemangioblast

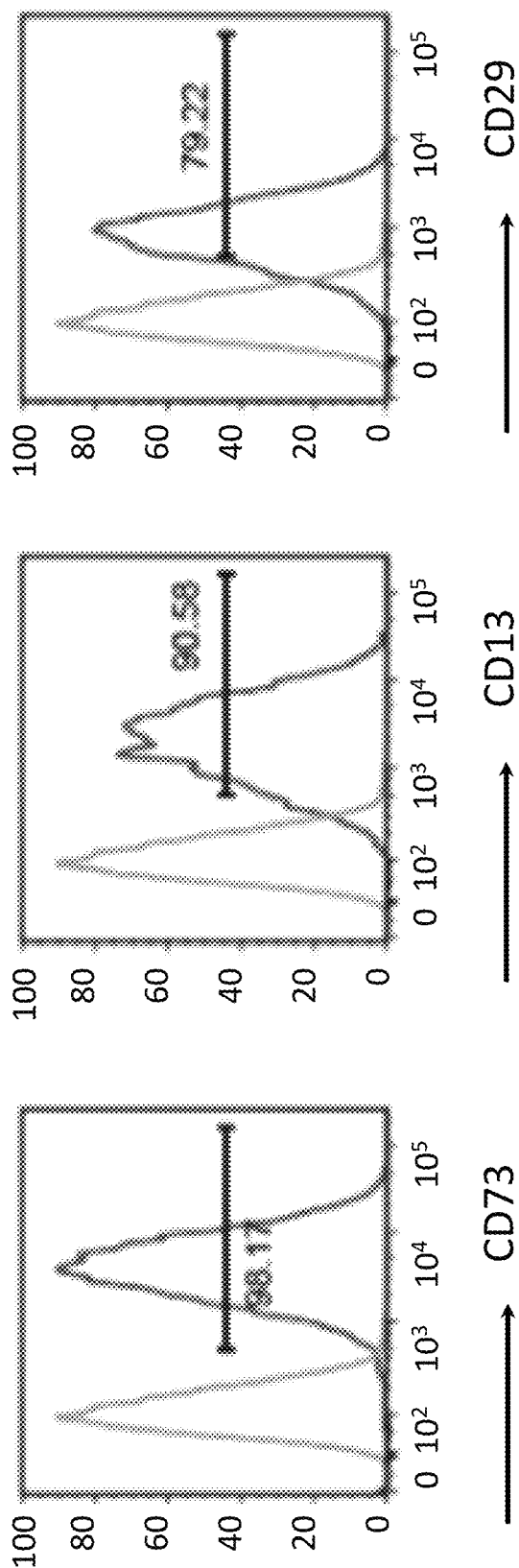

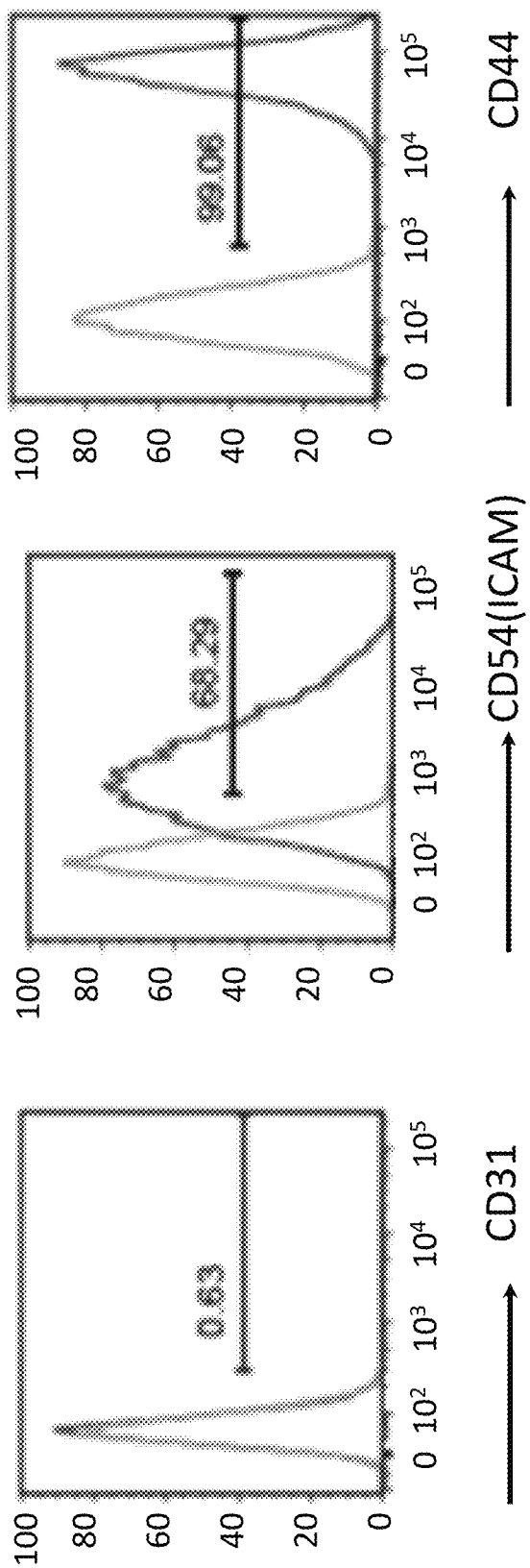

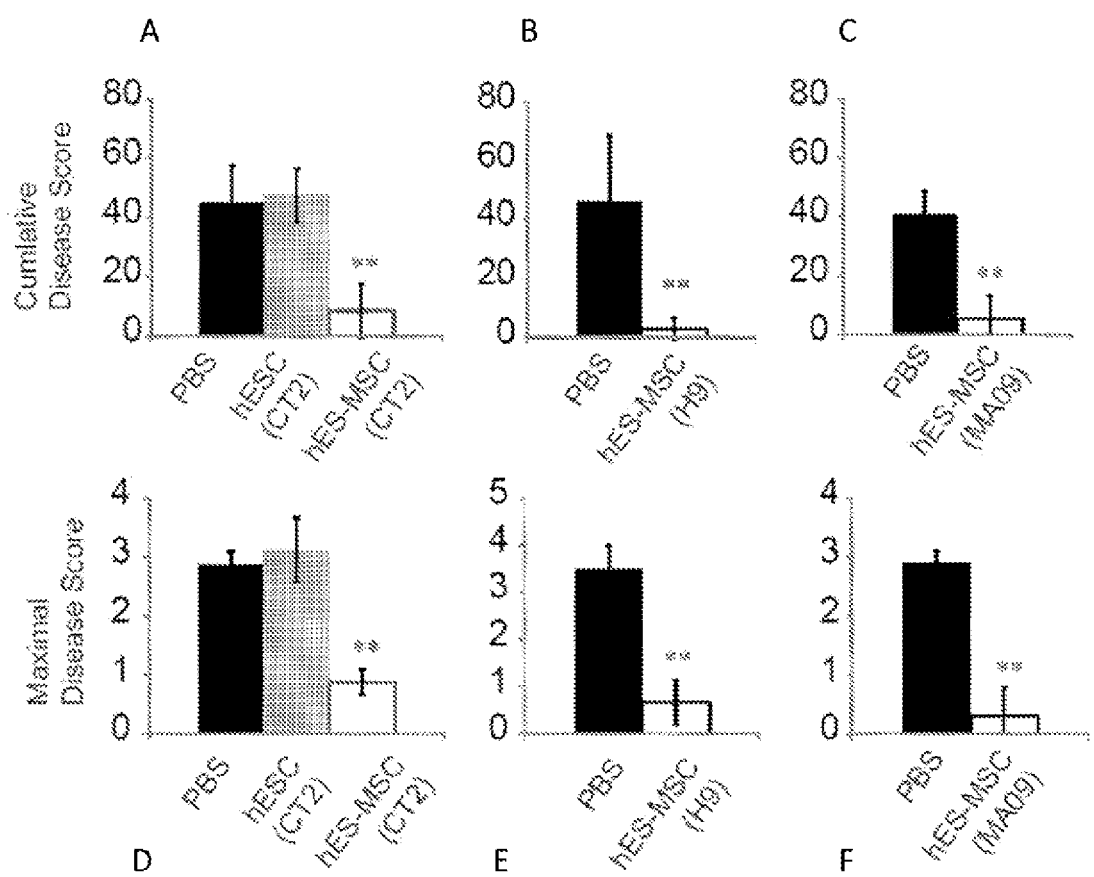
FIGS. 6 (A-F)

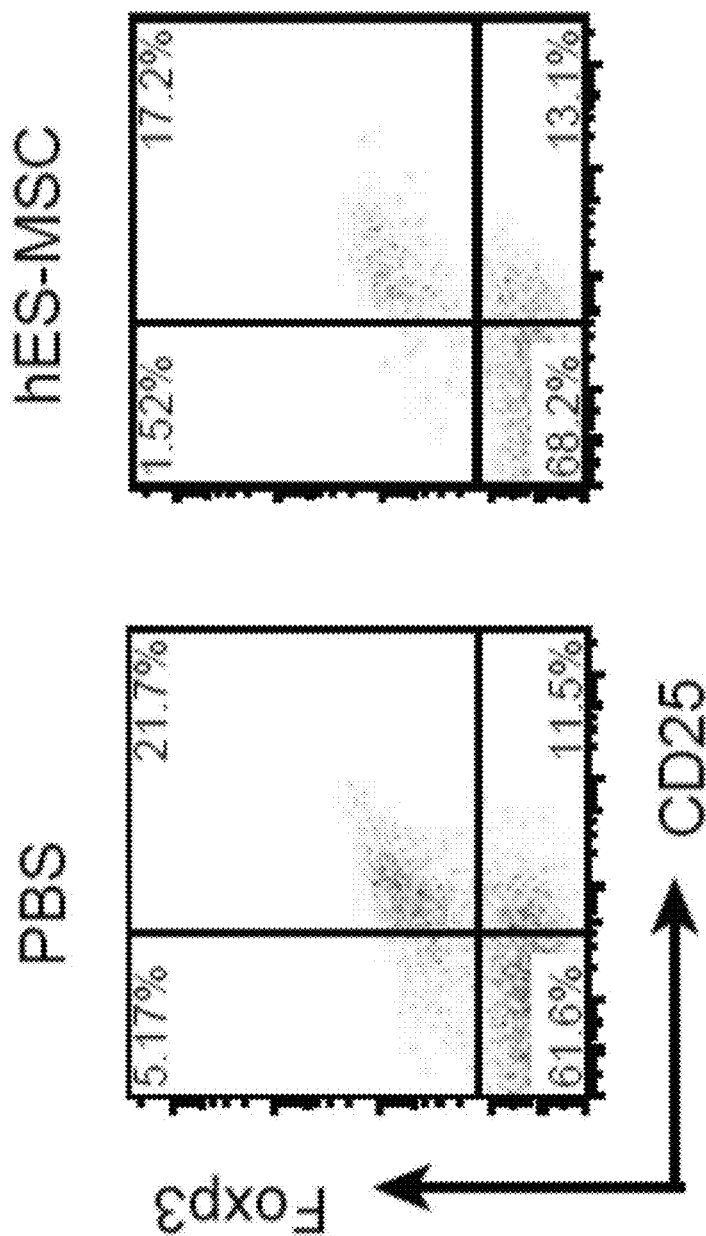

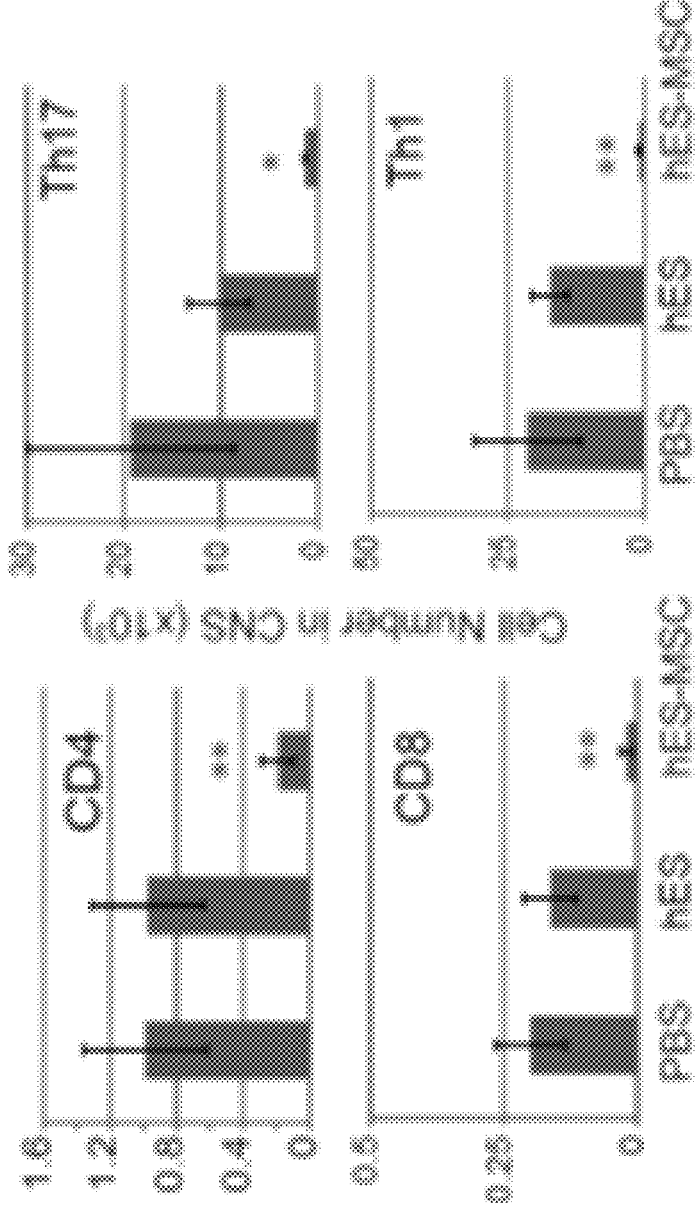

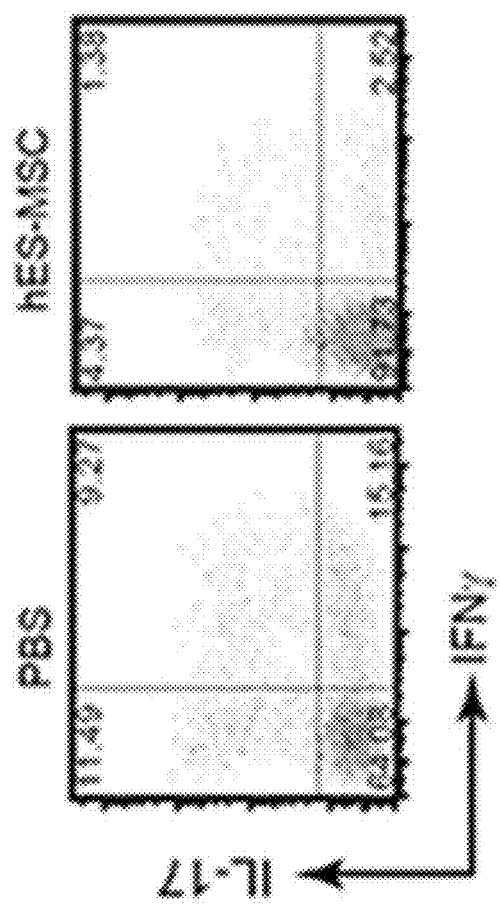

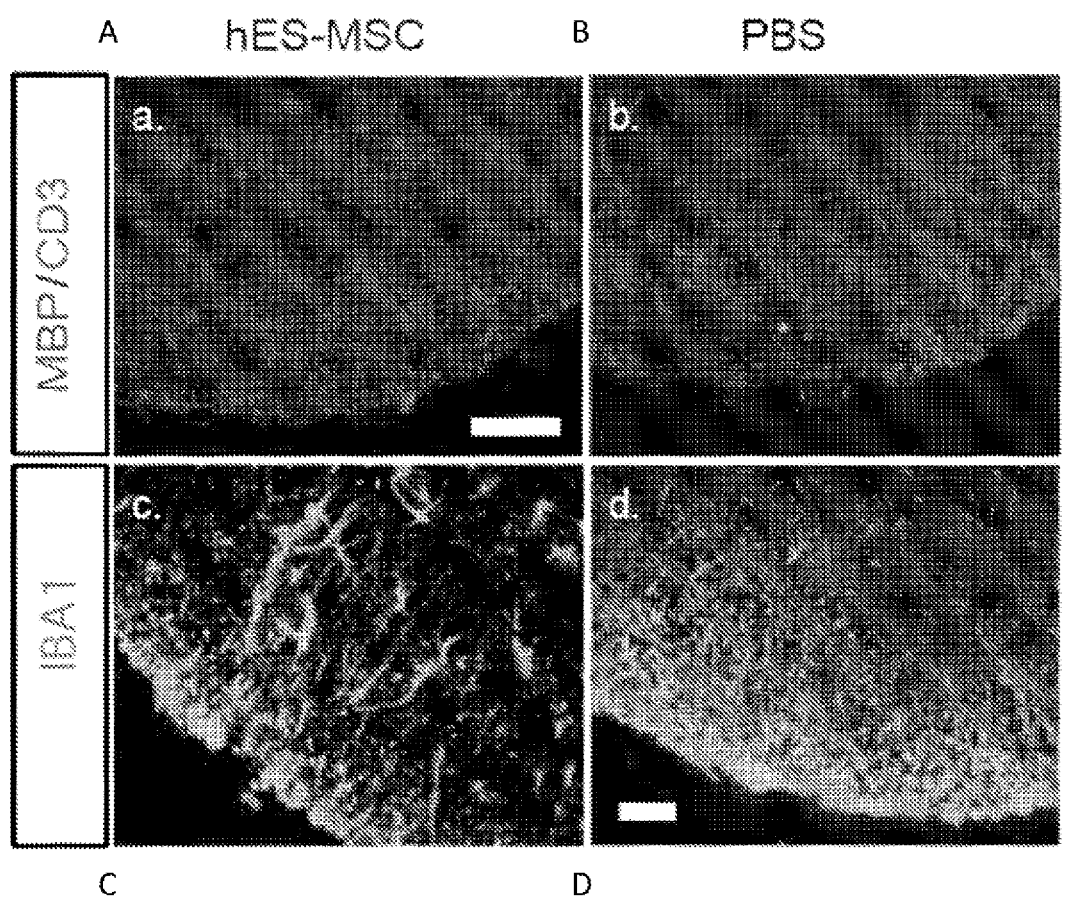
FIGS. 10 (A-D)

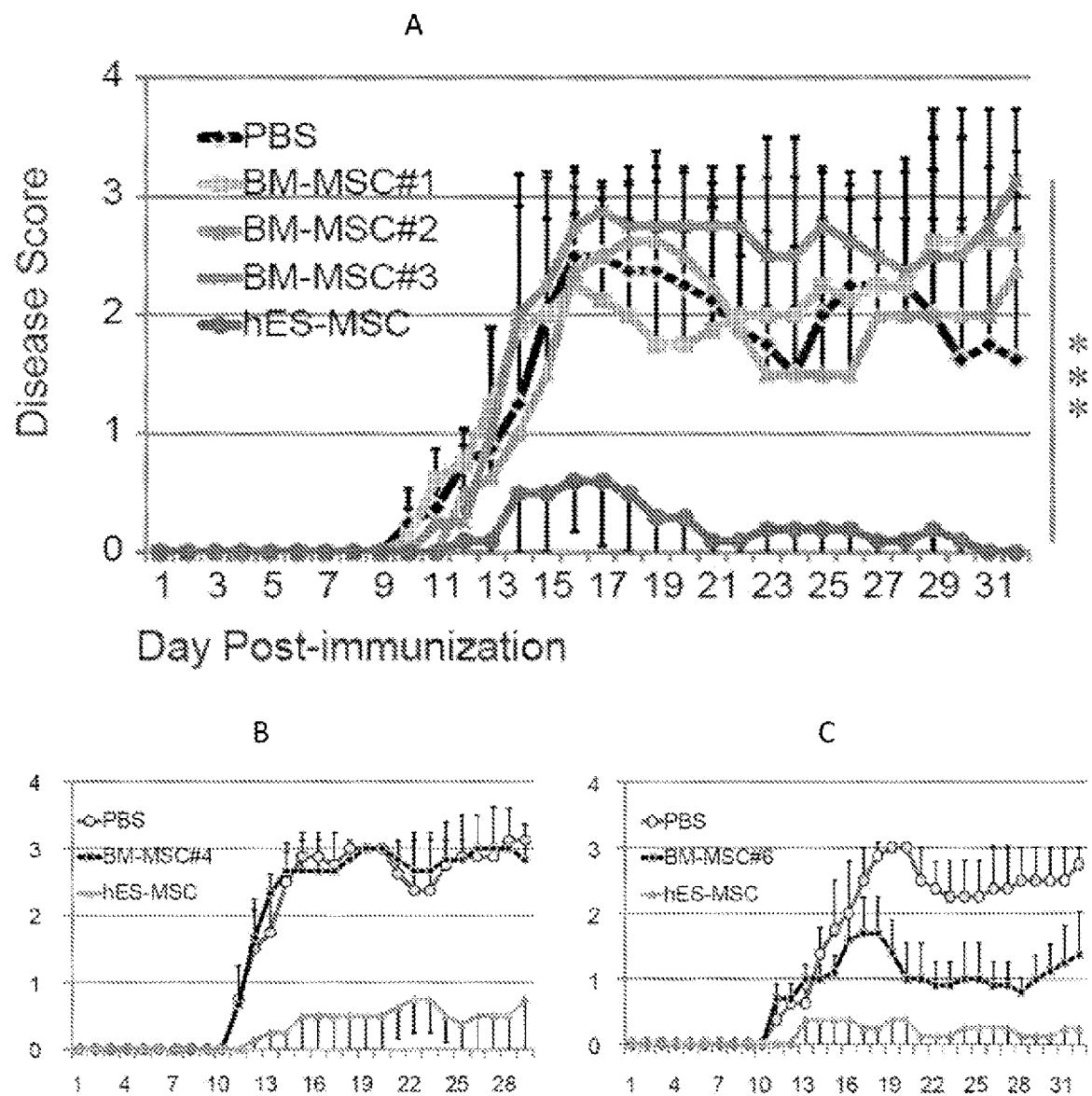
FIGS. 12 (A-C)

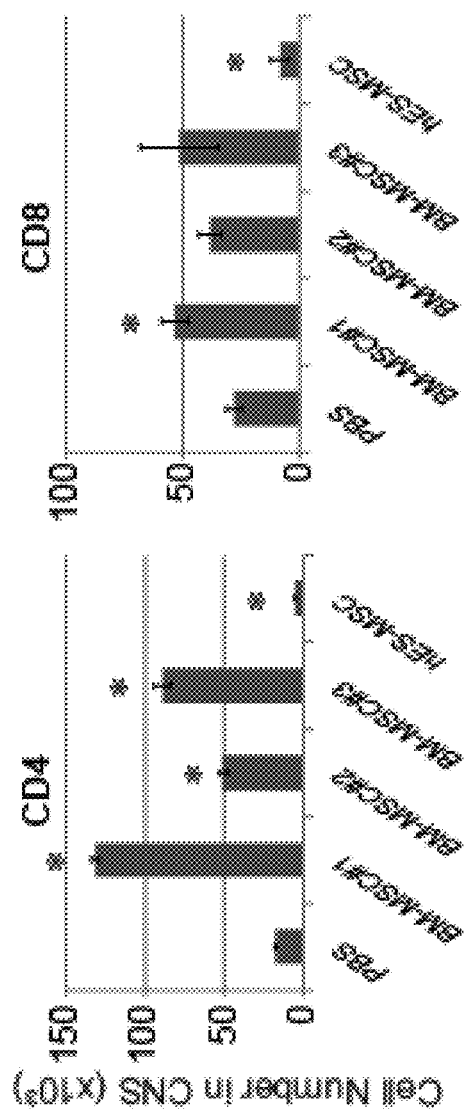
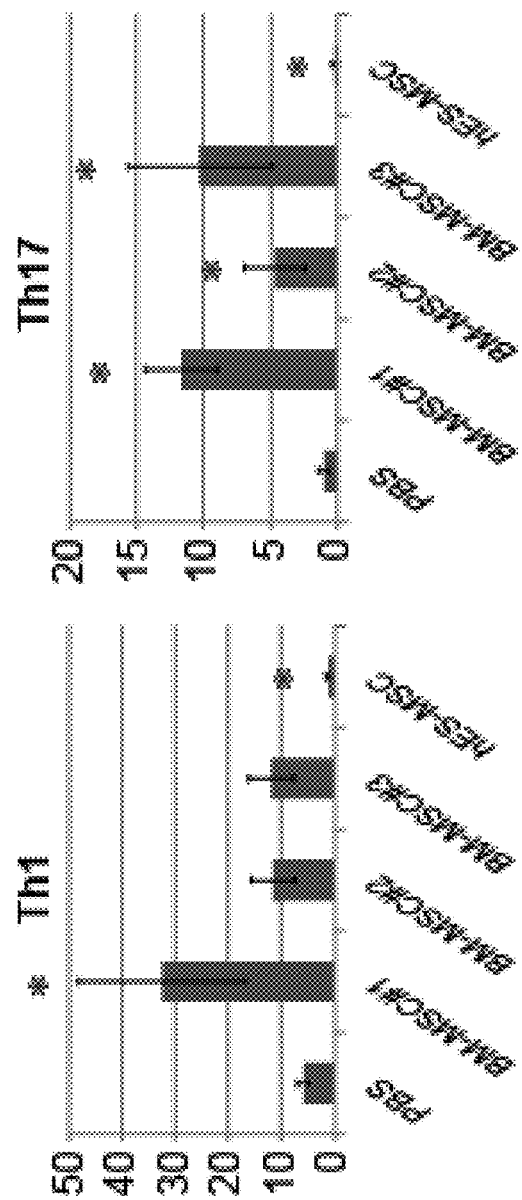
FIG. 13A
FIG. 13B
FIG. 13C
FIG. 13D

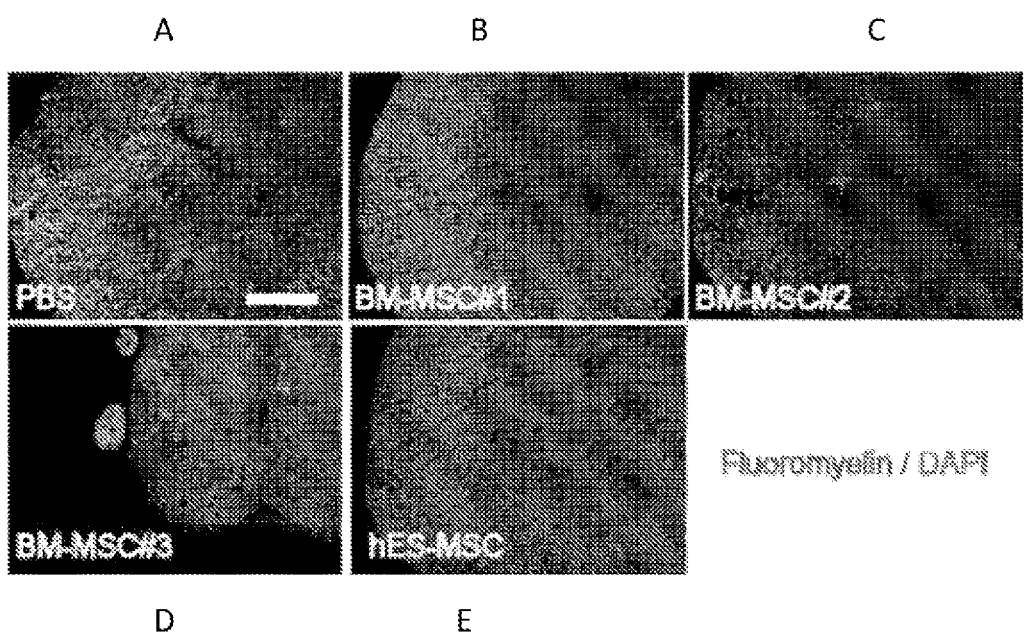
FIGS. 14 (A-E)

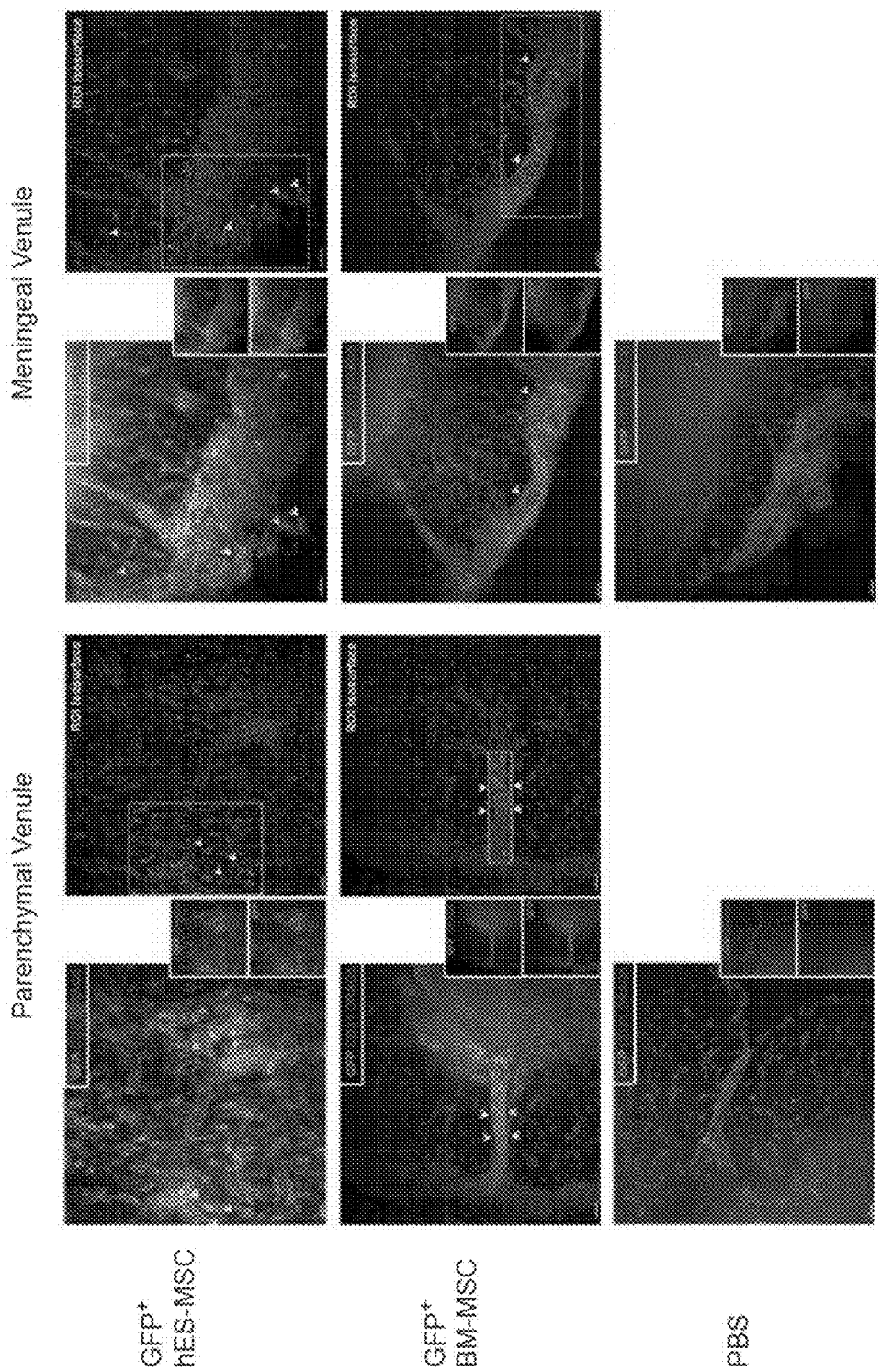

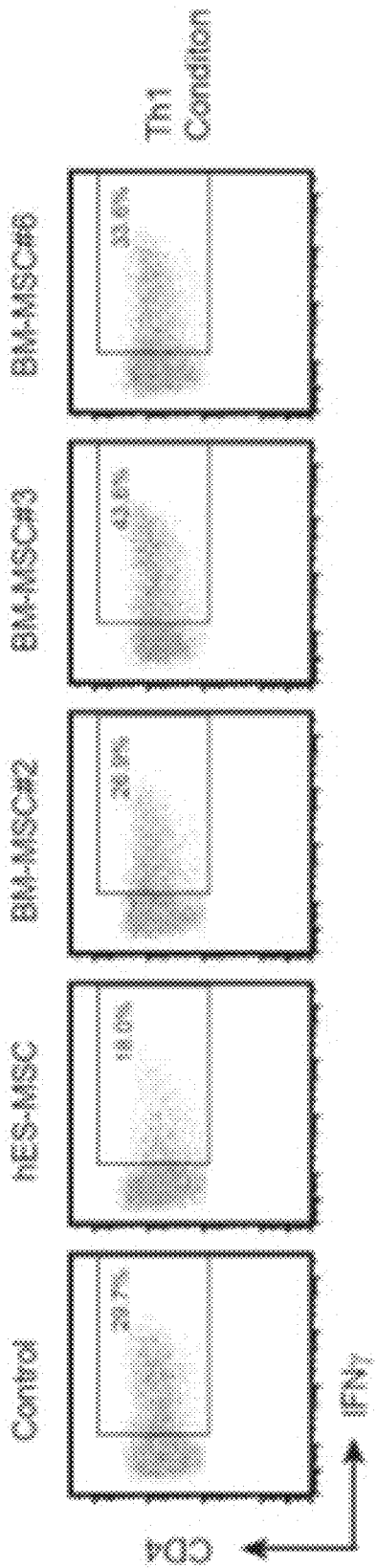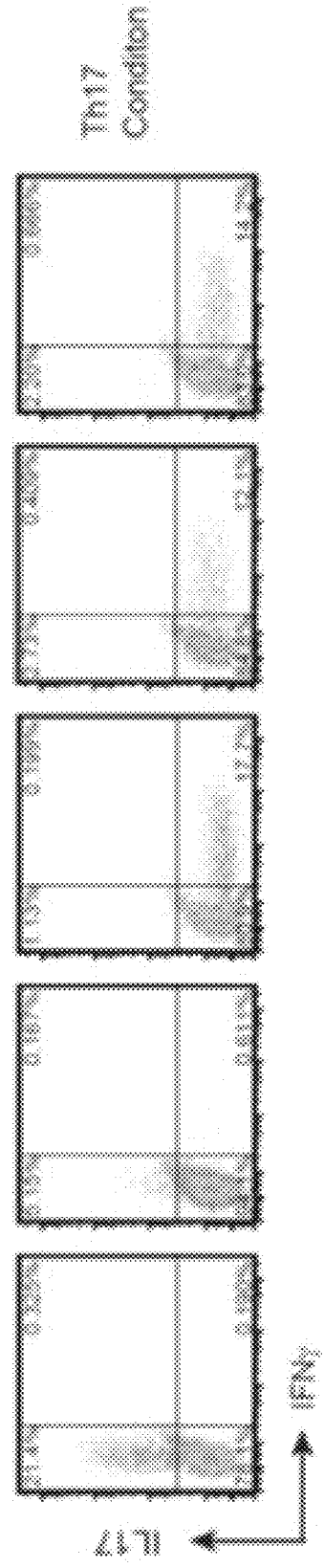

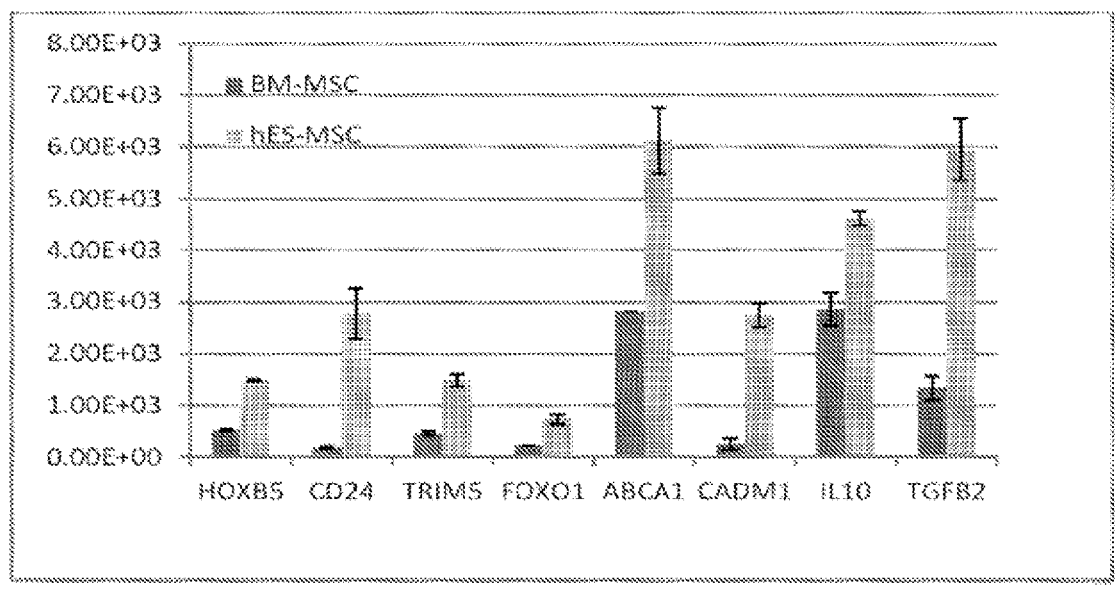
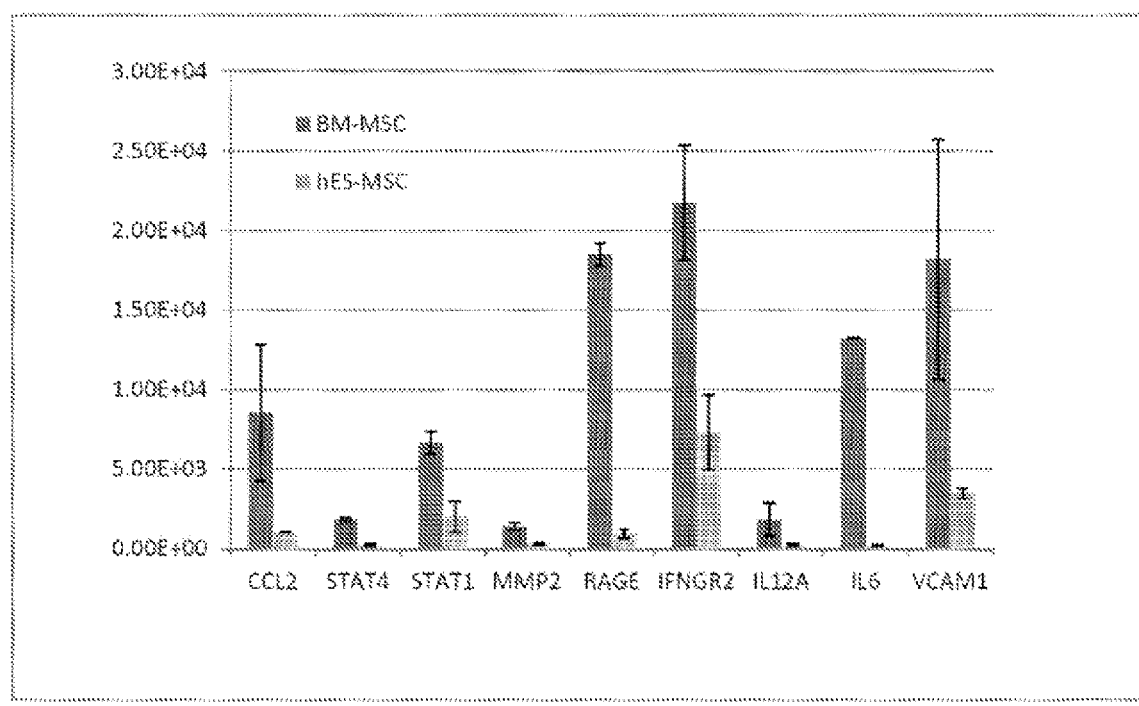
FIGS. 19 (A-B)

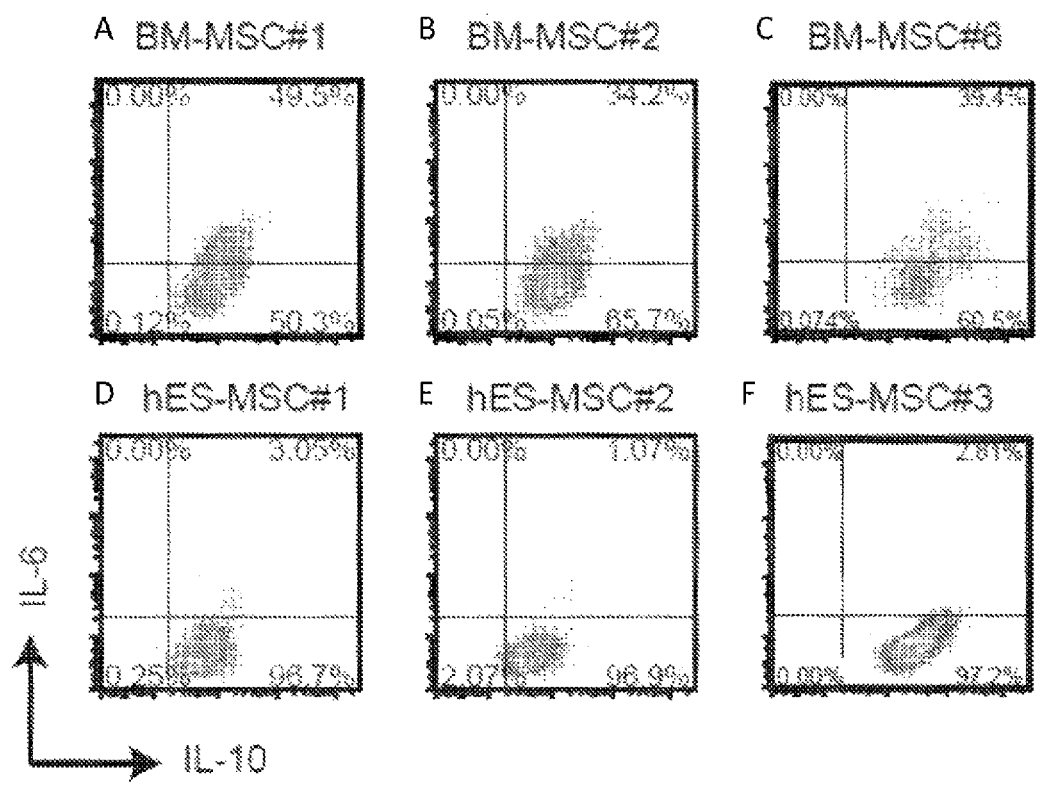
FIGS 20 (A-F)

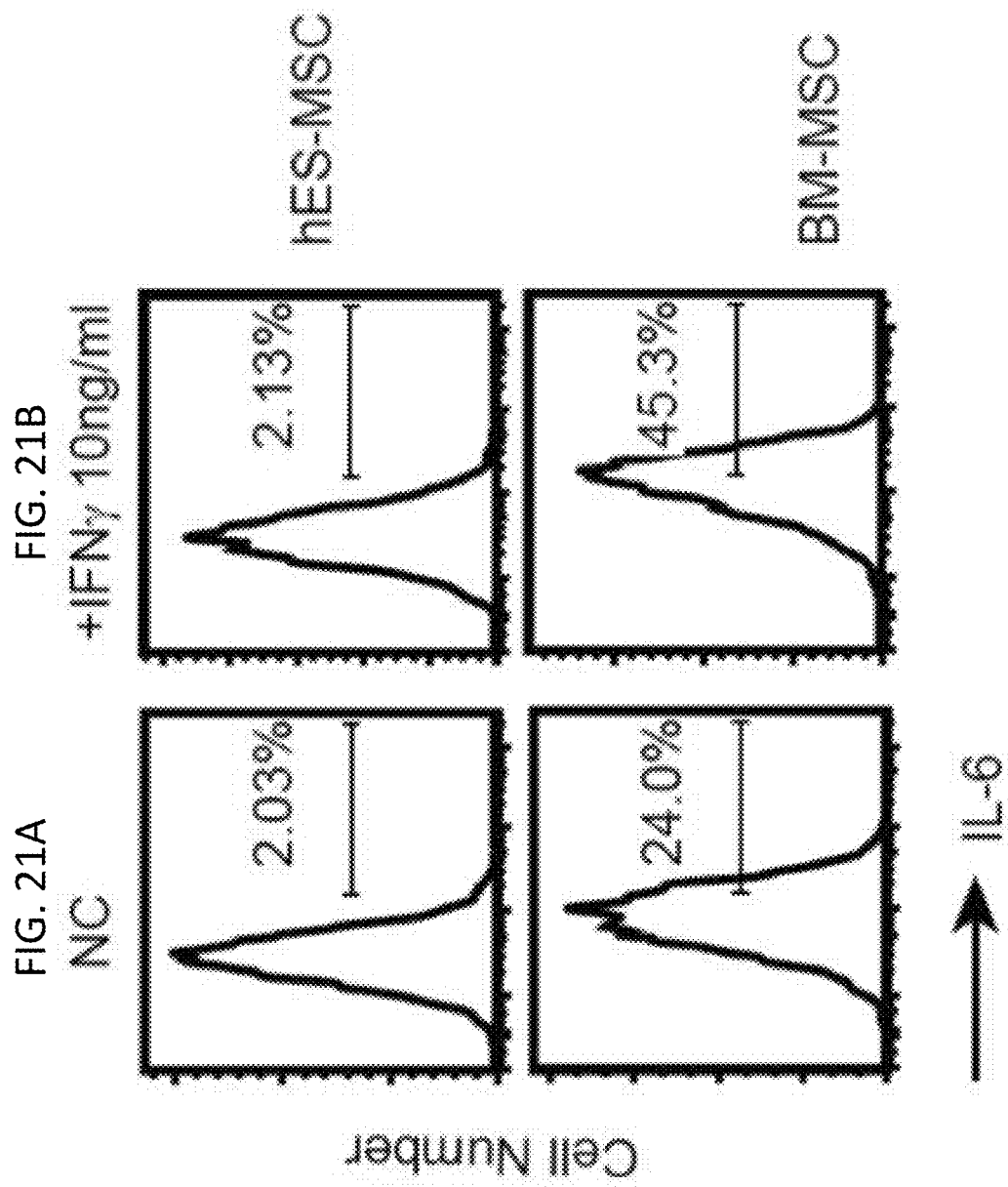

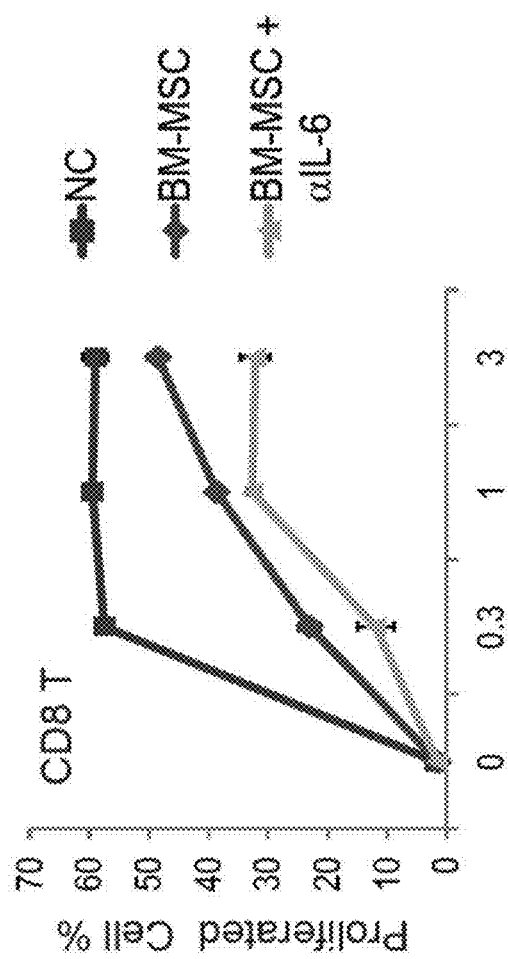
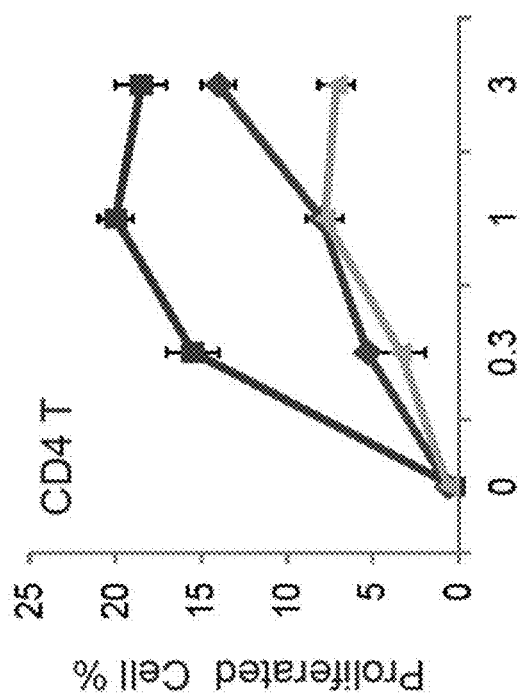
FIG. 23B
FIG. 23A

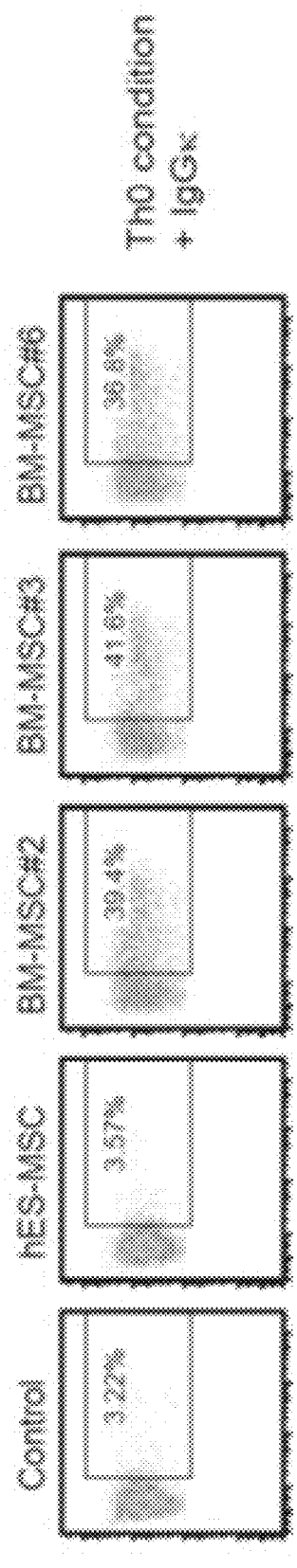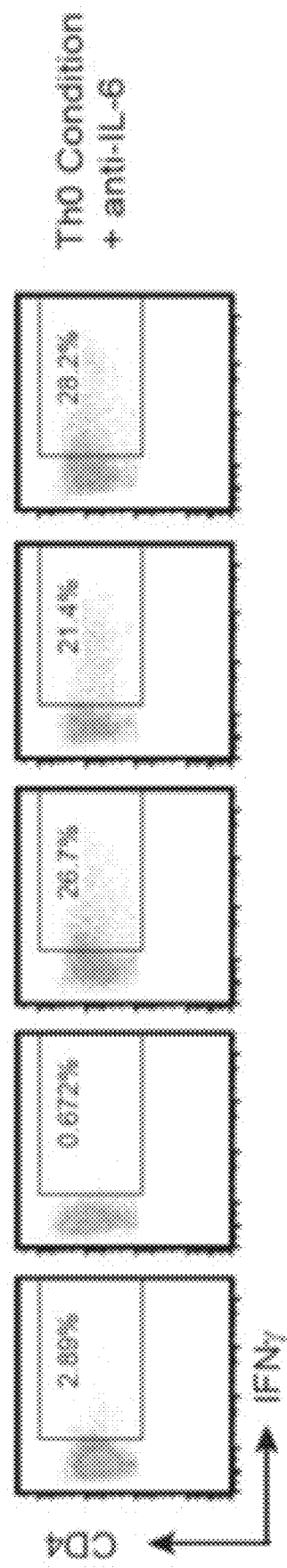
FIG. 24A  FIG. 24B  FIG. 24C  FIG. 24D  FIG. 24E  FIG. 24F  FIG. 24G  FIG. 24H  FIG. 24I  FIG. 24J

FIGS. 27 (A-B)

MESENCHYMAL-LIKE STEM CELLS DERIVED FROM HUMAN EMBRYONIC STEM CELLS, METHODS AND USES THEREOF

CROSS REFERENCE TO RELATED APPLICATION

The present application is a continuation application of U.S. patent application Ser. No. 15/656,473 now U.S. Pat. No. 10,557,122, which issued on Feb. 11, 2020, which was a divisional application of U.S. patent application Ser. No. 14/413,290 now U.S. Pat. No. 9,745,551, which issued on Aug. 29, 2017, which was a U.S. National Stage Application of PCT/US2013/048291 filed on Jun. 27, 2013, which claims priority to U.S. patent application Ser. No. 61/670,787 on Jul. 12, 2012 and U.S. provisional application Ser. No. 61/762,961, filed Feb. 11, 2013, all of which are hereby incorporated by reference in their entireties.

1. INTRODUCTION

The present invention relates to a method of generating mesenchymal stem cells from human embryonic stem cells using a multi-step method of culturing embryonic stem cells comprising culturing embryonic stem cells under conditions sufficient to produce embryoid bodies, culturing the embryoid bodies under conditions to expand hemangio-colony forming cells in the medium comprising the embryoid bodies, and culturing the hemangio-colony forming cells under conditions that induce differentiation into mesenchymal stem cells. Also disclosed are methods of identifying highly immunosuppressive human embryonic stem cell derived mesenchymal-like stem cells. The invention also relates to the human embryonic stem-cell derived mesenchymal stem cells, solutions and pharmaceutical preparations comprising the human embryonic stem cell-derived mesenchymal stem cells, methods of using the human embryonic stem-cell derived mesenchymal stem cells for treatment and prevention of disease, specifically, T cell related autoimmune diseases, and most specifically, multiple sclerosis, and methods of using the human embryonic stem cell-derived mesenchymal stem cells for the delivery of agents across the blood brain barrier and the blood spinal cord barrier. Also provided herein are methods of using hES-MSCs to modulate the immune system, inhibit immune response to individual's self-antigen and repair damaged central nerve systems. Provided herein are compositions comprising hES-MSCs for use in immunomodulation, methods of providing modified MSC with improved immunosuppressive function through modified gene expression. Also provided are methods of using hES-MSC as drug and/or gene delivery system.

2. BACKGROUND

Multiple sclerosis (MS) is a chronic autoimmune disease caused by infiltration of peripheral immune cells into the central nervous system (CNS) through damaged blood-brain barrier (BBB) or blood-spinal cord barrier (BSCB), which causes inflammation of the myelin sheaths around neuronal axons, and causes demyelination and scarring of the axons (McFarland and Martin (2007)). Almost any neurological symptom including physical and cognitive disability can appear with MS. The incidence of the disease is approximately 0.1% worldwide, and the disease onset usually occurs in young adults (more in females) (Benito-Leon (2011)). According to the National Multiple Sclerosis Society of United States, there are more than 70 FDA-approved medications for the treatment of MS, including Avonex (IFNβ-1a), Betaseron (IFNβ-1b), Gilenya (a sphingosine 1-phosphate receptor modulator), Glatiramer acetate (or Copolymer 1), and Tysabri (humanized anti-α-integrin antibody). However, these offer only palliative relief and are associated with serious adverse effects including increased infection, heart attack, stroke, progressive multifocal leukoencephalopathy, arrhythmia, pain, depression, fatigue, macula edema, and erectile dysfunction (Johnston and So (2012); Weber et al. (2012)).

Transplantation of mesenchymal stromal/stem cells (MSCs) has emerged as a potentially attractive therapy due to their immunomodulatory and neuroregenerative effects (Auletta et al., (2012); Pittenger et al. (1999)) and potential ability to repair the blood-brain barrier (Chao et al. (2009); Menge et al. (2012)). MSCs are multipotent meaning they can generate a variety of cell lineages including adipocyte, chondrocyte, and osteoblast cells. They can be derived from fetal, neonatal, and adult tissues such as the amniotic membrane, umbilical cord, bone marrow, and adipose. MSCs have several unique advantages over current pharmacotherapies, as these cells can serve as carriers of multiple and potentially synergistic therapeutic factors, and can migrate to injured tissues to exert local effects through secretion of mediators and cell-cell contact (Uccelli and Prockop (2010a)). Importantly, MSCs have been found efficacious in the treatment of mice with experimental autoimmune encephalomyelitis (EAE), a well-recognized animal model of MS (Gordon et al., 2008a; Gordon et al. (2010); Morando et al. (2012); Peron et al. (2012); Zappia et al. (2005); Zhang et al. (2005)), as well as MS patients in clinical trials (Connick et al. (2012); Karussis et al. (2010); Mohyeddin Bonab et al. (2007); Yamout et al. (2010)). Xenogeneity does not appear problematic as both mouse and human bone marrow-derived MSC (BM-MSC) can attenuate disease progression of EAE mice (Gordon et al. (2008a); Gordon et al. (2010); Morando et al. (2012); Peron et al. (2012); Zappia et al. (2005); Zhang et al. (2005)).

However, pitfalls exist for translating these findings from animals to patients. First, the limited sources and varying quality of human bone marrow (or other adult tissues) from different donors restrict the study and application of the MSCs, and prevent the standardization of the MSCs as a therapeutic product for large-scale clinical use. Second, these adult tissue-derived MSCs are highly mixed populations of cells, and perhaps only a portion of the cells exerts immunosuppressive effect. To obtain enough cells that are clinical grade for clinical use, one has to expand the MSC in vitro, which can decrease their immunosuppressive and homing abilities (Javazon et al. (2004)). Third, there are safety concerns about BM-MSC for possible malignant transformation of the cells (Wong (2011)), and potential transmission of pathogens from donors. Finally, varying effects were reported on EAE mice treated with BM-MSC in different reports (Gordon et al. (2008a); Payne et al. (2012); Zappia et al. (2005); Zhang et al. (2005)). Thus, the efficacy of BM-MSC on treatment of the disease is questionable.

Thus, there is a need for new therapies for the treatment of multiple sclerosis and other autoimmune diseases. There is also a need for an unlimited, safe, highly stable, efficient and consistent source of MSC to use as a treatment and prophylactic for these diseases as well as others.

It has been reported that human embryonic stem cells (hESC) can differentiate into embryoid bodies (EB), and then into a pool of cells with hemangioblast (HB) activities, i.e., they can further differentiate into vascular smooth muscle cells, endothelial cells, and hematopoietic cells (Chyou et al. (2008); Lu et al. (2007); Lu et al. (2009)). Therefore it was reasoned that a portion of these HB-containing cells could differentiate into MSCs, thus, eliminating the problems found with bone marrow-derived MSCs. These mesenchymal stem cells derived from human embryonic stem cell would be an unlimited, safe, and consistent supply of stem cells to be used to treat and prevent autoimmune diseases. Also disclosed herein are microarray analysis and other analysis, where several key factors are identified which differentially expressed in hES-MSC compared to BM-MSC.

3. SUMMARY OF THE INVENTION

The current invention is based on the surprising discovery that a portion of the HB-containing cells derived from embryonic stem cells (hES), can also differentiate into MSC, designated "hES-MSC", with high efficiency and consistency. These hES-MSCs produced from multiple hESC lines by the method of the invention, all remarkably inhibited T cell proliferation and differentiation in vitro and attenuated the disease score of EAE mice in vivo, accompanied by decreased demyelination, T cell infiltration, and microglial responses in the CNS. In contrast, BM-MSC from multiple sources had no effect at all on the EAE mice although they may reduce T cell proliferation and differentiation in vitro.

Thus, the present invention overcomes the problems described above by providing a method of generating mesenchymal stem cells (MSC) in vitro from human embryonic stem cells. The ability to generate the hES-MSC by the novel method disclosed herein allows the production of cells that can be used in a variety of therapeutic applications, including the treatment and prevention of multiple sclerosis, and other autoimmune diseases. Additionally, the hES-MSC produced by the novel method have the ability to cross the brain-blood barrier (BBB) and the blood-spinal cord barrier (BSCB) allowing them to be used for a variety of therapeutic applications, including drug delivery. The methods of the invention provide further utility in that they enable the generation of large numbers of hES-MSC that can be used at commercial scale.

Additionally, the present invention includes the human embryonic-derived mesenchymal stem cells produced by this method.

One embodiment of the present invention is a method for generating and expanding human embryonic-mesenchymal stem cells in vitro, said method comprising the steps of:
  a. culturing a cell culture comprising human embryonic stem cells in serum-free medium in the presence of at least one growth factor in an amount sufficient to induce the differentiation of said embryonic stem cells to differentiate into embryoid bodies;
  b. disaggregating the embryoid bodies into single cells and adding at least one growth factor to said culture comprising single cells from embryoid bodies and continuing to culture in serum-free medium, wherein said growth factor is in an amount sufficient to expand human hemangio-colony forming cells in said hemangio-colony culture;
  c. disaggregating the hemangio-colony forming cells into single cells;
  d. culturing the single cells in serum-containing media or serum-free media in an amount sufficient to induce the differentiation of said hemangio-colony forming single cells into mesenchymal stem cells, In certain embodiments, at least about 90%, 91%, 92%, 93%, 94%, 95%, 96%, 97%, 98%, or 99% of the resulting human embryonic-mesenchymal stem cells express CD73.

In certain embodiments, at least about 95% of the resulting human embryonic-mesenchymal stem cells express CD73. In certain embodiments, more than 95% of the resulting human embryonic-mesenchymal stem cells express CD73.

In certain embodiments, the medium contains growth factor including vascular endothelial growth factor (VEGF), bone morphogenic protein (BMP), stem cell factor (SCF), Flt-3L (FL), thrombopoietin (TPO), erythropoietin (EPO) or a combination thereof.

In certain embodiments, the serum-containing medium contains fetal calf serum, L-gultamine and the serum-free medium contains knockout serum replacement (KOSR) or bovine serum albumin (BSA).

In certain embodiments, there is an additional step of irradiating the resulting human embryonic-mesenchymal stem cells with gamma radiation ranging from 1 gy to 200 gy.

In certain embodiments, the method for generating and expanding human embryonic-mesenchymal stem cells results in at least 10,000 human embryonic-mesenchymal stem cells, at least 50,000 human embryonic-mesenchymal stem cells, at least 100,000 human embryonic-mesenchymal stem cells, at least 500,000 human embryonic-mesenchymal stem cells, at least $1\times10^6$ human embryonic-mesenchymal stem cells, at least $5\times10^6$ human embryonic-mesenchymal stem cells, at least $1\times10^7$ human embryonic-mesenchymal stem cells, at least $5\times10^7$ human embryonic-mesenchymal stem cells, at least $1\times10^8$ human embryonic-mesenchymal stem cells, at least $5\times10^8$ human embryonic-mesenchymal stem cells, at least $1\times10^9$ human embryonic-mesenchymal stem cells, at least $5\times10^9$ human embryonic-mesenchymal stem cells, or at least $1\times10^{10}$ human embryonic-mesenchymal stem cells. These methods result in cell solutions that may comprise between 10,000 and 10 billion human embryonic-mesenchymal stem cells. In certain embodiments, at least about 90%, 91%, 92%, 93%, 94%, 95%, 96%, 97%, 98%, or 99% of the resulting human embryonic-mesenchymal stem cells express one or more hES-MSC differential markers. In certain embodiment, the marker is CD73, CD90 and CD105.

In one embodiment, the hES-MSCs remarkably attenuate the disease score of the EAE mice, accompanied by decreased demyelination, T cell infiltration, and microglial responses. In addition, the hES-MSCs have much stronger immunosuppressive activity in vivo and in vitro when compared to bone marrow derived MSCs (BM-MSC). Also provided herein are key proteins/molecules that are differentially expressed between hES-MSC and BM-MSCs. Provided herein are methods of identifying hES-MSCs with improved immunosuppressive activity by measuring the expression level of the protein/molecular markers. Also disclosed are methods of genetic modification to improve immunosuppressive activity of hES-MSCs.

A further embodiment of the present invention is a solution comprising human embryonic-mesenchymal stem cells comprising at least 10,000 human embryonic-mesenchymal stem cells, at least 50,000 human embryonic-mesenchymal stem cells, at least 100,000 human embryonic-mesenchymal stem cells, at least 500,000 human embryonic-mesenchymal stem cells, at least $1\times10^6$ human embryonic-mesenchymal stem cells, at least $5\times10^6$ human embryonic-mesenchymal stem cells, at least $1\times10^7$ human embryonic-mesenchymal stem cells, at least $5\times10^7$ human embryonic-mesenchymal stem cells, at least $1 \times 10^8$ human embryonic-mesenchymal stem cells, at least $5 \times 10^8$ human embryonic-mesenchymal stem cells, at least $1 \times 10^9$ human embryonic-mesenchymal stem cells, at least $5 \times 10^9$ human embryonic-mesenchymal stem cells, or at least $1 \times 10^{10}$ human embryonic-mesenchymal stem cells.

In certain embodiments, the culture volume is from 2 ml for at least 10,000 cells, 10 ml for at least 100,000 cells, 100 ml for at least 1,000,000 cells, 1000 ml for at least 10,000,000 cells, and up to 4000 ml of media for $5 \times 10^8$ cell.

These solutions can be injected into a subject. These solutions can be frozen. These solutions can be used for the manufacture of a medicament for a disease that can be treated by the administration of human embryonic-mesenchymal stem cells.

This invention also provides a method for producing a solution of human embryonic-mesenchymal stem cells suitable for injection into a patient comprising the steps of isolating the solution of cells described in the preceding paragraph and placing the cells into solution suitable for injection into a patient. This invention also provides a method of producing a solution of human embryonic-mesenchymal stem cells suitable for freezing comprising the steps of isolating the cells described in the preceding paragraph and placing into a solution suitable for freezing.

Yet another embodiment of the present invention is a human embryonic-mesenchymal stem cell expressing one or more of cell marker proteins including CD73, CD90, CD105, CD13, CD29, CD54, CD44 or a combination thereof. In a further embodiment, the human embryonic-mesenchymal stem cell does not express or expresses low levels of one or more cell marker proteins including CD34, CD31, CD45 or a combination thereof. In a further embodiment, the human embryonic-mesenchymal stem cell does not express or expresses low levels of one or more pro-inflammatory proteins including MMP2, RAGE, IFNγR1, IFNγR2, IL-12, TNFα, IL-6, VCAM1 or a combination thereof. In certain embodiments, the human embryonic-mesenchymal stem cell expressed at least half of the level of the above markers as compared to Bone marrow derived MSC.

A further embodiment of the present invention is a cell culture comprising human embryonic-mesenchymal stem cells expressing one or more of cell marker proteins including CD73, CD90, CD105, CD13, CD29, CD54, and CD44. In a further embodiment, the human embryonic-mesenchymal stem cells in the cell culture do not express or express low levels of one or more cell marker proteins including CD34, CD31 and CD45. In a further embodiment, the human embryonic-mesenchymal stem cells in the cell culture do not express or express low levels of one or more pro-inflammatory proteins including MMP2, RAGE, IFNγR1, IFNγR2, IL-12, TNFα, IL-6, and VCAM1.

In certain embodiments, the cell culture comprises at least $1 \times 10^6$ human embryonic-mesenchymal stem cells, at least $1 \times 10^7$ human embryonic-mesenchymal stem cells at least $1 \times 10^8$ human embryonic-mesenchymal stem cells, at least $1 \times 10^9$ human embryonic-mesenchymal stem cells, or at least $1 \times 10^{10}$ human embryonic-mesenchymal stem cells. For $1 \times 10^6$ cell, the initial cell culture volume will be 10-20 ml.

In further embodiments, at least about 90% of the human embryonic-mesenchymal stem cells in the cell culture express the CD73 protein, at least more than 90%, 91%, 92%, 93%, 94%, 95%, 96%, 97%, 98%, 99% of the human embryonic-mesenchymal stem cells express the CD73 protein.

In further embodiments, at least about 75%, 80%, 85%, 90%, 95%, 99% of the human embryonic-mesenchymal stem cells in the cell culture express at least one cell marker protein selected from the group consisting of CD90, CD105, CD44, and CD29.

In further embodiments, at least about 80%, 85%, 90%, 95%, 99% of the human embryonic-mesenchymal stem cells in the cell culture do not express or express low levels of at least one cell marker including CD34, CD31, and CD45.

In further embodiments, at least about 75%, 80%, 85%, 90%, 95%, 99% of the human embryonic-mesenchymal stem cells in the cell culture do not express or express low levels of at least one pro-inflammatory protein including MMP2, RAGE, IFNγR1, IFNγR2, IL-12, TNFα, IL-6, and VCAM1. In certain embodiments, the hES-MSC express high levels of CD24, TGFβ2 or both.

In certain embodiments, the human embryonic-mesenchymal stem cells or cell cultures described in the preceding paragraphs are irradiated using gamma radiation.

Provided herein are pharmaceutical preparations comprising any one of the human embryonic-mesenchymal stem cells or cell cultures described in the preceding paragraphs and pharmaceutically acceptable carriers.

Provided herein are cryopreserved preparations of any of the human embryonic-mesenchymal stem cells or cell cultures described in the preceding paragraphs.

Provided herein are methods of treating or preventing a T cell related autoimmune disease in a subject in need thereof, comprising the steps of administering a therapeutically effective amount of solution, cell culture or pharmaceutical preparation comprising human embryonic-mesenchymal stem cells as described in the preceding paragraphs, to the subject in need thereof. The T cell related autoimmune diseases include but are not limited to Crohn's disease, inflammatory bowel disease, graft versus host disease, systemic lupus erythematosus, and rheumatoid arthritis, T cell mediated delayed type hypersensitivity (Type IV hypersensitivity) i.e. Type 1 diabetes mellitus, MS, RA, Hashimoto's thyroiditis, Crohn's, contact dermatitis, Scleroderma, etc.

In certain embodiments, the subject is preferably a mammal or avian, and most preferably human. In certain embodiments, the solution, cell culture or pharmaceutical preparation comprises irradiated or non-irradiated human embryonic-mesenchymal stem cells.

In certain embodiments, the method for treating or preventing disease includes combination therapy with one or more therapeutic agents for the treatment or prevention of disease.

In certain embodiments, the methods for treating or preventing multiple sclerosis disease in a subject in need thereof, comprise the steps of administering a therapeutically effective amount of solution, cell culture or pharmaceutical preparation comprising human embryonic-mesenchymal stem cells as described in the preceding paragraphs, to the subject in need thereof. Multiple sclerosis can be relapsing/remitting multiple sclerosis, progressive/relapsing multiple sclerosis, primary multiple sclerosis, or secondary multiple sclerosis. The subject is preferably a mammal or avian, and most preferably human. The solution, cell culture or pharmaceutical preparation can comprise irradiated or non-irradiated human embryonic-mesenchymal stem cells.

The method further comprises the administration of additional therapeutic agents to the subject, including but not limited to, fingolimod, adrenocorticotropic hormone (ACTH), methylprednisolone, dexamethasone, IFNβ-1a, IFN-1b, gliatriamer acetate, cyclophosphamide, methotrexate, azathioprine, cladribine, cyclosporine, mitoxantrone, and sulfasalazine. In yet another embodiment, one or more of these therapeutic agents can be attached to the hES-MSC in order to cross the blood-brain and/or blood-spinal cord barrier, for delivery of the therapeutic agent to the central nervous system.

Provided herein is a method of delivering an agent through the blood-brain barrier and/or the blood-spinal cord barrier, said method comprising the steps of: attaching or conjugating the agent to a human embryonic-mesenchymal stem cell to form a complex; and administering the human embryonic-mesenchymal stem cell-agent complex to a subject in need thereof, wherein the human embryonic-mesenchymal stem cell is capable of crossing the blood-brain barrier and/or the blood-spinal cord barrier and the agent is for the treatment, prevention or diagnosis of a disease or injury in the subject in need thereof. The human embryonic-mesenchymal stem cells may be in the form of a single cell, a cell culture, a solution or a pharmaceutical preparation. Agent would include but are not limited to drugs, proteins, DNA, RNA, and small molecules.

Provided herein is a method of selecting clinical grade hES-MSC for the treatment of autoimmune diseases, said hES-MSC having the following characteristics: (i) contain >95% of cells expressing group-1 markers; (ii) contain >80% of cells expressing group 2 markers; (iii) contain <5% of cells expressing group-3 markers (iv) expressing IL-10 and TGFβ; (v) contain <2% of cells expressing IL-6, IL-12 and TNFα; and (vi) contains <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4.

Provided herein is a method of modifying mesenchymal stem cells to produce a population of modified MSC having the following characteristics: (i) contain >95% of cells expressing group-1 markers; (ii) contain >80% of cells expressing group 2 markers; (iii) contain <5% of cells expressing group-3 markers (iv) expressing IL-10 and TGFβ; (v) contain <2% of cells expressing IL-6, IL-12 and TNFα; and (vi) contains <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4. Provided herein is a method of modifying MSC to produced a MSC with specific biomarker profile. Similar to hES-MSC, the modified MSC are useful for treatment of various diseases as listed in Section 5.14.

Provided herein are conditioned medium, concentrate of conditioned medium, cell lysate or other derivatives thereof that comprises one or more biomolecules secreted by the MSC as described. Provided herein is a method of using MSC as described herein as feeder cells for bone marrow hematopoietic stem cell expansion and umbilical-cord hematopoietic stem cell expansion. In certain embodiments, the MSC suitable for the disclosed method express Stro3. In certain embodiment, MSC is co-cultured with bone marrow hematopoietic stem cells and/or umbilical-cord hematopoietic stem cells. In certain embodiment, the MSC is mesenchymal stromal cells. Provided herein is a co-culture of MSC as described herein and bone marrow hematopoietic stem cells. Provided herein is a co-culture of MSC as described herein and umibilical-cord hematopoietic stem cells.

Also disclosed are kits comprising MSC described herein. In certain embodiments, the kits comprise hES-MSC and a cell delivery carrier.

4. BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIGS. 1A-D show a phase contrast images of hESC (CT2) differentiation into MSCs through multiple stages. (hESC: human embryonic stem cells; EB: embryo body; HB-enriched: hemagioblast-enriched; hES-MSC: hES cell derived mesenchymal stem cell)

FIGS. 2A-C depict flow cytometry analysis of cell surface markers on cells taken from a day 9 hemangioblast enriched cultures.

FIGS. 3A-I depict flow cytometry analysis of cell surface markers on cells taken from day 14 hemangioblast enriched cultures.

FIG. 4 shows the karyotyping of passage-10 hES-MSC derived from the H9-hESC line.

FIGS. 5A-C shows the disease scores of EAE mice treated with hES-MSCs prior to the onset of clinical disease. $10^6$ hES-MSC or undifferentiated hESC or saline control (PBS) was i.p. injected into the mice 6 days after the EAE inducing immunization. Panel A shows mice injected with hES-MSCs (CT2), panel B shows mice injected with hES-MSCs (MA09), and panel C shows mice injected with hES-MSCs (H9). N=5 mice per group, ***P<0.001.

FIGS. 6A-F are bar graphs depicting cumulative disease score (panels A-C) and the maximal disease scores (panels D-F) from days 28-32 post immunization for the mice shown in FIG. 5. N=5 mice per group, **P<0.01.

FIG. 7 is a graph of disease scores of EAE mice treated with hES-MSC or saline control (PBS) post-clinical disease onset. $10^6$ hES-MSC were i.p injected into mice 18 days post-immunization. N=6 mice per group, ***P<0.001.

FIGS. 8A-B show flow cytometric analyses of regulatory T cells (CD25$^+$FoxP3$^+$) in the CNS of EAE mice treated with saline (PBS) or hES-MSCs derived from hESC line CT2 15 days after immunization.

FIGS. 9A-F show a bar graph depicting the total numbers of CD4$^+$, CD8$^+$ cells, Th1 CD4$^+$ T cells, and Th17 CD4$^+$ T cells in the CNS of EAE mice treated with saline control (PBS), hESC or hES-MSC on day 15 post-immunization (panels A-D). Panels E-F show the expression of IL-17 and IFN-gamma in CD4$^+$ T cells from PBS or hES-MSC treated EAE mice. N=4 mice per group, *P<0.05, **P<0.01.

FIGS. 10A-D show immunohistochemical detection of myelin basic protein (MBP; red), CD3 for T cells (green) and IBA1 for microglia (green) on lumbar spinal cord cross sections from EAE mice treated with either hES-MSC (panels a and c) or saline (PBS) (panels b and d).

FIG. 11 shows a quantitative analysis of myelin basic protein (MBP) in the spinal cord was performed using relative fluorescent intensity (RFI) measurement of MBP expression in digitally captured spinal cord hemisections. N=4 to 6 mice per group, **P<0.02.

FIGS. 12A-C show graphs of disease scores of EAE mice treated with saline (PBS), bone marrow derived MSCs (BM-MSC) or hES-MSC prior to the onset of clinical disease. Panel A shows 5 groups of mice treated with either PBS, hES-MSCs (MA09) or BM-MSCs from one of three different sources. Panel B shows mice treated with PBS, BM-MSC or hES-MSC (CT2) prior to clinical disease onset. Panel C shows mice treated with PBS, BM-MSC or hES-MSC (MA09). For all experiments shown, N=5 mice per group, ***P<0.001 between hES-MSC and any of the three BM-MSC treated groups.

FIGS. 13A-D shows the total number of $CD4^+$, $CD8^+$, Th1 or Th17 T cells in the CNS of EAE mice treated with saline control (PBS), BM-MSCs (BM-MSC lines 1, 2 or 3) or hES-MSC. (N=4 mice per group, *P<0.05, **P<0.01).

FIGS. 14A-E show the qualitative analysis of myelin content in spinal cord cross-sections of EAE mice treated with saline (PBS), BM-MSCs (BM-MSC lines 1, 2, or 3), or hES-MSCs using Fluoromyelin stain (green) and counterstained with DAPI (blue) to indicate infiltration of nucleated cells.

FIGS. 15A-B show the localization of fluorescently labeled hES-MSC or BM-MSC in spinal cord cryosections (60 μm) taken from EAE mice 14 post immunization. Mice received an i.p. administration of $GFP^+$hESC-MSC or $GFP^+$ BM-MSC or PBS control. Mice were euthanized following the MSC cell administration and immunostained for GFP (green; to track the injected hES-MSC or BM-MSC cells), CD31 (red; vascular) and DRAQ5 (blue; cell nuclei). Panel A is parenchymal inflamed venules. Panel B shows meningeal venules. Isosurface rendered 3D reconstruction of the selected ROI (white dotted box) are shown next to the original images for enhanced spatial perspective. The insets show the GFP-DRAQ5 (upper inset image) and isolated GFP (lower inset image) channels separately.

FIGS. 16A-B show the proportion of proliferating $CD4^+$ or $CD8^+$ T cells, respectively, co-cultured in vitro with one of two hES-MSCs (MA09 or CT2) or one of three BM-MSC lines (1, 2 or 3) or no MSCs (PBS). T cells were stimulated with the indicated concentration of anti-CD3 antibody and proliferation was measured by CFSE dilution using flow cytometry. T cells and MSCs were mixed at a ratio of 10:1. N=3 replicates per group.

FIG. 17 shows the proliferation of $CD4^+$ or $CD8^+$ T cells co-cultured with BM-MSC, hES-MSC or no MSC (control) and stimulated with 0 μg/ml (NC), 0.1 μg/ml or 0.3 μg/ml anti-CD3 antibody. Flow cytometry histogram plots show the percentage of divided $CD4^+$ or $CD8^+$ T cells with diluted CFSE signal.

FIGS. 18A-J depicts intracellular FACS staining of $IFN\gamma^+$ or $IL-17^+$ naive $CD4^+$ T cells co-cultured with hES-MSC or one of three BM-MSC cell lines (#2, #3, or #6) or no MSCs (control) and stimulated with TPA/ionomycin stimulation of hES- or BM-MSC incubated with mouse naïve $CD4_+$ T cells, followed by Th1 or Th17 differentiation for 5 days. Data shown are from 1 of 4 independent experiments.

FIGS. 19A-B show relative gene expression levels from hES-MSC or BM-MSC as determined by microarray analysis. N=2, *P<0.05, **P<0.01.

FIGS. 20A-F show the expression of IL-6 and IL-10 in 3 individual BM-MSC and 3 individual hES-MSC lines by intracellular FACS staining.

FIGS. 21A-D shows the expression of IL-6 by intracellular FACS staining of IL-6 in BM-MSC or hES-MSC (CT2) cultured with IFNγ. NC is negative control.

FIGS. 22A-C show the percent of proliferating CFSE labeled $CD8^+$ T cells stimulated with various doses of anti-CD3 antibody and co-cultured with or without one of three BM-MSC lines (#2, #3 or #6) at a ratio of 10:1. Anti-human IL-6 antibody (10 μg/ml) or isotype control (IgGk) was added to the cultures as indicated. N=4 replicates per data point, **P<0.01.

FIGS. 23A-B show that IL-6 neutralizing antibody (αIL6) enhances suppression of BM-MSC on CD4 and CD8 T cell proliferation in vitro; NC=T cells cultured without MB-MSC or anti-IL6.

FIGS. 24A-J show the proportion of $IFN\gamma^+$ or $IL-17^+$ $CD4^+$ T cells detected via intracellular FACS staining after TPA/ionomycin stimulation in vitro. hES- or BM-MSC were incubated with mouse naïve $CD4^+$ T cells at a ratio of 1:10 under the Th17 differentiation conditions for 5 days, in the presence or absence of 10 μg/ml anti-human IL-6 antibody.

FIGS. 27A-B show the localization of non-irradiated hES-MSC or irradiated (Irr-hES-MSC) expressing D-Luciferin at various days following injection into EAE mice. Images were taken using the Xenogen IVIS 100 system. Non-irradiated (panels A) and irradiated (panels B) luciferase-expressing hES-MSCs (CT2) are shown in the dorsal and ventral images of EAE mice.

Figure 28:
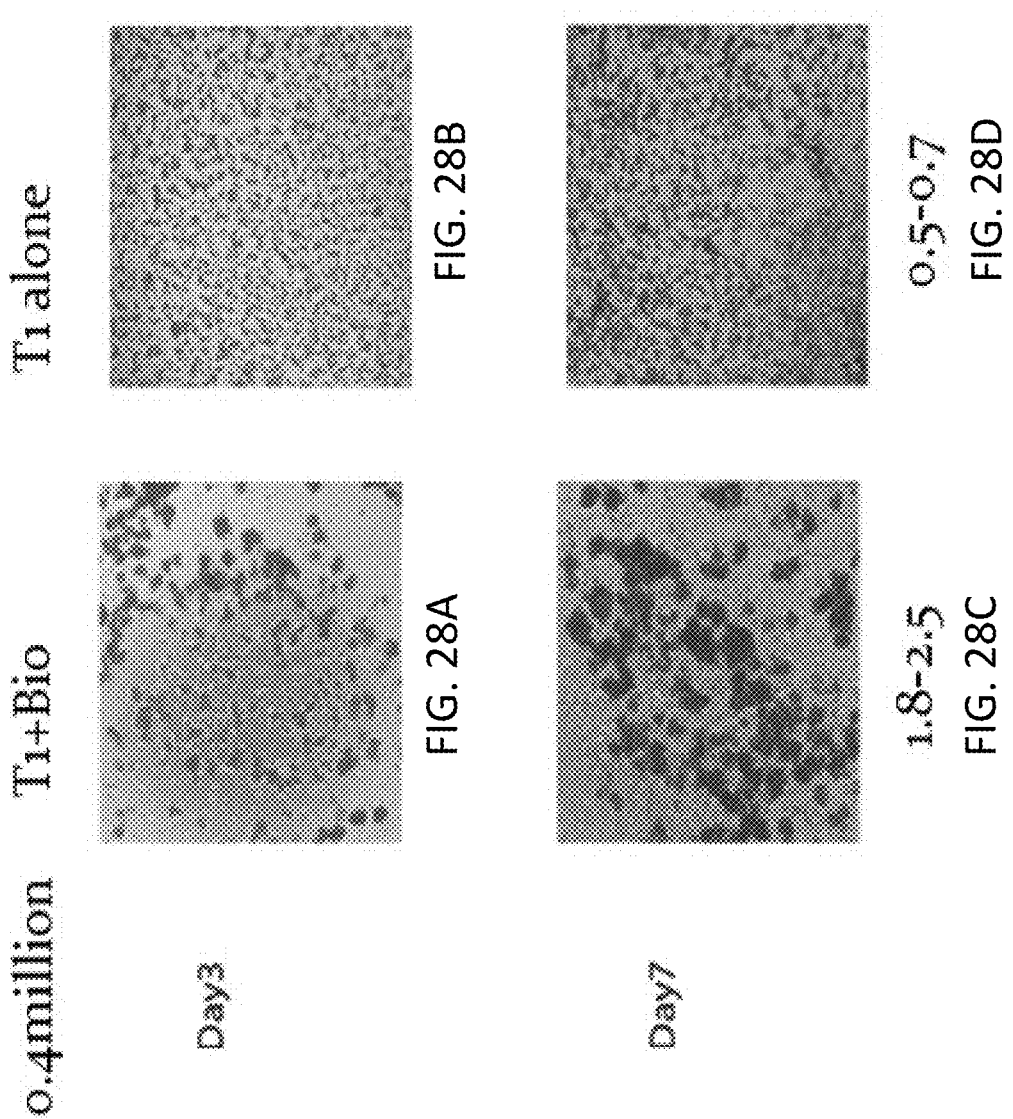
Figure 29:
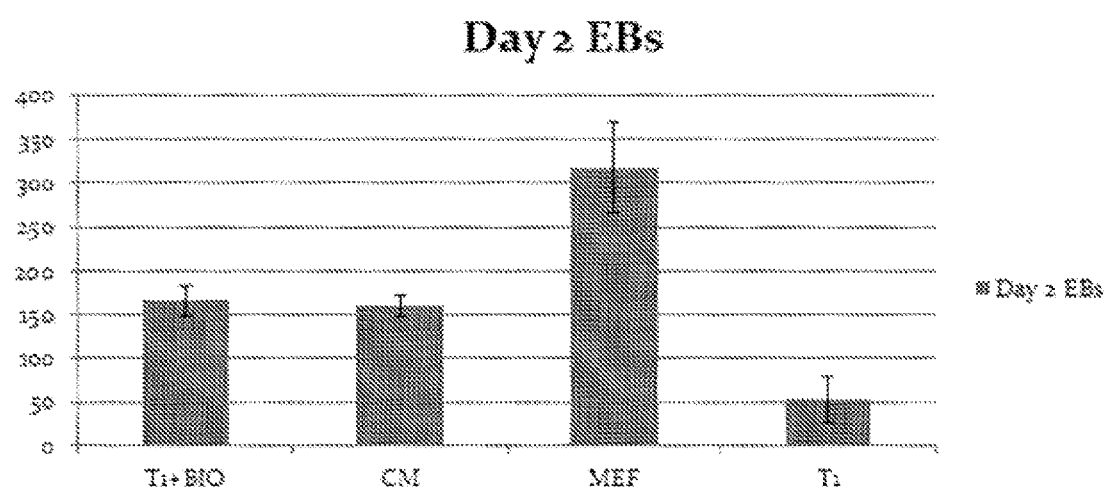
Figure 30:
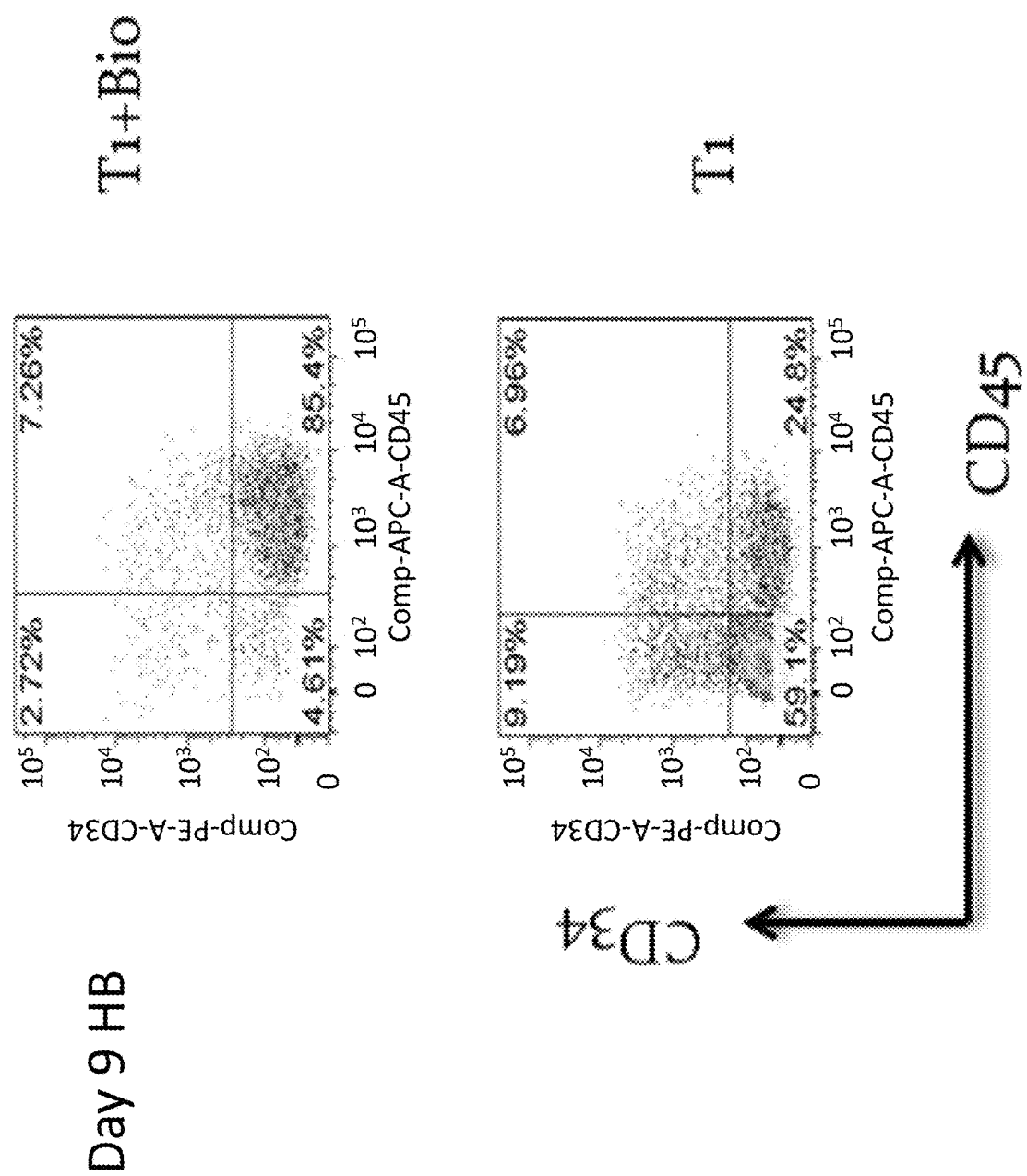

FIGS. 28A-D show the effect of the GSK3 inhibitor BIO ((2'Z,3'E)-6-Bromoindirubin-3'-oxime, 6-BIO) on the differentiation of embryoid bodies (EB) from hES cells. BIO significantly increases BM formation and the number of cells obtained by day 7 in culture FIG. 29 shows a bar chart show BIO increase the EB formation numbers FIG. 30 shows flow cytometry plots showing BIO treatment increases the hemangioblast forming efficiency.

Figure 31:
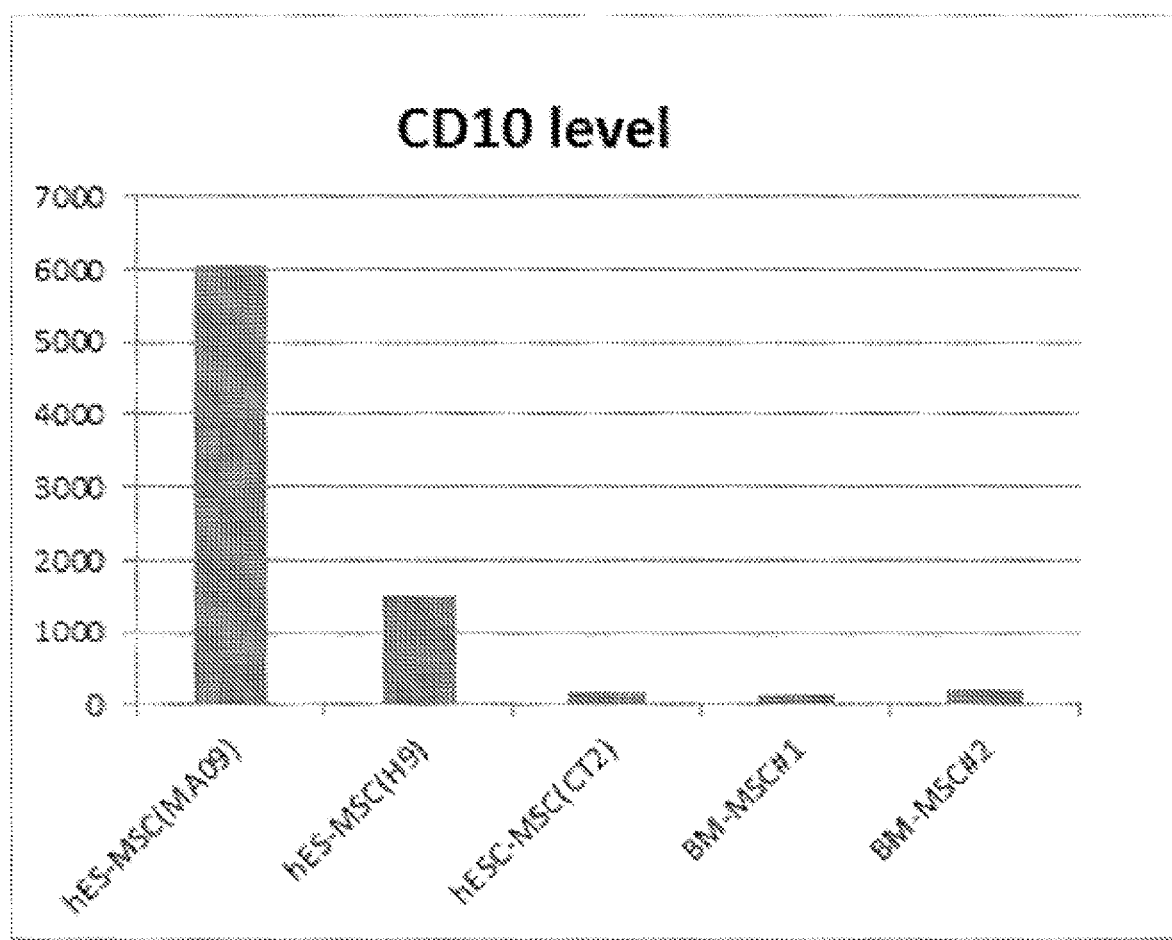

FIG. 31 shows microarray analysis of CD10 expression level of different hES-MSC lines and BM-MSC lines.

5. DETAILED DESCRIPTION OF THE INVENTION

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term hESC means human embryonic stem cells that encompass pluripotent stem cells produced from embryo, inner cell mass, blastomere or a cell line.

The term "hES-HB-MSC" are mesenchymal stem cells that are derived via hemangioblast or hemangio-colony forming middle step.

The term "hES-MSC" or hES-MSCs" or "human embryonic mesenchymal stem cells" or human embryonic stem cell derived mesenchymal stem cells" or "hES-MSC population" as used herein means mesenchymal-like stem cells, mesenchymal-like stromal cells, mesenchymal stem cells or mesenchymal stromal cells, derived from human embryonic stem cells or derived from induced pluripotent stem cells using any methods. hES-MSC as used herein includes individual cells, cell lines, batches, lots or populations of hES-MSC.

The term "clinical grade hES-MSC" as used herein means hES-MSC which contains characteristics that are suitable for use in clinical use for human, avian or other mammals. Clinical grade hES-MSC as used herein includes individual cells, cell lines, batches, lots or populations of MSC.

The term "hES-MSC population" as used herein means a population of hES-MSC cells which contains cells that have characteristics that are suitable for use in treatment and cells that do not have characteristics that are suitable for use in treatment.

The terms "iPS-MSC" and "iPS-MSCs" and "human induced pluripotent stem cells derived mesenchymal stem cells" are be used interchangeably throughout. These cells can be described based upon numerous structural and functional properties including but not limited to, expression or lack of expression of one or more markers. iPS-MSCs are multipotent and capable of differentiating to give rise to cell types of other lineages.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "in need thereof" would be a subject known or suspected of having or being at risk of developing a disease including but not limited to multiple sclerosis and other T cell related autoimmune diseases, or diseases related to the central nervous system or the blood-brain barrier or the blood-spinal cord barrier.

A subject in need of treatment would be one that has already developed the disease. A subject in need of prevention would be one with risk factors of the disease.

The term "agent" as used herein means a substance that produces or is capable of producing an effect and would include, but is not limited to, chemicals, pharmaceuticals, drugs, biologics, small molecules, antibodies, nucleic acids, peptides, and proteins.

5.2 In Vitro Differentiation of Embryonic Stem Cells Through Hemangioblasts to Obtain Mesenchymal-Like Stem Cells The present invention provides a method for generating and expanding mesenchymal-like stem cells (MSCs) from human hemangioblasts (HB) derived from embryonic stem cells (hES). These resulting cells are designated hES-MSCs. These hES-MSCs can be isolated and/or purified.

MSC-like cells have been derived from human embryonic stem cells by various methods (Barbieri et al. (2005); Olivier et al. (2006); Sanchez et al. (2011); Brown et al. (2009)). However, all of these methods involve co-culturing and hand-picking procedures that limit yield and purity and result in varying quality of cells.

To solve these problems, the method of the current invention derives MSCs from embryoid bodies and then hemangioblasts. It was hypothesized that because mesenchymal cells and hemangioblasts both originate from the mesodermal progenitors (MP) (Huber et al. (2004)), that a method to derive HB from hESC via EB would actually enrich MP that can further differentiate into either HB or MSCs depending on subsequent culture conditions. As shown in FIG. 1, MSCs were obtained by using a hESC to EB to HB to MSCs.

Although hESC express low levels of MHC antigens, it has been found that many cell types differentiated from hESC have increased expression of these antigens (Draper et al., 2002; Drukker et al., 2006; Drukker et al., 2002), thus, causing great concern for immunorejection of the differentiated cells if transplanted into patients. In contrast, MSC express low levels of costimulatory molecules and major MHC antigens, and have been used in allogeneic or xenograft models to treat autoimmune diseases (Gordon et al., 2008b; Grinnemo et al., 2004; Rafei et al., 2009a; Rafei et al., 2009b; Tse et al., 2003). hES-MSCs, like adult tissue-derived MSC, express low levels of the co-stimulatory molecules and MHC antigens, and do not require long-term engraftment to exert immunosuppressive effect, thus, there is no concern for immunorejection due to mismatch of MHC antigens between MSC and the recipient (Ohtaki et al., 2008; Uccelli and Prockop, 2010a). One hESC line is sufficient to generate hES-MSC at large scale, in an endless supply, and with easy quality control, suitable for industrial production as a potential therapy to treat patients with MS and other T cell-based autoimmune diseases.

The methods for obtaining EB from hES and then dissociating the EB into HB has been previously reported in Lu et al. (2007) and Lu et al. (2008) as well as in United States Patent Application Publication No. 2012/0027731 all hereby incorporated herein in their entirety.

Human hemangio-colony forming cells can be generated from human embryonic stem cells. Such embryonic stem cells include embryonic stem cells derived from or using, for example, blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means.

Additionally or alternatively, hemangio-colony forming cells can be generated from other embryo-derived cells. For example, hemangio-colony forming cells can be generated (without necessarily going through a step of embryonic stem cell derivation) from or using plated embryos, ICMs, blastocysts, trophoblast/trophectoderm cells, one or more blastomeres, trophoblast stem cells, embryonic germ cells, or other portions of a pre-implantation-stage embryo or embryo-like structure, regardless of whether produced by fertilization, somatic cell nuclear transfer (SCNT), parthenogenesis, androgenesis, or other sexual or asexual means. Similarly, hemangio-colony forming cells can be generated using cells or cell lines partially differentiated from embryo-derived cells. For example, if a human embryonic stem cell line is used to produce cells that are more developmentally primitive than hemangio-colony forming cells, in terms of development potential and plasticity, such embryo-derived cells could then be used to generate hemangio-colony forming cells.

Additionally or alternatively, hemangio-colony forming cells can be generated from other pre-natal or peri-natal sources including, without limitation, umbilical cord, umbilical cord blood, amniotic fluid, amniotic stem cells, and placenta.

It is noted that when hemangio-colony forming cells are generated from human embryonic tissue a step of embryoid body formation may be needed. However, given that embryoid body formation serves, at least in part, to help recapitulate the three dimensional interaction of the germ layers that occurs during early development, such a step is not necessarily required when the embryo-derived cells already have a structure or organization that serves substantially the same purpose as embryoid body formation. By way of example, when hemangio-colony forming cells are generated from plated blastocysts, a level of three dimensional organization already exists amongst the cells in the blastocyst. As such, a step of embryoid body formation is not necessarily required to provide intercellular signals, inductive cues, or three dimensional architecture.

Hemangio-colony forming cells can be generated from embryo-derived cells. In certain embodiments, the embryo-derived cells are embryonic stem cells. In certain other embodiments, the embryo-derived cells are plated embryos, ICMs, blastocysts, trophoblast/trophectoderm cells, one or more blastomeres, trophoblast stem cells, or other portions of an early pre-implantation embryo. For any of the foregoing, the embryo-derived cells may be from embryos produced by fertilization, somatic cell nuclear transfer (SCNT), parthenogenesis, androgenesis, or other sexual or asexual means.

The human embryonic stem cells or induced pluripotent stem cell may be the starting material of this method. The embryonic stem cells or iPS may be cultured in any way known in the art, such as in the presence or absence of feeder cells. Adding GSK3 inhibitor BIO at 0.05 uM-0.2 uM can increase the embryoid body formation and subsequent hemangioblast forming efficiency, shortening the culture time.

In the examples set forth herein, four hESC cell lines were used, H9 (derived from WiCell Research Institute) (Thomson et al. (1998), CT2 (derived from University of Connecticut Stem Cell Core (Lin et al. (2010)); MA09 (an FDA approved, clinical-grade cell line derived at Advanced Cell Technology, Inc.) (Klimanskaya et al (2006)); and ES03-Envy (Envy, a GFP-labeled line, derived at ES International) (Costa et al. (2005)).

In the first step of this method for generating and expanding human hemangioblast cells to obtain MSCs, human stem cells are grown in serum-free media and are induced to differentiate into embryoid bodies. To induce embryoid body formation, embryonic stem cells may be pelleted and resuspended in serum-free medium such as DMEM/F12, HPGM (Lonza), StemSpan H3000 (Stemcell Technologies), Stempro-34, QBSF-60, Xvivo-15, IMDM, Stemline I or II media (Sigma.™) supplemented with one or more morphogenic factors and cytokines and then plated on low attachment culture dishes. Morphogenic factors and cytokines may include, but are not limited to, bone morphogenic proteins (e.g., BMP-2, BMP-4, or BMP-7, but not BMP-3) and VEGF, SCF and FL. Bone morphogenic proteins and VEGF may be used alone or in combination with other factors. The morphogenic factors and cytokines may be added to the media from 0-72 hours of cell culture. Following incubation under these conditions, incubation in the presence of early hematopoietic expansion cytokines, including, but not limited to, thrombopoietin (TPO), Flt-3 ligand, and stem cell factor (SCF), allows the plated ES cells to form EBs. In addition to TPO, Flt-3 ligand, and SCF, VEGF, BMP-4, may also be added to the media. In one embodiment, human ES cells are first grown in the presence of BMP-4 and $VEGF_{165}$ (e.g., 25-100 ng/ml), followed by growing in the presence of BMP-4, $VEGF_{165}$, SCF, TPO, and FLT3 ligand (e.g., 10-50 ng/ml). The additional factors may be added 48-72 hours after plating.

Next, human hemangioblast cells are isolated from early embryoid bodies (EBs). Isolating hemangioblast cells from early EBs supports the expansion of the cells in vitro. For human cells, hemangioblast cells may be obtained from EBs grown for less than 10 days. In certain embodiments of the present invention, hemangioblast cells arise in human EBs grown for 2-6 days. According to one embodiment, hemangioblast cells are identified and may be isolated from human EBs grown for 4-6 days. In other embodiments, human EBs are grown for 2-5 days before hemangioblast cells are isolated. In certain embodiments, human EBs are grown for 3-4.5 days before hemangioblast cells are isolated.

In an embodiment of the method, early EBs are washed and dissociated, with TrypLE-LE (Invitrogen), Trypsin/EDTA or collagenase B. A select number of cells (e.g., $2-5 \times 10^5$ cells) are then mixed with serum-free methylcellulose medium optimized for hemangioblast cell growth, such as BL-CFU medium, for example Stem Cell Technologies Catalogue H4436, H4536, or hemangioblast cell expansion medium (HGM), or any medium containing 1.0% methylcellulose in MDM, 1-2% Bovine serum albumin, 0.1 mM 2-mercaptoethanol, 10 µg/ml rh-Insulin, 200 µg/ml iron saturated human transferrin, 20 ng/ml rh-GM-CSF, 20 ng/ml rh-IL-3, 20 ng/ml rh-IL-6, 20 ng/ml rh-G-CSF)("rh" stands for "recombinant human"). This medium may be supplemented with early stage cytokines including, but not limited to, EPO, TPO, SCF, FL, Flt-3, VEGF, BMPs such as BMP2, BMP4 and BMP7, but not BMP3 and HOXB4 (or another homeobox protein). In certain embodiments, erythropoietin (EPO) is added to the media. In further embodiments, EPO, SCF, VEGF, BMP-4 and HoxB4 are added to the media. In additional embodiments, the cells are grown in the presence of EPO, TPO and FL. In certain embodiments where H9 is the starting human ES cell line, EPO, TPO and FL are added to the media. In addition to EPO, TPO and FL, media for cells derived from H9 or other ES cells may further comprise VEGF, BMP-4, and HoxB4.

The cells so obtained by this method (the cells may be in BL-CFU medium), which include hemangioblast cells, are plated onto ultra-low attachment culture dishes and incubated in a $CO_2$ incubator to grow hemangioblast colonies. Some cells may be able to form secondary EBs. Following approximately 3-6 days, and in some instances 3-4.5 days, hemangioblast colonies are observed. Hemangioblast colonies may be distinguished from other cells such as secondary EBs by their distinctive grape-like morphology and/or by their small size. In addition, hemangioblasts may be identified by the expression of certain markers (e.g., the expression of both early hematopoietic and endothelial cell markers) as well as their ability to differentiate into at least both hematopoietic and endothelial cells. For example, while hemangioblasts lack certain features characteristic of mature endothelial or hematopoietic cells, these cells may be identified by the presence of certain markers (such as, for example, CD133, SCA-1, CD34, CD45, CD31, cKit, Nestin$^+$, Stro-1, Stro-3, CD71$^+$). Hemangioblasts may also express GATA-1 and GATA-2 proteins, CXCR-4, and TPO and EPO receptors. Further, hemangioblasts may be characterized by the expression of certain genes, those genes associated with hemangioblasts and early primitive erythroblast development, such as, for example, SCL, LMO2, FLT-1, embryonic fetal globin genes, NF-E2, GATA-1, EKLF, ICAM-4, glycophoriuns, and EPO receptor).

The hemangioblast cells may be isolated by size and/or morphology by the following procedure. After 3 to 7 days of growth, the cell mixture contains EBs, which are round and represent a clump of multiple cells, and hemangioblasts, which are grape-like, smaller than the EBs, and are single cells. Accordingly, hemangioblasts may be isolated based on their morphology and size. The hemangioblast cells may be manually picked, for example, when observing the cell mixture under a microscope. The cells may subsequently grow into colonies, each colony having between 100-150 cells.

In one embodiment, hemangioblast cells are digested to form single cells with TrypLE, Trypsin or collagenase B. The single cells are re-suspended in a medium optimized for mesenchymal stem cell growth such as alpha-MEM containing 2-20% of fetal bovine serum, human AB serum, DMEM-high glucose containing 2-20% of fetal bovine serum, the FBS can be replaced with 5-20% of knock-out serum replacement (KOSR) or bovine serum albumin (BSA), or any other commercial available serum free MSC culture mediums. In certain embodiments, Serum, KOSR or BSA is added in a concentration of from about 5-20%. In certain embodiments, Fetal bovine serum is preferred. In certain embodiments, cells are cultured at a density of about 10-1000 cells/cm$^2$. In certain embodiments, the cells are cultured in an environment that mimics the extracellular environment of tissues, such as Matrigel.

After approximately 24 hours, a number of cells (5-10%) attached to the culture plate and approximately 6-14 days later, mesenchymal stem cells begin to differentiate from the HBs. MSCs are identified by a small cell with spindle-like morphology. MSCs can also be identified by the cell surface expression of CD146 and CD166 and by the absence or low expression of certain cell surface markers such as CD31, CD34, and CD45. MSCs are also characterized as multipotent and able to differentiate into chondrocytes, osteocytes, and adipocytes. CD10 expression level maybe different from the cell source, CT2 and H9-MSC express low level of CD10 whereas MA09-MSC express high level of CD10, which is not related to its immunosuppressive function but may related to other function like fibrosis and downstream differentiation. In certain embodiments, less than 28%, 27%, 26%, 25%, 20%, 15%, 10%, 5%, 4%, 3%, 2%, 1% of the hES-MSC express CD10.

In a further embodiment of the present invention, an additional step of irradiating the hES-MSCs is performed. This irradiation can be accomplished with the use of any method known in the art that emits radiation including but not limited to gamma irradiation e.g. Cesium-137 gamma irradiation, or photon radiation using X-ray. The preferred amount of radiation to be administered is about between 5 and 20000 gy, more preferably about between 50 and 100 gy, and most preferably 80 gy.

5.3 Human Embryonic Stem Cell Derived Mesenchymal Stem Cells (hES-MSC) and iPS-MSC One embodiment of the present invention is the human embryonic stem cell derived mesenchymal stem cells, designated hES-MSC. These cells are unique and have a variety of therapeutic and other uses. Thus, the present invention included various preparations, including pharmaceutical preparations, and compositions comprising hES-MSCs.

The terms "hES-MSC" and "hES-MSCs" and "human embryonic stem cell derived mesenchymal stem cells" and "human embryonic mesenchymal stem cells" will be used interchangeably throughout. These cells can be described based upon numerous structural and functional properties including but not limited to, expression or lack of expression of one or more markers. hESC-MSCs are multipotent and capable of differentiating to give rise to cell types of other lineages.

The terms "iPS-MSC" and "iPS-MSCs" and "human induced pluripotent stem cells derived mesenchymal stem cells" will be used interchangeably throughout. These cells can be described based upon numerous structural and functional properties including but not limited to, expression or lack of expression of one or more markers. iPS-MSCs are multipotent and capable of differentiating to give rise to cell types of other lineages.

Human embryonic stem cell derived mesenchymal stem cells are identified and characterized based upon their structural properties. Specifically, hES-MSCs are characterized by small cell bodies with a fibroblast like and spindle like morphology.

hES-MSCs and iPS-MSC are identified or characterized by the expression or lack of expression as assessed on the level of DNA, RNA or protein, of one or more cell markers. hESC-MSCs can be identified as expressing cell surface marker CD73, or expressing at least one or more of the following cell surface markers: CD90, CD105, CD13, CD29, CD54, CD44, or CD146 and CD166 or not expressing or expressing at a low level at least one of the following cell surface markers: CD34, CD31, or CD45.

Alternatively or additionally, hES-MSCs are identified or characterized based upon their low level of expression of one or more pro-inflammatory proteins, MMP2, RAGE, IFNγR1, IFNγR2, IL-12, TNFα, IL-6, and VCAM1. This profile of gene expression is in contrast to bone marrow derived mesenchymal stem cells. In particular, IL-6 was expressed much higher in BM-MSCs than in hES-MSCs. IL-6 is a pleiotropic cytokine involved in crosstalk between hematopoietic/immune cells and stromal cells, including the onset and resolution of inflammation.

Alternatively or additionally, hES-MSCs, similar to other kind of MSC, are identified by the expression of high levels of immunosuppressive non-classical MHC antigen HLA-G and HLA-ABC and low levels or no expression of MHC class-II antigen HLA-DR and co-stimulatory molecule CD80.

The hES-MSCs are also characterized in their ability to inhibit T cell proliferation after stimulation in vitro. This characteristic is in contrast to BM-MSCs which has less potency in inhibiting T cell proliferation after stimulation in vitro.

Thus, the human embryonic stem cell-derived mesenchymal stem cells described herein have at least one of the following characteristics: 1. Differentiate into chondrocytes, osteocytes and/or adipocytes; 2. Have a fibroblast-like morphology; 3. Express CD73, CD90, CD105, CD13, CD29, CD54, CD44, CD146 and/or CD166; 5. Express at low levels or do not express CD34, CD31, and/or CD45; 6. Express at low levels or do not express MMP2, RAGE, IFNγR1, IFNγR2, IL-12, TNFα, IL-6, and/or VCAM1, particularly IL-6; 7. Express MHC antigen HLA-G and/or HLA-ABC and express at low levels or do not express HLA-DR and/or CD80; and 8. Inhibit T cell proliferation after stimulation in vitro. In certain embodiments, the hES-MSCs have at least two, at least three, at least four, at least five, at least six, at least seven or all eight six characteristics.

Additionally, the human embryonic stem cell derived mesenchymal stem cells described herein have the unique ability to cross the blood-brain barrier (BBB) and the blood-spinal cord barrier (BSCB), making them uniquely suited for therapeutic and diagnostic applications. As shown herein, the hES-MSCs described herein have the ability to migrate in and out of the vessels of the spinal cord, across the BSCB, to fulfill functions in the CNS, including but not limited to the delivery of therapeutic and diagnostic agents. This is in contrast to BM-MSCs which do not have this ability.

In certain embodiments, the hES-MSC is irradiated either by gamma or x-ray radiation. This embodiment would include human embryonic stem cell derived mesenchymal stem cells with at least one of the following characteristics listed above, having at least two, at least three, at least four, at least five, at least six, at least seven, all eight characteristics and that the hES-MSC have been subjected to irradiation.

In another embodiment, the cell culture comprises human embryonic stem cell derived mesenchymal stem cells. In certain embodiments, the hES-MSCs differentiate into chondrocytes, osteocytes and/or adipocytes. In certain embodiments, the cells express CD73, CD90, CD105, CD13, CD29, CD54, CD44, CD146, and/or CD166. In certain embodiments, the cells express at low levels or do not express CD34, CD31, and/or CD45. In certain other embodiments, the cells express at low levels or do not express MMP2, RAGE, IFNγR1, IFNγR2, IL-12, TNFα, IL-6, and/or VCAM1, especially IL-6. In certain other embodiments, the cells express MHC antigen HLA-G and/or HLA-ABC and express at low levels or do not express HLA-DR and/or CM. In certain other embodiments, the cells inhibit T cell proliferation after stimulation in vitro. In certain embodiments, the cells can cross the blood-brain barrier and the blood-spinal cord barrier. In certain embodiments, the cells have been irradiated.

In another aspect, provided herein is a pharmaceutical preparation comprising human embryonic stem cell derived mesenchymal stem cells. In certain embodiments, the hES-MSCs can differentiate into chondrocytes, osteocytes and/or adipocytes. In certain embodiments, the cells express CD73, CD90, CD105, CD13, CD29, CD54, CD44, CD146 and/or CD166. In certain embodiments, the cells express at low levels or do not express CD34, CD31, and/or CD45. In certain other embodiments, the cells express at low levels or do not express MMP2, RAGE, IFNγR1, IFNγR2, IL-12, TNFα, IL-6, and/or VCAM1, especially IL-6. In certain other embodiments, the cells express MHC antigen HLA-G and/or HLA-ABC and express at low levels or do not express HLA-DR and/or CM. In certain other embodiments, the cells inhibit T cell proliferation after stimulation in vitro.

In certain embodiments, the cells can cross the blood-brain barrier and the blood-spinal cord barrier. In certain embodiments, the cells have been irradiated. The pharmaceutical preparation can be prepared using any pharmaceutically acceptable carrier or excipient.

In certain embodiments, the composition or pharmaceutical preparation comprises at least at least 10,000 human embryonic-mesenchymal stem cells, at least 50,000 human embryonic-mesenchymal stem cells, at least 100,000 human embryonic-mesenchymal stem cells, at least 500,000 human embryonic-mesenchymal stem cells, at least $1 \times 10^6$ human embryonic-mesenchymal stem cells, at least $5 \times 10^6$ human embryonic-mesenchymal stem cells, at least $1 \times 10^7$ human embryonic-mesenchymal stem cells, at least $5 \times 10^7$ human embryonic-mesenchymal stem cells, at least $1 \times 10^8$ human embryonic-mesenchymal stem cells, at least $5 \times 10^8$ human embryonic-mesenchymal stem cells, at least $1 \times 10^9$ human embryonic-mesenchymal stem cells, at least $5 \times 10^9$ human embryonic-mesenchymal stem cells, or at least $1 \times 10^{10}$ human embryonic-mesenchymal stem cells.

In certain embodiments, the invention provides a cryopreserved preparation of human hemangio-colony cells or cells partially or terminally differentiated therefrom.

In certain embodiments, the invention provides the therapeutic use of hES-MSCs, or compositions or preparations of hES-MSCs, including irradiated hES-MSCs. Such cells and preparations can be used in the treatment of any of the conditions or diseases detailed throughout the specification, as well as in a delivery system for agents across the blood-brain barrier and the blood-spinal cord barrier.

5.4 Selecting and Producing hES-MSC Populations

Provided herein is a method of identifying highly immunosuppressive hES-MSC by identifying a biomarker profile of the highly immunosuppressive hES-MSC that are clinical grade for use in therapy. In certain embodiment, the clinical grade hES-MSC have the following characteristics: (i) contain >95% of cells expressing group-1 markers; (ii) contain >80% of cells expressing group 2 markers; (iii) contain <5% of cells expressing group-3 markers (iv) expressing IL-10 and TGFβ; (v) contain <2% of cells expressing IL-6, IL-12 and TNFα; and (vi) contains <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4.

In certain embodiments, the method comprises measuring the differential expression of markers that encode anti-inflammatory factors ("AIF") and pro-inflammatory factors ("PIF"). In certain embodiments, the AIF is IL-10, TGFβ2. In certain embodiments, the PIF is upregulated. In certain embodiments, hES-MSC express at least 1.5 fold of the above markers as compared to BM-MSC. In certain embodiments, the PIF is IL-6, IL-12, TNFα, CCL2, VCAM1, RAGE, MMP2. In certain embodiment, the PIF is down-regulated. In certain embodiments, hES-MSC express at least half of the above markers as compared to BM-MSC In another embodiment, highly immunosuppressive hES-MSC has a lower ratio of IL-6+ cells as compared to BM-MSC. In certain embodiments, highly immunosuppressive hES-MSC has less than 5%, 4%, 3%, 2%, 1% of IL-6 positive cells. In certain embodiment, hES-MSC express low level of IL12, TNFα, RAGE and other PIF. In certain embodiment, hES- MSC may express high level of TGFβ2 and IL-10. In certain embodiments, the expression of markers are compared to expression in BM-MSC.

Provided herein is a qualification procedure for clinical grade hES-MSC population. Expression of specific markers are measured in a population of hES-MSC to determine whether they are suitable for therapeutic use. The markers include, for example, (1) MSC-specific markers (set 1): CD73, CD90, CD105, CD166, and CD44, (2) MSC-specific markers (set 2): CD13, CD29, CD54, CD49E, SCA-1, and STRO-1, (3) hematopoietic stem/progenitor markers: CD45 and CD34, and endothelial cell marker CD31, (4) immunogenic markers: HLA-ABC, HLA-G, CD80, and CD86, (5) cytokines: IL-10, TGFβ, IL-6, and IL-12, and (6) pluripotency markers: OCT4, NANOG, TRA-1-60, and SSEA-4. In certain embodiments, hES-MSC population contains more than 95%, 96%, 97%, 98%, 99% of cells that express at least one group 1 markers. In certain embodiments, hES-MSC population contains more than 80%, 85%, 90%, 95%, 99% of cells that express at least one group 2 markers. In certain embodiments, hES-MSC population contains less than 0.1%, 0.08%, 0.05%, 0.03%, 0.02%, 0.01% of cells that express at least one group 3 marker. In certain embodiments, hES-MSC population contains more than 80%, 85%, 90%, 95%, 99% of cells that express IL-10 and/or TGFβ. In certain embodiments, hES-MSC population contains less than 5%, 4%, 3%, 2%, 1% of cells that express IL-6 and/or IL-12. In certain embodiments, hES-MSC population contains less 0.001% of cells that express at least one group 6 marker. The clinical-grade hES-MSC is compared with the preclinical-grade hES-MSC as a positive control. In certain embodiment, the hES-MSC is characterized through multicolor flow cytometry analyses and/or immunofluorescence. In certain embodiments, hES-MSC population express CCL2, CCL3, CCL4, CCL5, IL-1, IL-2, IL-4, IL-6, IL-8, IL-10, IL-17, TNFα, TGFβ, IFNγ, GM-CSF, G-CSF, bFGF, CXCL5, VEGF, TPO or a combination thereof. In certain embodiments, the hES-MSC population will also be analyzed for (1) presence of exogenous materials such as endotoxin and residual cytokines/growth factors, and/or (2) genomic abnormalities (via karyotyping and whole-genome sequencing).

Methods for determining the expression profile of the MSC are known in the art, including but not limited to, flow cytometry, multiplex microarray, RT-PCT, northern blot and western blot. In certain embodiments, the expression profile of the MSC are determined by cytometric bead array based multiplex cytokine analysis, luminex system based multiplex cytokine analysis, microarray RNA-seq, quantitative RT-PCR, Elispot Elisa, Elisa cytokine array, flow cytometry luciferase reporter system, fluroscence reporter system, histology staining, and Immunofluroscence staining.

5.4.1 Methods of Detecting Nucleic Acid Biomarkers

In specific embodiments, biomarkers in a biomarker profile are nucleic acids. Such biomarkers and corresponding features of the biomarker profile may be generated, for example, by detecting the expression product (e.g., a polynucleotide or polypeptide) of one or more markers. In a specific embodiment, the biomarkers and corresponding features in a biomarker profile are obtained by detecting and/or analyzing one or more nucleic acids expressed from a markder disclosed herein using any method well known to those skilled in the art including, but not limited to, hybridization, microarray analysis, RT-PCR, nuclease protection assays and Northern blot analysis.

In certain embodiments, nucleic acids detected and/or analyzed by the methods and compositions of the invention include RNA molecules such as, for example, expressed RNA molecules which include messenger RNA (mRNA) molecules, mRNA spliced variants as well as regulatory RNA, cRNA molecules (e.g., RNA molecules prepared from cDNA molecules that are transcribed in vitro) and discriminating fragments thereof.

In specific embodiments, the nucleic acids are prepared in vitro from nucleic acids present in, or isolated or partially isolated from a cell culture. which are well known in the art, and are described generally, e.g., in Sambrook et al., 2001, Molecular Cloning: A Laboratory Manual. 3.sup.rd ed. Cold Spring Harbor Laboratory Press (Cold Spring Harbor, N.Y.), which is incorporated by reference herein in its entirety.

5.4.1.1 Nucleic Acid Arrays

In certain embodiments, nucleic acid arrays are employed to generate features of biomarkers in a biomarker profile by detecting the expression of any one or more of the markers described herein. In one embodiment of the invention, a microarray such as a cDNA microarray is used to determine feature values of biomarkers in a biomarker profile. Exemplary methods for cDNA microarray analysis are described below, and in the examples.

In certain embodiments, the feature values for biomarkers in a biomarker profile are obtained by hybridizing to the array detectably labeled nucleic acids representing or corresponding to the nucleic acid sequences in mRNA transcripts present in a biological sample (e.g., fluorescently labeled cDNA synthesized from the sample) to a microarray comprising one or more probe spots.

Nucleic acid arrays, for example, microarrays, can be made in a number of ways, of which several are described herein below. Preferably, the arrays are reproducible, allowing multiple copies of a given array to be produced and results from said microarrays compared with each other. Preferably, the arrays are made from materials that are stable under binding (e.g., nucleic acid hybridization) conditions. Those skilled in the art will know of suitable supports, substrates or carriers for hybridizing test probes to probe spots on an array, or will be able to ascertain the same by use of routine experimentation.

Arrays, for example, microarrays, used can include one or more test probes. In some embodiments each such test probe comprises a nucleic acid sequence that is complementary to a subsequence of RNA or DNA to be detected. Each probe typically has a different nucleic acid sequence, and the position of each probe on the solid surface of the array is usually known or can be determined. Arrays useful in accordance with the invention can include, for example, oligonucleotide microarrays, cDNA based arrays, SNP arrays, spliced variant arrays and any other array able to provide a qualitative, quantitative or semi-quantitative measurement of expression of a marker described herein. Some types of microarrays are addressable arrays. More specifically, some microarrays are positionally addressable arrays. In some embodiments, each probe of the array is located at a known, predetermined position on the solid support so that the identity (e.g., the sequence) of each probe can be determined from its position on the array (e.g., on the support or surface). In some embodiments, the arrays are ordered arrays. Microarrays are generally described in Draghici, 2003, Data Analysis Tools for DNA Microarrays, Chapman & Hall/CRC, which is hereby incorporated herein by reference in its entirety.

5.4.1.2 RT-PCR

In certain embodiments, to determine the feature values of biomarkers in a biomarker profile of level of expression of one or more of the markers described herein is measured by amplifying RNA from a sample using reverse transcription (RT) in combination with the polymerase chain reaction (PCR). In accordance with this embodiment, the reverse transcription may be quantitative or semi-quantitative. The RT-PCR methods taught herein may be used in conjunction with the microarray methods described above. For example, a bulk PCR reaction may be performed, the PCR products may be resolved and used as probe spots on a microarray.

Total RNA, or mRNA is used as a template and a primer specific to the transcribed portion of the marker(s) is used to initiate reverse transcription. Methods of reverse transcribing RNA into cDNA are well known and described in Sambrook et al., 2001, supra. Primer design can be accomplished based on known nucleotide sequences that have been published or available from any publicly available sequence database such as GenBank. For example, primers may be designed for any of the markders described herein. Further, primer design may be accomplished by utilizing commercially available software (e.g., Primer Designer 1.0, Scientific Software etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts. The method of PCR is well known in the art. PCR, is performed, for example, as described in Mullis and Faloona, 1987, Methods Enzymol. 155:335, which is hereby incorporated herein by reference in its entirety.

PCR can be performed using template DNA or cDNA (at least 1 fg; more usefully, 1-1000 ng) and at least 25 µmol of oligonucleotide primers. A typical reaction mixture includes: 2 .mu.l of DNA, 25 µmol of oligonucleotide primer, 2.5 µl of 10 M PCR buffer 1 (Perkin-Elmer, Foster City, Calif.), 0.4 µl of 1.25 M dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

Quantitative RT-PCR ("QRT-PCR"), which is quantitative in nature, can also be performed to provide a quantitative measure of marker expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.) or as provided by Applied Biosystems (Foster City, Calif.) is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96-well plates so that samples derived from many individuals are processed and measured simultaneously. The Taqman system has the additional advantage of not requiring gel electrophoresis and allows for quantification when used with a standard curve.

A second technique useful for detecting PCR products quantitatively is to use an intercolating dye such as the commercially available QuantiTect SYBR Green PCR (Qiagen, Valencia Calif.). RT-PCR is performed using SYBR green as a fluorescent label which is incorporated into the PCR product during the PCR stage and produces a fluorescence proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol). Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the fluorescence increases giving a quantitative measurement of gene expression.

5.4.1.3 Northern Blot Assays

Any hybridization technique known to those of skill in the art can be used to generate feature values for biomarkers in a biomarker profile. In other particular embodiments, feature values for biomarkers in a biomarker profile can be obtained by Northern blot analysis (to detect and quantify specific RNA molecules. A standard Northern blot assay can be used to ascertain an RNA transcript size, identify alternatively spliced RNA transcripts, and the relative amounts of one or more genes described herein (in particular, mRNA) in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

5.4.2 Methods of Detecting Proteins

In specific embodiments of the invention, feature values of biomarkers in a biomarker profile can be obtained by detecting proteins, for example, by detecting the expression product (e.g., a nucleic acid or protein) of one or more markers described herein, or post-translationally modified, or otherwise modified, or processed forms of such proteins. In a specific embodiment, a biomarker profile is generated by detecting and/or analyzing one or more proteins and/or discriminating fragments thereof expressed from a marker disclosed herein using any method known to those skilled in the art for detecting proteins including, but not limited to protein microarray analysis, immunohistochemistry and mass spectrometry.

Standard techniques may be utilized for determining the amount of the protein or proteins of interest present in a cell culture. For example, standard techniques can be employed using, e.g., immunoassays such as, for example Western blot, immunoprecipitation followed by sodium dodecyl sulfate polyacrylamide gel electrophoresis, (SDS-PAGE), immunocytochemistry, and the like to determine the amount of protein or proteins of interest present in a sample. One exemplary agent for detecting a protein of interest is an antibody capable of specifically binding to a protein of interest, preferably an antibody detectably labeled, either directly or indirectly.

For such detection methods, if desired a protein from the cell culture to be analyzed can easily be isolated using techniques which are well known to those of skill in the art. Protein isolation methods can, for example, be such as those described in Harlow and Lane, 1988, Antibodies: A Laboratory Manual, Cold Spring Harbor Laboratory Press (Cold Spring Harbor, N.Y.), which is incorporated by reference herein in its entirety.

In certain embodiments, methods of detection of the protein or proteins of interest involve their detection via interaction with a protein-specific antibody. For example, antibodies directed to a protein of interest. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or F(ab')$_2$) can, for example, be used.

For example, antibodies, or fragments of antibodies, specific for a protein of interest can be used to quantitatively or qualitatively detect the presence of a protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a biological sample (e.g., a biopsy specimen) from a patient, and applying thereto a labeled antibody that is directed to a protein of interest. The antibody (or fragment) is preferably applied by overlaying the antibody (or fragment) onto a biological sample. Through the use of such a procedure, it is possible to determine not only the presence of the protein of interest, but also its distribution, in a particular sample. A wide variety of well-known histological methods (such as staining procedures) can be utilized to achieve such in situ detection.

Immunoassays for a protein of interest typically comprise incubating a sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a protein of interest can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, J. Clin. Pathol. 31:507-520; Butler, J. E., 1981, Meth. Enzymol. 73:482-523; Maggio (ed.), 1980, Enzyme Immunoassay, CRC Press, Boca Raton, Fla.; Ishikawa et al., (eds.), 1981, Enzyme Immunoassay, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, 1986, Principles of Radioimmunoassays, Seventh Training Course on Radioligand Assay Techniques, The Endocrine Society, which is hereby incorporated by reference herein). The radioactive isotope (e.g., $^{125}I$, $^{131}I$, $^{35}S$ or $^{3}H$) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In another embodiment, specific binding molecules other than antibodies, such as aptamers, may be used to bind the biomarkers. In yet another embodiment, the biomarker profile may comprise a measurable aspect of an infectious agent (e.g., lipopolysaccharides or viral proteins) or a component thereof.

In some embodiments, a protein chip assay (e.g., The ProteinChip® Biomarker System, Ciphergen, Fremont, Calif.) is used to measure feature values for the biomarkers in the biomarker profile. See also, for example, Lin, 2004, Modern Pathology, 1-9; Li, 2004, Journal of Urology 171, 1782-1787; Wadsworth, 2004, Clinical Cancer Research, 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, each of which is hereby incorporated by reference in its entirety.

In some embodiments, a bead assay is used to measure feature values for the biomarkers in the biomarker profile. One such bead assay is the Becton Dickinson Cytometric Bead Array (CBA). CBA employs a series of particles with discrete fluorescence intensities to simultaneously detect multiple soluble analytes. CBA is combined with flow cytometry to create a multiplexed assay. The Becton Dickinson CBA system, as embodied for example in the Becton Dickinson Human Inflammation Kit, uses the sensitivity of amplified fluorescence detection by flow cytometry to measure soluble analytes in a particle-based immunoassay. Each bead in a CBA provides a capture surface for a specific protein and is analogous to an individually coated well in an ELISA plate. The BD CBA capture bead mixture is in suspension to allow for the detection of multiple analytes in a small volume sample.

In some embodiments the multiplex analysis method described in U.S. Pat. No. 5,981,180 ("the '180 patent"), herein incorporated by reference in its entirety, and in particular for its teachings of the general methodology, bead technology, system hardware and antibody detection, is used to measure feature values for the biomarkers in a biomarker profile. For this analysis, a matrix of microparticles is synthesized, where the matrix consists of different sets of microparticles. Each set of microparticles can have thousands of molecules of a distinct antibody capture reagent immobilized on the microparticle surface and can be color-coded by incorporation of varying amounts of two fluorescent dyes. The ratio of the two fluorescent dyes provides a distinct emission spectrum for each set of microparticles, allowing the identification of a microparticle a set following the pooling of the various sets of microparticles. U.S. Pat. Nos. 6,268,222 and 6,599,331 also are incorporated herein by reference in their entirety, and in particular for their teachings of various methods of labeling microparticles for multiplex analysis.

5.4.3 Use of Other Methods of Detection

In some embodiments, a separation method may be used to determine feature values for biomarkers in a biomarker profile, such that only a subset of biomarkers within the sample is analyzed. For example, the biomarkers that are analyzed in a sample may be mRNA species from a cellular extract which has been fractionated to obtain only the nucleic acid biomarkers within the sample, or the biomarkers may be from a fraction of the total complement of proteins within the sample, which have been fractionated by chromatographic techniques.

Feature values for biomarkers in a biomarker profile can also, for example, be generated by the use of one or more of the following methods described below. For example, methods may include nuclear magnetic resonance (NMR) spectroscopy, a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS).sup.n, atmospheric pressure photoionization mass spectrometry (APPI-MS), APPI-MS/MS, and APPI-(MS).sup.n. Other mass spectrometry methods may include, inter alia, quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

In one embodiment, laser desorption/ionization time-of-flight mass spectrometry is used to create determine feature values in a biomarker profile where the biomarkers are proteins or protein fragments that have been ionized and vaporized off an immobilizing support by incident laser radiation and the feature values are the presence or absence of peaks representing these fragments in the mass spectra profile. A variety of laser desorption/ionization techniques are known in the art (see, e.g., Guttman et al., 2001, Anal. Chem. 73:1252-62 and Wei et al., 1999, Nature 399:243-246, each of which is hereby incorporated by herein be reference in its entirety).

Laser desorption/ionization time-of-flight mass spectrometry allows the generation of large amounts of information in a relatively short period of time. A biological sample is applied to one of several varieties of a support that binds all of the biomarkers, or a subset thereof, in the sample. Cell lysates or samples are directly applied to these surfaces in volumes as small as 0.5 .mu.L, with or without prior purification or fractionation. The lysates or sample can be concentrated or diluted prior to application onto the support surface. Laser desorption/ionization is then used to generate mass spectra of the sample, or samples, in as little as three hours.

5.4.4 Data Analysis Algorithms

Biomarker expression profile of hES-MSC are factors discriminating between clinical grade hES-MSC and non-clinical grade hES-MSC. The identity of these biomarkers and their corresponding features (e.g., expression levels) can be used to develop a decision rule, or plurality of decision rules, that discriminate between clinical grade and non-clinical grade hES-MSC. Specific data analysis algorithms for building a decision rule, or plurality of decision rules, that discriminate between clinical grade hES-MSC and non-clinical grade hES-MSC. Once a decision rule has been built using these exemplary data analysis algorithms or other techniques known in the art, the decision rule can be used to classify a hES-MSC population into one of the two or more phenotypic classes (e.g. a clinical grade or a non-clinical grade hES-MSC). This is accomplished by applying the decision rule to a biomarker profile obtained from the cell culture. Such decision rules, therefore, have enormous value as defining the quality of hES-MSC.

In certain embodiment, provided herein is a method for the evaluation of a biomarker profile from a test cell culture to biomarker profiles obtained from a cell culture in a control population. In some embodiments, each biomarker profile obtained from the control population, as well as the test cell culture, comprises a feature for each of a plurality of different biomarkers. In some embodiments, this comparison is accomplished by (i) developing a decision rule using the biomarker profiles from the control population and (ii) applying the decision rule to the biomarker profile from the test cell culture. As such, the decision rules applied in some embodiments of the present invention are used to determine whether a test cell culture is clinical grade or non-clinical grade. In certain embodiment, the control population is a clinical grade hES-MSC. In another embodiment, the control population is BM-MSC.

In some embodiments of the present invention, when the results of the application of a decision rule indicate that the test cell culture is clinical grade hES-MSC, it is used for treatment. If the results of an application of a decision rule indicate that the test cell culture is non-clinical grade hES-MSC, the test cell culture is not used for treatment.

5.5 Modification of MSC

Provided herein is a method of modifying mesenchymal stem cells to produce a population of modified MSC that has improved immunosuppressive function. The MSC have the following characteristics: (i) contain >95% of cells expressing group-1 markers; (ii) contain >80% of cells expressing group 2 markers; (iii) contain <5% of cells expressing group-3 markers (iv) expressing IL-10 and TGFβ; (v) contain <2% of cells expressing IL-6, IL-12 and TNFα; and (vi) contains <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4.

Provided herein is a method of increasing immunosuppressive function of hES-MSC by increasing the expression of AIF. In an embodiment, the method comprises decreasing the expression of PIF. In an embodiment, the method comprises decreasing the expression of IL6, IL12, TNFα, RAGE and other PIF in hES-MSC. In an embodiment, the method comprises increasing the expression of TGFβ and IL-10 in hES-MSC.

In certain embodiments, the method comprises genetic and epigenetic modification of hES-MSC that are known in the art. In certain embodiments, the genetic modification or epigenetic regulation includes, but are not limited to, knockout, small hair pin RNA ("shRNA"), micro RNA ("miRNA"), non-coding RNA ("ncRNA"), mopholino oligo, decoy RNA, DNA methylation regulation, histone methylation regulation, translation inhibition and/or antibody blocking. In certain embodiment, MSC are modified through transposomes, toll-like receptor ligands, small molecules.

In certain embodiments, small molecules are used to target any of the signaling pathway components of IL-6 signaling. In certain embodiments, the target includes, but not limited to, gp130, STATS, Cathepsin S, NFkappaB, IRF5. In certain embodiments, IL-12 expression is decreased in hES-MSC by activation of the prostaglandin E2 pathway, by increasing intracellular cyclic AMP levels with cAMP agonists that include but are not limited to forskolin, cholera toxin, β1- and β2 adrenoreceptor agonists, by inhibition of the NF-κB Rel-B pathway, by treating hES-MSC with apoptotic cells, by treatment with phosphatidylserine, by treatment with butyrate, by treatment with Triptolide or extracts from *Tripterygium wiilordii* or synthetic forms or Triptolide (i.e. Minnelide).

In certain embodiments, MSC may be modified to express a certain marker using methods known in the art of recombinant DNA. In certain embodiment, MSC may be modified by transfection using the nucleotide sequence encoding the marker. The marker can be inserted into an appropriate expression vector, i.e., a vector which contains the necessary elements for the transcription and translation of the inserted coding sequence. The necessary transcriptional and translational elements can also be present. The regulatory regions and enhancer elements can be of a variety of origins, both natural and synthetic. A variety of host-vector systems may be utilized to express the marker. These include, but are not limited to, mammalian cell systems infected with virus (e.g., vaccinia virus, adenovinis, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. The expression elements of vectors vary in their strengths and specificities. Depending on the host-vector system utilized, any one of a number of suitable transcription and translation elements may be used.

Once a vector encoding the appropriate marker has been synthesized, the MSC is transformed or transfected with the vector of interest.

Standard methods of introducing a nucleic acid sequence of interest into the MSC can be used. Transformation may be by any known method for introducing polynucleotides into a host cell, including, for example packaging the polynucleotide in a virus and transducing a host cell with the virus, and by direct uptake of the polynucleotide. Mammalian transformations (i.e., transfections) by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well-known to one of skill in the art.

In a preferred embodiment, stable cell lines containing the constructs of interest are generated for high throughput screening. Such stable cells lines may be generated by introducing a construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, anti-metabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

5.6 Stem Cell Collection Composition

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The stem cell collection composition can comprise one or more components that tend to preserve stem cells, that is, prevent the stem cells from dying, or delay the death of the stem cells, reduce the number of stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from Clostridium histolyticum, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., Pseudomonas aeruginosa, Staphylococcus aureus, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 μM to about 100 μM); a reducing agent (e.g., N-acetylcysteine present at about 0.1 mM to about 5 mM); an agent that prevents calcium entry into cells (e.g., verapamil present at about 2 μM to about 25 μM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

5.7 Immunomodulation Using hES-MSC or iPS-MSC

Provided herein is the modulation of the activity (e.g. reduced cell proliferation, reduced cell survival, impaired cell migration to sites of inflammation, reduced ability of the cells to promote or prolong inflammation or enhanced cell functions that promote the restoration of healthy tissue or organ homeostasis) of an immune cell, or plurality of immune cells, by contacting the immune cell(s) with a plurality of hES-MSC or iPS-MSC. In one embodiment, the method of modulating an immune response comprises contacting a plurality of immune cells with a plurality of hES-MSC or iPS-MSC for a time sufficient for said hES-MSC or iPS-MSC to detectably suppress an immune response, wherein said hES-MSC or iPS-MSC detectably suppress T cell proliferation in a mixed lymphocyte reaction (MLR) assay.

Since BM-MSC or other adult tissue derived MSC has been used to treat many autoimmune disease, BM-MSC is also used for tissue repairing by limit inflammation and secret growth and protective factors, replace damaged tissues. We have showed here in our examples that hES-MSC have superior immunosuppressive function than BM-MSC, thus hES-MSC can be used in all areas and diseases that currently targeted by BM-MSC. hES-MSC or iPS-MSC used for immunomodulation may be derived or obtained from an embryonic stem cell line or induced pluripotent stem cell line, respectively. hES-MSC or iPS-MSC used for immunomodulation may also be derived from a the same species as the immune cells whose activity is to be modulated or from a different species as that of the immune cells whose activity is to be modulated.

An "immune cell" in the context of this method means any cell of the immune system, particularly T cells and NK (natural killer) cells. Thus, in various embodiments of the method, hES-MSC are contacted with a plurality of immune cells, wherein the plurality of immune cells are, or comprises, a plurality of T cells (e.g., a plurality of CD3.sup.+ T cells, CD4.sup.+ T cells and/or CD8.sup.+ T cells) and/or natural killer cells. An "immune response" in the context of the method can be any response by an immune cell to a stimulus normally perceived by an immune cell, e.g., a response to the presence of an antigen. In various embodiments, an immune response can be the proliferation of T cells (e.g., CD3.sup.+ T cells, CD4.sup.+ T cells and/or CD8.sup.+ T cells) in response to a foreign antigen, such as an antigen present in a transfusion or graft, or to a self-antigen, as in an autoimmune disease. The immune response can also be a proliferation of T cells contained within a graft. The immune response can also be any activity of a natural killer (NK) cell, the maturation of a dendritic cell, or the like. The immune response can also be a local, tissue- or organ-specific, or systemic effect of an activity of one or more classes of immune cells, e.g. the immune response can be graft versus host disease, inflammation, formation of inflammation-related scar tissue, an autoimmune condition (e.g., rheumatoid arthritis, Type I diabetes, lupus erythematosus, etc.). and the like.

"Contacting" in this context encompasses bringing the hES-MSC and immune cells together in a single container (e.g., culture dish, flask, vial, etc.) or in vivo, for example, the same individual (e.g., mammal, for example, human). In a preferred embodiment, the contacting is for a time sufficient, and with a sufficient number of hES-MSC and immune cells, that a change in an immune function of the immune cells is detectable. More preferably, in various embodiments, said contacting is sufficient to suppress immune function (e.g., T cell proliferation in response to an antigen) by at least 50%, 60%, 70%, 80%, 90% or 95%, compared to the immune function in the absence of the hES-MSC. Such suppression in an in vivo context can be determined in an in vitro assay; that is, the degree of suppression in the in vitro assay can be extrapolated, for a particular number of hES-MSC and a number of immune cells in a recipient individual, to a degree of suppression in the individual.

The invention in certain embodiments provides methods of using hES-MSC to modulate an immune response, or the activity of a plurality of one or more types of immune cells, in vitro. Contacting the hES-MSC and plurality of immune cells can comprise combining the hES-MSC and immune cells in the same physical space such that at least a portion of the plurality of hES-MSC interacts with at least a portion of the plurality of immune cells; maintaining the hES-MSC and immune cells in separate physical spaces with common medium; or can comprise contacting medium from one or a culture of hES-MSC or immune cells with the other type of cell (for example, obtaining culture medium from a culture of hES-MSC and resuspending isolated immune cells in the medium). In a specific example, the contacting is a Mixed Lymphocyte Reaction (MLR).

Such contacting can, for example, take place in an experimental setting designed to determine the extent to which a particular plurality of hES-MSC is immunomodulatory, e.g., immunosuppressive. Such an experimental setting can be, for example, a mixed lymphocyte reaction (MLR) or regression assay. Procedures for performing the MLR and regression assays are well-known in the art. See, e.g. Schwarz, "The Mixed Lymphocyte Reaction: An In Vitro Test for Tolerance," J. Exp. Med. 127(5):879-890 (1968); Lacerda et al., "Human Epstein-Barr Virus (EBV)-Specific Cytotoxic T Lymphocytes Home Preferentially to and Induce Selective Regressions of Autologous EBV-Induced B Lymphoproliferations in Xenografted C.B-17 Scid/Scid Mice," J. Exp. Med. 183:1215-1228 (1996). In a preferred embodiment, an MLR is performed in which a plurality of hES-MSC are contacted with a plurality of immune cells (e.g., lymphocytes, for example, $CD3^+$ $CD4^+$ and/or $CD8^+$ T lymphocytes).

The MLR can be used to determine the immunosuppressive capacity of a plurality of hES-MSC. For example, a plurality of hES-MSC can be tested in an MLR comprising combining $CD4^+$ or $CD8^+$ T cells, dendritic cells (DC) and hES-MSC in a ratio of about 10:1:2, wherein the T cells are stained with a dye such as, e.g., CFSE that partitions into daughter cells, and wherein the T cells are allowed to proliferate for about 6 days. The plurality of hES-MSC is immunosuppressive if the T cell proliferation at 6 days in the presence of hES-MSC is detectably reduced compared to T cell proliferation in the presence of DC and absence of hES-MSC. In such an MLR, hES-MSC are either thawed or harvested from culture. About 20,000 hES-MSC are resuspended in 100 µl of medium (RPMI 1640, 1 mM HEPES buffer, antibiotics, and 5% pooled human serum), and allowed to attach to the bottom of a well for 2 hours. $CD4^+$ and/or $CD8^+$ T cells are isolated from whole peripheral blood mononuclear cells Miltenyi magnetic beads. The cells are CFSE stained, and a total of 100,000 T cells ($CD4^+$ T cells alone, $CD8^+$ T cells alone, or equal amounts of $CD4^+$ and $CD8^+$ T cells) are added per well. The volume in the well is brought to 200 .µl, and the MLR is allowed to proceed.

In one embodiment, therefore, the invention provides a method of suppressing an immune response comprising contacting a plurality of immune cells with a plurality of hES-MSC for a time sufficient for said hES-MSC to detectably suppress T cell proliferation in a mixed lymphocyte reaction (MLR) assay.

Populations of hES-MSC obtained from different embryonic stem cell line, can differ in their ability to modulate an activity of an immune cell, e.g., can differ in their ability to suppress T cell activity or proliferation or NK cell activity. It is thus desirable to determine, prior to use, the capacity of a particular population of hES-MSC for immunosuppression. Such a capacity can be determined, for example, by testing a sample of the stem cell population in an MLR or regression assay. In one embodiment, an MLR is performed with the sample, and a degree of immunosuppression in the assay attributable to the hES-MSC is determined. This degree of immunosuppression can then be attributed to the stem cell population that was sampled. Thus, the MLR can be used as a method of determining the absolute and relative ability of a particular population of hES-MSC to suppress immune function. The parameters of the MLR can be varied to provide more data or to best determine the capacity of a sample of hES-MSC to immunosuppress. For example, because immunosuppression by hES-MSC appears to increase roughly in proportion to the number of hES-MSC present in the assay, the MLR can be performed with, in one embodiment, two or more numbers of stem cells, e.g., $1 \times 10^3$, $3 \times 10^3$, $1 \times 10^4$ and/or $3 \times 10^4$ hES-MSC per reaction. The number of hES-MSC relative to the number of T cells in the assay can also be varied. For example, hES-MSC and T cells in the assay can be present in any ratio of, e.g. about 10:1 to about 1:10, preferably about 1:5, though a relatively greater number of hES-MSC or T cells can be used.

The invention also provides methods of using hES-MSC to modulate an immune response, or the activity of a plurality of one or more types of immune cells, in vivo. hES-MSC and immune cells can be contacted, e.g., in an individual that is a recipient of a plurality of hES-MSC. Where the contacting is performed in an individual, in one embodiment, the contacting is between exogenous hES-MSC (that is, hES-MSC not derived from the individual) and a plurality of immune cells endogenous to the individual. In specific embodiments, the immune cells within the individual are $CD3^+$ T cells, $CD4^+$ T cells, $CD8^+$ T cells, and/or NK cells.

Such immunosuppression using hES-MSC would be advantageous for any condition caused or worsened by, or related to, an inappropriate or undesirable immune response. hES-MSC-mediated immunomodulation, e.g., immunosuppression, would, for example, be useful in the suppression of an inappropriate immune response raised by the individual's immune system against one or more of its own tissues. In various embodiments, therefore, the invention provides a method of suppressing an immune response, wherein the immune response is an autoimmune disease, e.g., lupus erythematosus, diabetes, rheumatoid arthritis, or multiple sclerosis.

The contacting of the plurality of hES-MSC with the plurality of one or more types of immune cells can occur in vivo in the context of, or as an adjunct to, for example, grafting or transplanting of one or more types of tissues to a recipient individual. Such tissues may be, for example, bone marrow or blood; an organ; a specific tissue (e.g., skin graft); composite tissue allograft (i.e., a graft comprising two or more different types of tissues); etc. In this regard, the hES-MSC can be used to suppress one or more immune responses of one or more immune cells contained within the recipient individual, within the transplanted tissue or graft, or both. The contacting can occur before, during and/or after the grafting or transplanting. For example, hES-MSC can be administered at the time of the transplant or graft. The hES-MSC can also, or alternatively, be administered prior to the transplanting or grafting, e.g., about 1, 2, 3, 4, 5, 6 or 7 days prior to the transplanting or grafting. hES-MSC can also, or alternatively, be administered to a transplant or graft recipient after the transplantation or grafting, for example, about 1, 2, 3, 4, 5, 6 or 7 days after the transplanting or grafting. Preferably, the plurality of hES-MSC are contacted with the plurality of hES-MSC before any detectable sign or symptom of an immune response, either by the recipient individual or the transplanted tissue or graft, e.g., a detectable sign or symptom of graft-versus-host disease or detectable inflammation, is detectable.

In another embodiment, the contacting within an individual is primarily between exogenous hES-MSC and exogenous progenitor cells or stem cells, e.g., exogenous progenitor cells or stem cells that differentiate into immune cells. For example, individuals undergoing partial or full immunoablation or myeloablation as an adjunct to cancer therapy can receive hES-MSC in combination with one or more other types of stem or progenitor cells. For example, the hES-MSC can be combined with a plurality of $CD34^+$ cells, e.g., $CD34^+$ hematopoietic stem cells. Such $CD34^+$ cells can be, e.g., $CD34^+$ cells from a tissue source such as peripheral blood, umbilical cord blood, placental blood, or bone marrow. The $CD34^+$ cells can be isolated from such tissue sources, or the whole tissue source (e.g., units of umbilical cord blood or bone marrow) or a partially purified preparation from the tissue source (e.g., white blood cells from cord blood) can be combined with the hES-MSC.

The hES-MSC are administered to the individual preferably in a ratio, with respect to the known or expected number of immune cells, e.g., T cells, in the individual, of from about 10:1 to about 1:10, preferably about 1:5. However, a plurality of hES-MSC can be administered to an individual in a ratio of in non-limiting examples, about 10,000:1, about 1,000:1, about 100:1, about 10:1, about 1:1, about 1:10, about 1:100, about 1:1,000 or about 1:10,000. Generally, about $1 \times 10^5$ to about $1 \times 10^8$ hES-MSC per recipient kilogram, preferably about $1 \times 10^6$ to about $1 \times 10^7$ hES-MSC recipient kilogram can be administered to effect immunosuppression. In various embodiments, a plurality of hES-MSC administered to an individual or subject comprises at least, about, or no more than, $1 \times 10^5$, $3 \times 10^5$, $1 \times 10^6$, $3 \times 10^6$, $1 \times 10^7$, $3. \times 10^7$, $1 \times 10^8$, $3 \times 10^8$, $1 \times 10^9$, $3 \times 10^9$ hES-MSC, or more.

The hES-MSC can also be administered with one or more second types of stem cells, e.g., mesenchymal stem cells from bone marrow. Such second stem cells can be administered to an individual with HES-MSC in a ratio of, e.g., about 1:10 to about 10:1.

To facilitate contacting the hES-MSC and immune cells in vivo, the hES-MSC can be administered to the individual by any route sufficient to bring the hES-MSC and immune cells into contact with each other. For example, the hES-MSC can be administered to the individual, e.g., intravenously, intramuscularly, intraperitoneally, or directly into an organ, e.g., pancreas. For in vivo administration, the hES-MSC can be formulated as a pharmaceutical composition.

The method of immunosuppression can additionally comprise the addition of one or more immunosuppressive agents, particularly in the in vivo context. In one embodiment, the plurality of hES-MSC are contacted with the plurality of immune cells in vivo in an individual, and a composition comprising an immunosuppressive agent is administered to the individual. Immunosuppressive agents are well-known in the art and include, e.g., anti-T cell receptor antibodies (monoclonal or polyclonal, or antibody fragments or derivatives thereof), anti-IL-2 receptor antibodies (e.g., Basiliximab (SIMULECT®) or daclizumab (ZENAPAX)®), anti T cell receptor antibodies (e.g., Muromonab-CD3), azathioprine, corticosteroids, cyclosporine, tacrolimus, mycophenolate mofetil, sirolimus, calcineurin inhibitors, and the like. In a specific embodiment, the immunosuppressive agent is a neutralizing antibody to macrophage inflammatory protein (MIP)-1α or MIP-1β.

5.8 Preservation of hES-MSC hES-MSC can be preserved, that is, placed under conditions that allow for long-term storage, or conditions that inhibit cell death by, e.g., apoptosis or necrosis. hES-MSC can be preserved using, e.g., a composition comprising an apoptosis inhibitor, necrosis inhibitor. In one embodiment, the invention provides a method of preserving a population of stem cells comprising contacting said population of stem cells with a stem cell collection composition comprising an inhibitor of apoptosis, wherein said inhibitor of apoptosis is present in an amount and for a time sufficient to reduce or prevent apoptosis in the population of stem cells, as compared to a population of stem cells not contacted with the inhibitor of apoptosis. In a specific embodiment, said inhibitor of apoptosis is a caspase-3 inhibitor. In another specific embodiment, said inhibitor of apoptosis is a JNK inhibitor. In a more specific embodiment, said JNK inhibitor does not modulate differentiation or proliferation of said stem cells. In another embodiment, said stem cell collection composition comprises said inhibitor of apoptosis and said oxygen-carrying perfluorocarbon in separate phases. In another embodiment, said stem cell collection composition comprises said inhibitor of apoptosis and said oxygen-carrying perfluorocarbon in an emulsion. In another embodiment, the stem cell collection composition additionally comprises an emulsifier, e.g., lecithin. In another embodiment, said apoptosis inhibitor and said perfluorocarbon are between about 0° C. and about 25° C. at the time of contacting the stem cells. In another more specific embodiment, said apoptosis inhibitor and said perfluorocarbon are between about 2° C. and 10° C., or between about 2° C. and about 5° C., at the time of contacting the stem cells. In another more specific embodiment, said contacting is performed during transport of said population of stem cells. In another more specific embodiment, said contacting is performed during freezing and thawing of said population of stem cells.

In certain embodiments, rock-inhibitor Y27632 may be added as a preservation helper. In certain embodiments, the rock-inhibitor is added at concentration of 10 uM.

In another embodiment, the invention provides a method of preserving a population of hES-MSC comprising contacting said population of stem cells with an inhibitor of apoptosis and an organ-preserving compound, wherein said inhibitor of apoptosis is present in an amount and for a time sufficient to reduce or prevent apoptosis in the population of stem cells, as compared to a population of stem cells not contacted with the inhibitor of apoptosis.

Typically, during hES-MSC collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than six hours during said preservation, wherein a hypoxic condition is a concentration of oxygen that is less than normal blood oxygen concentration. In a more specific embodiment, said population of stem cells is exposed to said hypoxic condition for less than two hours during said preservation. In another more specific embodiment, said population of stem cells is exposed to said hypoxic condition for less than one hour, or less than thirty minutes, or is not exposed to a hypoxic condition, during collection, enrichment or isolation. In another specific embodiment, said population of stem cells is not exposed to shear stress during collection, enrichment or isolation.

The HES-MSC can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 5-10% (v/v). Cryopreservation medium may comprise additional agents, for example, methylcellulose and/or glycerol. HES-MSC are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.9 Cryopreserved hES-MSC

The hES-MSC disclosed herein can be preserved, for example, cryopreserved for later use. Methods for cryopreservation of cells, such as stem cells, are well known in the art. hES-MSC can be prepared in a form that is easily administrable to an individual. For example, provided herein are hES-MSC that are contained within a container that is suitable for medical use. Such a container can be, for example, a sterile plastic bag, flask, jar, or other container from which the hES-MSC can be easily dispensed. For example, the container can be a blood bag or other plastic, medically-acceptable bag suitable for the intravenous administration of a liquid to a recipient. The container is preferably one that allows for cryopreservation of the combined stem cell population. Cryopreserved hES-MSC can comprise hES-MSC derived from a single donor, or from multiple donors. The hES-MSC can be completely HLA-matched to an intended recipient, or partially or completely HLA-mismatched.

In another specific embodiment, the container is a bag, flask, or jar. In more specific embodiment, said bag is a sterile plastic bag. In a more specific embodiment, said bag is suitable for, allows or facilitates intravenous administration of the hES-MSC. The bag can comprise multiple lumens or compartments that are interconnected to allow mixing of the hES-MSC and one or more other solutions, e.g., a drug, prior to, or during, administration. In another specific embodiment, the composition comprises one or more compounds that facilitate cryopreservation of the combined stem cell population. In another specific embodiment, said hES-MSC is contained within a physiologically-acceptable aqueous solution. In a more specific embodiment, said physiologically-acceptable aqueous solution is a 0.9% NaCl solution. In another specific embodiment, said hES-MSC are HLA-matched to a recipient of said stem cell population. In another specific embodiment, said combined stem cell population comprises hES-MSC that are at least partially HLA-mismatched to a recipient of said stem cell population.

5.10 Pharmaceutical Preparations

As discussed above, one embodiment of the present invention is a pharmaceutical composition comprising a therapeutically effective amount of the human embryonic stem cell derived mesenchymal stem cells and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

These compositions can take the form of solutions, suspensions, emulsions, tablets, pills, capsules, powders, sustained-release formulations, cachets, troches, lozenges, dispersions, suppositories, ointments, cataplasms (poultices), pastes, powders, dressings, creams, plasters, patches, aerosols, gels, liquid dosage forms suitable for parenteral administration to a patient, and sterile solids (e.g., crystalline or amorphous solids) that can be reconstituted to provide liquid dosage forms suitable for parenteral administration to a patient. Such compositions will contain a therapeutically effective amount of the compound, preferably in purified form, together with a suitable form of carrier so as to provide the form for proper administration to the patient. The formulation should suit the mode of administration.

Pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient over a prolonged period of time.

Pharmaceutical compositions adapted for nasal and pulmonary administration may comprise solid carriers such as powders which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for parenteral administration include aqueous and non-aqueous sterile injectable solutions or suspensions, which may contain anti-oxidants, buffers, baceriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Selection of a therapeutically effective dose will be determined by the skilled artisan considering several factors which will be known to one of ordinary skill in the art. Such factors include the particular form of the inhibitor, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

In certain embodiments, patients are treated with antipyretic and/or antihistamine (acetaminophen and diphenhydramine hydrochloride) to minimize any possible DMSO infusion toxicity related to the cryopreserve component in the hES-MSC treatment.

5.11 hES-MSC Conditioned Medium and Derivatives

The hES-MSC disclosed herein can be used to produce conditioned medium, concentrate of conditioned medium, cell lysate or other derivatives that is immunosuppressive, that is, medium comprising one or more biomolecules secreted or excreted by the stem cells that have a detectable immunosuppressive effect on a plurality of one or more types of immune cells. In various embodiments, the conditioned medium comprises medium in which hES-MSC have grown for at least 1, 2, 3, 4, 5, 6, 7, 8, 9, 10, 11, 12, 13, 14 or more days. In other embodiments, the conditioned medium comprises medium in which hES-MSC have grown to at least 30%, 40%, 50%, 60%, 70%, 80%, 90% confluence, or up to 100% confluence. Such conditioned medium can be used to support the culture of a separate population of hES-MSC, or stem cells of another kind. In another embodiment, the conditioned medium comprises medium in which hES-MSC have been differentiated into an adult cell type. In another embodiment, the conditioned medium of the invention comprises medium in which hES-MSC and non-hES-MSC have been cultured. In various embodiments, cell lysate comprises of hES-MSC cells lysed by repeat frozen-thaw procedures, or by hypertonic or hypotonic solution treatment.

Thus, in one embodiment, the invention provides a composition comprising culture medium, cell lysate and/or other derivatives from a culture of hES-MSC, wherein said hES-MSC (a) adhere to a substrate; (b) express CD73, CD105, CD90, CD29, CD44, CD146, IL-10, TGFb2, HGF, but do not express IL-6, TNFα, IL-12 and/or RAGE. In another specific embodiment, the composition comprises an antiproliferative agent, e.g., an anti-MIP-1α or anti-MIP-1β antibody.

Provided herein is a method of using hES-MSC as described herein as feeder cells for bone marrow hematopoietic stem cell, peripheral blood hematopoietic stem cell and umbilical-cord hematopoietic stem cell expansion. In certain embodiments, the hES-MSC suitable for the disclosed method express Stro-3, Stro-1, DL1, and/or Nestin. In certain embodiment, hES-MSC is co-cultured with bone marrow hematopoietic stem cells, peripheral blood hematopoietic stem cells and/or umbilical-cord hematopoietic stem cells. In certain embodiment, the hES-MSC is mesenchymal stromal cells. Provided herein is a co-culture of hES-MSC as described herein and bone marrow hematopoietic stem cells. Provided herein is a co-culture of hES-MSC as described herein and umbilical-cord hematopoietic stem cells.

5.12 Matrices Comprising hES-MSC

The invention further comprises matrices, hydrogels, scaffolds, and the like that comprise hES-MSC. hES-MSC can be seeded onto a natural matrix, e.g., a biomaterial. In certain embodiments, the scaffold is obtained by 3D printing. The hES-MSC can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. hES-MSC in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are crosslinked ionically, or block polymers such as polyethylene oxide-polypropylene glycol block copolymers which are crosslinked by temperature or pH, respectively. In some embodiments, the hydrogel or matrix of the invention is biodegradable. In some embodiments of the invention, the formulation comprises an in situ polymerizable gel (see., e.g., U.S. Patent Application Publication 2002/0022676; Anseth et al., J. Control Release, 78(1-3): 199-209 (2002); Wang et al., Biomaterials, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The hES-MSC or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve the practice of the invention. Examples of scaffolds that can be used in the present invention include nonwoven mats, porous foams, or self-assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(s-caprolactone)/poly(glycolic acid) (PCL/PGA) copolymer, formed by processes such as freeze-drying, or lyophilization (see, e.g., U.S. Pat. No. 6,355,699), can also be used as scaffolds.

The hES-MSC can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, hES-MSC can be seeded onto, or contacted with, a felt, which can be, e.g., composed of a multifilament yarn made from a bioabsorbable material such as PGA, PLA, PCL copolymers or blends, or hyaluronic acid.

The hES-MSC can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells of the invention in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with stem cells.

5.13 Immortalized hES-MSC

Mammalian hES-MSC can be conditionally immortalized by transfection with any suitable vector containing a growth-promoting gene, that is, a gene encoding a protein that, under appropriate conditions, promotes growth of the transfected cell, such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. In one embodiment, a tetracycline (tet)-controlled gene expression system can be employed (see Gossen et al., Proc. Natl. Acad. Sci. USA 89:5547-5551, 1992; Hoshimaru et al., Proc. Natl. Acad. Sci. USA 93:1518-1523, 1996). In the absence of tet, a tet-controlled transactivator (tTA) within this vector strongly activates transcription from ph.sub.CMV*-1, a minimal promoter from human cytomegalovirus fused to tet operator sequences. tTA is a fusion protein of the repressor (tetR) of the transposon-10-derived tet resistance operon of Escherichia coli and the acidic domain of VP 16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the present invention. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a stem cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized hES-MSC cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human hES-MSC cell line prepared as described above. In general, such clonal cell lines may be isolated using standard techniques, such as by limit dilution or using cloning rings, and expanded. Clonal cell lines may generally be fed and passaged as described above.

Conditionally-immortalized human hES-MSC cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.14 Assays

The hES-MSC can be used in assays to determine the influence of culture conditions, environmental factors, molecules (e.g., biomolecules, small inorganic molecules. Etc.) and the like on stem cell proliferation, expansion, and/or differentiation, compared to hES-MSC not exposed to such conditions.

In a preferred embodiment, the hES-MSC are assayed for changes in proliferation, expansion or differentiation upon contact with a molecule. In one embodiment, for example, the invention provides a method of identifying a compound that modulates the proliferation of a plurality of hES-MSC, comprising contacting said plurality of hES-MSC with said compound under conditions that allow proliferation, wherein if said compound causes a detectable change in proliferation of said hES-MSC compared to a plurality of hES-MSC not contacted with said compound, said compound is identified as a compound that modulates proliferation of hES-MSC. In a specific embodiment, said compound is identified as an inhibitor of proliferation. In another specific embodiment, said compound is identified as an enhancer of proliferation.

In another embodiment, the invention provides a method of identifying a compound that modulates the expansion of a plurality of hES-MSC, comprising contacting said plurality of hES-MSC with said compound under conditions that allow expansion, wherein if said compound causes a detectable change in expansion of said plurality of hES-MSC compared to a plurality of hES-MSC not contacted with said compound, said compound is identified as a compound that modulates expansion of hES-MSC. In a specific embodiment, said compound is identified as an inhibitor of expansion. In another specific embodiment, said compound is identified as an enhancer of expansion.

In another embodiment, disclosed herein is a method of identifying a compound that modulates the differentiation of a hES-MSC, comprising contacting said hES-MSC with said compound under conditions that allow differentiation, wherein if said compound causes a detectable change in differentiation of said hES-MSC compared to a hES-MSC not contacted with said compound, said compound is identified as a compound that modulates proliferation of hES-MSC. In a specific embodiment, said compound is identified as an inhibitor of differentiation. In another specific embodiment, said compound is identified as an enhancer of differentiation.

5.15 Therapeutic Uses of Human Embryonic Stem Cell Derived Mesenchymal Stem Cells Mesenchymal stem cells derived from bone marrow (BM-MSCs) have been used as cell based therapy for T cell related autoimmune diseases, including multiple sclerosis, but due to limited sources, unstable quality, and biosafety concerns of using cells derived from adult tissue, their use as a therapeutic aid has been limited.

The novel method for generating mesenchymal stem cells from embryonic stem cells set forth herein, and the novel hES-MSCs generated from this method, provide new therapies for T cell related autoimmune disease, in particular multiple sclerosis.

In certain embodiments, hES-MSC given to mice pre-onset of EAE, remarkably attenuated the disease score of these animals. The decrease in score was accompanied by decreased demyelination, T cell infiltration, and microglial responses in the central nervous system, as well as repressed immune cell proliferation, and differentiation in vitro.

In certain embodiments, a gradual decline of disease score in EAE mice after treatment with hES-MSC, post disease onset, was observed. In certain embodiments, hES-MSC have both prophylactic and therapeutic effects on the disease.

In certain embodiment, the immunosuppressive activity of the hES-MSC account for the prophylactic effect on the disease as irradiated hES-MSC, which are unlikely to replace damage myelin, were also effective in reducing disease score. In one embodiment, irradiation does not shorten the lifespan of the hES-MSC.

In certain embodiment, the therapeutic effects of the hES-MSC involve immunosuppression as well as neural repair and regeneration.

In certain embodiment, EAE mice treated with hES-MSC have much fewer inflammatory T cells in their central nervous system and less T cells infiltrating the spinal cord. The hES-MSC can reduce damage and symptoms caused by inflammatory T cells, making them useful in therapy and prevention of all T cell related autoimmune diseases. hES-MSC also decreased demyelination.

In certain embodiment, the therapeutic method comprises the use of hES-MSC in combination with other therapeutic agent. In certain embodiment, hES-MSC is administered in combination with anti-IL-6 antibody, anti-IL-12 antibody, and/or other immunosuppressive agents.

As shown by the results herein, hES-MSCs from three different hES cell lines, given to mice pre-onset of EAE, remarkably attenuated the disease score of these animals. The decrease in score was accompanied by decreased demyelination, T cell infiltration, and microglial responses in the central nervous system, as well as repressed immune cell proliferation, and differentiation in vitro.

Additionally, a gradual decline of disease score in EAE mice after treatment with hES-MSCs, post disease onset, was observed. These data suggest that hES-MSCs have both prophylactic and therapeutic effects on the disease.

It is believed that the immunosuppressive activity of the hES-MSCs account for the prophylactic effect on the disease as irradiated hES-MSCs, which are unlikely to replace damage myelin, were also effective in reducing disease score. Moreover, irradiation does not shorten the lifespan of the hES-MSCs.

The therapeutic effect of the hES-MSCs may involve immunosuppression as well as neural repair and regeneration.

More surprisingly, EAE mice treated with hES-MSCs have much fewer inflammatory T cells in their central nervous system and less T cells infiltrating the spinal cord, showing that the hES-MSCs can reduce damage and symptoms caused by inflammatory T cells, making them useful in therapy and prevention of all T cell related autoimmune diseases. HES-MSCs also decreased demyelination.

These favorable results are all in marked contrast to the results obtained with bone marrow-derived mesenchymal stem cells. BM-MSCs only suppressed mouse T cell proliferation in response to anti-CD3 stimuli at low doses in vitro, and even enhanced Th1 and Th17 cell infiltration into the CNS. Autoreactive effector CD4+ T cells have been associated with the pathogenesis of several autoimmune disorders, including multiple sclerosis, Crohn's disease, and rheumatoid arthritis. These CD4+ T cells include Th1 and Th17 cells.

Moreover, BM-MSCs had no effect at all on the score of EAE mice. These observations are surprising but consistent with previous reports that show only mild or negligible effects of human BM-MSCs on EAE mice (Gordon et al. 2008a; Zhang et al. 2005; Payne et al. 2012). A recent report showed a reduction of disease score of only 3.5 to 3.0 of EAE mice treated with human umbilical-derived MSCs (Liu et al. 2012). The results herein and those from these studies highlight the novelty and usefulness of the present invention.

Additionally, BM-MSC and hES-MSC have very similar global transcriptional profiles, but differentially express some pro- and anti-inflammatory factors. Among them, IL-6 is expressed at a much higher level in BM-MSCs than hES-MSCs. Moreover, IL-6 expression in BM-MSCs was double upon IFNγ stimulation in vitro, whereas it remained low in the hES-MSCs.

IL-6 is pleiotropic cytokine involved in crosstalk between hematopoietic/immune cells and stromal cells, including the onset and resolution of inflammation. IL-6 can promote the differentiation and functions of Th17 cells (Dong, 2008). The levels of IL-6 are elevated in mononuclear cells in blood and in brain tissue from MS patients (Patanella et al., 2010), as well as in serum in aged humans (Sethe et al., 2006). Mice lacking IL-6 receptor a at the time of T cell priming are resistant to EAE (Leech et al., 2012). Site-specific production of IL-6 in the CNS can re-target and enhance the inflammatory response in EAE (Quintana et al., 2009), whereas IL-6-neutralizing antibody can reduce symptoms in EAE mice (Gijbels et al., 1995). Thus, IL-6 has become a promising therapeutic target for treatment of MS.

Immunomodulation of peripheral T cell activity and regeneration and repair of neural cells are widely recognized modes of MSC therapeutic action in MS and in EAE (Al Jumah and Abumaree 2012; Auletta et al. 2012; Morando et al. (2012). However, long-term functional neuronal recovery and sustained disease remission in MS needs repair of the damaged BBB and BSCB (Correale and Villa 2007; Minagar et al. 2012). In other words, MS is an inflammatory, neurodegenerative, and vascular disease, and effective treatment need to target all three component.

The characteristics of hES-MSCs make them uniquely suited for the treatment of T cell related autoimmune diseases especially multiple sclerosis. In particular, the hES-MSCs can decrease disease scores of EAE mice, but also decrease demyelination and decrease Th1 and Th17 proliferation, and have low expression of IL-6. These latter two characteristics make them suitable to treat other T cell related autoimmune diseases. Additionally, the ability of the hESC-MSCs to cross the blood-brain barrier and blood-spinal cord barrier, makes them superior as a treatment and prevention of multiple sclerosis and other autoimmune diseases related to the central nervous system.

Thus, one embodiment of the present invention is a method of treating or preventing a T cell related autoimmune disease comprising the steps of administering a therapeutically effective amount of solution, cell culture or pharmaceutical preparation comprising human embryonic-mesenchymal stem cells as described in the preceding paragraphs, to the subject in need thereof. The T cell related autoimmune diseases would include but are not limited to multiple sclerosis, inflammatory bowel disease, Crohn's disease, graft versus host disease, systemic lupus erythematosus, and rheumatoid arthritis. The subject is preferably a mammal or avian, and most preferably human. The solution, cell culture or pharmaceutical preparation can comprise irradiated or non-irradiated human embryonic-mesenchymal stem cells. The solution, cell culture or pharmaceutical preparation is preferably administered by injection.

Multiple sclerosis has been categorized into four subtypes: relapsing/remitting; secondary progressive; primary progressive; and progressive relapsing. The relapsing/remitting subtype is characterized by unpredictable relapses followed by long periods of remission. Secondary progressive MS often happens in individuals who start with relapsing/remitting MS and then have a progressive decline with not periods of remission. Primary progressive MS describes a small number of individuals who never have remission after their initial symptoms. Progressive relapsing, the least common subtype, have a steady neurologic decline, and suffer from acute Thus, further embodiments of the present invention is a method for treating or preventing multiple sclerosis disease in a subject in need thereof, comprising the steps of administering a therapeutically effective amount of solution, cell culture or pharmaceutical preparation comprising human embryonic-mesenchymal stem cells as described in the preceding paragraphs, to the subject in need thereof. The multiple sclerosis can be relapsing/remitting multiple sclerosis, progressive/relapsing multiple sclerosis, primary multiple sclerosis, or secondary multiple sclerosis. The subject is preferably a mammal, and most preferably human. The solution, cell culture or pharmaceutical preparation can comprise irradiated or non-irradiated human embryonic-mesenchymal stem cells. The solution, cell culture or pharmaceutical preparation is preferably administered by injection.

Multiple sclerosis manifests in a variety of symptom including sensory disturbance of the limbs, optic nerve disfunction, pryramidal tract dysfunction, bladder dysfunction, bowel dysfunction, sexual dysfuntion, ataxia and diplopia attacks.

A further embodiment of the present invention is a method of treating multiple sclerosis comprising the steps of administering a therapeutically effective amount of solution, cell culture or pharmaceutical preparation comprising human embryonic-mesenchymal stem cells as described in the preceding paragraphs, to the subject in need thereof, wherein there is detectable improvement in at least one of these symptoms, at least two of these symptoms, at least four of these symptoms, at least five of these symptoms or all of these symptoms.

The Expanded Disability Status Scale (EDSS) is the most commonly used rating scale to evaluate the clinical status of patients with MS. It measures disability along several separate parameters: strength, sensation, brainstem functions (speech and swallowing), coordination, vision, cognition, and bowel/bladder continence. It is a well-accepted measure of disability in MS and it is not particularly difficult or time consuming to perform. The EDSS quantifies disability in eight Functional Systems (FS) and allows neurologists to assign a Functional System Score (FSS) in each of these (Kurtzke 1983).

Kurtzke defines functional systems as follows:
pyramidal
cerebellar
brainstem
sensory
bowel and bladder
visual cerebral
other The EDSS steps 1.0 to 4.5 refer to people with MS who are fully ambulatory. EDSS steps 5.0 to 9.5 are defined by the impairment to ambulation. The clinical meaning of each possible result is the following:
0.0: Normal Neurological Exam
1.0: No disability, minimal signs on 1 FS
1.5: No disability, minimal signs on 2 of 7 FS
2.0: Minimal disability in 1 of 7 FS
2.5: Minimal disability in 2 FS
3.0: Moderate disability in 1 FS; or mild disability in 3-4 FS, though fully ambulatory
3.5: Fully ambulatory but with moderate disability in 1 FS and mild disability in 1 or 2 FS; or moderate disability in 2 FS; or mild disability in 5 FS
4.0: Fully ambulatory without aid, up and about 12 hrs a day despite relatively severe disability. Able to walk without aid 500 meters
4.5: Fully ambulatory without aid, up and about much of day, able to work a full day, may otherwise have some limitations of full activity or require minimal assistance. Relatively severe disability. Able to walk without aid 300 meters
5.0: Ambulatory without aid for about 200 meters. Disability impairs full daily activities
5.5: Ambulatory for 100 meters, disability precludes full daily activities
6.0: Intermittent or unilateral constant assistance (cane, crutch or brace) required to walk 100 meters with or without resting
6.5: Constant bilateral support (cane, crutch or braces) required to walk 20 meters without resting
7.0: Unable to walk beyond 5 meters even with aid, essentially restricted to wheelchair, wheels self, transfers alone; active in wheelchair about 12 hours a day
7.5: Unable to take more than a few steps, restricted to wheelchair, may need aid to transfer; wheels self, but may require motorized chair for full day's activities
8.0: Essentially restricted to bed, chair, or wheelchair, but may be out of bed much of day; retains self care functions, generally effective use of arms
8.5: Essentially restricted to bed much of day, some effective use of arms, retains some self care functions
9.0: Helpless bed patient, can communicate and eat
9.5: Unable to communicate effectively or eat/swallow
10.0: Death due to MS Therefore, a further embodiment of the present invention is a method for treating multiple sclerosis disease in a subject in need thereof, comprising the steps of administering a therapeutically effective amount of solution, cell culture or pharmaceutical preparation comprising human embryonic-mesenchymal stem cells as described in the preceding paragraphs, to the subject in need thereof wherein the subject demonstrates improvement on the Expanded Disability Status Scale of at least one point, and preferably at least two points.

There are other therapeutic agents that have been used to treat and prevent multiple sclerosis, including but not limited to, fingolimod, adrenocorticotropic hormone (ACTH), methylprednisolone, dexamethasone, IFNβ-1a, IFN-1b, gliatriamer acetate, cyclophosphamide, methotrexate, azathioprine, cladribine, cyclosporine, mitoxantrone, and sulfasalazine.

Therefore, the method of the present invention can further comprise the administration of one or more additional therapeutic agents to the subject, including but not limited to, fingolimod, adrenocorticotropic hormone (ACTH), methylprednisolone, dexamethasone, IFNβ-1a, IFN-1b, gliatriamer acetate, cyclophosphamide, methotrexate, azathioprine, cladribine, cyclosporine, mitoxantrone, and sulfasalazine. In a further embodiment, these additional therapeutic agents can be administered prior to, after, or at the same time as the hES-MSCS, or can be conjugated or attached to the hES-MSCS, as described below.

Other T cell or B cell related autoimmune diseases that can be treated by the disclosed hES-MSC includes, but are not limited to, Alopecia Areata, Anklosing Spondylitis, Antiphospholipid Syndrome, Autoimmune Addison's Disease, Autoimmune Hemolytic Anemia, Autoimmune Hepatitis, Autoimmune Inner Ear Disease, Autoimmune Lymphoproliferative Syndrome (ALPS), Autoimmune Thrombocytopenic Purpura (ATP), Behcet's Disease, Bullous Pemphigoid, Cardiomyopathy, Celiac Sprue-Dermatitis, Chronic Fatigue Syndrome Immune Deficiency Syndrome (CFIDS), Chronic Inflammatory Demyelinating Polyneuropathy, Cicatricial Pemphigoid, Cold Agglutinin Disease, CREST Syndrome, Crohn's Disease, Dego's Disease, Dermatomyositis, Dermatomyositis-Juvenile, Discoid Lupus, Essential Mixed Cryoglobulinemia, Fibromyalgia—Fibromyositis, Grave's Disease, Guillain-Barre, Hashimoto's Thyroiditis, Idiopathic Pulmonary Fibrosis, Idiopathic Thrombocytopenia Purpura (ITP), IgA Nephropathy, Insulin Dependent Diabetes (Type I), Type II diabetes, Juvenile Arthritis, Lupus, Meniere's Disease, Mixed connective Tissue Disease, Multiple Sclerosis, Myasthenia Gravis, Pemphigus Vulgaris, Pernicious Anemia, Polyarteritis Nodosa, Polychondritis, Polyglancular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjogren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis. Or any acute or chronic inflammation related to burning, surgery, injury, and allergy.

5.16 Uses of Human Embryonic Stem Cell Derived Mesenchymal Stem Cells as Delivery Systems Because it has been shown that the hES-MSCs of the present invention have the unique ability to cross the blood-brain barrier and the blood-spinal cord barrier, a further embodiment of the present invention is a method of using human embryonic-mesenchymal stem cells for delivery of agents through the blood brain barrier and/or the blood spinal cord barrier, by attaching or conjugating the agent to the human embryonic mesenchymal stem cells to form a complex; and administering the human embryonic mesenchymal stem cells-agent complex to a subject, wherein the human embryonic mesenchymal stem cells cross the blood-brain and/or the blood-spinal cord barrier and deliver the agent to the central nervous system. The human embryonic mesenchymal stem cells may be in the form of a single cell, a cell culture, a solution or a pharmaceutical preparation. Agents would include but are not limited to chemicals, drugs, proteins, DNA, RNA, antibodies, and small molecules.

A further embodiment of the present invention is a delivery system for the delivery of agents through the blood brain barrier and/or the blood spinal cord barrier comprising human embryonic-mesenchymal stem cells and an agent conjugated or attached to the human embryonic-mesenchymal stem cells.

The ability to permeate the blood-brain barrier and the blood-spinal cord barrier would be useful in the treatment and prevention of diseases including but not limited to neurological disorders, multiple sclerosis, cancer, Parkinson's Disease, Alzheimer's Disease, Huntington's Disease, meningitis, encephalitis, rabies, epilepsy, dementia, Lyme's Disease, stroke, and amyotrophic lateral sclerosis, as well as brain and spinal cord injury. Thus, a subject in need thereof would have a disease or be at risk for a disease in which the blood-brain barrier and/or blood-spinal cord barrier is involved. Thus, a further embodiment of the present invention is a method of treating a disease or injury, by attaching or conjugating an agent to the human embryonic mesenchymal stem cells to form a complex; and administering the human embryonic mesenchymal stem cells-agent complex to a subject in need thereof, wherein the human embryonic mesenchymal stem cells cross the blood-brain and/or the blood-spinal cord barrier and deliver the agent to the central nervous system, and the agent is used as a treatment or prevention of the disease or injury of the subject. Since the hES-MSC have strong ability migration and infiltration ability, it can also been used as carrier for tumor/cancer therapy to carry anti-tumor drugs and proteins. The human embryonic mesenchymal stem cells may be in the form of a single cell, a cell culture, a solution or a pharmaceutical preparation. Agents include, but are not limited to, chemicals, drugs, proteins, DNA, RNA, micro-RNA, non-coding RNA, antibodies, small molecules and/or nano particles.

Agents that are useful in the treatment and prevention of diseases include, but not limited to, antibiotics, anti-viral agents, anti-fungal agents, steroids, chemotherapeutics, anti-inflammatories, cytokines, and/or synthetic peptides.

Proteins and peptides would also be useful to conjugate to the hES-MSCs and would include erythropoietin (EPO), anti-beta-amyloid peptides, tissue plasminogen activator (TPA), granulocyte colony stimulating factor (G-CSF), interferon (IFN), growth factor/hormone, anti-VEGF peptides, anti-TNF peptides, NGF, HGF, IL-2, CX3CL1, GCV, CPT-11, cytosine deaminase, HSV-TK, carboxyesterase, oncolytic virus, TSP-1, TRAIL, FASL, IL-10, TGFb Proteins and peptides that bind to particular receptors and block these receptors would also be useful and are contemplated by the current invention to be attached to the hES-MSCs.

DNA and RNA that coded for therapeutic proteins and peptide would also be useful to conjugate to the hES-MSCs for delivery across the blood-brain barrier and/or the blood-spinal cord barrier.

The terms "antibody" and "antibodies" include polyclonal antibodies, monoclonal antibodies, humanized or chimeric antibodies, single chain Fv antibody fragments, Fab fragments, and $F(ab')_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Any agent that would block the activation, expression and/or action of a molecule or the receptor of the molecule in the pathway related to any disease in which crossing the blood-brain barrier and/or blood-spinal cord barrier is useful could be attached or conjugated to the hES-MSCs. Such agents include but are not limited to chemicals, phytochemicals, pharmaceuticals, biologics, small organic molecules, antibodies, nucleic acids, peptides, and proteins.

Inhibiting a pathway can also be effected using "decoy" molecules which mimic the region of a target molecule in the pathway binds and activates. The activating molecule would bind to the decoy instead of the target, and activation could not occur.

Inhibition can also be effected by the use of a "dominantly interfering" molecule, or one in which the binding portion of activating molecule is retained but the molecule is truncated so that the activating domain is lacking. These molecules would bind to receptors in the pathway but be unproductive and block the receptors from binding to the activating molecule. Such decoy molecules and dominantly interfering molecule can be manufactured by methods known in the art, and attached or conjugated to the hES-MSCs for delivery across the blood-brain or blood-spinal cord barrier.

A method for delivery of agents across the blood-brain and/or blood-spinal cord barrier is also useful for diagnostic agents, including but not limited to chemicals, antibodies, peptides, proteins, DNA, and RNA. Such agents in order to be useful for diagnosis must have a means of being visualized and/or quantified. Such means include, but are not limited to, fluorescence, biomarkers, dyes, radioactive isotypes labels and/or nanoparticles.

Such a method for delivery and a delivery system would be useful for the diagnosis neurological disorders, multiple sclerosis, cancer, Parkinson's Disease, Alzheimer's Disease, Huntington's Disease, meningitis, encephalitis, rabies, epilepsy, dementia, Lyme's Disease, stroke, and amyotrophic lateral sclerosis, as well as brain and spinal cord injury. Thus, a further embodiment of the present invention is a method of diagnosing a disease or injury, by attaching or conjugating the agent to the human embryonic mesenchymal stem cells to form a complex; and administering the human embryonic mesenchymal stem cells-agent complex to a subject in which a disease is suspected, wherein the human embryonic mesenchymal stem cells cross the blood-brain and/or the blood-spinal cord barrier and deliver the agent to the central nervous system. The human embryonic-mesenchymal stem cells may be in the form of a single cell, a cell culture, a solution or a pharmaceutical preparation. Agents would include but are not limited to chemicals, drugs, proteins, DNA, RNA, antibodies, and small molecules.

Agents, no matter the type and whether for treatment, prevention, or diagnosis, can be conjugated or attached to the hES-MSCs by any method known in the art including but not limited to synthetic extracellular matrix, alginate-poly-L-Lysine encapsulate and/or container.

In certain embodiments, large scale production at industrial level of manufacturing is included in the present disclosure, methods of which are well known in the art. In certain embodiment, the large scale production includes the use of Hyper-STACK 2D culture system and/or Microcarrier 3D bioreactor.

6. EXAMPLES

The present invention may be better understood by reference to the following non-limiting examples, which are presented in order to more fully illustrate the preferred embodiments of the invention. They should in no way be construed to limit the broad scope of the invention.

6.1 Example 1—Derivation of hES-HB-MSCs

Using a method to derive HB from hESC via EB, mesodermal cells (MP) were enriched and further differentiated into either HB or MSC depending on subsequent culture conditions.

Material and Methods

Four hESC cell lines were used: H9 (derived from WiCell Research Institute) (Thomson et al. (1998)); CT2 (derived from University of Connecticut Stem Cell Core (Lin et al. (2010)); MA09 (an FDA approved, clinical-grade cell line derived at Advanced Cell Technology, Inc.) (Klimanskaya et al. (2006)); and ES03-Envy (Envy, a GFP-labeled line, derived at ES International) (Costa et al. (2005)). These cell lines were cultured on Matrigel (BD Biosciences, San Jose, California) and cultured in TeSR1 medium, (Stem Cell Technologies, Vancouver, Canada), with or without adding of 0.05-0.2 µM of BIO (6-Bromoindirubin-3'-oxime (CAS 667463-62-9)).

hESC cells were then differentiated into EB cells and then enriched for HB as previously described (Lu et al. (2008); Lu et al. (2007)). 50-80% confluent hEs cell on the Matrigel plate were digested with Dispase (1 mg/ml for 5 to 10 minutes) and then washed with EB formation basal medium, HPGM (Lonza, Walksville, Maryland), or STEMLINE I/II Hematopoietic Stell Cell Expansion Medium (Sigma, St. Louis, Missouri), or StemSpan H3000 (Stem Cell Technologies, Vancouver, Canada), or IMDM with 10% FBS, or DMEDM/F12 with 10% FBS. Cells were then cultured in EB formation medium supplemented with 50 ng/ml of VEGF (Peprotech) and 50 ng/ml of BMP4 (Stemgent) for 48 hours on ultra-low plate at a density of about 2-3 million cells/ml. After 48 hours, half the culture medium was replaced with fresh EB formation medium plus 25-50 ng/ml of bFGF.

Four days later, EB cells formed in the medium were harvested and dissociated into single cells with TrypLE (Invitrogen) at 37° C. for 2-3 minutes. Cells were washed and resuspended at 1-5 million cells/ml in EB formation basal medium. The single cell suspension were then mixed at 1:10 with Hemangioblast Growth Medium (Stem Cell Technologies, Vancouver, Canada).

Blast cell growth medium (BGM) were made as follows: To 100 ml Serum-free methylcellulose CFU medium (Stem Cell Technologies, H4436 or H4536), added with VEGF, TPO and FLT3-Ligand to 50 ng/ml, bFGF to 20-50 ng/ml, 1 ml of EX-CYTE Growth Enhancement Media Supplement and 1 ml of Pen/Strap, mix well.

The mixtures were vortexed and plated onto ultralow plates by passing through a 16G needle and cultured for 5-9 days at 37° C. with 5% $CO_2$.

Single cells were then re-suspended in MSC medium containing: 1) 10-20% FBS in alpha-MEM (Invitrogen) or 2) 10-20% KOSR alpha-MEM, 3) 10-20% FBS DMEM high-glucose, or 4) 10-20% KOSR DMEM high-glucose, and cultured on either Matrigel, gelatin, vitronectin, fibronectin, collagen I coated plates at a density of 100-5,000 cell/cm². The medium was changed after 24 hours and refreshed every 2-4 days. After 6-12 days the cells gradually differentiated into spindle-like cells similar to typical MSCs.

Flow cytometry staining was used to characterize the hES-MSCs. Cells were washed and blocked with 2% BSA in PBS, and stained with antibodies for various cell surface markers CD31, CD34, CD29, CD73, CD90, CD105, CD44, CD45, CD146, CD166, HLA-ABC, HLA-DR, HLA-G (BD Bioscience or eBioscience) by following the manufacturers' instructions. Data were collected on FACS LSR II Flow Cytometer using FACSDiva software (BD Bioscience). Post-acquisition analysis was performed with the FlowJo software (Treestar).

Results

Figure 2A:
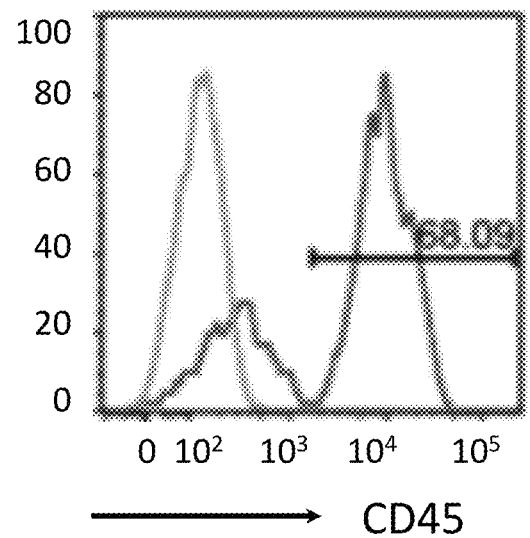
Figure 2B:
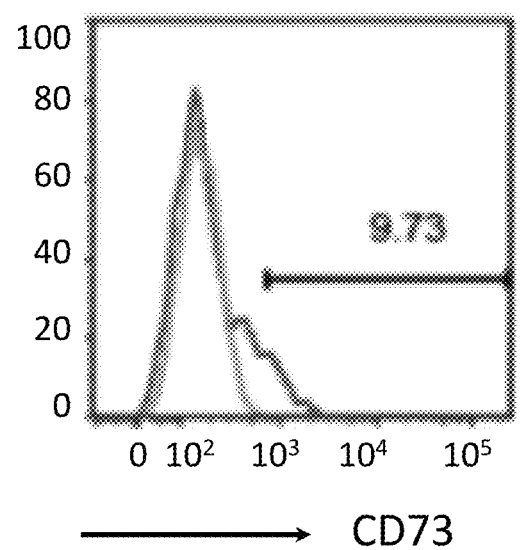
Figure 2C:
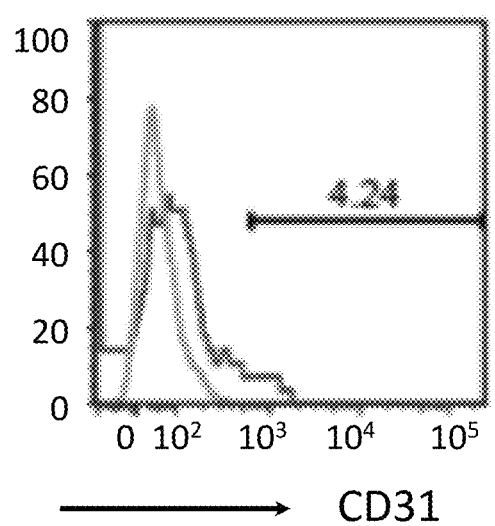

On day 9 of the culture (HB-d9), characterization by flow cytometry showed 68.1% CD45+ cells (hematopoietic progenitors), 22-1% CD31+ cells (epithelial progenitors), and 9.7% CD+ 73 cells (MSC). (FIG. 2)

These cells were replated onto Matrigel-coated plates containing MSC growth medium (Invitrogen). Twenty-four (24) hours later 5-10% of the cells attached to the plate and 9-14 days later, the attached cells fully differentiated into MSC-like cells.

We have also found that by adding GSK3 inhibitor BIO in the feeder free serum free hESC culture can significantly increase the EB and HB formation efficiency. As shown in FIG. 28, adding BIO in the mTersr1 medium can increase the size and yield of the EB culture afterwards. As shown in FIG. 29, total EB number was increase 3 folds after using BIO in the mTesr1 Medium. As shown in FIG. 30, the percentage of CD45 cell differentiation which is an indicator of the hemangioblast differentiation efficiency is also tripled with BIO treatment compare to traditional mTersr1 Medium.

We also found that after differentiation, CD10 expression level varies between different lines of hESC lines. As shown in FIG. 31, hES-MSC from MA09 have extreme high level of CD10, but hES-MSC from H9 and CT2 has lower CD10 expression similar to that from BM-MSC. This is confirmed by both microarray and FACS staining

6.2 Example 2—Further Characterization of hES-HB-MSC Cells

The MSC cells obtained in Example 1 were further analyzed using flow cytometry, immunofluorescence staining, multi-lineage differentiation, and karyotyping.

Materials and Methods

Flow cytometry was performed as described in Example 1.

Immunofluorescence was performed by fixing cells with 4% paraformaldehyde for 15 minutes, and incubating in PBS containing 0.2% Triton X-100 (for permeabilization) and 5% goat serum (for blocking). PBS containing 5% goat serum was used to dilute the primary antibodies. The cells were incubated with the primary antibodies at 4° C. overnight, followed by washing with PBS for three times. Afterwards, the cells were incubated with fluorochrome-conjugated, corresponding secondary antibodies at room temperature for 30 minutes and washed with PBS for three times. Finally, the cells were examined under fluorescence microscope to capture both phase and fluorescent images.

The G-banded karyotyping of hES-MSC was conducted through an outsourced service at University of Connecticut-Storrs Laboratory.

Microarray Analysis: HumanHT-12 V3 expression BeadChip (illumina) was used for microarray, genomic studio V2011.1 was used for data analysis.

Results

The attached cells obtained 9-14 days later, fully differentiated into MSC-like cells with cell surface markers similar to those of BM-MSCs. The hES-MSCs expressed high levels of CD73 (greater than 99%), CD90 (greater than 90%), CD105 (greater than 90%), CD13 (greater than 85%), CD29 (greater than 90%), CD54 (greater than 80%), CD44

Figure 3A:
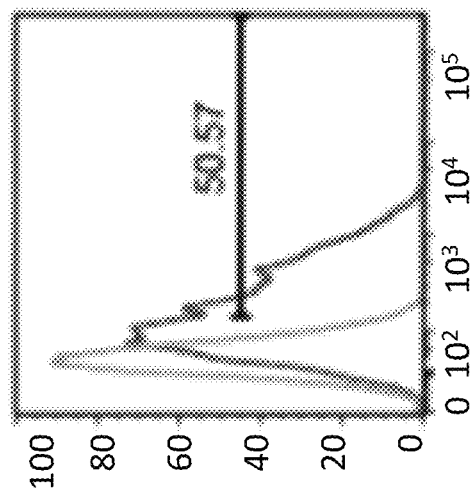
Figure 3B:
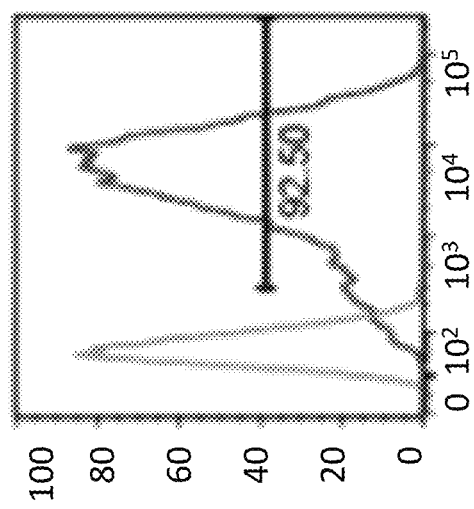
Figure 3C:
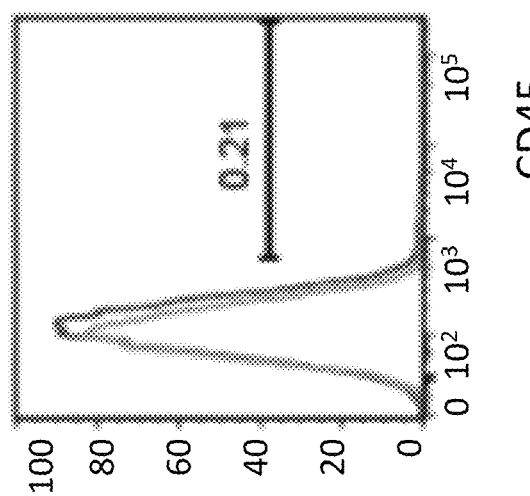

(greater than 99%), and CD166 (greater than 90%), but did not express non-MSC markers such as CD31, CD34 and CD45 (FIGS. 2 and 3).

Figure 4:
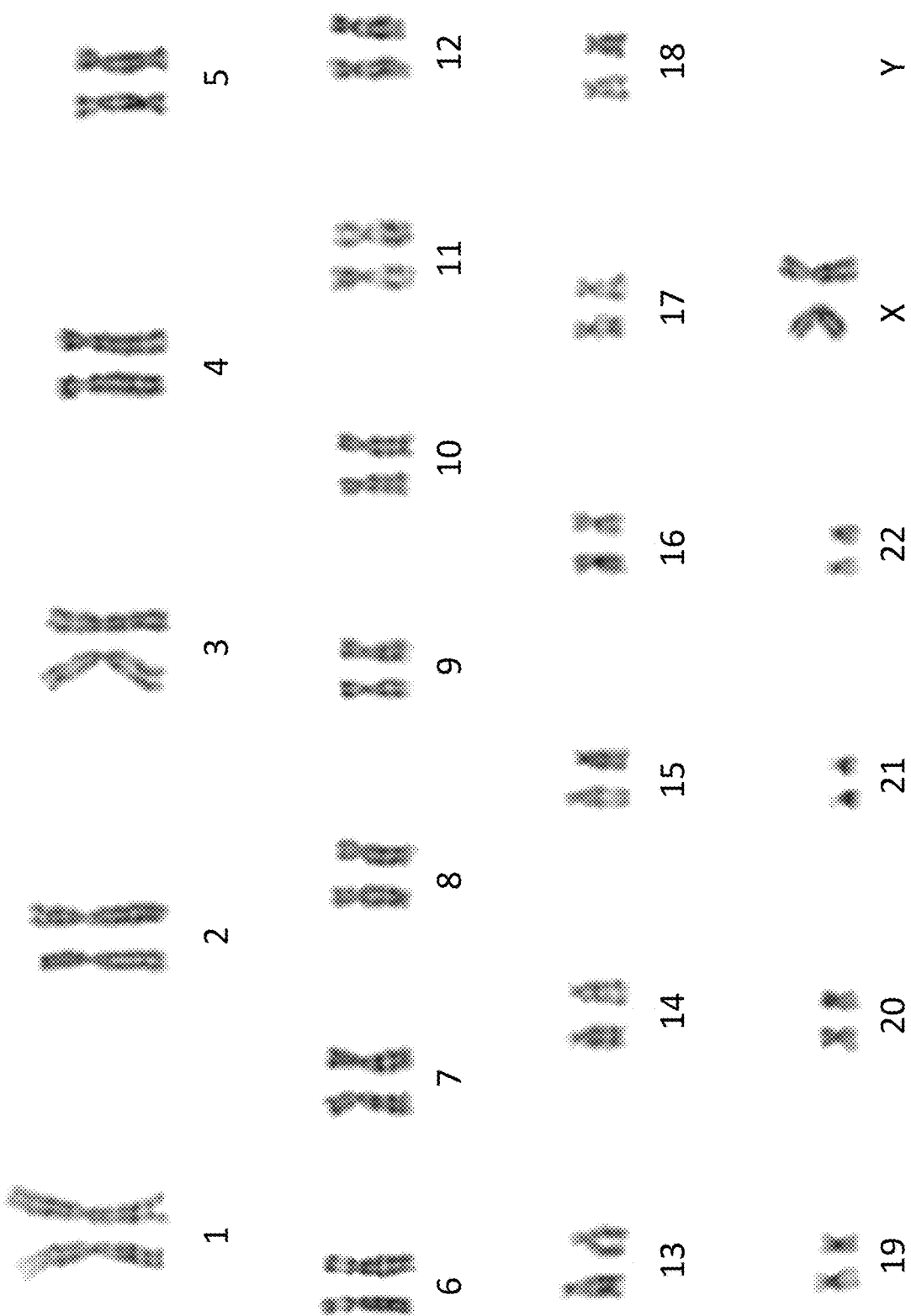

The hES-MSCs could be cultured in vitro for up to 10 passages with normal karyotyping (FIG. 4) and sustained expressional profiles of their cell surface markers and differentiation capability.

6.3 Example 3—hES-MSCs Attenuate the Disease Score of EAE Mice in Both Prophylactic and Therapeutic Modes Because it has been shown that BM-MSCs can attenuate the disease progression of the mouse model of multiple sclerosis, experimental autoimmune encephalomyelitis (EAE), the hES-MSCs obtained in Example 1 were injected into mice with EAE to determine if they would have the same effect.

Materials and Methods

The mouse EAE model was induced as previously described (Stromnes and Goverman (2006)). C57BL/6 mice were subcutaneously injected with a mixture of myelin oligodendrocyte glycoprotein peptide 35-55 ($MOG^{35-55}$), Freund's adjuvant, and pertussis toxin contained in the EAE Induction Kit (Hooke Laboratories, Inc, MA. (Cat. #EK-0114)) following the manufacturer's protocol and as described in Ge et al. (2012).

BM- or hES-MSC at $10^6$ cells/mouse or PBS (a vehicle control) was intraperitoneal (i.p.) injected on day 6 (for pre-onset) or 18 (for post-onset) after the immunization. The disease score was monitored on the mice every day for up to 31 days.

The disease scoring system is as follows:
0: no sign of disease;
1: loss of tone in the tail;
2: partial hind limb paralysis;
3: complete hind limb paralysis;
4: front limb paralysis; and
5: moribund
(Stromnes and Goverman, 2006).

Results

Figures 5A, 5B, 5C:
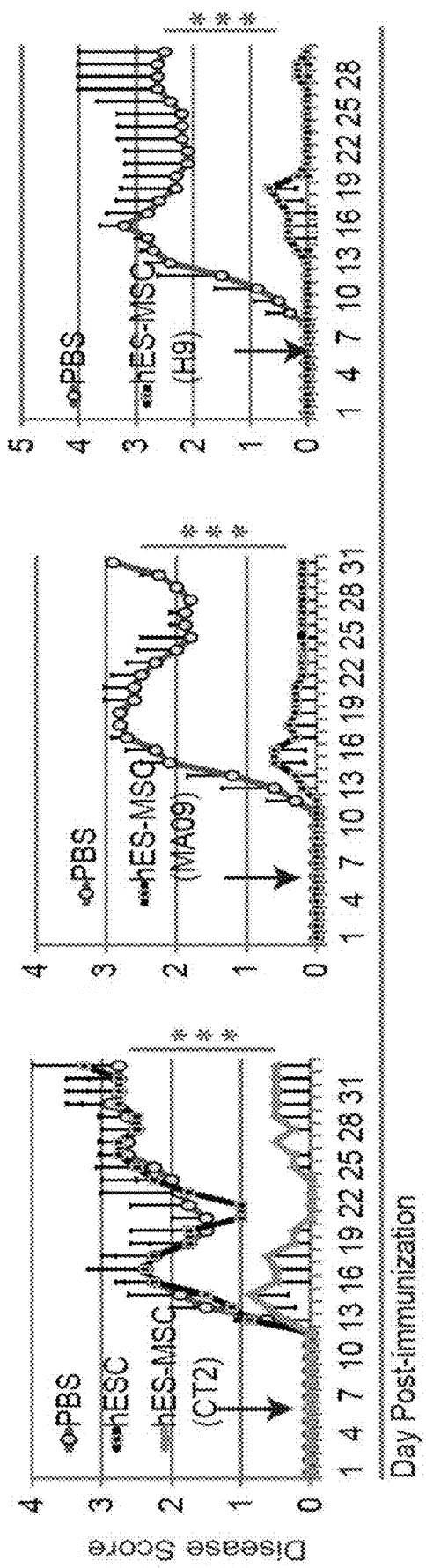

As shown in FIG. 5, the hES-MSCs derived from the three hESC lines CT2, MA09, and H9 all significantly attenuated the daily disease scores, as well as the cumulative and maximal disease scores (FIG. 6) when injected at 6 days or pre-onset of disease, showing a prophylactic effect of the hES-MSCs. Mice injected with CT2 hEScs manifested high disease scores similar to those seen with control mice receiving PBS injection, ruling out the possibility of the effect of human xenograft in mice.

Figure 7:
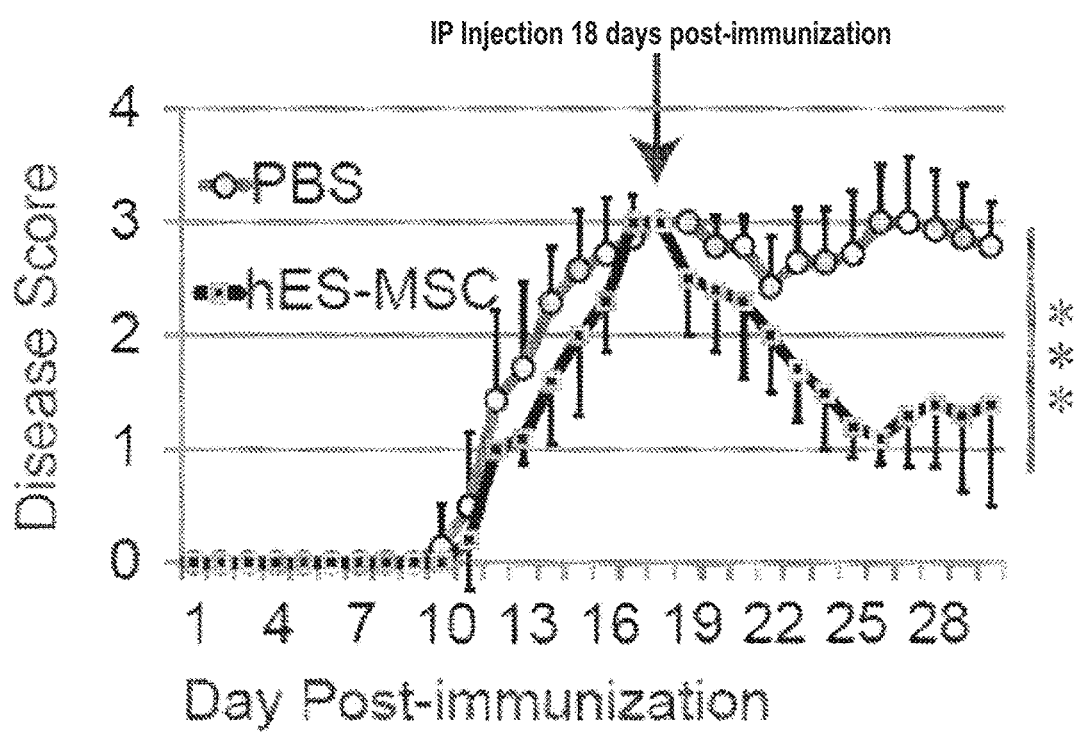

As shown in FIG. 7, treatment with hES-MSCs also had a therapeutic effect on mice that have already developed EAE. When injected with hES-MSCs on day 18 post-immunization (right after the disease score peaked in mice), there was a gradual decline of the disease score in hES-MSC-treated EAE mice with an average score of 1.67 at day 30, whereas the PBS-treated EAE mice had an average score of 2.8 at the same day.

6.4 Example 4—Characterization of the Central Nervous System of the EAE Mice Treated with hES-MSCs The central nervous system of the EAE mice treated with hES-MSCs was further analyzed.

Materials and Methods

Flow cytometry as described in Example 1 was used. Regulatory T cells in the CNS of EAE mice treated with PBS or hES-MSC (CT2) as described in Example 3 were analyzed day 15 post-immunization through FACS analysis of Foxp3 and CD25.

Th1 and Th17 cells from the CNS of EAE mice treated with PBS or hES-MSC (CT2) as described in Example 3 were analyzed day 15 post-immunization by perfusing EAE mice with 20 ml cold PBS through the left ventricle. The brain and spinal cord were harvested from the perfused mice and ground into small pieces. After digestion with collagenase (1 mg/ml) and Dispase (1 mg/ml) for 20 minutes. at 37° C., the tissues were further ground and passed through a 40-µm strainer. Cells were washed and re-suspended in 4 ml of 40% Percoll and overlaid onto 5 ml of 70% Percoll. After centrifugation at 2,000 rpm for 20 minutes cells in the inter layer were collected. The cells were then stimulated with 12-Otetradecanoylphorbol-13-acetate (TPA) at 50 ng/ml (Sigma, MO) and ionomycin at 500 ng/ml (Sigma, MO) in the presence of GolgiStop (BD Bioscience, CA) for 6 hours. Cells were then immunostained with anti-CD4-FITC and anti-CD8-Pacific Blue antibodies (BD Bioscience, CA). For intracellular staining of IFN γ and IL-17A, cells were fixed and permeabilized using an intracellular staining kit (BD Bioscience, CA) by following the manufacturer's instructions.

Pathology of the Spinal Cord

Paraffin-embedded spinal cord cross sections were immunostained for CD3 (Biocare Medical) or Iba1 (Waco) and counterstained with anti-MBP (Millipore) or fluoromyelin as previously described (Crocker et al., 2006; Moore et al., 2011). Quantification of anti-MBP staining intensity was performed on the lateral columns of sections from the thoracic and lumbar levels of spinal cord samples using ImageJ (NIH) (Crocker et al., 2006). At least three regions of interest were analyzed for each subject in each treatment group.

Results

Because of the important role of immune-suppressive regulatory T cells ($T_{reg}$ cells detected as Foxp3+ and CD25+) in suppressing inflammation (Hansen et al., (2008)), the ratio of $T_{reg}$ cells among T cells infiltrated into the CNS of EAE mice treated with hES-MSCs and PBS was looked at, and it was found that the ratio did not increase (FIG. 8), suggesting that $T_{reg}$ cells may not be responsible for the immunosuppressive effect of hES-MSCs. This is similar to the case with BM-MSC on EAE mice reported by others (Zappia et al. (2005)).

Much fewer $CD4_+$, $CD8_+$, Th1, and Th17 T cells were isolated from the CNS in the hES-MSC treat group than in the control PBS or hESC-injected group (FIG. 9), suggesting that reduction of these inflammatory T cells may contribute to the improvement of the symptoms of the hES-MSC-treated mice.

Pathologically, the microglial response in the spinal cord was analyzed which is a sign of inflammatory responses in the CNS, via immunostaining for ionized calcium-binding adapter molecule 1 (IBA1). IBA1 staining was diminished in the spinal cord of EAE mice treated with hES-MSC compared to those treated with PBS (FIG. 10). Consistently, infiltration of total T cells (stained as $CD3_+$ cells) into the spinal cord was decreased in the hES-MSC-treated EAE mice compared to the control (FIG. 10).

Figure 11:
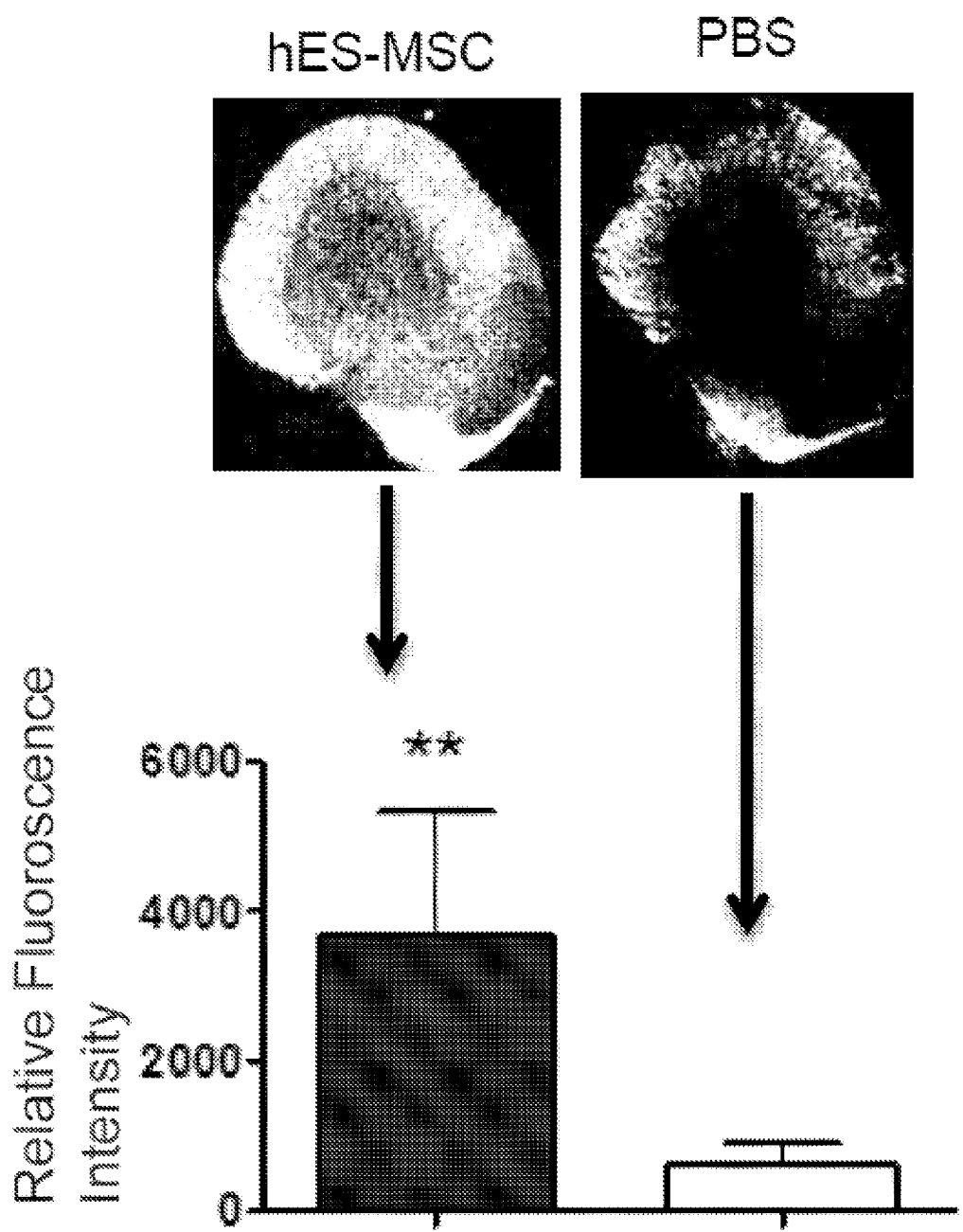

Immunostaining for myelin-binding protein (MBP) in the spinal cord indicates that demyelination was reduced in the mice treated with hES-MSC compared to the mice treated with PBS (FIGS. 10 and 11), suggesting that hES-MSC can prevent and/or repair the inflammatory damages in the CNS and preserve the integrity of myelin.

6.5 Example 5—hES-MSCs have a Stronger Anti-EAE Effect In Vivo than BM-MSC with Evidence in the CNS BM-MSC have long been used to treat autoimmune diseases including MS on various animal models and clinical trials, however the outcomes include mixed or improved response or no change (Tyndall, 2011). Thus, hES-MSCs were compared with human BM-MSC in this study.

Materials and Methods

EAE mice as described in Example 3 were i.p. injected at 6 days post-immunization with PBS, BM-MSC or hES-MSCs (MA09) ($10^6$ cells from three different sources). Disease scoring was done as described in Example 3.

Flow cytometry of T cells infiltrated into the CNS of the BM-MSC-treated mice was performed as described in Example 4.

Results

Five of human BM-MSC line obtained from six sources failed to attenuate the disease score of EAE mice, only one BM-MSC line mildly decreased disease score by 1, in marked contrast to hES-MSC that again showed strong anti-EAE effect (FIG. 12).

T cells infiltrated in the CNS of the EAE mice treated with BM-MSC were found to have higher ratio of Th17 cells among the CD4 T cells in the CNS than both the PBS- and hES-MSC-treated mice, suggesting that BM-MSC can increase the differentiation of Th17 cells. After calculating the total infiltrated cell Th1 and Th17 cells, it was found that all 3 lines of BM-MSC significantly increased the total Th17 cell number (FIG. 13), and only one line can increase the total Th1 cell number, whereas hES-MSCs can decrease both Th1 and Th17 as shown in Example 4. Together, this indicates that BMMSC not only failed to inhibit the Th1 response, rather they increased the Th17 response in vivo. Reduced fluoromyelin staining of MBP in the spinal cord confirms severe damage in both PBS-treated and BM-MSC-treated mice while MBP levels were preserved in hES-MSC-treated mice (FIG. 14). The damaged regions in BM-MSC-treated mice also show a high number of DAPI positive cells, suggesting more inflammatory cells infiltration.

6.6 Example 6—hES-MSCs can Enter the Central Nervous System

Since it is well known that the BBB and BSCB play a key role in preventing T cells from entry into the CNS, it was asked whether they also play a role in the entry of MSC into the CNS.

Materials and Methods

MSC differentiated from the hESC line Envy that constitutively expressed GFP (Costa et al., 2005) as described in Example 1, and GFP-labeled human BM-MSC (Hofstetter et al., 2002), were injected them into EAE mice 6 days post-immunization, and isolated the spinal cord 14 days post-immunization.

The migration of the $GFP_+$ cells through the BSCB in the spinal cord

Results

As shown in FIG. 18, only the $GFP_+$ hES-MSC migrated out of the vessels and aggregated in the parenchyma of the perivascular regions of the spinal cord, however, the $GFP_+$ BM-MSC were observed only inside the vessels. Parenchymal inflamed venules showed "parenchymal localization" of GFP+hES-MSC, indicating they have extravasated. In contrast, the mice with GFP+BM-MSC appeared to have more "lumen restricted" GFP immunoreactivity (FIG. 15A). Inflamed meningeal venules also displayed limited extravasation of GFP+BM-MSCs when compared to mice receiving GFP+hES-MSCs (FIG. 15B).

These results indicate that only hES-MSC, and not BM-MSC, have the requisite mechanism to exit the vessels efficiently to fulfill enter into the CNS.

6.7 Example 6—hES-MSCs have a Stronger Inhibition on T Cell Functions In Vitro than BM-MSC hEs-MSCs and BM-MSCs were compared for their ability to inhibit T cell proliferation in vitro following antigen stimulation.

Materials and Methods

The in vitro assay for T cell proliferation was performed using lymphocytes isolated from mouse peripheral lymph nodes. These lymphocytes were labeled with 5 µM of and labeled the cells with carboxyfluorescein succinimidyl ester (CFSE) to track their proliferation by monitoring CFSE dilution in their daughter cells, for 10 minutes at 37° C. 10,000 hES-MSCs or BM-MSCs were mixed with 100,000 lymphocytes per well in a 96-well plate, and the cells were stimulated for proliferation with plate-bound anti-CD3 (at 0.2, 0.6, 2, and 6 µg/ml) and soluble anti-CD28 antibodies (eBioscience, CA). The cells were collected 3 days after the stimulation, followed by FACS staining with anti-CD4 and anti-CD8 antibodies (BD Bioscience, CA). CFSE dilution was gated on $CD4_+$ and $CD8_+$ T cells, respectively.

Results

Figure 16A:
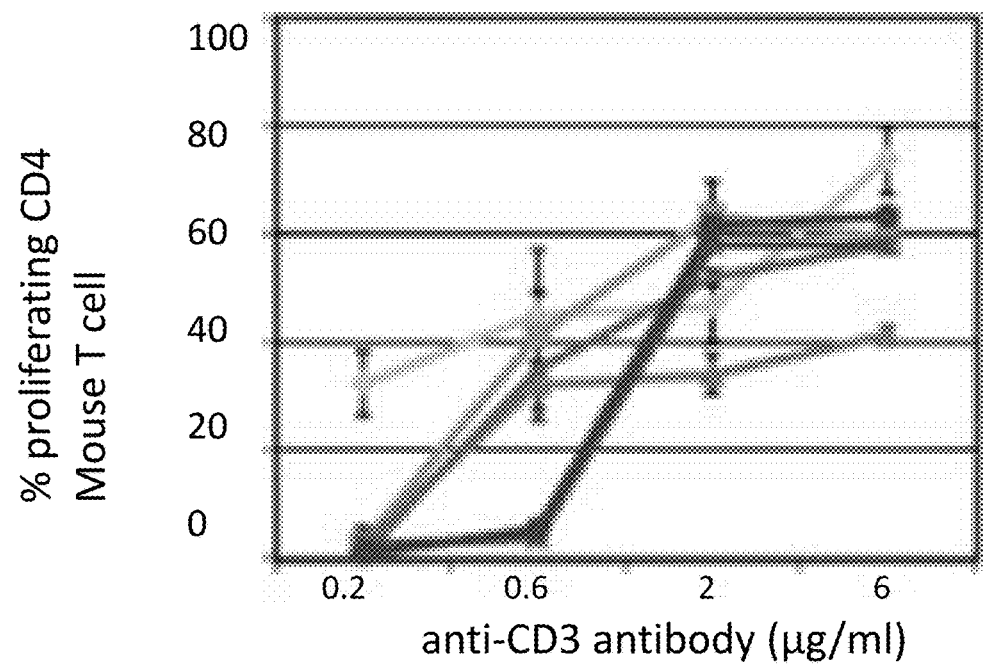
Figure 16B:
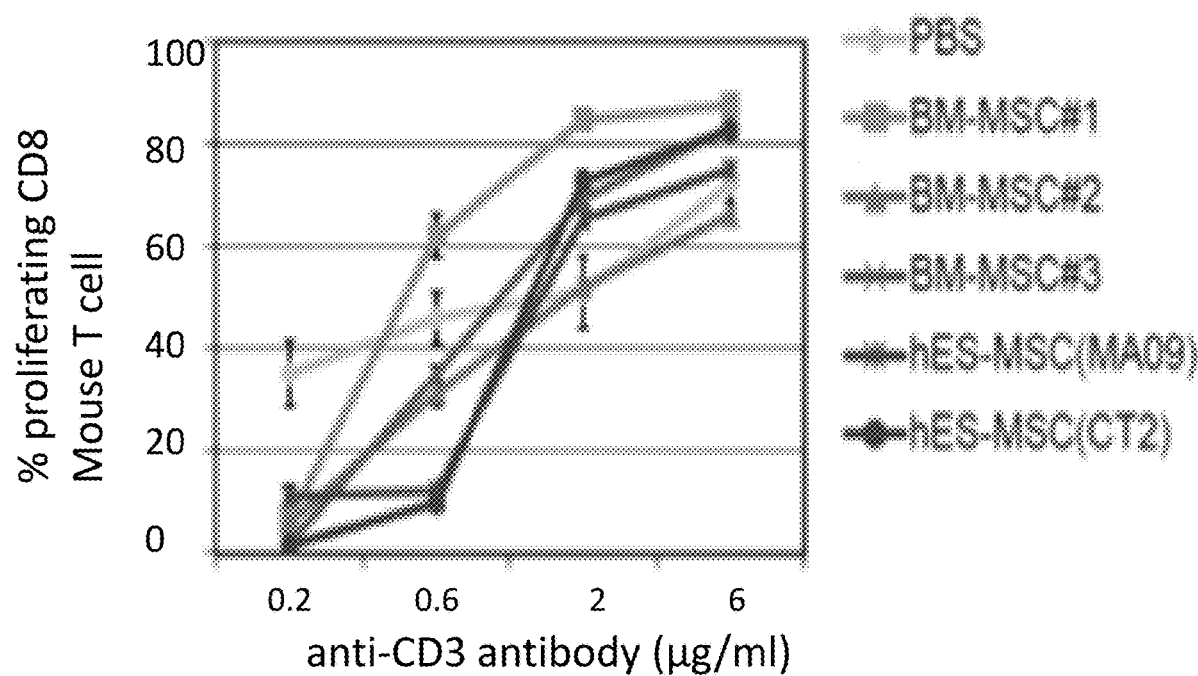
Figure 17:
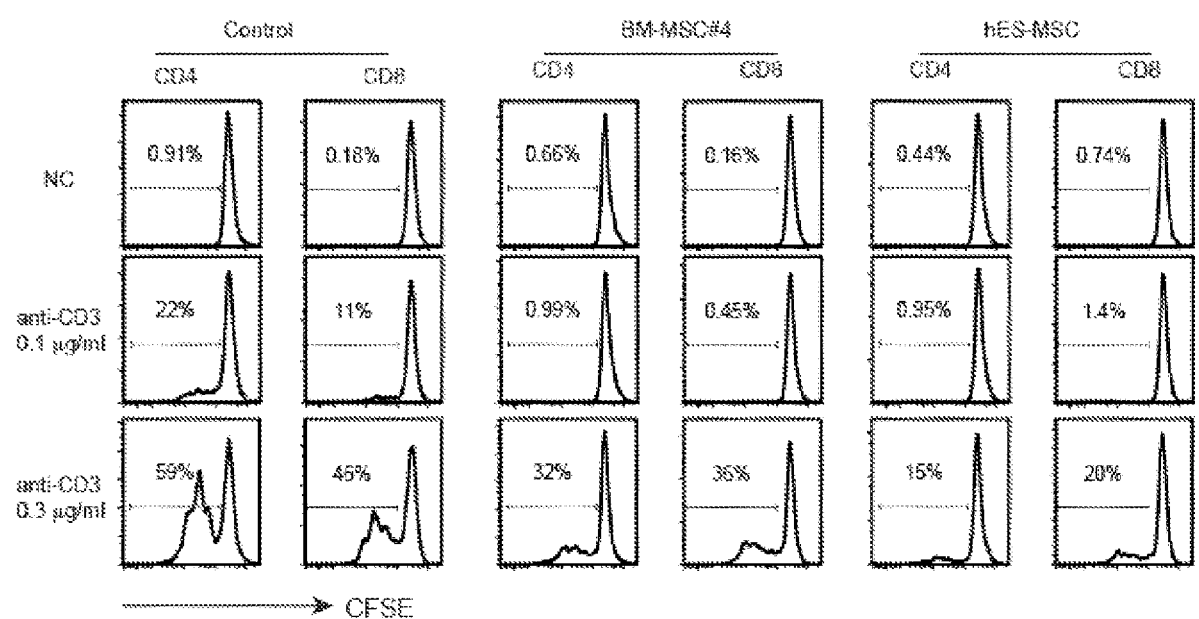

Using the in vitro assay with mouse lymphocytes, it was found hES-MSCs inhibited the proliferation of mouse $CD4_+$ and $CD8_+$ T cells when stimulated with anti-CD3 antibody at 0.2 and 0.6 µg/ml, or 0.1 and 0.3 µg/ml, whereas BM-MSC only did so when the T cells were stimulated with anti-CD3 antibody at low doses, i.e., 0.2 or 0.1 µg/ml (FIG. 16, 17)'

6.8 Example 7—Further Evidence that hES-MSCs have a Stronger Inhibition on T Cell Functions In Vitro than BM-MSC Materials and Methods In vitro assays of Th0, Th1, and Th17 cells were performed using naive mouse $CD4_+$ T cells isolated from mouse spleen and purified with the Naive CD4 T Cell Enrichment kit (Stem Cell Technologies, Canada). The cells were incubated with hES-MSCs or BM-MSCs at a ratio of 1:10 or PBS, followed by Th1 or Th17 differentiation for 5 days. Cells activated with anti-CD3 and anti-CD28 antibodies under the following conditions. Cells were cultured with rhIL-2 at 5 ng/ml to remain in Th0 status, with anti-mIL-4 at 5 µg/ml (eBioscience, CA), rhIL-2 at 5 ng/ml (eBioscience, CA), and mIL-12 at 10 ng/ml (PeproTech, CA) for Th1 differentiation, and with anti-mIL4 at 5 ug/ml, anti-mIFNγ at 5 ug/ml (eBioscience, CA), rmIL-6 at 20 ng/ml (Peprotech, CA), and rhTGF-β1 at 1 ng/ml (Peprotech, CA) for Th17 differentiation. For some groups, anti-hIL-6 antibody (eBioscience, CA) was added to culture at 10 µg/ml. Naïve CD4 T cells were plated at $0.3 \times 10^6$ cells/well in 24-well plates. hES- or BM-MSC that had been mitotically-arrested through irradiation at 80 Gy, were added 1 hour after. IFNγ+ and IL-17$^+$ cells were determined via FACS.

Results

Since EAE mice treated with BM-MSC had more Th17 and Th1 cell infiltration into the CNS than mice treated with hES-MSC as shown in Example 5 and FIG. 18, these T cell subtypes were examined in vitro in the presence or absence of hES- and BM-MSC, As shown in FIG. 18, under the Th1 condition, differentiation into Th1 (IFNγ+/IL-17−) cells was reduced by hES-MSC (from 29.70 to 18.0%) In comparison, all BM-MSC lines either did not change or increased the Th1 differentiation (26.9% to 43.6%).

Under the Th17 differentiation condition, both hES- and BM-MSC reduced the ratio of Th17 cells, but surprisingly all BM-MSC lines significantly increased the percentage of IFNγ producing cells but not hES-MSCs.

These results suggest that BM-MSC cannot inhibit Th1 differentiation under the Th1 condition, and increased Th1 cell differentiation under Th17 conditions. These complex effects of BM-MSC in vitro may mirror the mixed effects on EAE mice.

6.9 Example 8 Gene Expression Profiles of hES-MSCs and BM-MSCs

Microarray analysis was performed to compare the gene expression profile of hES-MSCs and BM-MSCs.

Materials and Methods

For microarray analysis RNA of hES-MSC at passages 2-4 or BM-MSC at passage 3 were harvested with Trizol (Invitrogen, CA) following manufacturer's protocol. The HumanHT-12 v4 Expression BeadChip (Illumina, San Diego, CA) was used to analyze the gene expression profile of the cells. Data were analyzed using Genome Studio V2011.1. Two BM-MSC cell lines from different sources were used, and two hES-MSC cell lines, derived from H9 and MA09, were used.

Flow cytometry analysis was performed as in Example 1.

Results

As shown in Table 1, the overall expressional profiles of the hES- and BMMSC samples were quite similar with most of the anti-inflammatory genes such as HLA-G, HGF, COX2, IDO1, and iNOS expressed at similar levels among these samples.

TABLE 1

|  | hES-MSC | BM-MSC |
| --- | --- | --- |
| HLA-G | 359.1 ± 52.2 | 726.8 ± 51.3 |
| HGF | 116.9 ± 19.1 | 115 ± 15.3 |
| PTGS1/COX-1 | 136.3 ± 2.5 | 122.7 ± 14.1 |
| PTGS2/COX-2 | 346.2 ± 244.5 | 964 ± 674.7 |
| IDO1 | 121.9 ± 3.9 | 127.6 ± 12.4 |
| IDO2 | 119.9 ± 1.8 | 123.5 ± 5.46 |
| NOS2/iNOS | 129.5 ± 10.6 | 154.2 ± 11.2 |

However, a small set of genes was expressed differentially between the hES-MSCs and BM-MSCs samples. These genes include those encoding anti-inflammatory factors, such as IL-10 and TGFβ and pro-inflammatory factors, such as, CCL2, MMP2, RAGE, IFNγR1, IFNγR2, IL-12, IL-6, and VCAM1 (FIG. 19).

The higher expression of IL-6 in BM-MSC than hES-MSC was confirmed through intracellular staining followed by flow cytometry analysis as shown in FIG. 20.

Based on microarray analysis, the transcriptomic profiles of hES-MSC and BM-MSC are quite similar. Only a small set of genes has differential expression between hES-MSC and BM-MSC. These genes include those encoding potential anti-inflammatory factors (AIFs) and pro-inflammatory factors (PIFs). Among the differentially expressed factors in hES-MSC and BM-MSC, some potential AIFs such as IL-10 (Dai et al., 2012) and TGFβ2 (Huss et al., 2011) are expressed higher in hES-MSC than BM-MSC, whereas some potential PIFs such as IL-6 (Quintana et al., 2009), IL-12 (Becher et al., 2002), CCL2 (Mahad and Ransohoff, 2003), VCAM1 (Chaudhary et al., 2006), RAGE (Cuccurullo et al., 2006), and MMP2 (Cunnea et al., 2010) have lower expression in hES-MSC than BM-MSC. The lower ratio of IL-6$^+$ cells among hES-MSC than BM-MSC was confirmed via FACS.

Provided herein is a method of identification of highly immunosuppressive hES-MSC., The method comprises using expression level of IL-6 and other factors mentioned above as indicator of the quality of hES-MSC and BM-MSC. Provided herein are hES-MSC that has <5% of IL-6 positive cells, and low level of IL12, TNFα, RAGE, and other pro-inflammatory cytokines. Also preferred are hES-MSC that express high level of TGFβ and IL-10. Provided herein are methods of producing hES-MSC that has improved immunosuppressive function by genetic and epigenetic modification of differentially expressed factors.

6.10 Example 9—BM-MSCS, but not hES-MSCS, Produce IL-6 in Response to Activated T Cells Since it is known that MSCs can be activated to produce cytokines including IL-6 following stimulation with factors such as IFNγ (Ryan et al., 2007), TNFα (English et al., 2007), Toll-like receptor, CCL2, CCL5, and IL-8 in vitro and in vivo (Anton et al., 2012; Waterman et al., 2010), it is possible that MSC may produce more IL-6 in contact with activated T cells as the latter produces high levels of IFNγ and TNFα.

Materials and Methods

BM-MSCs and hES-MSCs (MA09) were co-cultured with human PBMC for four days. 2.5 ng/ml of PHA was added for the final two days to stimulate T cells. The PBMC was washed away and quantitative RT-PCR was performed as described in Example 8.

MSCs were stimulated with directly with IFNγ in vitro at 10 ng/ml for 12 hours, and IL-6 was detected via intracellular FACs.

Results

When the MSC were directly stimulated with IFNγ in vitro, it was found that IL-6 expression in hES-MSC did not change following the stimulation, but IL-6 level was almost doubled in IFNγ-treated BM-MSC compared to the already high, basal level in the untreated BM-MSC (FIG. 21). These results suggest that BM-MSC, but not hES-MSC, produce high levels of the proinflammatory factor IL-6 in response to activated T cells or inflammatory cytokines, probably another reason for the compromised immunosuppressive effect of BM-MSC.

6.11 Example 10—Further Evidence of IL-6 Involvement in BM-MSC Limited Ant-EAE Activity Since IL-6 enhances T cell proliferation and survival, and promote T17 cell differentiation (Dienz and Rincon, 2009; Rochman et al., 2005), elevated IL-6 production in BM-MSC may counteract the otherwise anti-inflammatory activity of BM-MSC. To test this possibility, we used a neutralizing anti-human IL-6 antibody in the following experiments.

Materials and Methods

The in vitro assay for T cell proliferation described in Example 6 was used. CFSE labeled mouse lymphocytes were incubated with and without BM-MSCs at a ratio of 1:10 and anti-human IL-6 antibody at 10 μg/ml. Ratios of divided CD4+ and CD8+ T cell was determined CFSE FACS staining.

hES-MSCs or BM-MSCs were incubated with mouse naïve CD4+ T cells at a ratio of 1:10 under the Th17 differentiation conditions for five days as described in Example 7 in the presence or absence of 10 μg/ml of anti-human IL-6 antibody. IFNγ+ and IL-17$^+$ cells were determined via intracellular FACS staining after TPA/ionomycin stimulation.

Results

Figures 22A, 22B, 22C:
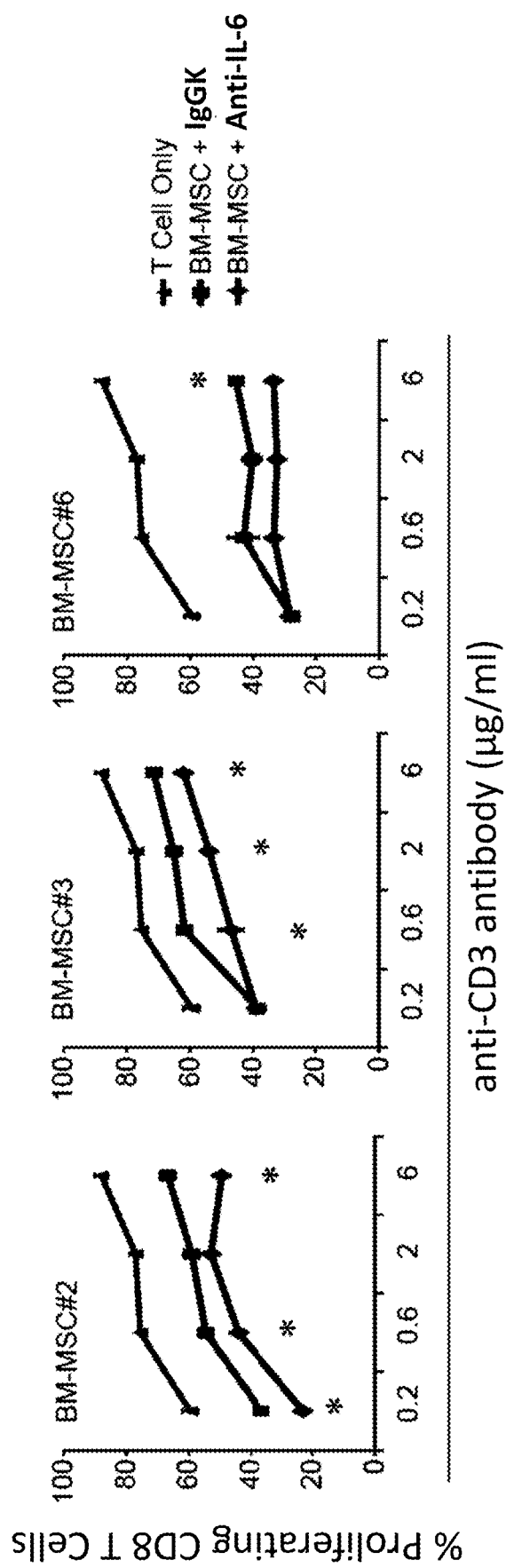

As shown in FIG. 22, 23, the anti-IL-6 antibody enhanced the suppressive effect of different BM-MSC lines on mouse $CD8_+$ T cell (FIG. 22, 23B) and CD4+ T cell (FIG. 23A) proliferation in response to anti-CD3 antibody stimulation.

Next, it was examined whether adding anti-human-IL-6 antibody can reverse the increase of Th1 differentiation in vitro. Under a special differentiation condition, so called Th0 condition, no mouse cytokine was added but anti-mouse-IFNγ and anti-mouse-IL-4 was used to inhibit both Th1 and Th2 differentiation. Co-cultured mouse T cells with human BM-MSC but not hES-MSC can dramatically increase the Th1 differentiation of mouse T cells. Using anti-human-IL-6 antibody can reduce this effect by 30%-50% (FIG. 24). Thus, the elevated IL-6 production in BM-MSC may be at least partially responsible for the compromised anti-inflammatory and anti-EAE effects of the cells, in sharp contrast to hES-MSC which have low IL-6 production.

6.12 Example 11—Irradiated hES-MSCs Retain Anti-EAE Effect

Mouse embryonic fibroblasts (MEF) are routinely irradiated to stop mitosis without affecting their feeder activity to sustain self-renewal and pluripotency of hESC, as used since the first derivation of hESC lines (Thomson et al. (1998)). Based upon this, it was hypothesized that irradiated MSC may also sustain the anti-EAE effect exerted by non-irradiated MSC.

Materials and Methods hES-MSC, derived from MA09 hESC were irradiated at 80 Gy right before injecting them into EAE mice at $10^6$ cells/mouse at day 6 post-immunization as described in Example 2. Disease scoring was done as described in Example 2.

Results

Figure 25:
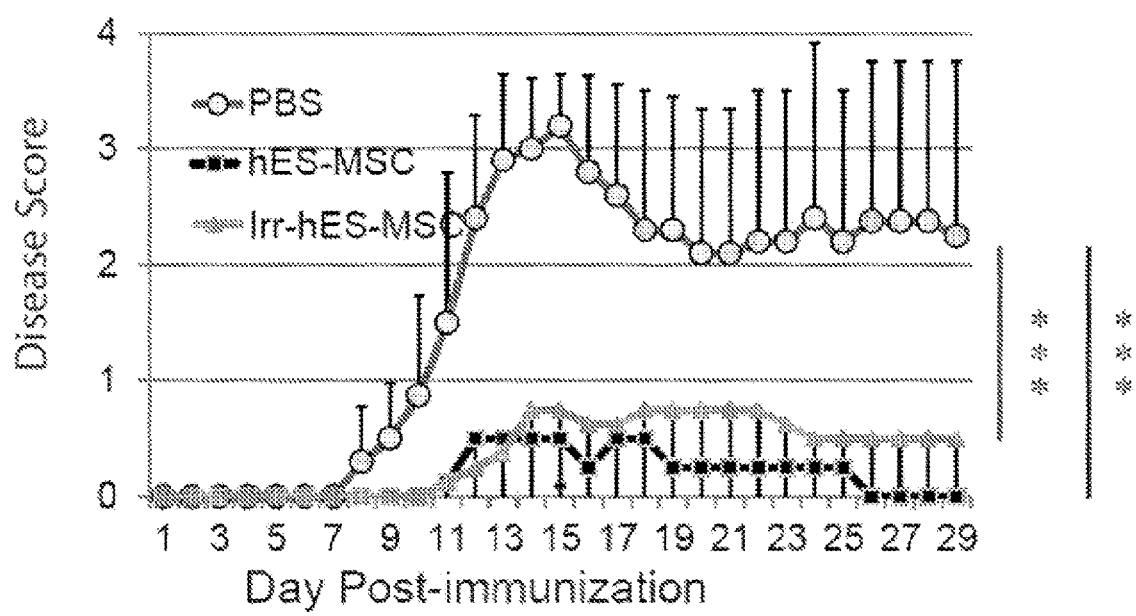
FIG. 25 shows the clinical disease scores of EAE mice injected with irradiated hES-MSC (Irr-hES-MSC; from MA09), hES-MSCs (from MA09) or saline (PBS). N=5 mice per group, ***P<0.001.

As shown in FIG. 25, a decrease of the disease score in the injected mice was found although milder than the decrease caused by non-irradiated hES-MSC. When the dose of hES-MSC was increased to $2 \times 10^6$ cells/mouse, similar anti-EAE effects were seen between the irradiated and non-irradiated hES-MSC groups 6.13 Example 12—Irradiated hES-MSCs have a Similar Lifespan to the Host Mice The lifespan of irradiated hES-MSCs in vivo was established to determine if the irradiated cells would be effective on EAE.

Materials and Methods

Figure 26:
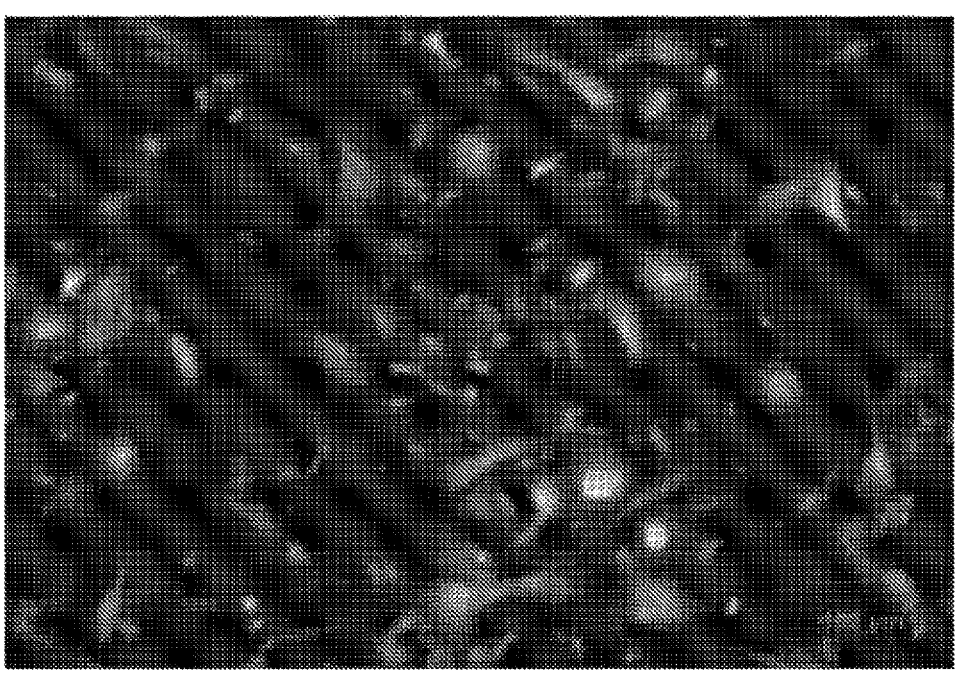
FIG. 26 shows immunostaining of luciferase-expressing hES-MSC (CT2). The luciferase expressing hES-MSCs cultured in Petri dish were immunostained with an anti-luciferase antibody (green) and counterstained for nuclei with DAPI (blue).

To determine the lifespan of irradiated hES-MSC in vivo, CT2 hESC clone with constitutive expression of luciferase in the hESC and their progeny was produced by transducing the cells with a lentiviral vector (Pomper et al. (2009)). The cells were stained with an anti-luciferase antibody (green) and counterstained for nuclei with DAPI (blue) and were confirmed to be luciferase positive by fluorescence microscopy (FIG. 26).

The luciferase-expressing hES-MSCs (CT2) were irradiated, and non-irradiated and irradiated cells were injected into EAE mice as described in Example 2.

Results

Figure 27:
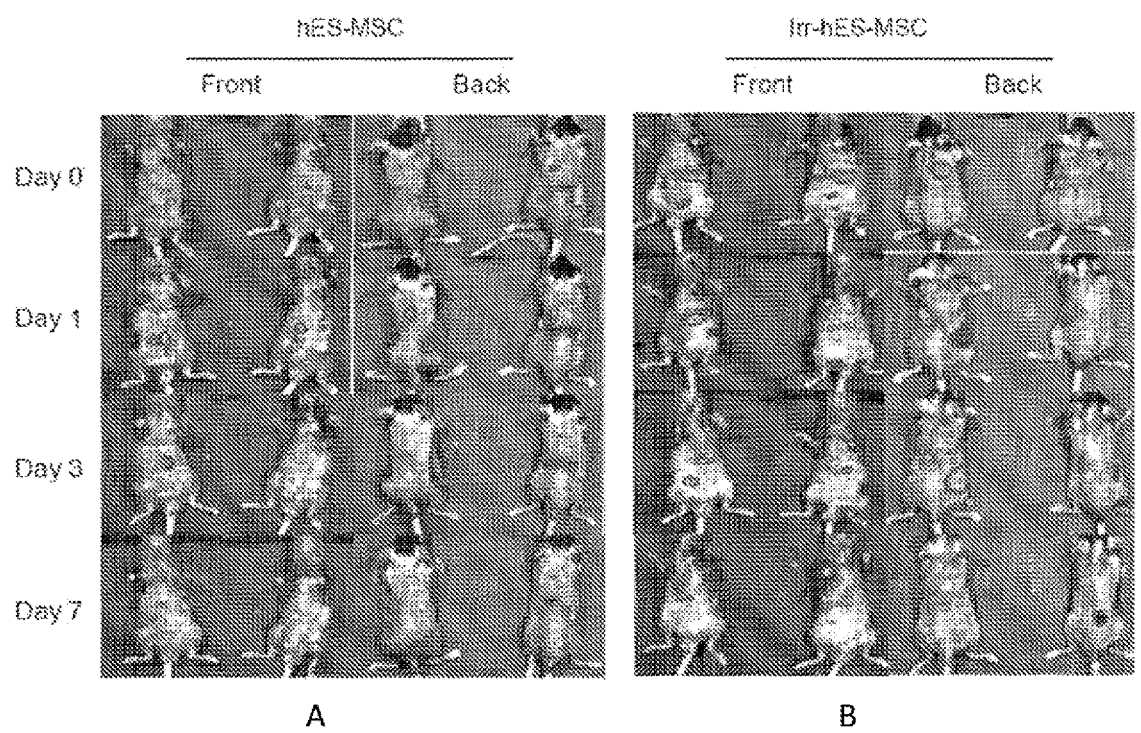

It was found that the irradiated hES-MSC had about the same lifespan of 7-10 days in the mice post-injection as the non-irradiated hES-MSC (FIG. 27). These data, together, suggest that irradiated hES-MSC have similar lifespan in the host mice and can achieve similar efficacy on EAE (when given at doubled dose) compared to non-irradiated hES-MSC, and no tumors are found in the immune-compromised mice transplanted with hES-MSCs.

6.14 Example 14—Qualification Procedure for Clinical Grade hES-MSCs hES-MSC are characterized through multi-color flow cytometry analyses and immunofluorescence staining using six groups of markers: (1) MSC-specific markers (set 1): CD73, CD90, CD105, CD146, CD166, and CD44, (2)

MSC-specific markers (set 2): CD13, CD29, CD54, CD49E, SCA-1, and STRO-1, (3) hematopoietic stem/progenitor markers: CD45 and CD34, and endothelial cell marker CD31, (4) immunogenic markers: HLA-ABC, HLA-G, CD80, and CD86, (5) cytokines: IL-10, TGFβ, IL-6, IL-12 and TNFα, and (6) pluripotency markers: OCT4, NANOG, TRA-1-60, and SSEA-4. A clinical grade MSC contains >95% of the cells positive for group-1 markers, >80% positive for group 2, <5% for group 3, >80% positive for IL-10 and/or TGFβ, <5% positive for IL-6, IL-12 and TNFα, and <0.001% co-expressing group 6. Heterogeneity and purity of the cells can be tested as described above. The clinical-grade MSC will be compared side-by-side with the preclinical-grade MSC validated in Aim 3.1 as a positive control.

To examine whether the hES-MSC have a consistent cytokine secretion profile, 24 hr condition medium of hES-MSC will be analyzed for secreted cytokines expression using Multiplex System with R&D Fluorokine MAP multiplex Human Cytokine Panel A and TGF-beta 3-plex. All important cytokines that are critical for MSC function will be analyzed simultaneously with only 50-100 ul sample needed, including, but not limited to, CCL2, CCL3, CCL4, CCL5, IL-1, IL-2, IL-4, IL-6, IL-8, IL-10, IL-17, TNFα, TGFβ, IFNγ, IFNα, IFNβ, GM-CSF, G-CSF, bFGF, CXCL5, VEGF, TPO, CXCL10, CCL11, CD40 ligand, EGF, HGF, IL12A, IL12, IL-13 and/or Leptin.

hES-MSC are also analyzed for: (1) presence of exogenous materials such as endotoxin and residual cytokines/growth factors used to differentiate hES-MSC, and (2) genomic abnormalities (via karyotyping and whole-genome sequencing).

All references, including publications, patent applications and patents, cited herein are hereby incorporated by reference to the same extent as if each reference was individually and specifically indicated to be incorporated by reference and was set forth in its entirety herein.

REFERENCES

Al Jumah, M. A., and Abumaree, M. H. (2012). The Immunomodulatory and Neuroprotective Effects of Mesenchymal Stem Cells (MSCs) in Experimental Autoimmune Encephalomyelitis (EAE): A Model of Multiple Sclerosis (MS). International journal of molecular sciences 13, 9298-9331.

Anton, K., Banerjee, D., and Glod, J. (2012). Macrophage-associated mesenchymal stem cells assume an activated, migratory, pro-inflammatory phenotype with increased IL-6 and CXCL10 secretion. PLoS One 7, e35036.

Auletta, J. J., Bartholomew, A. M., Maziarz, R. T., Deans, R. J., Miller, R. H., Lazarus, H. M., and Cohen, J. A. (2012). The potential of mesenchymal stromal cells as a novel cellular therapy for multiple sclerosis. Immunotherapy 4, 529-547.

Barberi, T., Willis, L. M., Socci, N. D., and Studer, L. (2005). Derivation of multipotent mesenchymal precursors from human embryonic stem cells. PLoS Med 2, e161.

Becher B, Durell B G, Noelle R J (2002) Experimental autoimmune encephalitis and inflammation in the absence of interleukin-12. The Journal of clinical investigation 110: 493-497.

Benito-Leon, J. (2011). Are the prevalence and incidence of multiple sclerosis changing? Neuroepidemiology 36, 148-149.

Brown, S. E., Tong, W., and Krebsbach, P. H. (2009). The derivation of mesenchymal stem cells from human embryonic stem cells. Cells Tissues Organs 189, 256-260.

Chao, Y. X., He, B. P., and Tay, S. S. (2009). Mesenchymal stem cell transplantation attenuates blood brain barrier damage and neuroinflammation and protects dopaminergic neurons against MPTP toxicity in the substantia nigra in a model of Parkinson's disease. Journal of neuroimmunology 216, 39-50.

Chaudhary P, Marracci G H, Bourdette D N (2006) Lipoic acid inhibits expression of ICAM-1 and VCAM-1 by CNS endothelial cells and T cell migration into the spinal cord in experimental autoimmune encephalomyelitis. Journal of neuroimmunology 175: 87-96.

Chyou, S., Elland, E. H., Carpenter, A. C., Tzeng, T. C., Tian, S., Michaud, M., Madri, J. A., and Lu, T. T. (2008). Fibroblast-type reticular stromal cells regulate the lymph node vasculature. J Immunol 181, 3887-3896.

Connick, P., Kolappan, M., Crawley, C., Webber, D. J., Patani, R., Michell, A. W., Du, M. Q., Luan, S. L., Altmann, D. R., Thompson, A. J., et al. (2012). Autologous mesenchymal stem cells for the treatment of secondary progressive multiple sclerosis: an open-label phase 2a proof-of concept study. Lancet neurology 11, 150-156.

Correale, J., and Villa, A. (2007). The blood-brain-barrier in multiple sclerosis: functional roles and therapeutic targeting. Autoimmunity 40, 148-160.

Costa, M., Dottori, M., Ng, E., Hawes, S. M., Sourris, K., Jamshidi, P., Pera, M. F., Elefanty, A. G., and Stanley, E. G. (2005). The hESC line Envy expresses high levels of GFP in all differentiated progeny. Nat Methods 2, 259-260.

Cuccurullo C, Iezzi A, Fazia M L, De Cesare D, Di Francesco A, et al. (2006) Suppression of RAGE as a basis of simvastatin-dependent plaque stabilization in type 2 diabetes. Arteriosclerosis, thrombosis, and vascular biology 26: 2716-2723.

Cunnea P, McMahon J, O'Connell E, Mashayekhi K, Fitzgerald U, et al. (2010) Gene expression analysis of the microvascular compartment in multiple sclerosis using laser microdissected blood vessels. Acta neuropathologica 119: 601-615.

Dai H, Ciric B, Zhang G X, Rostami A (2012) Interleukin-10 plays a crucial role in suppression of experimental autoimmune encephalomyelitis by Bowman-Birk inhibitor. Journal of neuroimmunology 245: 1-7.

Dienz, O., and Rincon, M. (2009). The effects of IL-6 on CD4 T cell responses. Clinical immunology 130, 27-33.

Djouad, F., Plence, P., Bony, C., Tropel, P., Apparailly, F., Sany, J., Noel, D., and Jorgensen, C. (2003) Immunosuppressive effect of mesenchymal stem cells favors tumor growth in allogeneic animals. Blood 102, 3837-3844.

Dong, C. (2008). TH17 cells in development: an updated view of their molecular identity and genetic programming Nat Rev Immunol 8, 337-348.

Draper, J. S., Pigott, C., Thomson, J. A., and Andrews, P. W. (2002). Surface antigens of human embryonic stem cells: changes upon differentiation in culture. Journal of anatomy 200, 249-258.

Drukker, M., Katchman, H., Katz, G., Even-Toy Friedman, S., Shezen, E., Hornstein, E., Mandelboim, O., Reisner, Y., and Benvenisty, N. (2006). Human embryonic stem cells and their differentiated derivatives are less susceptible to immune rejection than adult cells. Stem Cells 24, 221-229.

Drukker, M., Katz, G., Urbach, A., Schuldiner, M., Markel, G., Itskovitz-Eldor, J., Reubinoff, B., Mandelboim, O., and Benvenisty, N. (2002). Characterization of the expression of MHC proteins in human embryonic stem cells. Proceedings of the National Academy of Sciences of the United States of America 99, 9864-9869.

English, K., Barry, F. P., Field-Corbett, C. P., and Mahon, B. P. (2007). IFN-gamma and TNF alpha differentially regulate immunomodulation by murine mesenchymal stem cells. Immunol Lett 110, 91-100.

Ge, S., Shrestha, B., Paul, D., Keating, C., Cone, R., Guglielmotti, A., and Pachter, J. S. (2012). The CCL2 synthesis inhibitor bindarit targets cells of the neurovascular unit, and suppresses experimental autoimmune encephalomyelitis. J Neuroinflammation 9, 171.

Gijbels, K., Brocke, S., Abrams, J. S., and Steinman, L (1995). Administration of neutralizing antibodies to interleukin-6 (IL-6) reduces experimental autoimmune encephalomyelitis and is associated with elevated levels of IL-6 bioactivity in central nervous system and circulation. Mol Med 1, 795-805.

Gordon, D., Pavlovska, G., Glover, C. P., Uney, J. B., Wraith, D., and Scolding, N. J. (2008a). Human mesenchymal stem cells abrogate experimental allergic encephalomyelitis after intraperitoneal injection, and with sparse CNS infiltration. Neurosci Lett 448, 71-73.

Gordon, D., Pavlovska, G., Glover, C. P., Uney, J. B., Wraith, D., and Scolding, N. J. (2008b). Human mesenchymal stem cells abrogate experimental allergic encephalomyelitis after intraperitoneal injection, and with sparse CNS infiltration. Neuroscience letters 448, 71-73.

Gordon, D., Pavlovska, G., Uney, J. B., Wraith, D. C., and Scolding, N. J. (2010). Human mesenchymal stem cells infiltrate the spinal cord, reduce demyelination, and localize to white matter lesions in experimental autoimmune encephalomyelitis. J Neuropathol Exp Neurol 69, 1087-1095.

Grinnemo, K. H., Mansson, A., Dellgren, G., Klingberg, D., Wardell, E., Drvota, V., Tammik, C., Holgersson, J., Ringden, O., Sylven, C., et al. (2004). Xenoreactivity and engraftment of human mesenchymal stem cells transplanted into infarcted rat myocardium. J Thorac Cardiovasc Surg 127, 1293-1300.

Hansen, W., Westendorf, A. M., and Buer, J. (2008). Regulatory T cells as targets for immunotherapy of autoimmunity and inflammation. Inflamm Allergy Drug Targets 7, 217-223.

Hofstetter, C. P., Schwarz, E. J., Hess, D., Widenfalk, J., El Manira, A., Prockop, D. J., and Olson, L. (2002). Marrow stromal cells form guiding strands in the injured spinal cord and promote recovery. Proceedings of the National Academy of Sciences of the United States of America 99, 2199-2204.

Huber, T. L., Kouskoff, V., Fehling, H. J., Palis, J., and Keller, G. (2004). Haemangioblast commitment is initiated in the primitive streak of the mouse embryo. Nature 432, 625-630.

Hwang, N. S., Varghese, S., Lee, H. J., Zhang, Z., Ye, Z., Bae, J., Cheng, L., and Elisseeff, J. (2008). In vivo commitment and functional tissue regeneration using human embryonic stem cell derived mesenchymal cells. Proc Natl Acad Sci USA 105, 20641-20646.

Huss D J, Winger R C, Cox G M, Guerau-de-Arellano M, Yang Y, et al. (2011) TGF-beta signaling via Smad4 drives IL-10 production in effector Th1 cells and reduces T-cell trafficking in EAE. European journal of immunology 41: 2987-2996.

Javazon, E. H., Beggs, K. J., and Flake, A. W. (2004). Mesenchymal stem cells: paradoxes of passaging. Exp Hematol 32, 414-425.

Johnston, J., and So, T. Y. (2012). First-line disease-modifying therapies in paediatric multiple sclerosis: a comprehensive overview. Drugs 72, 1195-1211.

Karussis, D., Karageorgiou, C., Vaknin-Dembinsky, A., Gowda-Kurkalli, B., Gomori, J. M., Kassis, I., Bulte, J. W., Petrou, P., Ben-Hur, T., Abramsky, O., et al. (2010). Safety and immunological effects of mesenchymal stem cell transplantation in patients with multiple sclerosis and amyotrophic lateral sclerosis. Arch Neurol 67, 1187-1194.

Klimanskaya, I., Chung, Y., Becker, S., Lu, S. J., and Lanza, R. (2006). Human embryonic stem cell lines derived from single blastomeres. Nature 444, 481-485.

Kurtzke J F (1983). "Rating neurologic impairment in multiple sclerosis: an expanded disability status scale (EDSS)". Neurology 33 (11): 1444-52

Leech, M. D., Barr, T. A., Turner, D. G., Brown, S., O'Connor, R. A., Gray, D., Mellanby, R. J., and Anderton, S. M. (2012). Cutting Edge: IL-6-Dependent Autoimmune Disease: Dendritic Cells as a Sufficient, but Transient, Source. J Immunol.

Lin, G., Martins-Taylor, K., and Xu, R. H. (2010). Human embryonic stem cell derivation, maintenance, and differentiation to trophoblast. Methods in molecular biology 636, 1-24.

Liu, R., Zhang, Z., Lu, Z., Borlongan, C., Pan, J., Chen, J., Qian, L., Liu, Z., Zhu, L., Zhang, J., et al. (2012). Human Umbilical Cord Stem Cells Ameliorate Experimental Autoimmune Encephalomyelitis by Regulating Immunoinflammation and Remyelination. Stem cells and development.

Lu, S. J., Feng, Q., Caballero, S., Chen, Y., Moore, M. A., Grant, M. B., and Lanza, R. (2007). Generation of functional hemangioblasts from human embryonic stem cells. Nat Methods 4, 501-509.

Lu, S. J., Ivanova, Y., Feng, Q., Luo, C., and Lanza, R. (2009). Hemangioblasts from human embryonic stem cells generate multilayered blood vessels with functional smooth muscle cells. Regenerative medicine 4, 37-47.

Lu, S. J., Luo, C., Holton, K., Feng, Q., Ivanova, Y., and Lanza, R. (2008). Robust generation of hemangioblastic progenitors from human embryonic stem cells. Regen Med 3, 693-704.

Ludwig T E, Levenstein M E, Jones J M, Berggren W T, Mitchen E R, et al. (2006) Derivation of human embryonic stem cells in defined conditions. Nat Biotechnol 24: 185-187.

Mahad D J, Ransohoff R M (2003) The role of MCP-1 (CCL2) and CCR2 in multiple sclerosis and experimental autoimmune encephalomyelitis (EAE). Seminars in immunology 15: 23-32.

McFarland, H. F., and Martin, R. (2007). Multiple sclerosis: a complicated picture of autoimmunity. Nat Immunol 8, 913-919.

Menge, T., Zhao, Y., Zhao, J., Wataha, K., Gerber, M., Zhang, J., Letourneau, P., Redell, J., Shen, L., Wang, J., et al. (2012). Mesenchymal Stem Cells Regulate Blood-Brain Barrier Integrity Through TIMP3 Release After Traumatic Brain Injury. Science translational medicine 4, 161ra150.

Minagar, A., Maghzi, A. H., McGee, J. C., and Alexander, J. S. (2012). Emerging roles of endothelial cells in multiple sclerosis pathophysiology and therapy. Neurological research 34, 738-745.

Mohyeddin Bonab, M., Yazdanbakhsh, S., Lotfi, J., Alimoghaddom, K., Talebian, F., Hooshmand, F., Ghavamzadeh, A., and Nikbin, B. (2007). Does mesenchymal stem cell therapy help multiple sclerosis patients? Report of a pilot study. Iranian journal of immunology: IJI 4, 50-57.

Morando, S., Vigo, T., Esposito, M., Casazza, S., Novi, G., Principato, M. C., Furlan, R., and Uccelli, A. (2012). The therapeutic effect of mesenchymal stem cell transplantation in experimental autoimmune encephalomyelitis is mediated by peripheral and central mechanisms. Stem Cell Res Ther 3, 3.

Ohtaki, H., Ylostalo, J. H., Foraker, J. E., Robinson, A. P., Reger, R. L., Shioda, S., and Prockop, D. J. (2008). Stem/progenitor cells from bone marrow decrease neuronal death in global ischemia by modulation of inflammatory/immune responses. Proc Natl Acad Sci USA 105, 14638-14643.

Olivier, E. N., Rybicki, A. C., and Bouhassira, E. E. (2006). Differentiation of human embryonic stem cells into bipotent mesenchymal stem cells. Stem Cells 24, 1914-1922.

Patanella, A K, Zinno, M., Quaranta, D., Nociti, V., Frisullo, G., Gainotti, G., Tonali, P. A., Batocchi, A. P., and Marra, C. (2010). Correlations between peripheral blood mononuclear cell production of BDNF, TNF-alpha, IL-6, IL-10 and cognitive performances in multiple sclerosis patients. J Neurosci Res 88, 1106-1112.

Payne, N. L., Sun, G., McDonald, C., Layton, D., Moussa, L., Emerson-Webber, A., Veron, N., Siatskas, C., Herszfeld, D., Price, J., et al. (2012). Distinct immunomodulatory and migratory mechanisms underpin the therapeutic potential of human mesenchymal stem cells in autoimmune demyelination. Cell Transplant.

Peron, J. P., Jazedje, T., Brandao, W. N., Perin, P. M., Maluf, M., Evangelista, L. P., Halpern, S., Nisenbaum, M. G., Czeresnia, C. E., Zatz, M., et al. (2012). Human endometrial-derived mesenchymal stem cells suppress inflammation in the central nervous system of EAE mice. Stem Cell Rev 8, 940-952.

Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human mesenchymal stem cells. Science 284, 143-147.

Pomper, M. G., Hammond, H., Yu, X., Ye, Z., Foss, C. A., Lin, D. D., Fox, J. J., and Cheng, L. (2009). Serial imaging of human embryonic stem-cell engraftment and teratoma formation in live mouse models. Cell Res 19, 370-379.

Quintana, A., Muller, M., Frausto, R. F., Ramos, R., Getts, D. R., Sanz, E., Hofer, M. J., Krauthausen, M., King, N. J., Hidalgo, J., et al. (2009). Site-specific production of IL-6 in the central nervous system retargets and enhances the inflammatory response in experimental autoimmune encephalomyelitis. Journal of immunology 183, 2079-2088.

Rafei, M., Birman, E., Forner, K., and Galipeau, J. (2009a). Allogeneic mesenchymal stem cells for treatment of experimental autoimmune encephalomyelitis. Mol Ther 17, 1799-1803.

Rafei, M., Campeau, P. M., Aguilar-Mahecha, A., Buchanan, M., Williams, P., Birman, E., Yuan, S., Young, Y. K., Boivin, M. N., Forner, K., et al. (2009b). Mesenchymal stromal cells ameliorate experimental autoimmune encephalomyelitis by inhibiting CD4 Th17 T cells in a CC chemokine ligand 2-dependent manner J Immunol 182, 5994-6002.

Rochman, I., Paul, W. E., and Ben-Sasson, S. Z. (2005). IL-6 increases primed cell expansion and survival. Journal of immunology 174, 4761-4767.

Ryan, J. M., Barry, F., Murphy, J. M., and Mahon, B. P. (2007). Interferon-gamma does not break, but promotes the immunosuppressive capacity of adult human mesenchymal stem cells. Clin Exp Immunol 149, 353-363.

Sanchez, L., Gutierrez-Aranda, I., Ligero, G., Rubio, R., Munoz-Lopez, M., Garcia-Perez, J. L., Ramos, V., Real, P. J., Bueno, C., Rodriguez, R., et al. (2011). Enrichment of human ESC derived multipotent mesenchymal stem cells with immunosuppressive and anti-inflammatory properties capable to protect against experimental inflammatory bowel disease. Stem Cells 29, 251-262.

Sethe, S., Scutt, A., and Stolzing, A. (2006). Aging of mesenchymal stem cells. Ageing Res Rev 5, 91-116.

Solchaga, L. A., Penick, K. J., and Welter, J. F. (2011). Chondrogenic differentiation of bone marrow-derived mesenchymal stem cells: tips and tricks. Methods in molecular biology 698, 253-278.

Stromnes, I. M., and Goverman, J. M. (2006). Active induction of experimental allergic encephalomyelitis. Nat Protoc 1, 1810-1819.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tse, W. T., Pendleton, J. D., Beyer, W. M., Egalka, M. C., and Guinan, E. C. (2003). Suppression of allogeneic T-cell proliferation by human marrow stromal cells: implications in transplantation. Transplantation 75, 389-397.

Tyndall, A. (2011). Successes and failures of stem cell transplantation in autoimmune diseases. Hematology Am Soc Hematol Educ Program 2011, 280-284.

Uccelli, A., and Prockop, D. J. (2010a). Why should mesenchymal stem cells (MSCs) cure autoimmune diseases? Curr Opin Immunol 22, 768-774.

Uccelli, A., and Prockop, D. J. (2010b). Why should mesenchymal stem cells (MSCs) cure autoimmune diseases? Curr Opin Immunol, 7.

Waterman, R. S., Tomchuck, S. L., Henkle, S. L., and Betancourt, A. M. (2010). A new mesenchymal stem cell (MSC) paradigm: polarization into a pro-inflammatory MSC1 or an Immunosuppressive MSC2 phenotype. PLoS One 5, e10088.

Weber, M. S., Menge, T., Lehmann-Horn, K., Kronsbein, H. C., Zettl, U., Sellner, J., Hemmer, B., and Stuve, O. (2012). Current treatment strategies for multiple sclerosis—efficacy versus neurological adverse effects. Current pharmaceutical design 18, 209-219.

Wong, R. S. (2011). Mesenchymal stem cells: angels or demons? J Biomed Biotechnol 2011, 459510.

Yamout, B., Hourani, R., Salti, H., Barada, W., El-Hajj, T., Al-Kutoubi, A., Herlopian, A., Baz, E. K., Mahfouz, R., Khalil-Hamdan, R., et al. (2010). Bone marrow mesenchymal stem cell transplantation in patients with multiple sclerosis: a pilot study. J Neuroimmunol 227, 185-189.

Zappia, E., Casazza, S., Pedemonte, E., Benvenuto, F., Bonanni, I., Gerdoni, E., Giunti, D., Ceravolo, A., Cazzanti, F., Frassoni, F., et al. (2005). Mesenchymal stem cells ameliorate experimental autoimmune encephalomyelitis inducing T-cell anergy. Blood 106, 1755-1761.

Zhang, J., Li, Y., Chen, J., Cui, Y., Lu, M., Elias, S. B., Mitchell, J. B., Hammill, L, Vanguri, P., and Chopp, M.

(2005). Human bone marrow stromal cell treatment improves neurological functional recovery in EAE mice. Exp Neurol 195, 16-26.

Becher, B., Durell, B. G., and Noelle, R. J. (2002). Experimental autoimmune encephalitis and inflammation in the absence of interleukin-12. The Journal of clinical investigation 110, 493-497.

Chaudhary, P., Marracci, G. H., and Bourdette, D. N. (2006). Lipoic acid inhibits expression of ICAM-1 and VCAM-1 by CNS endothelial cells and T cell migration into the spinal cord in experimental autoimmune encephalomyelitis. Journal of neuroimmunology 175, 87-96.

Crocker, S. J., Milner, R., Pham-Mitchell, N., and Campbell, I. L. (2006). Cell and agonist-specific regulation of genes for matrix metalloproteinases and their tissue inhibitors by primary glial cells. Journal of neurochemistry 98, 812-823.

Cuccurullo, C., Iezzi, A., Fazia, M. L., De Cesare, D., Di Francesco, A., Muraro, R., Bei, R., Ucchino, S., Spigonardo, F., Chiarelli, F., et al. (2006). Suppression of RAGE as a basis of simvastatin-dependent plaque stabilization in type 2 diabetes. Arteriosclerosis, thrombosis, and vascular biology 26, 2716-2723.

Cunnea, P., McMahon, J., O'Connell, E., Mashayekhi, K., Fitzgerald, U., and McQuaid, S. (2010). Gene expression analysis of the microvascular compartment in multiple sclerosis using laser microdissected blood vessels. Acta neuropathologica 119, 601-615.

Dai, H., Ciric, B., Zhang, G. X., and Rostami, A. (2012). Interleukin-10 plays a crucial role in suppression of experimental autoimmune encephalomyelitis by Bowman-Birk inhibitor. Journal of neuroimmunology 245, 1-7.

Huss, D. J., Winger, R. C., Cox, G. M., Guerau-de-Arellano, M., Yang, Y., Racke, M. K., and Lovett-Racke, A. E. (2011). TGF-beta signaling via Smad4 drives IL-10 production in effector Th1 cells and reduces T-cell trafficking in EAE. Eur J Immunol 41, 2987-2996.

Mahad, D. J., and Ransohoff, R. M. (2003). The role of MCP-1 (CCL2) and CCR2 in multiple sclerosis and experimental autoimmune encephalomyelitis (EAE). Semin Immunol 15, 23-32.

Moore, C. S., Milner, R., Nishiyama, A., Frausto, R. F., Serwanski, D. R., Pagarigan, R. R., Whitton, J. L., Miller, R. H., and Crocker, S. J. (2011). Astrocytic tissue inhibitor of metalloproteinase-1 (TIMP-1) promotes oligodendrocyte differentiation and enhances CNS myelination. The Journal of neuroscience: the official journal of the Society for Neuroscience 31, 6247-6254.

Quintana, A., Muller, M., Frausto, R. F., Ramos, R., Getts, D. R., Sanz, E., Hofer, M. J., Krauthausen, M., King, N. J., Hidalgo, J., et al. (2009). Site-specific production of IL-6 in the central nervous system retargets and enhances the inflammatory response in experimental autoimmune encephalomyelitis. Journal of immunology 183, 2079-2088.

The invention claimed is:

1. A method for producing embryoid bodies (EB) comprising:
   a. culturing human embryonic stem cells under adherent conditions in a serum-free medium comprising a GSK3 inhibitor at a concentration ranging from 0.05 µM to 0.2 µM in the absence of feeder cells, wherein the GSK3 inhibitor is (2'Z,3'E)-6-Bromoindirubin-3'-oxime (BIO);
   b. dissociating the cultured human embryonic stem cells; and
   c. culturing the dissociated human embryonic stem cells in an EB formation medium in an ultra-low-attachment dish to form embryoid bodies, wherein the inclusion of BIO in the serum-free medium results in an increase in the yield of embryoid bodies.

2. A method for producing hemangioblast comprising:
   a. culturing human embryonic stem cells under adherent conditions in a serum-free medium comprising a GSK3 inhibitor at a concentration ranging from 0.05 µM to 0.2 µM in the absence of feeder cells, wherein the GSK3 inhibitor is (2'Z,3'E)-6-Bromoindirubin-3'oxime (BIO);
   b. dissociating the cultured human embryonic stem cells; and
   c. culturing the dissociated human embryonic stem cells in an embryoid body formation medium in an ultra-low-attachment dish to form embryoid bodies, wherein the inclusion of BIO in the serum-free medium of step a) results in an increase in the yield of embryoid bodies; and
   d. disaggregating the embryoid bodies resulting from step c) into single cells and culturing the single cells in a culture comprising growth factors vascular endothelial growth factor (VEGF), Flt-3L (FL), thrombopoietin (TPO), and bFGF in an amount sufficient for the formation of human hemangio-colony forming cells.

3. The method of claim 1, wherein the dissociated human embryonic stem cells are cultured in step c) for less than 10 days.

4. The method of claim 1, wherein the dissociated human embryonic stem cells are cultured in step c) for 2-6 days.

5. The method of claim 1, wherein the dissociated human embryonic stem cells are cultured in step c) for 4-6 days.

6. The method of claim 2, wherein the dissociated human embryonic stem cells are cultured in step c) for less than 10 days.

7. The method of claim 2, wherein the dissociated human embryonic stem cells are cultured in step c) for 2-6 days.

8. The method of claim 2, wherein the dissociated human embryonic stem cells are cultured in step c) for 4-6 days.

9. The method of claim 2, wherein the step of disaggregating further comprises isolating the human hemangio-colony forming cells by size or morphology.

* * * * *